US012227524B2

(12) United States Patent
Kim et al.

(10) Patent No.: US 12,227,524 B2
(45) Date of Patent: Feb. 18, 2025

(54) ANTI-INFECTIVE COMPOUNDS

(71) Applicant: INSTITUT PASTEUR KOREA, Gyeonggi-do (KR)

(72) Inventors: Jaeseung Kim, Seoul (KR); Sunhee Kang, Yongin-si (KR); Juhee Kang, Gyeonggi-do (KR); Sumi Lee, Busan (KR); Jeong Jea Seo, Seoul (KR); Mooyoung Seo, Gyeonggi-do (KR)

(73) Assignee: INSTITUT PASTEUR KOREA, Gyeonggi-Do (KR)

( * ) Notice: Subject to any disclaimer, the term of this patent is extended or adjusted under 35 U.S.C. 154(b) by 0 days.

(21) Appl. No.: 17/588,947

(22) Filed: Jan. 31, 2022

(65) Prior Publication Data

US 2022/0153756 A1 May 19, 2022

Related U.S. Application Data

(62) Division of application No. 15/319,983, filed as application No. PCT/EP2015/063982 on Jun. 22, 2015, now Pat. No. 11,279,714.

(60) Provisional application No. 62/015,056, filed on Jun. 20, 2014.

(51) Int. Cl.
| | |
|---|---|
| *C07D 519/00* | (2006.01) |
| *C07D 215/48* | (2006.01) |
| *C07D 277/82* | (2006.01) |
| *C07D 401/04* | (2006.01) |
| *C07D 417/04* | (2006.01) |
| *C07D 495/04* | (2006.01) |
| *C07D 513/04* | (2006.01) |

(52) U.S. Cl.
CPC ......... *C07D 519/00* (2013.01); *C07D 215/48* (2013.01); *C07D 277/82* (2013.01); *C07D 401/04* (2013.01); *C07D 417/04* (2013.01); *C07D 495/04* (2013.01); *C07D 513/04* (2013.01)

(58) Field of Classification Search
CPC .. C07D 513/04; C07D 417/04; C07D 401/04; C07D 519/00
See application file for complete search history.

(56) References Cited

U.S. PATENT DOCUMENTS

| | | | |
|---|---|---|---|
| 3,551,443 A | 12/1970 | Duennenberger et al. | |
| 6,087,380 A | 7/2000 | Hauel et al. | |
| 6,414,008 B1 | 7/2002 | Hauel et al. | |
| 7,622,481 B2 * | 11/2009 | Axten | C07D 513/04 546/122 |
| 8,163,753 B2 * | 4/2012 | Tsubouchi | A61P 31/06 514/323 |
| 8,232,410 B2 * | 7/2012 | Ojima | A61P 31/00 548/310.7 |

FOREIGN PATENT DOCUMENTS

| | | |
|---|---|---|
| CN | 104718213 B | 2/2018 |
| RU | 2244717 C2 | 1/2005 |
| WO | WO 2008156676 | * 12/2008 |
| WO | 2009034546 A2 | 3/2009 |
| WO | 2009034546 A3 | 3/2009 |
| WO | 2011163610 A2 | 12/2011 |
| WO | 2014015167 A2 | 1/2014 |

OTHER PUBLICATIONS

Huang et al., J. Med. Chem. 2009, vol. 52, No. 21, pp. 6757-6767.*
Akerkar, A.S., Naftchi, N.E et al., "Antimycobacterial activity of some quinolyl aryl sulfides, sulfones, and ethers, in vitro." Antimicrobial Agents and Chemotherapy, May 1972, 1(5):392-396.
Ananthan, S. et al., "High-throughput screening for inhibitors of *Mycobacterium tuberculosis* H37Rv." Tuberculosis, Sep. 2009, 89(5):334-353, doi:10.1016/j.tube.2009.05.008.
Ban, S., "Studies on Chemotherapeutics. XXXIX. Synthesis of imidazo compounds. IV. Imidazo[2, 1-b]thiadiazole derivatives. (2)." Yakugaku Zasshi; Journal of the Pharmaceutical Society of Japan, Jan. 1954, 74(6):Summary.
CAS Registry No. 1287873-51-1, May 1, 2011; CAS Registry No. 1189667-13-7, Oct. 23, 2009; CAS Registry No. 1185157-28-1, Sep. 16, 2009; CAS Registry No. 1216531-94-0, Apr. 4, 2010; CAS Registry No. 1216474-47-3, Apr. 4, 2010; CAS Registry No. 1189944-69-1, Oct. 25, 2009; CAS Registry No. 1185166-46-4, Sep. 16, 2009; retrieved from STN International [online].
CAS Registry No. 924455-53-8, Mar. 2, 2007; CAS Registry No. 919879-00-8, Feb. 8, 2007; CAS Registry No. 930480-88-9, Apr. 17, 2007; CAS Registry No. 906253-79-0, Sep. 10, 2006; CAS Registry No. 1211512-82-1, Mar. 18, 2010; retrieved from STN International [online].
Clarke, K. et al., "Condensed isothiazoles. Part 5. Thieno[2,3-d]isothiazoles and Thieno[3,2-d]isothiazoles." Journal of the Chemical Society, Jan. 1980, pp. 1029-1037.
De Souza, M.V.N. et al., "Synthesis and in vitro antitubercular activity of a series of quinolone derivatives." Bioorganic & Medicinal Chemistry, Feb. 2009, 17(4):1474-1480, doi:10.1016/j.bmc.2009.01.013.
Grehn, L., "Bromine-induced Cyclization of I-Acyl-3-(3-thienyl)-2-thioureas to 2-Acylaminothieno[3,2-d]thiazoles." Journal of Heterocyclic Chemistry, Jan. 1978, 15(1):81-87.
Knudson, S.E. et al., "A Trisubstituted Benzimidazole Cell Division Inhibitor with Efficacy against *Mycobacterium tuberculosis*." Plos One, Apr. 2014, 9(4):1-7.
Kvitko, N.Ya. et al., "Synthesis of 2-phenylthieno[3,2-d]oxazole and 2-phenylthieno[3,2-d]thiazole." Chemistry of Heterocyclic Compounds, Apr. 1979, 15(4):384-386.
Efranc et al. European Journal of Medicinal Chemistry 63 (2013) 213-223.
Michael, J.P., "Quinoline, quinazoline and acridone alkaloids." Natural Product Reports, Jan. 2000, 17(6):603-620, doi:10.1039/a904850b.
Nayyar, A. et al., "3D-QSAR study of ring-substituted quinolone class of anti-tuberculosis agents." Bioorganic & Medicinal Chemistry, Feb. 2006, 14(3):847-856, doi:10.1016/j.bmc.2005.09.018.

(Continued)

*Primary Examiner* — Rebecca L Anderson
(74) *Attorney, Agent, or Firm* — SALIWANCHIK, LLOYD & EISENSCHENK

(57) ABSTRACT

The present invention relates to small molecule compounds and their use in the treatment of bacterial infections, in particular Tuberculosis.

5 Claims, No Drawings

(56) References Cited

OTHER PUBLICATIONS

Office Action dated Oct. 10, 2018 issued in parallel Russian Patent Application No. 016150134/04(080453), filed Jun. 22, 2015 with English translation wherein RU 2244717 C2 was cited.
Office Action dated Oct. 31, 2019 issued in parallel European Patent Application No. 15 730 7836.
Office Action dated Sep. 16, 2019 issued in parallel Chinese Patent Application No. 2015800442692 with English translation.
Terzioglu, N., Gursoy, A., "Synthesis and anticancer evaluation of some new hydrazine derivatives of 2,6-dimethylimidazo[2, 1-b]-[1,3,4]thiadiazole-5-carbohydrazide." European Journal of Medicinal Chemistry, Jul. 2003, 38(7-8):781-786, doi: 10.1016/S0223-5234(03)00138-7.
Vangapandu, S. et al., "Ring-substituted quinolones as potential anti-tuberculosis agents." Bioorganic & Medicinal Chemistry, Jan. 2004, 12:2501-2508, doi:10.1016/j.bmc.2004.03.045.
Waddell, S.T. et al., "Benzothiazolylthio Carbapenems: Potent Anti-MRSA Agents." Bioorganic & Medicinal Chemistry Letters, Jul. 1995, 5(13):1427-1432.
Yadav, R. et al., "Novel Biphenyl Imidazo[2,1-b][1,3,4]-Thiadiazole -a versatile scaffold." DHR International Journal of Pharmaceutical Sciences, Jan. 2012, 2(1):20-37.

* cited by examiner

ANTI-INFECTIVE COMPOUNDS

CROSS REFERENCE TO A RELATED APPLICATION

This application is a divisional application of co-pending application Ser. No. 15/319,983, filed Dec. 19, 2016; which is a National Stage Application of International Application Number PCT/EP2015/063982, filed Jun. 22, 2015; which claims priority to U.S. Provisional Application No. 62/015,056, filed Jun. 20, 2014.

FIELD OF THE INVENTION

The present invention relates to small molecule compounds and their use in the treatment of bacterial infections, in particular Tuberculosis.

BACKGROUND OF THE INVENTION

Tuberculosis (TB) still claims the life of more than 1.8 million people each year. Inadequate use of chemotherapy has led to an increasing number of multi-drug resistant (MDR) TB, and the situation is likely to worsen with the emergence and spread of extensively drug resistant forms of the disease (Chaisson R. E. & Nuermberger E. L., N Engl J Med 2012). The most urgent clinical need is to discover potent agents capable of reducing the time of M/XDR tuberculosis therapy with a success rate comparable to susceptible tuberculosis. The last decade has seen the discovery of promising new agent classes for the management of tuberculosis (Stover C. K. et al. Nature 2000; Andreis K. et al. Science 2005), several of which are currently under clinical development (Diacon A.H. et al. Antimicrob Agents Chemother 2012; Gler M. T. et al. N Engl J Med 2012). However, given the high attrition rate during clinical development and the emergence of resistance, the discovery of additional clinical candidates is clearly needed.

Current chemotherapy consists of compounds that directly target *Mycobacterium tuberculosis* bacillus, by targeting either the synthesis of macromolecules such as DNA, RNA or protein synthesis, or key components of the cell-wall. The most widely used dedicated anti-tubercular drugs isoniazid, ethionamide and pyrazinamide are pro-drugs that first require activation. As active forms, they demonstrate inhibitory activity on primarily cell-wall synthesis and/or on a wide range of mycobacterial targets, which have not yet been fully characterized.

One of the most challenging obstacles in the discovery of new anti-TB drugs is the lack of predictive in vitro screening methods that reproduce critical features found in vivo. Although there is still a lack of understanding of the biological mechanisms behind tubercle bacillus persistence, i.e. the location and state of latent bacteria in humans, *M. tuberculosis* is thought to persists in primary granulomas and within various cell types (Houben et al., 2006; Neyrolles et al., 2006). The bacillus mainly localizes inside phagocytic cells, such as macrophages and dendritic cells, where it adapts drastically its metabolism to survive the harsh environment found in professional phagocytic cells (Rohde et al., 2007). Therefore, we developed and used a phenotypic high-content screening technology in infected macrophages to identify novel antitubercular compounds (WO2010003533A2), overcoming many of the numerous and burdensome steps involved with other methodologies (Arain et al., 1996). The technology has several advantages compared to traditional phenotypic screening approaches since it allows i) screening under physiologically relevant conditions, which is notoriously challenging in the field (Stanley S. A. et al., ACS Chem Biol 2012), ii) selection of non-cytotoxic compounds that penetrate effectively inside macrophages (Pethe K. et al. Nat Med. 2013), and iii) selection of compounds that are poor substrates for macrophage-induced efflux mechanisms, thereby compressing the discovery and optimization time of new lead molecules.

It was an object of the present invention to identify compounds effective against bacterial infections, in particular compounds that would prevent *M. tuberculosis* multiplication inside the host macrophage.

DESCRIPTION OF THE INVENTION

In one aspect, the present invention relates to compounds having the general formula I:

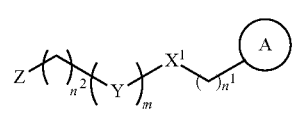

wherein
$n^1$ and $n^2$ are independently 0, 1, 2, or 3;
m is 0 or 1;
A is a moiety selected from the group consisting of

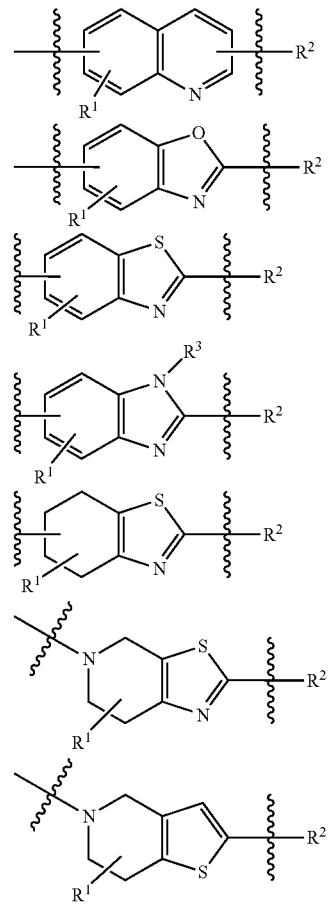

-continued

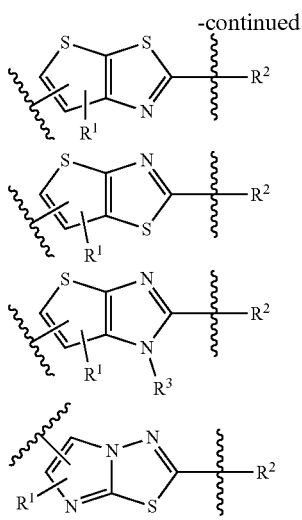

R¹ is selected from the group consisting of hydrogen, halogen. $C_1$-$C_{10}$ alkyl, $C_3$-$C_{10}$cycloalkyl, $C_1$-$C_3$haloalkyl, hydroxyl, —OR³, —CN, —NO$_2$, —NH$_2$, —NR$^b$R$^c$, aryl, heteroaryl and heterocyclyl group wherein each of said alkyl, cycloalkyl, aryl heteroaryl and heterocyclyl is optionally substituted with one to four R$^a$ groups;

R² is selected from the group consisting of hydrogen, halogen, $C_1$-$C_{10}$ alkyl, $C_3$-$C_{10}$cycloalkyl, $C_1$-$C_3$haloalkyl, hydroxyl, —OR³, —CN, —NO$_2$, —NH$_2$, —NR$^b$R$^c$, —NR⁶C(O)R$^c$, —(NR$^d$)(V)$_p$R$^e$, aryl, heteroaryl, heterocyclyl group and groups of formula Ia shown below, wherein each of said alkyl, cycloalkyl, aryl, heteroaryl and heterocyclyl is optionally substituted with one to four R$^a$ groups;

formula Ia

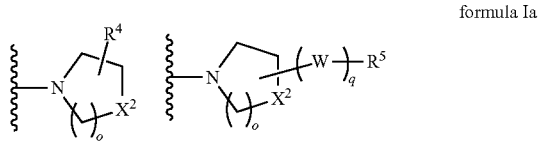

wherein,
o is independently, at each occurrence, 0, 1, 2 or 3;
p is 0 or 1,
q is 0 or 1;
X¹ is C=O, O, S, —S(O)$_2$—, —S(O)$_2$NR⁶—, —C(O)O—, —C(O)NR⁶—, —NHC(O)— or —(NR⁶)—;
X² is selected from CR$^b$R$^c$, O, S, or NR⁶;
Y is $C_1$-$C_6$ alkylene, O, S or NR⁶;
V and W are independently, at each occurrence, $C_1$-$C_6$ alkylene;

R³ is selected from the group consisting of hydrogen, $C_1$-$C_{10}$ alkyl, $C_3$-$C_{10}$cycloalkyl, haloalkyl in particular, $C_1$-$C_3$haloalkyl, $C_1$-$C_6$alkyl-O-alkyl, $C_2$-$C_{10}$ alkenyl, $C_3$-$C_{10}$ cycloalkenyl, $C_2$-$C_{10}$ alkynyl, aryl, heteroaryl and heterocyclyl group, wherein each of said alkyl, cycloalkyl, aryl, heteroaryl and heterocyclyl is optionally substituted with one to four R$^a$ groups;

R⁴ is selected from the group consisting of hydrogen, halogen, $C_1$-$C_{10}$ alkyl, $C_3$-$C_{10}$cycloalkyl, $C_1$-$C_3$haloalkyl, hydroxyl, —OR⁶, —CN, —NO$_2$, —NH$_2$, —NR$^b$R$^c$, —N(R⁶)C(O)R⁶, —C(O)R⁶, —C(O)OR⁶, —C(O)NR$^b$R$^c$, —S(O)R⁶, —S(O)$_2$R⁶, —S(O)$_2$NR$^b$R$^c$, aryl, heteroaryl and heterocyclyl group wherein each of said alkyl, cycloalkyl, —OR⁶ aryl, heteroaryl and heterocyclyl is optionally substituted with one to four R$^a$ groups;

R⁵ is selected from the group consisting of hydrogen, halogen, $C_1$-$C_{10}$ alkyl, $C_3$-$C_{10}$cycloalkyl, $C_1$-$C_3$haloalkyl, hydroxyl, —OR⁶, —CN, —NO$_2$, —NH$_2$, —NR$^b$R$^c$, —N(R⁶)C(O)R⁶, —N(R⁶)C(O)OR⁶, —C(O)R⁶, —C(O)OR⁶, —C(O)NR$^b$R$^c$, —CHOHR⁶, —S(O)R⁶, —S(O)$_2$R⁶, —S(O)$_2$NR$^b$R$^c$, aryl, e.g. phenyl, benzyl, heteroaryl and heterocyclyl group wherein each of said alkyl, cycloalkyl, aryl, heteroaryl, and heterocyclyl is optionally substituted with one to four R$^a$ groups;

R⁶ is independently, at each occurrence, selected from the group consisting of hydrogen, $C_1$-$C_{10}$ alkyl, $C_3$-$C_{10}$cycloalkyl, $C_1$-$C_3$haloalkyl, aryl, heteroaryl and heterocyclyl group, wherein each of said alkyl, cycloalkyl, aryl, heteroaryl and heterocyclyl is optionally substituted with one to four R$^a$ groups;

Z is selected from the group consisting of $C_1$-$C_{10}$ alkyl, $C_3$-$C_{10}$cycloalkyl, $C_1$-$C_3$haloalkyl, OR⁷, aryloxy, aryl, e.g., phenyl or benzyl, heteroaryl, heterocyclyl group, e.g., piperidinyl, morpholinyl, and groups of formula Ib shown below, wherein each of said alkyl, cycloalkyl, aryl, heteroaryl, heterocyclyl and groups of formula Ib is optionally substituted with one to four R$^a$ groups;

Formula Ib

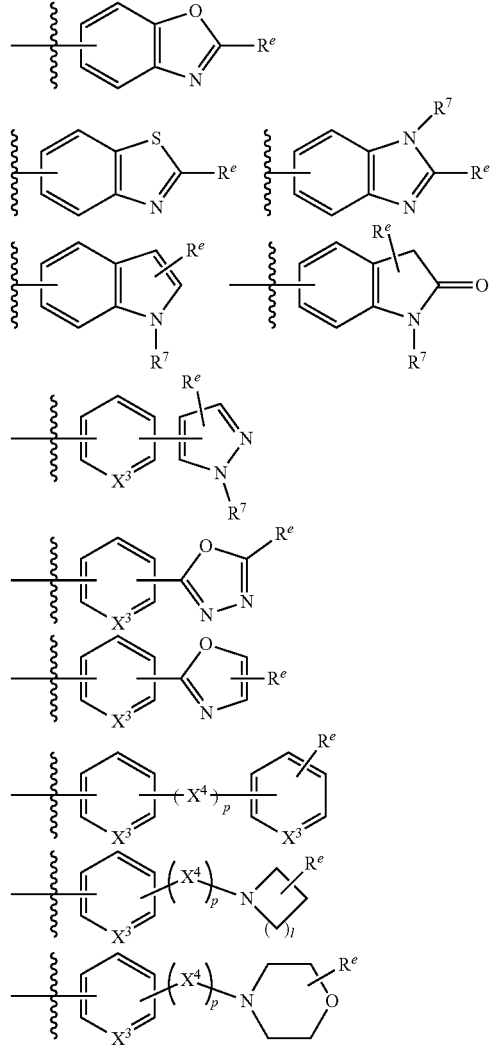

-continued

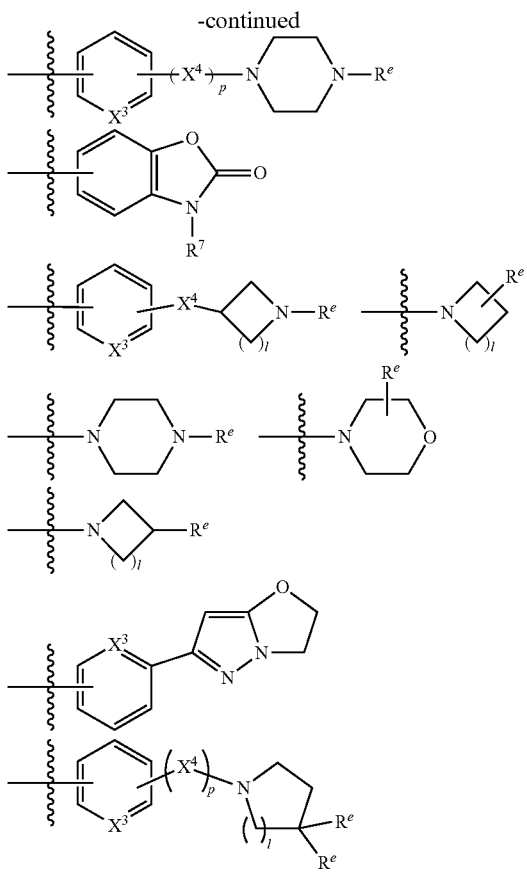

wherein, p is 0 or 1;

l is 1, 2 or 3;

$X^3$ is, independently at each occurrence, selected from CH or N;

$X^4$ is selected from C=O, $CR^bR^c$, O, S, or $NR^7$;

$R^e$, if denoted in formula Ib, may also occur twice as substituent at the same carbon atom wherein $R^e$ is independently selected at each occurrence;

$R^a$ is independently, at each occurrence, selected from the group consisting of hydrogen, halogen, $C_1$-$C_3$ alkyl, $C_1$-$C_4$ alkoxy, $C_1$-$C_4$ alkoxy substituted with aryl, e.g., phenyl or benzyl, aryloxy; $C_1$-$C_3$ haloalkyl, hydroxyl, $C_1$-$C_3$ alkylhydroxyl, —CN, $NO_2$, $—NR^bR^c$, $—C(O)NR^bR^c$, $—OR^c$, $—C(O)R^c$, $—C(O)OR^c$, sulfonyl, sulfoxide, $C_3$-$C_{10}$ cycloalkyl, heterocyclyl, heteroaryl and aryl, e.g., phenyl, benzyl, alkylaryl wherein each of said alkyl, cycloalkyl, aryl, heteroaryl and heterocyclyl is optionally substituted with one to four $C_1$-$C_3$ alkyl, $C_1$-$C_4$ alkoxy, aryl, e.g., phenyl, benzyl, halogen, $C_1$-$C_3$ haloalkyl, hydroxyl, $—NH_2$, wherein such substitution, if present, may occur in such a manner that there is more than one substituent. e.g., two or three substituents, per carbon atom, wherein these two or three substituents may be the same or different;

$R^b$ and $R^c$ are independently, at each occurrence selected from the group consisting of hydrogen, $C_1$-$C_{10}$ alkyl, $C_3$-$C_{10}$ cycloalkyl, $C_1$-$C_6$ alkyl-O-alkyl, $C_2$-$C_{10}$ alkenyl, $C_1$-$C_4$ alkoxy, $C_1$-$C_3$ alkylhydroxyl, $C_3$-$C_{10}$ cycloalkenyl, $C_2$-$C_{10}$ alkynyl, $C_1$-$C_{10}$ haloalkyl, in particular $C_1$-$C_3$ haloalkyl, aryl, e.g., phenyl or benzyl, alkylaryl, heteroaryl, and heterocyclyl, wherein each of said alkyl, cycloalkyl, aryl, heteroaryl and heterocyclyl is optionally substituted with one to four $C_1$-$C_3$ alkyl, $C_1$-$C_4$ alkoxy, e.g., methoxy, halogen, aryloxy, $C_1$-$C_3$ haloalkyl, e.g., trifluoromethyl, hydroxyl, $C_1$-$C_3$ alkylhydroxyl, —CN, $—NO_2$, $—NH_2$, sulfonyl, sulfoxide, $C_3$-$C_{10}$ cycloalkyl, heterocyclyl, aryl, e.g. phenyl, benzyl, heteroaryl, wherein such substitution, if present, may occur in such a manner that there is more than one substituent, e.g. two or three substituents, per carbon atom, wherein such two or three substituents may be the same or different; or $R^b$ and $R^c$ are connected to each other to make a four, five or six membered saturated or unsaturated cyclic or heterocyclic ring, or they are connected to make a fused cyclic or heterocyclic ring structure;

$R^d$ is independently, at each occurrence, selected from the group consisting of hydrogen, $C_1$-$C_{10}$ alkyl, $C_3$-$C_{10}$ cycloalkyl, $C_1$-$C_3$ haloalkyl, aryl, e.g. phenyl or benzyl, heteroaryl and heterocyclyl group, wherein each of said alkyl, cycloalkyl, aryl, heteroaryl and heterocyclyl is optionally substituted with one to four $R^a$ groups;

$R^e$ is independently, at each occurrence, selected from the group consisting of hydrogen, halogen, $C_1$-$C_{10}$ alkyl, $C_3$-$C_{10}$ cycloalkyl, $C_1$-$C_3$ haloalkyl, hydroxyl, —CN, $—(CH_2)_lR^7$, with l being 0, 1, 2 or 3, $—NO_2$, $—NH_2$, $—NR^bR^c$, $—N(R)C(O)R^7$, $—C(O)R^7$, $—C(O)OR^7$, $—C(O)NR^bR^c$, $—S(O)R^7$, $—S(O)_2R^7$, $—S(O)_2NR^bR^c$, aryl, e.g., phenyl or benzyl, heteroaryl and heterocyclyl group, wherein each of said alkyl, cycloalkyl, aryl, heteroaryl and heterocyclyl is optionally substituted with one to four $R^a$ groups;

$R^7$ is independently, at each occurrence, selected from the group consisting of hydrogen, $C_1$-$C_{10}$ alkyl, $C_3$-$C_{10}$ cycloalkyl, $C_1$-$C_3$ haloalkyl, aryl, e.g., phenyl or benzyl, heteroaryl, and heterocyclyl, wherein each of said alkyl, cycloalkyl, aryl, heteroaryl and heterocyclyl is optionally substituted with one to four $R^a$ groups, and pharmaceutically acceptable salts thereof.

In one embodiment, the compound has the general formula II:

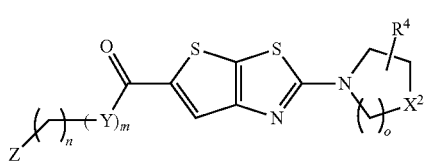

II wherein n is 0, 1, 2 or 3;

m is 0 or 1;

is 0, 1, 2 or 3;

$X^2$ is selected from $CR^bR^c$, O, S, or $NR^6$;

Y is $C_1$-$C_6$ alkylene, O, S or $NR^6$;

$R^4$ is selected from the group consisting of hydrogen, halogen, $C_1$-$C_{10}$ alkyl, $C_3$-$C_{10}$ cycloalkyl, $C_1$-$C_3$ haloalkyl, hydroxyl, $—OR^6$, —CN, $—NO_2$, $—NH_2$, $—NR^bR^c$, $—N(R^6)C(O)R^6$, $—C(O)R^6$, $—C(O)OR^6$, $—C(O)NR^bR^c$, $—S(O)R^6$, $—S(O)_2R^6$, $—S(O)_2NR^bR^c$, aryl, e.g., phenyl or benzyl, heteroaryl and heterocyclyl group wherein each of said alkyl, cycloalkyl, aryl, heteroaryl and heterocyclyl is optionally substituted with one to four $R^a$ groups;

$R^6$ is independently, at each occurrence, selected from the group consisting of hydrogen, $C_1$-$C_{10}$ alkyl, $C_3$-$C_{10}$ cycloalkyl, $C_1$-$C_3$ haloalkyl, aryl, e.g. phenyl or benzyl, heteroaryl and heterocyclyl group, wherein each of said alkyl, cycloalkyl, aryl, heteroaryl and heterocyclyl is optionally substituted with one to four $R^a$ groups;

Z is selected from the group consisting of $C_1$-$C_{10}$ alkyl, $C_3$-$C_{10}$cycloalkyl, $C_1$-$C_3$haloalkyl, $OR^6$, aryloxy, aryl, e.g., phenyl or benzyl, heteroaryl, heterocyclyl group, and groups of formula Ib shown below, wherein each of said alkyl, cycloalkyl, aryl, heteroaryl, heterocyclyl and groups of formula Ib is optionally substituted with one to four $R^a$ groups;

Formula Ib

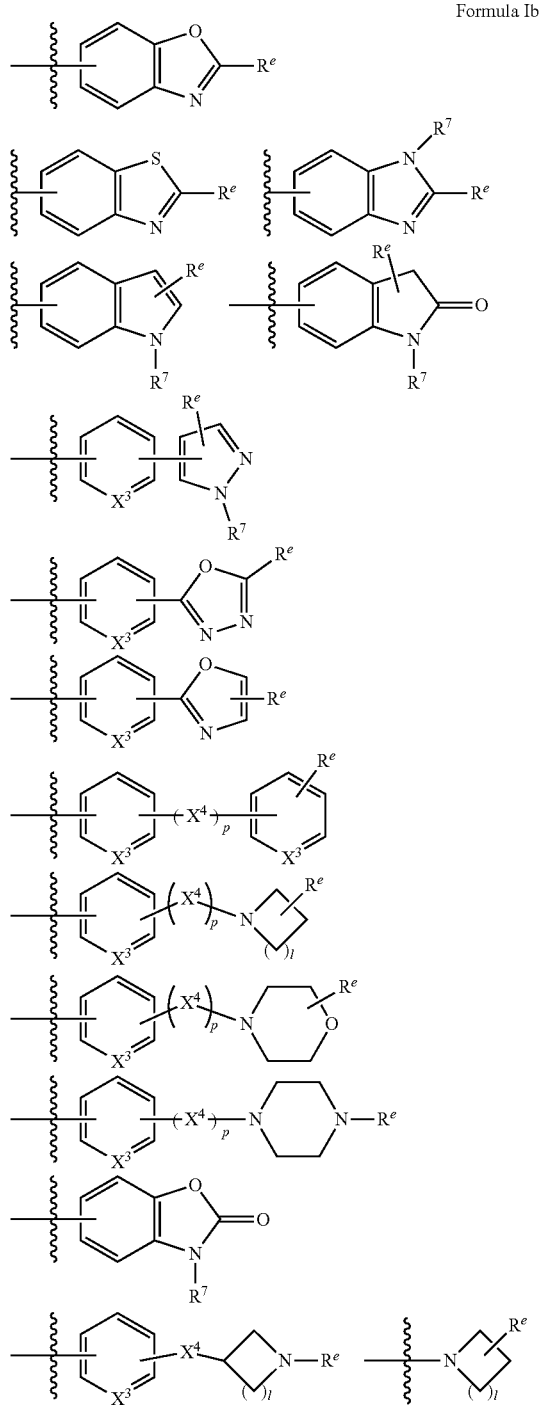

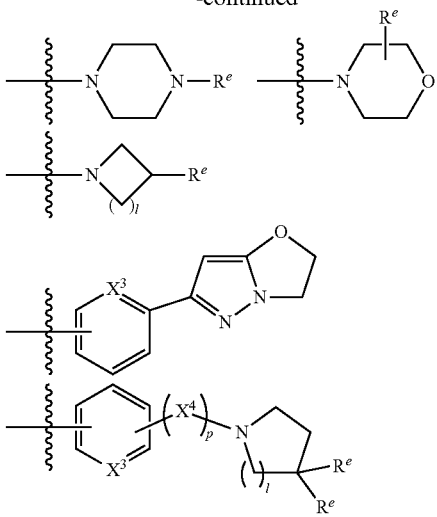

wherein,
p is 0 or 1;
l is 1, 2 or 3;
$X^3$ is, independently at each occurrence, selected from CH or N;
$X^4$ is selected from C=O, $CR^bR^c$, O, S, or $NR^7$;
$R^e$, if denoted in formula Ib, may also occur twice as substituent at the same carbon atom wherein $R^e$ is independently selected at each occurrence;
$R^a$ is independently, at each occurrence, selected from the group consisting of hydrogen, halogen, $C_1$-$C_3$ alkyl, $C_1$-$C_4$ alkoxy, alkoxy substituted with aryl, e.g., phenyl, benzyl, aryloxy;
$C_1$-$C_3$ haloalkyl, hydroxyl, $C_1$-$C_3$ alkylhydroxyl, —CN, $NO_2$, —$NR^bR^c$, —$C(O)NR^bR^c$, —$OR^c$, —$C(O)R^c$, —$C(O)OR^c$, sulfonyl, sulfoxide, $C_3$-$C_{10}$ cycloalkyl, heterocyclyl, heteroaryl and aryl, e.g., phenyl or benzyl, alkylaryl wherein each of said alkyl, cycloalkyl, aryl, heteroaryl and heterocyclyl is optionally substituted with one to four $C_1$-$C_3$ alkyl, $C_1$-$C_4$ alkoxy, aryl, e.g., phenyl or benzyl, halogen, $C_1$-$C_3$ haloalkyl, hydroxyl, —$NH_2$ wherein such substitution, if present, may occur in such a manner that there is more than one substituent, e.g. two or three substituents, per carbon atom, wherein such two or three substituents may be the same or different;
$R^b$ and $R^c$ are, independently at each occurrence, selected from the group consisting of hydrogen, $C_1$-$C_{10}$ alkyl, $C_3$-$C_{10}$ cycloalkyl, $C_1$-$C_6$ alkyl-O-alkyl, $C_2$-$C_{10}$ alkenyl, $C_1$-$C_4$ alkoxy, $C_1$-$C_3$ alkylhydroxyl, $C_3$-$C_{10}$ cycloalkenyl, $C_2$-$C_{10}$ alkynyl, $C_1$-$C_{10}$ haloalkyl, in particular $C_1$-$C_3$ haloalkyl, aryl, e.g., phenyl or benzyl, alkylaryl, heteroaryl, and heterocyclyl, wherein each of said alkyl, cycloalkyl, aryl, heteroaryl and heterocyclyl is optionally substituted with one to four $C_1$-$C_3$ alkyl, $C_1$-$C_4$ alkoxy, e.g., methoxy, halogen, aryloxy, $C_1$-$C_3$ haloalkyl, e.g., trifluoromethyl, hydroxyl, $C_1$-$C_3$ alkylhydroxyl, —CN, —$NO_2$, —$NH_2$, sulfonyl, sulfoxide, $C_3$-$C_{10}$ cycloalkyl, heterocyclyl, aryl, e.g., phenyl, benzyl, heteroaryl, wherein such substitution, if present, may occur in such a manner that there is more than one substituent, e.g., two or three substituents, per carbon atom, wherein such two or three substituents may be the same or different or they are connected to make a fused cyclic or heterocyclic ring structure; or $R^b$ and $R^c$ are connected to each other to make a four, five or six membered saturated or unsaturated cyclic or heterocyclic ring, or they are connected to make a fused cyclic or heterocyclic ring structure;

$R^e$ is independently, at each occurrence, selected from the group consisting of hydrogen, halogen, $C_1$-$C_{10}$ alkyl, $C_3$-$C_{10}$cycloalkyl, $C_1$-$C_3$haloalkyl, hydroxyl, —$OR^7$, —CN, —(CH2)$_l$$R^7$ with l being 0, 1, 2 or 3, —$NO_2$, —$NH_2$, —$NR^bR^c$, —$N(R^7)C(O)R^7$, —$C(O)R^7$, —$C(O)OR^7$, —$C(O)NR^bR^c$, —$S(O)R^7$, —$S(O)_2R^7$, —$S(O)_2NR^bR^c$, aryl, heteroaryl and heterocyclyl group, wherein each of said alkyl, cycloalkyl, aryl, heteroaryl and heterocyclyl is optionally substituted with one to four $R^a$ groups;

$R^7$ is independently, at each occurrence, selected from the group consisting of hydrogen, $C_1$-$C_{10}$ alkyl, $C_3$-$C_{10}$ cycloalkyl, haloalkyl, aryl, heteroaryl and heterocyclyl, wherein each of said alkyl, cycloalkyl, aryl and heterocyclyl is optionally substituted with one to four $R^a$ groups, and pharmaceutically acceptable salts thereof.

In one embodiment, the compound has the general formula III:

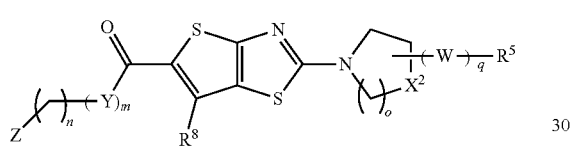

III wherein
n is 0, 1, 2 or 3;
m is 0 or 1;
is 0, 1, 2 or 3;
q is 0 or 1;
$X^2$ is selected from $CR^bR^c$, O, S, or $NR^6$;
Y is $C_1$-$C_6$ alkylene, O, S or $NR^6$;
W is $C_1$-$C_6$ alkylene;
$R^5$ is selected from the group consisting of hydrogen, halogen, $C_1$-$C_{10}$ alkyl, $C_3$-$C_{10}$cycloalkyl, $C_1$-$C_3$haloalkyl, hydroxyl, —$OR^6$, —CN, —$NO_2$, —$NH_2$, —$NR^bR^c$, —$N(R^6)C(O)R^6$, —$N(R^6)C(O)OR^6$, —$C(O)R^6$, —$C(O)OR^6$, —$C(O)NR^bR^c$, —$CHOHR^6$, —$S(O)R^6$, —$S(O)_2R^6$, —$S(O)_2NR^bR^c$, aryl, e.g., phenyl or benzyl, heteroaryl and heterocyclyl group wherein each of said alkyl, cycloalkyl, aryl, heteroaryl, and heterocyclyl is optionally substituted with one to four $R^a$ groups;

$R^6$ is independently, at each occurrence, selected from the group consisting of hydrogen, $C_1$-$C_{10}$ alkyl, $C_3$-$C_{10}$cycloalkyl, $C_1$-$C_3$haloalkyl, aryl, e.g., phenyl or benzyl, heteroaryl and heterocyclyl group, wherein each of said alkyl, cycloalkyl, aryl, heteroaryl and heterocyclyl is optionally substituted with one to four $R^a$ groups;

$R^8$ is selected from the group consisting of hydrogen, halogen, $C_1$-$C_{10}$ alkyl, $C_3$-$C_{10}$cycloalkyl, $C_1$-$C_3$haloalkyl, hydroxyl, —$OR^9$, —CN, —$NO_2$, —$NH_2$, aryl, e.g. phenyl or benzyl, heteroaryl and heterocyclyl group wherein each of said alkyl, cycloalkyl, aryl, heteroaryl and heterocyclyl is optionally substituted with one to four $R^a$ groups;

$R^9$ is selected from the group consisting of $C_1$-$C_{10}$ alkyl, $C_3$-$C_{10}$cycloalkyl, $C_1$-$C_3$haloalkyl, aryl, e.g., phenyl or benzyl, heteroaryl and heterocyclyl group wherein each of said alkyl, cycloalkyl, aryl, heteroaryl and heterocyclyl is optionally substituted with one to four $R^a$ groups;

Z is selected from the group consisting of $C_1$-$C_{10}$ alkyl, $C_3$-$C_{10}$cycloalkyl, $C_1$-$C_3$haloalkyl, $OR^6$, aryloxy, aryl, e.g., phenyl or benzyl, heteroaryl, heterocyclyl group, and groups of formula Ib shown below, wherein each of said alkyl, cycloalkyl, aryl, heteroaryl, heterocyclyl and groups of formula Ib is optionally substituted with one to four $R^a$ groups;

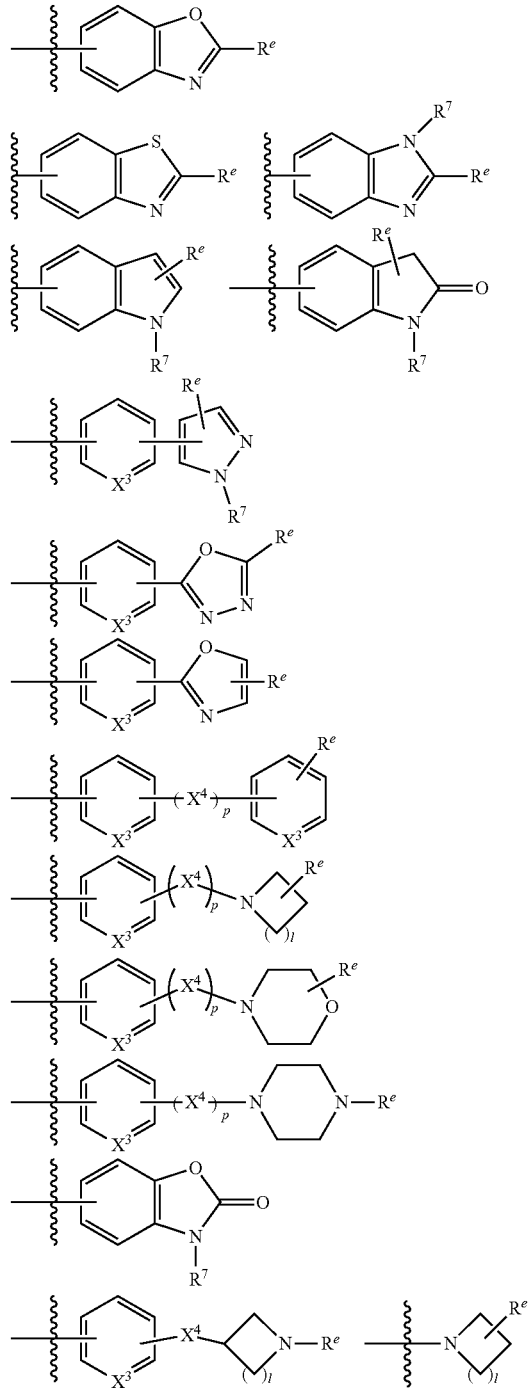

Formula Ib

-continued

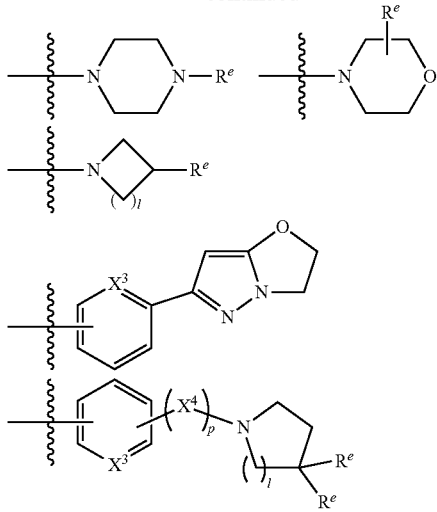

wherein, p is 0 or 1;

l is 1, 2 or 3;

$X^3$ is, independently at each occurrence, selected from CH or N;

$X^4$ is selected from C=O, $CR^bR^c$, O, S, or $NR^7$;

$R^e$, if denoted in formula Ib, may also occur twice as substituent at the same carbon atom wherein $R^e$ is independently selected at each occurrence;

$R^a$ is independently, at each occurrence, selected from the group consisting of hydrogen, halogen, $C_1$-$C_3$ alkyl, $C_1$-$C_4$ alkoxy, $C_1$-$C_4$ alkoxy substituted with aryl, e.g. phenyl, aryloxy; $C_1$-$C_3$ haloalkyl, hydroxyl, $C_1$-$C_3$ alkylhydroxyl, —CN, $NO_2$, —$NR^bR^c$, —$C(O)NR^bR^c$, —$C(O)R^c$, —$C(O)OR^c$, sulfonyl, sulfoxide, $C_3$-$C_{10}$ cycloalkyl, heterocyclyl, heteroaryl and aryl, e.g. phenyl or benzyl, benzyl, alkylaryl wherein each of said alkyl, cycloalkyl, aryl, heteroaryl and heterocyclyl is optionally substituted with one to four $C_1$-$C_3$ alkyl, $C_1$-$C_4$ alkoxy, halogen, $C_1$-$C_3$ haloalkyl, hydroxyl, —$NH_2$ wherein such substitution, if present, may occur in such a manner that there is more than one substituent, e.g. two or three substituents, per carbon atom, wherein such two or three substituents may be the same or different;

$R^b$ and $R^c$ are independently, at each occurrence, selected from the group consisting of hydrogen, $C_1$-$C_{10}$ alkyl, $C_3$-$C_{10}$ cycloalkyl, $C_1$-$C_6$ alkyl-O-alkyl, $C_2$-$C_{10}$ alkenyl, $C_1$-$C_4$ alkoxy, $C_1$-$C_3$ alkylhydroxyl, $C_3$-$C_{10}$cycloalkenyl, $C_2$-$C_{10}$ alkynyl, haloalkyl, in particular $C_1$-$C_3$ haloalkyl, aryl, e.g., phenyl or benzyl, alkylaryl, heteroaryl, and heterocyclyl; wherein each of said alkyl, cycloalkyl, aryl, heteroaryl and heterocyclyl is optionally substituted with one to four $C_1$-$C_3$ alkyl, $C_1$-$C_4$ alkoxy, e.g., methoxy, halogen, aryloxy, $C_1$-$C_3$ haloalkyl, e.g., trifluoromethyl, hydroxyl, $C_1$-$C_3$ alkylhydroxyl, —CN, —$NO_2$, —$NH_2$, sulfonyl, sulfoxide, $C_3$-$C_{10}$ cycloalkyl, heterocyclyl, aryl, e.g., phenyl, benzyl, heteroaryl, wherein such substitution, if present, may occur in such a manner that there is more than one substituent, e.g., two or three substituents, per carbon atom, wherein such two or three substituents may be the same or different; or $R^b$ and $R^c$ are connected to each other to make a four, five or six membered saturated or unsaturated cyclic or heterocyclic ring, or they are connected to make a fused cyclic or heterocyclic ring structure;

$R^e$ is independently, at each occurrence, selected from the group consisting of hydrogen, halogen, $C_1$-$C_{10}$ alkyl, $C_3$-$C_{10}$cycloalkyl, $C_1$-$C_3$haloalkyl, hydroxyl, —$OR^7$, —CN, —$(CH_2)_lR^7$ with l being 0, 1, 2 or 3, —$NO_2$, —$NH_2$, —$NR^bR^c$, —$N(R^7)C(O)R^7$, —$C(O)R^7$, —$C(O)OR^7$, —$C(O)NR^bR^c$, —$S(O)R^7$, —$S(O)_2R^7$, —$S(O)_2NR^bR^c$, aryl, e.g., phenyl or benzyl, heteroaryl and heterocyclyl group, wherein each of said alkyl, cycloalkyl, aryl, heteroaryl and heterocyclyl is optionally substituted with one to four $R^a$ groups;

$R^7$ is independently, at each occurrence, selected from the group consisting of hydrogen, $C_1$-$C_{10}$ alkyl, $C_3$-$C_{10}$ cycloalkyl, $C_1$-$C_3$ haloalkyl, aryl, e.g. phenyl or benzyl, heteroaryl, and heterocyclyl, wherein each of said alkyl, cycloalkyl, aryl, heteroaryl and heterocyclyl is optionally substituted with one to four $R^a$ groups, and pharmaceutically acceptable salts thereof.

In one embodiment, the compound has the general formula IV:

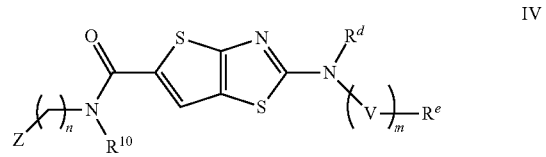

IV wherein n is 0, 1, 2 or 3;

m is 0 or 1;

V is $C_1$-$C_6$ alkylene $R^{10}$ and $R^d$ are independently at each occurrence, selected from the group consisting of hydrogen, $C_1$-$C_{10}$ alkyl, $C_3$-$C_{10}$cycloalkyl, $C_1$-$C_3$haloalkyl, aryl, heteroaryl and heterocyclyl group, wherein each of said alkyl, cycloalkyl, aryl, heteroaryl and heterocyclyl is optionally substituted with one to four $R^a$ groups;

$R^e$ is independently, at each occurrence, selected from the group consisting of hydrogen, halogen, $C_1$-$C_{10}$ alkyl, $C_3$-$C_{10}$cycloalkyl, $C_1$-$C_3$haloalkyl, hydroxyl, —$OR^7$, —CN, —$(CH_2)_lR^7$ with l being 0, 1, 2 or 3, —$NO_2$, —$NH_2$, —$NR^bR^c$, —$N(R^7)C(O)R^7$, —$C(O)R^7$, —$C(O)OR^7$, —$C(O)NR^bR^c$, —$S(O)R^7$, —$S(O)_2R^7$, —$S(O)_2NR^bR^c$, aryl, heteroaryl and heterocyclyl group, wherein each of said alkyl, cycloalkyl, aryl, e.g., phenyl or benzyl, heteroaryl and heterocyclyl is optionally substituted with one to four $R^a$ groups;

$R^7$ is independently, at each occurrence, selected from the group consisting of hydrogen, $C_1$-$C_{10}$ alkyl, $C_3$-$C_{10}$cycloalkyl, $C_1$-$C_3$haloalkyl, aryl, heteroaryl and heterocyclyl group, wherein each of said alkyl, cycloalkyl, aryl, e.g., phenyl or benzyl, heteroaryl and heterocyclyl is optionally substituted with one to four $R^a$ groups;

Z is selected from the group consisting of $C_1$-$C_{10}$ alkyl, $C_3$-$C_{10}$cycloalkyl, $C_1$-$C_3$haloalkyl, $OR^7$, aryloxy, aryl, e.g., phenyl or benzyl, heteroaryl, heterocyclyl group, and groups of formula Ib shown below, wherein each of said alkyl, cycloalkyl, aryl, heteroaryl, heterocyclyl and groups of formula Ib is optionally substituted with one to four $R^a$ groups;

Formula Ib

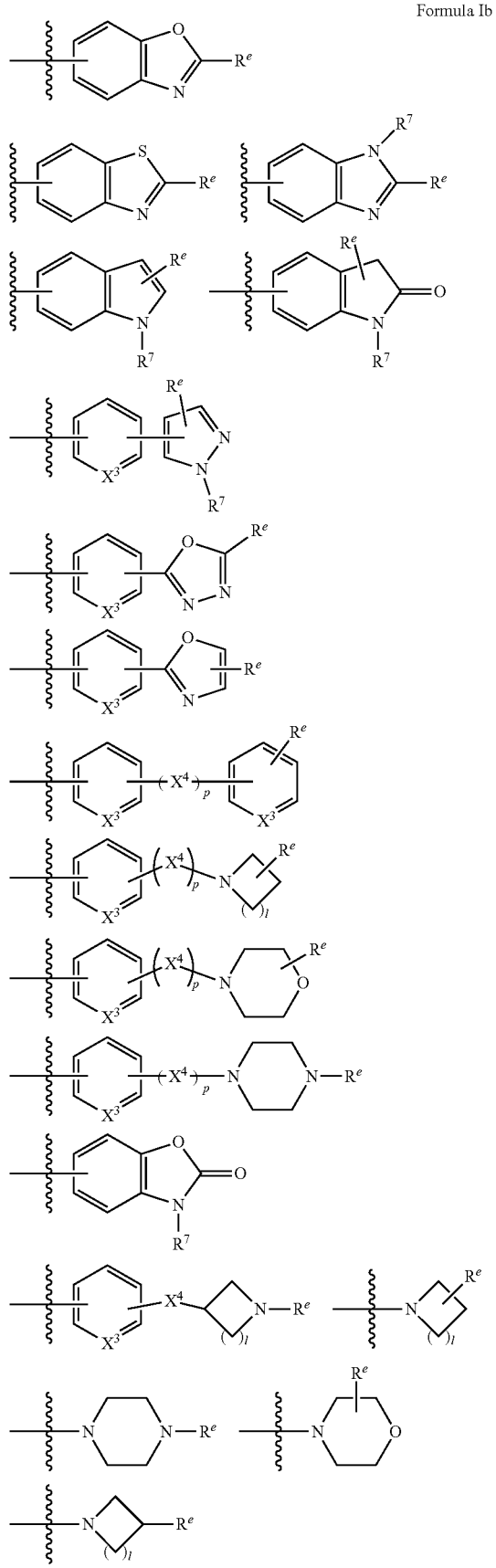

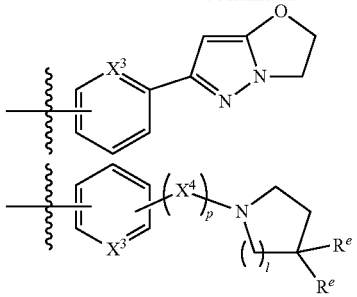

wherein,
p is 0 or 1;
l is 1, 2 or 3;
$X^3$ is, independently at each occurrence, selected from CH or N;
$X^4$ is selected from C=O, $CR^bR^c$, O, S, or $NR^7$;
$R^e$, if denoted in formula Ib, may also occur twice as substituent at the same carbon atom wherein $R^c$ is independently selected at each occurrence;
$R^a$ is independently, at each occurrence, selected from the group consisting of hydrogen, halogen, $C_1$-$C_3$ alkyl, $C_1$-$C_4$ alkoxy, $C_1$-$C_4$ alkoxy substituted with aryl, e.g. phenyl or benzyl, aryloxy; $C_1$-$C_3$ haloalkyl, hydroxyl, $C_1$-$C_3$ alkylhydroxyl, —CN, $NO_2$, —C(O)$NR^bR^c$, —$OR^e$, —C(O)$R^e$, —C(O)$OR^e$, sulfonyl, sulfoxide, $C_3$-$C_{10}$ cycloalkyl, heterocyclyl, heteroaryl and aryl, e.g., phenyl, benzyl, alkylaryl wherein each of said alkyl, cycloalkyl, aryl, heteroaryl and heterocyclyl is optionally substituted with one to four $C_1$-$C_3$ alkyl, $C_1$-$C_4$ alkoxy, aryl, e.g., phenyl or benzyl, halogen, $C_1$-$C_3$ haloalkyl, hydroxyl, —$NH_2$, wherein such substitution, if present, may occur in such a manner that there is more than one substituent, e.g., two or three substituents, per carbon atom, wherein such two or three substituents may be the same or different;
$R^b$ and $R^c$ are independently, at each occurrence, selected from the group consisting of hydrogen, $C_1$-$C_{10}$ alkyl, $C_3$-$C_{10}$ cycloalkyl, $C_1$-$C_3$ haloalkyl, $C_1$-$C_6$ alkyl-O-alkyl, $C_2$-$C_{10}$alkenyl, $C_1$-$C_4$ alkoxy, $C_1$-$C_3$ alkylhydroxyl, $C_3$-$C_{10}$ cycloalkenyl, $C_2$-$C_{10}$ alkynyl, $C_1$-$C_{10}$ haloalkyl, aryl, e.g., phenyl, benzyl, alkylaryl, heteroaryl, and heterocyclyl, wherein each of said alkyl, cycloalkyl, aryl, heteroaryl and heterocyclyl is optionally substituted with one to four $C_1$-$C_3$ alkyl, $C_1$-$C_4$ alkoxy, e.g., methoxy, halogen, aryloxy, $C_1$-$C_3$ haloalkyl, e.g., trifluoromethyl, hydroxyl, $C_1$-$C_3$ alkylhydroxyl, —CN, —$NO_2$, —$NH_2$, sulfonyl, sulfoxide, $C_3$-$C_{10}$ cycloalkyl, heterocyclyl, aryl, e.g., phenyl, benzyl, heteroaryl, wherein such substitution, if present, may occur in such a manner that there is more than one substituent, e.g., two or three substituents, per carbon atom, wherein such two or three substituents may be the same or different; or
$R^b$ and $R^c$ are connected to each other to make a four, five or six membered saturated or unsaturated cyclic or heterocyclic ring, or they are connected to make a fused cyclic or heterocyclic ring structure;
$R^d$ is independently, at each occurrence, selected from the group consisting of hydrogen, $C_1$-$C_{10}$ alkyl, $C_3$-$C_{10}$cycloalkyl, $C_1$-$C_3$haloalkyl, aryl, e.g., phenyl or benzyl, heteroaryl and heterocyclyl group, wherein each of said alkyl, cycloalkyl, aryl, heteroaryl and heterocyclyl is optionally substituted with one to four $R^a$ groups;

$R^e$ is independently, at each occurrence, selected from the group consisting of hydrogen, halogen, $C_1$-$C_{10}$ alkyl, $C_3$-$C_{10}$cycloalkyl, $C_1$-$C_3$haloalkyl, hydroxyl, —$OR^7$, —CN, —$(CH_2)_lR^7$ with l being 0, 1, 2 or 3, —$NO_2$, —$NH_2$, —$NR^bR^c$, —$N(R^7)C(O)R^7$, —$C(O)R^7$, —$C(O)OR^7$, —$C(O)NR^bR^c$, —$S(O)R^7$, —$S(O)_2R^7$, —$S(O)_2NR^bR^c$, aryl, e.g., phenyl or benzyl, heteroaryl and heterocyclyl group, wherein each of said alkyl, cycloalkyl, aryl, heteroaryl and heterocyclyl is optionally substituted with one to four $R^a$ groups;

$R^7$ is independently, at each occurrence, selected from the group consisting of hydrogen, $C_1$-$C_{10}$ alkyl, $C_3$-$C_{10}$ cycloalkyl, $C_1$-$C_3$ haloalkyl, aryl, e.g., phenyl or benzyl, heteroaryl, and heterocyclyl, wherein each of said alkyl, cycloalkyl, aryl, heteroaryl and heterocyclyl is optionally substituted with one to four $R^a$ groups, and pharmaceutically acceptable salts thereof.

In one embodiment, the present invention also relates to pharmaceutically acceptable salts of the compounds according to the present invention.

The term "alkyl" refers to a monovalent straight or branched chain, saturated aliphatic hydrocarbon radical having a number of carbon atoms in the specified range. Thus, for example, "$C_1$-$C_6$ alkyl" refers to any of the hexyl alkyl and pentyl alkyl isomers as well as n-, iso-, sec-, and t-butyl, n- and isopropyl, ethyl and methyl.

Alkyl groups may be optionally substituted with one or more substituents with one or more substituents as defined herein. Alkyl groups may be straight or branched. Representative branched alkyl groups have one, two, or three branches. In one embodiment, "alkyl" refers to $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{11}$, $C_{15}$, $C_{16}$ $C_{17}$, $C_{18}$, $C_{19}$, $C_{20}$, $C_{21}$, $C_{22}$, $C_{23}$ and/or $C_{24}$, alkyl, and combinations of any of the foregoing including the ranges $C_1$ to $C_4$, alkyl, $C_2$-$C_4$ alkyl, $C_2$-$C_{12}$ alkyl, $C_3$-$C_6$ alkyl, $C_3$-$C_{12}$ alkyl, $C_4$-$C_6$ alkyl, $C_4$-$C_8$ alkyl, $C_4$-$C_{10}$ alkyl, $C_4$-$C_{12}$ alkyl, $C_5$-$C_8$ alkyl, $C_5$-$C_{10}$ alkyl, $C_5$-$C_{12}$ alkyl, $C_5$-$C_{14}$ alkyl, $C_6$-$C_8$ alkyl, $C_6$-$C_{10}$ alkyl, $C_6$-$C_{12}$ alkyl.

The term "alkoxy" means a group having the formula —O-alkyl, in which an alkyl group, as defined above, is attached to the parent molecule via an oxygen atom. The alkyl portion of an alkoxy group can have 1 to 20 carbon atoms (i.e., $C_1$-$C_{20}$ alkoxy), 1 to 12 carbon atoms (i.e., $C_1$-$C_{12}$ alkoxy), or 1 to 6 carbon atoms (i.e., $C_1$-$C_6$ alkoxy). Examples of suitable alkoxy groups include, but are not limited to, methoxy (—O—$CH_3$ or OMe), ethoxy (—$OCH_2CH_3$ or —OEt), t-butoxy (—O—$C(CH_3)_3$ or —OtBu) and the like.

The term "alkenyl" refers to a monovalent straight or branched chain aliphatic hydrocarbon radical containing one or more carbon-carbon double bonds and having a number of carbon atoms in the specified range. Thus, for example, "$C_2$-$C_6$ alkenyl" refers to all of the hexenyl and pentenyl isomers as well as 1-butenyl, 2-butenyl, 3-butenyl, isobutenyl, 1-propenyl, 2-propenyl, and ethenyl (or vinyl). Examples of alkenyls useful in accordance with the present invention are $C_2$-$C_{10}$, $C_2$-$C_9$, $C_2$-$C_8$, $C_2$-$C_7$, $C_2$-$C_6$, $C_2$-$C_5$ and $C_2$-$C_4$ alkenyl.

The term "alkynyl" refers to a monovalent straight or branched chain aliphatic hydrocarbon radical containing one carbon-carbon triple bond and having a number of carbon atoms in the specified range. Thus, for example, "$C_2$-$C_6$ alkynyl" refers to all of the hexynyl and pentynyl isomers as well as 1-butynyl, 2-butynyl, 3-butynyl, 1-propynyl, 2-propynyl, and ethynyl. Examples of alkynyls useful in accordance with the present invention are $C_2$-$C_{10}$, $C_2$-$C_9$, $C_2$-$C_8$, $C_2$-$C_7$, $C_2$-$C_6$, $C_2$-$C_5$ and $C_2$-$C_4$ alkynyl.

The term "alkylene" refers to a saturated, branched or straight chain or cyclic hydrocarbon radical having two monovalent radical centers derived by the removal of two hydrogen atoms from the same or two different carbon atoms, 1 to 10 carbon atoms, or 1 to 6 carbon atoms. Typical alkylene radicals include, but are not limited to, methylene (—$CH_2$—), 1,1-ethyl (—$CH(CH_3)$—), 1,2-ethyl (—$CH_2CH_2$—), 1,1-propyl (—$CH(CH_2CH_3)$—), 1,2-propyl (—$CH_2CH(CH_3)$—), 1,3-propyl (—$CH_2CH_2CH_2$—), 1,4-butyl (—$CH_2CH_2CH_2CH_2$—), and the like.

The term "alkenylene" refers to an unsaturated, branched or straight chain or cyclic hydrocarbon radical having two monovalent radical centers derived by the removal of two hydrogen atoms from the same or two different carbon atoms of parent alkene. For example, an alkenylene group can have 1 to 20 carbon atoms, 1 to 10 carbon atoms, or 1 to 6 carbon atoms. Typical alkenylene radicals include, but are not limited to, 1,2-ethenyl (—CH=CH—).

The term "alkynylene" refers to an unsaturated, branched or straight chain or cyclic hydrocarbon radical having two monovalent radical centers derived by the removal of two hydrogen atoms from the same or two different carbon atoms of parent alkyne. For example, an alkynylene group can have 1 to 20 carbon atoms, 1 to 10 carbon atoms or 1 to 6 carbon atoms. Typical alkynylene radicals include, but are not limited to, acetylene (—C≡C—), propargyl (—$CH_2$C≡C—), and 4-pentynyl (—$CH_2CH_2CH_2$C≡CH—).

The term "cycloalkyl", alone or in combination with any other term, refers to a group, such as optionally substituted or non-substituted cyclic hydrocarbon, having from three to eight carbon atoms, unless otherwise defined. Thus, for example, "$C_3$-$C_8$ cycloalkyl" refers to cyclopropyl, cyclobutyl, cyclopentyl, cyclohexyl, cycloheptyl, and cyclooctyl. Cycloalkyl groups may be optionally substituted with one or more substituents as defined herein. Cycloalkyl includes cyclopropyl, cyclobutyl, cyclopentyl, cyclohexyl, and cycloheptyl. Examples of substituents that are suitable include but are not limited to hydroxyl, halogen, cyano, sulfonyl, further aryl(s), $C_1$-$C_5$ alkyl, $C_1$-$C_4$ alkoxy, oxo, $C_3$-$C_6$ cycloalkyl, heteroaryl, heterocycloalkyl, $C_1$-$C_3$ sulfanyl.

The term "haloalkyl" refers to an alkyl group, as defined herein that is substituted with at least one halogen. Examples of straight or branched chained "haloalkyl" groups useful in the present invention include, but are not limited to, methyl, ethyl, propyl, isopropyl, n-butyl, and t-butyl substituted independently with one or more halogens, e.g., 2, 3, 4, 5 or 6 substituent halogens. The term "haloalkyl" should be interpreted to include such substituents such as —$CH_2F$, —$CHF_2$, —$CF_3$, —$CH_2$—$CH_2$—F, —CHF—$CH_2F$, —$CH_2$—$CF_3$, and the like.

The term "heteroalkyl" refers to an alkyl group where one or more carbon atoms have been replaced with a heteroatom, such as, O, N, or S. For example, if the carbon atom of alkyl group which is attached to the parent molecule is replaced with a heteroatom (e.g., O, N, or S) the resulting heteroalkyl groups are, respectively, an alkoxy group (e.g., —$OCH_3$, etc.), an amine (e.g., —$NHCH_3$, —$N(CH_3)_2$, etc.), or thioalkyl group (e.g., —$SCH_3$, etc.). If a non-terminal carbon atom of the alkyl group which is not attached to the parent molecule is replaced with a heteroatom (e.g., O, N, or S) and the resulting heteroalkyl groups are, respectively, an alkyl ether (e.g., —CH$_2$CH$_2$—O—CH$_3$, etc.), alkyl amine (e.g., —CH$_2$NHCH$_3$, —CH$_2$N(CH$_3$)$_2$, etc.), or thioalkyl ether (e.g., —CH$_2$—S—CH$_3$).

The term "halogen" refers to fluorine, chlorine, bromine, or iodine.

The term "aryl" refers to (i) optionally substituted phenyl, (ii) optionally substituted benzyl, (iii) optionally substituted 9- or 10 membered bicyclic, fused carbocyclic ring systems in which at least one ring is aromatic, and (iv) optionally substituted 11- to 14-membered tricyclic, fused carbocyclic ring systems in which at least one ring is aromatic. Suitable aryls include, for example, phenyl, biphenyl, naphthyl, tetrahydronaphthyl (tetralinyl), indenyl, anthracenyl, and fluorenyl. Aryl groups may be optionally substituted with one or more substituents as defined herein. Examples of substituents that are suitable include but are not limited to hydroxyl, halogen, cyano, sulfonyl, further aryl(s), C$_1$-C$_5$ alkyl, C$_1$-C$_4$ alkoxy, oxo, C$_3$-C$_6$ cycloalkyl, heteroaryl, heterocycloalkyl, C$_1$-C$_3$ sulfanyl.

The term "benzyl" as used herein is meant to indicate an optionally substituted or non-substituted benzyl group.

The term "heteroaryl" refers to (i) optionally substituted 5- and 6-membered heteroaromatic rings and (ii) optionally substituted 9- and 10-membered bicyclic, fused ring systems in which at least one ring is aromatic, wherein the heteroaromatic ring or the bicyclic, fused ring system contains from 1 to 4 heteroatoms independently selected from N, O, and S, where each N is optionally in the form of an oxide and each S in a ring which is not aromatic is optionally S(O) or S(O)$_2$. Suitable 5- and 6-membered heteroaromatic rings include, for example, pyridyl, pyrrolyl, pyrazinyl, pyrimidinyl, pyridazinyl, triazinyl, thienyl, furanyl, imidazolyl, pyrazolyl, triazolyl, tetrazolyl, oxazolyl, isooxazolyl, oxadiazolyl, thiazolyl, isothiazolyl, and thiadiazolyl. Suitable 9- and 10-membered heterobicyclic, fused ring systems include, for example, benzofuranyl, indolyl, indazolyl, naphthyridinyl, isobenzofuranyl, benzopiperidinyl, benzisoxazolyl, benzoxazolyl, chromenyl, quinolinyl, isoquinolinyl, cinnolinyl, quinazolinyl, tetrahydroquinolinyl, tetrahydroisoquinolinyl, isoindolyl, benzodioxolyl, benzofuranyl, imidazo[1,2-a]pyridinyl, benzotriazolyl, dihydroindolyl, dihydroisoindolyl, indazolyl, indolinyl, isoindolinyl, quinoxalinyl, quinazolinyl, 2,3-dihydrobenzofuranyl, and 2,3-dihydrobenzo-1,4-dioxinyl. The term "heterocyclyl" refers to (i) optionally substituted 4- to 8-membered, saturated and unsaturated but non-aromatic monocyclic rings containing at least one carbon atom and from 1 to 4 heteroatoms, (ii) optionally substituted bicyclic ring systems containing from 1 to 6 heteroatoms, and (iii) optionally substituted tricyclic ring systems, wherein each ring in (ii) or (iii) is independent of fused to, or bridged with the other ring or rings and each ring is saturated or unsaturated but nonaromatic, and wherein each heteroatom in (i), (ii), and (iii) is independently selected from N, O, and S, wherein each N is optionally in the form of an oxide and each S is optionally oxidized to S(O) or S(O)2. Suitable 4- to 8-membered saturated heterocyclyls include, for example, azetidinyl, piperidinyl, morpholinyl, thiomorpholinyl, thiazolidinyl, isothiazolidinyl, oxazolidinyl, isoxazolidinyl, pyrrolidinyl, imidazolidinyl, piperazinyl, tetrahydrofuranyl, tetrahydrothienyl, pyrazolidinyl, hexahydropyrimidinyl, thiazinanyl, thiazepanyl, azepanyl, diazepanyl, tetrahydropyrany I, tetrahydrothiopyranyl, dioxanyl, and azacyclooctyl. Suitable unsaturated heterocyclic rings include those corresponding to the saturated heterocyclic rings listed in the above sentence in which a single bond is replaced with a double bond. It is understood that the specific rings and ring systems suitable for use in the present invention are not limited to those listed in this and the preceding paragraphs. These rings and ring systems are merely representative.

"Optionally substituted" indicates that a group, such as alkyl, alkenyl, alkynyl, aryl, cycloalkyl, cycloalkenyl, heterocycloalkyl, heterocyclyl or heteroaryl, may be unsubstituted, or the group may be substituted with one or more substituents as defined herein.

"Pharmaceutically acceptable" refers to those compounds, materials, compositions, and dosage forms which are, within the scope of sound medical judgment, suitable for use in contact with the tissues of human beings or animals without excessive toxicity, irritation, or other problem or complication, commensurate with a reasonable benefit/risk ratio.

"Substituted" in reference to a group indicates that one or more hydrogen atoms attached to a member atom within the group is replaced with a substituent selected from the group of defined or suitable substituents. It should be understood that the term "substituted" includes the implicit provision that such substitution be in accordance with the permitted valence of the substituted atom and the substituent, and that the substitution results in a stable compound. When it is stated that a group may contain one or more substituents, one or more member atom within the group may be substituted. In addition, a single member atom within the group may be substituted with more than one substituent as long as such substitution is in accordance with the permitted valence of the atom. The term "MIC50" refers to the concentration of compound which inhibits bacterial growth, preferably growth of *M. tuberculosis*, in comparison to a control without any drug after five days by 50%.

In a further aspect, the present invention relates to compounds having one of the formulae 1-360, as shown in Tables 1-2, preferably 3, 6, 8, 13,14, 17-20, 22, 24, 25, 27-29, 32, 35, 36, 38-58, 60-68, 72, 74-80, 82-87, 90-92, 95-97, 99-101, 103-108, 110-112, 114-116, 118-122, 124-127, 129, 130, 132-140, 142-146, 149, 151-156, 158-162, 165, 167-169, 171, 174, 177, 178, 180, 183, 186, 188, 192-197, 199, 201-204, 206-209, 211-229, 231-254, 256, 258-262, 264-268, 271-279, 281-285, 287-294, 296-299, 301, 302, 304-309, 311, 313-325, 327-346, 348-355, 357-360, more preferably 3, 13, 14, 32, 35, 36, 38-50, 53-55, 58, 61, 63, 66-68, 72, 74, 76-80, 83-86, 90, 91, 95, 96, 99-101, 103-108, 110-112, 114, 115, 118-122, 124, 125, 127, 129, 130, 132-138, 142-146, 151, 153-156, 158-162, 167, 168, 171, 174, 177, 180, 183, 186, 188, 193-195, 197, 199, 201-204, 206-209, 211-222, 224-226, 228, 231-252, 254, 256, 258-262, 265, 266, 268, 271-278, 282-285, 287-294, 296, 298, 299, 301, 302, 304-309, 314-320, 323-325, 328-334, 336-346, 348-352, 358-360 as shown in Tables 1-2.

Preferably, the compounds as defined above have an inhibitory activity on bacterial growth, preferably on the growth of *M. tuberculosis*, inside a host cell, preferably a macrophage, at a concentration between 1-20 μM, preferably less than 1 μM.

In one aspect, the present invention relates to compounds as defined above for use in the treatment of a bacterial infection, e.g., tuberculosis.

In one aspect, the present invention relates to compounds as defined above for use in the treatment of Tuberculosis.

In one aspect, the present invention relates to a composition, preferably a pharmaceutical composition comprising a compound as defined above, and a pharmaceutically acceptable carrier.

In one aspect, the present invention relates to a method of treatment of a bacterial infection, in particular Tuberculosis, comprising the application of a suitable amount of a compound as defined above or of a pharmaceutical composition as defined above to a person in need thereof.

In one embodiment, a "suitable amount", as used herein, is meant to refer to an amount in the range of from 0.01 mg/kg body weight to 1 g/kg body weight.

The objects of the present invention are also solved by a compound that competitively inhibits the specific binding of a compound according to the present invention. Preferably, such specific binding is with respect to a target protein of said compound according to the present invention. The objects of the invention are also solved by a pharmaceutical composition comprising such competitively inhibiting compound, as defined above, and a pharmaceutically acceptable carrier.

The objects of the present invention are also solved by a method of treatment of a bacterial infection, in particular tuberculosis comprising the application of a suitable amount of a compound which compound is characterized by an ability to competitively inhibit the specific binding of a compound according to the present invention to a target protein, or the application of a suitable amount of the pharmaceutical composition comprising such competitively inhibiting compound, to a person in need thereof.

Pharmaceutical Compositions
Pharmaceutically Acceptable Salts

Examples of pharmaceutically acceptable addition salts include, without limitation, the non-toxic inorganic and organic acid addition salts such as the acetate derived from acetic acid, the aconate derived from aconitic acid, the ascorbate derived from ascorbic acid, the benzenesulfonate derived from benzensulfonic acid, the benzoate derived from benzoic acid, the cinnamate derived from cinnamic acid, the citrate derived from citric acid, the embonate derived from embonic acid, the enantate derived from enanthic acid, the formate derived from formic acid, the fumarate derived from fumaric acid, the glutamate derived from glutamic acid, the glycolate derived from glycolic acid, the hydrochloride derived from hydrochloric acid, the hydrobromide derived from hydrobromic acid, the lactate derived from lactic acid, the maleate derived from maleic acid, the malonate derived from malonic acid, the mandelate derived from mandelic acid, the methanesulfonate derived from methane sulphonic acid, the naphthalene-2-sulphonate derived from naphtalene-2-sulphonic acid, the nitrate derived from nitric acid, the perchlorate derived from perchloric acid, the phosphate derived from phosphoric acid, the oxalate derived from oxalic acid, the phthalate derived from phthalic acid, the salicylate derived from salicylic acid, the sorbate derived from sorbic acid, the stearate derived from stearic acid, the succinate derived from succinic acid, the sulphate derived from sulphuric acid, the tartrate derived from tartaric acid, the toluene-p-sulphonate derived from p-toluene sulphonic acid, and the like. Such salts may be formed by procedures well known and described in the art.

Other acids, which may not be considered pharmaceutically acceptable, may be useful in the preparation of salts useful as intermediates in obtaining a chemical compound of the invention and its pharmaceutically acceptable acid addition salt.

In another embodiment, the compounds of the invention are used in their respective free base form according to the present invention.

Metal salts of a chemical compound of the invention include alkali metal salts, such as the sodium salt of a chemical compound of the invention containing a carboxy group.

The chemical compounds of the invention may be provided in unsolvated or solvated forms together with a pharmaceutically acceptable solvent(s) such as water, ethanol, and the like. Solvated forms may also include hydrated forms such as the monohydrate, the dihydrate, the hemihydrate, the trihydrate, the tetrahydrate, and the like. In general, solvated forms are considered equivalent to unsolvated forms for the purposes of this invention.

Administration and Formulation

The production of medicaments containing the compounds of the invention, its active metabolites or isomers and salts according to the invention and their application can be performed according to well-known pharmaceutical methods.

While the compounds of the invention, useable according to the invention for use in therapy, may be administered in the form of the raw chemical compound, it is preferred to introduce the active ingredient, optionally in the form of a physiologically acceptable salt in a pharmaceutical composition together with one or more adjuvants, excipients, carriers, buffers, diluents, and/or other customary pharmaceutical auxiliaries. Such salts of the compounds of the invention may be anhydrous or solvated.

In a preferred embodiment, the invention provides medicaments comprising a compound useable according to the invention, or a pharmaceutically acceptable salt or derivative thereof, together with one or more pharmaceutically acceptable carriers therefor, and, optionally, other therapeutic and/or prophylactic ingredients. The carrier(s) must be "acceptable" in the sense of being compatible with the other ingredients of the formulation and not harmful to the recipient thereof.

A medicament of the invention may be those suitable for oral, rectal, bronchial, nasal, topical, buccal, sub-lingual, transdermal, vaginal or parenteral (including cutaneous, subcutaneous, intramuscular, intraperitoneal, intravenous, intraarterial, intracerebral, intraocular injection or infusion) administration, or those in a form suitable for administration by inhalation or insufflation, including powders and liquid aerosol administration, or by sustained release systems. Suitable examples of sustained release systems include semipermeable matrices of solid hydrophobic polymers containing the compound of the invention, which matrices may be in form of shaped articles, e.g., films or microcapsules.

The compounds useable according to the invention, together with a conventional adjuvant, carrier, or diluent, may thus be placed into the form of medicament and unit dosages thereof. Such forms include solids, and in particular tablets, filled capsules, powder and pellet forms, and liquids, in particular aqueous or non-aqueous solutions, suspensions, emulsions, elixirs, and capsules filled with the same, all for oral use, suppositories for rectal administration, and sterile injectable solutions for parenteral use. Such medicament and unit dosage forms thereof may comprise conventional ingredients in conventional proportions, with or without additional active compounds or principles, and such unit dosage forms may contain any suitable effective amount of the active ingredient commensurate with the intended daily dosage range to be employed.

The compounds useable according to the invention can be administered in a wide variety of oral and parenteral dosage forms. It will be obvious to those skilled in the art that the following dosage forms may comprise, as the active component, either a compound(s) useable according to the invention or a pharmaceutically acceptable salt of a compound(s) useable according to the invention.

For preparing a medicament from a compound useable according to the invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavouring agents, solubilizers, lubricants, suspending agents, binders, preservatives, tablet disintegrating agents, or an encapsulating material.

In powders, the carrier is a finely divided solid which is in a mixture with the finely divided active component. In tablets, the active component is mixed with the carrier having the necessary binding capacity in suitable proportions and compacted in the shape and size desired. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier providing a capsule in which the active component, with or without carriers, is surrounded by a carrier, which is thus in association with it. Similarly, cachets and lozenges are included. Tablets, powders, capsules, pills, cachets, and lozenges can be used as solid forms suitable for oral administration.

For preparing suppositories, a low melting wax, such as a mixture of fatty acid glyceride or cocoa butter, is first melted and the active component is dispersed homogeneously therein, as by stirring. The molten homogenous mixture is then poured into convenient sized moulds, allowed to cool, and thereby to solidify. Compositions suitable for vaginal administration may be presented as pessaries, tampons, creams, gels, pastes, foams or sprays containing in addition to the active ingredient such carriers as are known in the art to be appropriate. Liquid preparations include solutions, suspensions, and emulsions, for example, water or water-propylene glycol solutions. For example, parenteral injection liquid preparations can be formulated as solutions in aqueous polyethylene glycol solution.

The chemical compounds according to the present invention may thus be formulated for parenteral administration (e.g., by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulation agents such as suspending, stabilising and/or dispersing agents. Alternatively, the active ingredient may be in powder form, obtained by aseptic isolation of sterile solid or by lyophilization from solution, for constitution with a suitable vehicle, e.g., sterile, pyrogen-free water, before use.

Aqueous solutions suitable for oral use can be prepared by dissolving the active component in water and adding suitable colorants, flavours, stabilising and thickening agents, as desired. Aqueous suspensions suitable for oral use can be made by dispersing the finely divided active component in water with viscous material, such as natural or synthetic gums, resins, methylcellulose, sodium carboxymethylcellulose, or other well known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavours, stabilisers, buffers, artificial and natural sweeteners, dispersants, thickeners, solubilizing agents, and the like.

In one embodiment of the present invention, the medicament is applied topically or systemically or via a combination of the two routes.

For administration, the compounds of the present invention may, in one embodiment, be administered in a formulation containing 0.001% to 70% per weight of the compound, preferably between 0.01% to 70% per weight of the compound, even more preferred between 0.1% and 70% per weight of the compound. In one embodiment, a suitable amount of compound administered is in the range of from 0.01 mg/kg body weight to 1 g/kg body weight.

Compositions suitable for administration also include lozenges comprising the active agent in a flavoured base, usually sucrose and acacia or tragacanth; pastilles comprising the active ingredient in an inert base such as gelatin and glycerol or sucrose and acacia; and mouthwashes comprising the active ingredient in a suitable liquid carrier.

Solutions or suspensions are applied directly to the nasal cavity by conventional means, for example with a dropper, pipette or spray. The compositions may be provided in single or multi-dose form. In the latter case of a dropper or pipette, this may be achieved by the patient administering an appropriate, predetermined volume of the solution or suspension. In the case of a spray, this may be achieved for example by means of a metering atomising spray pump.

Administration to the respiratory tract may also be achieved by means of an aerosol formulation in which the active ingredient is provided in a pressurised pack with a suitable propellant such as a chlorofluorocarbon (CFC) for example dichlorodifluoromethane, trichlorofluoromethane, or dichlorotetrafluoroethane, carbon dioxide, or other suitable gas. The aerosol may conveniently also contain a surfactant such as lecithin. The dose of drug may be controlled by provision of a metered valve.

Alternatively the active ingredients may be provided in the form of a dry powder, for example a powder mix of the compound in a suitable powder base such as lactose, starch, starch derivatives such as hydroxypropylmethyl cellulose and polyvinylpyrrolidone (PVP). Conveniently the powder carrier will form a gel in the nasal cavity. The powder composition may be presented in unit dose form for example in capsules or cartridges of, e.g., gelatin, or blister packs from which the powder may be administered by means of an inhaler.

In compositions intended for administration to the respiratory tract, including intranasal compositions, the compound will generally have a small particle size for example of the order of 5 microns or less. Such a particle size may be obtained by means known in the art, for example by micronization.

When desired, compositions adapted to give sustained release of the active ingredient may be employed.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packaged tablets, capsules, and powders in vials or ampoules. Also, the unit dosage form can be a capsule, tablet, cachet, or lozenge itself, or it can be the appropriate number of any of these in packaged form. Tablets or capsules for oral administration and liquids for intravenous administration and continuous infusion are preferred compositions.

Further details on techniques for formulation and administration may be found in the latest edition of Remington's Pharmaceutical Sciences (Maack Publishing Co. Easton, Pa.).

Tables

Reference is now made to the tables, wherein

Table 1 summarizes compounds 1-360 in terms of their structures and corresponding characteristics.

Table 2 summarizes the compounds (general scaffolds I-IV) with their respective inhibitory activities; the in vitro growth fluorescence assay (QUM) and the intracellular growth assay (QIM).

Table 3 shows anti-bacterial activity for compound 83, 127, 144 and compound 202 on several multi-drug resistant (MDR) strains.

EXAMPLES

The invention is now further described by reference to the following examples which are intended to illustrate, not to limit the scope of the invention.

Example 1

Determination the Minimum Inhibitory Concentration (MIC) or $MIC_{50}$ of New Chemical Entities against M. tuberculosis The intracellular (QIM) assay and in vitro (QUM) assay, wherein the abbreviation "QIM" stands for Quantification of Intracellular Mycobacteria and the abbreviation "QUM" stands for Quantification of in vitro grown Mycobacteria, along with the Resazurin Microtitre Assay (REMA) were used to determine the $MIC_{50}$ value.

The QIM assay to determine $MIC_{50}$ was performed as now described. Briefly, Raw 264.7 cells were infected with H37Rv-GFP in suspension at a MOI 2:1 in RPMI 1640 supplemented with 10% heat-inactivated FCS for 2 hours at 37° C. with shaking. After three washes with RPMI-1% FCS (fetal calf serum) by centrifugation, 45 µl of 15000 infected cells were dispensed into each plate well pre-plated with 5 µl of compounds to be tested and controls. Infected cells were incubated for 5 days at 37° C., 5% $CO_2$. After five days, macrophages were stained with SYTO 60, 5 µM (Invitrogen, S11342) for 1 hour at 37° C. and image acquisition was performed on an EVOscreeen-Mark III fully automated platform (PerkinElmer) integrated with an Opera™ (10x-air objective) and located in a BSL-3 safety laboratory. Mycobacteria-GFP were detected using a 488-nm laser filter and SYTO 60 labelled cells with a 635-nm laser filter. Two fields were recorded for each plate well and each image was then processed using dedicated in-house image analysis software. The results are summarized in Table 2. The QUM assay to determine $MIC_{50}$ was performed as now described. Briefly, 384 plates (Greiner, #781091) were first prepared with 0.5 µl of compound to be tested dispensed by EVOBird (Evotec) in 10 ul of 7H9-10% ADS-0.05% Tween80. M. tuberculosis H37Rv expressing the green fluorescent protein (H37Rv-GFP) precultured in separate test tubes at 37° C. in Middlebrook 7H9 broth (Difco) supplemented with 0.05% Tween 80 (Sigma, P8074), 0.02% Glycerol, 10% Albumin-Dextrose Saline (ADS) and 50 µg/ml Hygromycine (Invitrogen) for 5 days until the Optical density (OD) reached between 0.4~0.5. For the assay, the precultured H37Rv-GFP bacteria were then placed into 7H9-10% ADS-0.05% media after centrifugation. Forty microliters of H37Rv-GFP bacterial suspension diluted to $2 \times 10^6$ CFU/mL (based on GFP fluorescence assessment and a reference curve) was then added to the pre-prepared 384 plates resulting in a final volume of 50 µl containing 1% DMSO. Plates were incubated at 37° C., 5% $CO_2$ for 5 days. Mycobacterial growth was determined by measuring GFP-fluorescence using a Victor 3 reader (Perkin-Elmer Life Science). The results are summarized in Table 2.

The REMA using concentrations of compounds, to be tested, from 60 µM to 3 nM was performed as now described. Briefly, 66.6 µl of 7H9-10% ADS-0.05% Tween80 medium was prepared through 3-fold serial dilutions of drugs in every well of 96-well microtitre plates except peripheral wells where 200 µl sterilized water was added to prevent evaporation during incubation. 33.3 µl of the Mycobacterium multi-drug resistant (MDR) strains (MDR-33, 137 and 146 are clinical isolates) were added to pre-prepared plates resulting in a final volume of 100 µl (final bacterial OD=0.005) Plates were sealed and incubated at 37° C. for 1 week. Twenty-five microliters of 0.02% resazurin (Sigma Chem. Co.) solution was added to each well; plates were re-incubated for an additional 1 day. A change in color from blue to pink indicated the growth of bacteria, and the MIC was read as the minimum compound concentration that prevented the color change in resazurin solution. The results are summarized in Table 3.

Example 2

Derivatization of the General Scaffolds

The compounds (scaffolds I-IV, see Table 1) underwent derivatization according to the methods outlined below (Schemes 1-31). Resulting derivatives were examined for inhibitory activity (MIC) using the assays described above (Example 1) and the results are summarized in Tables 2-3. The synthesized compounds 1-360 are shown in Table 1.

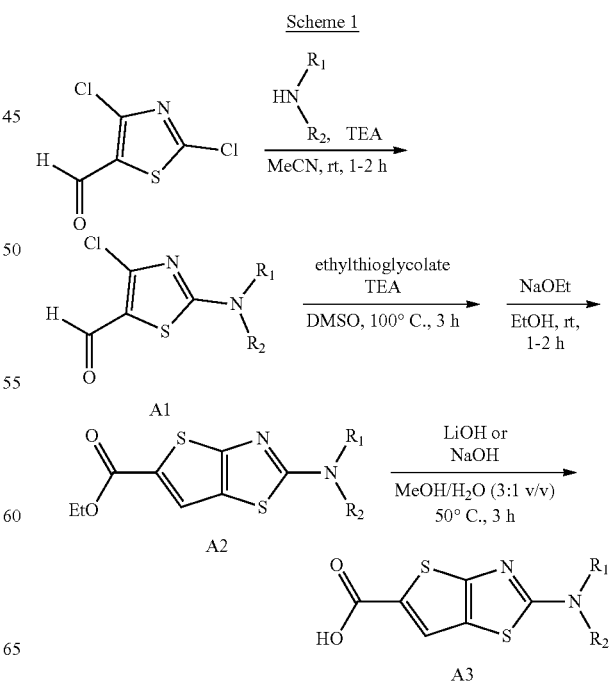

Scheme 1

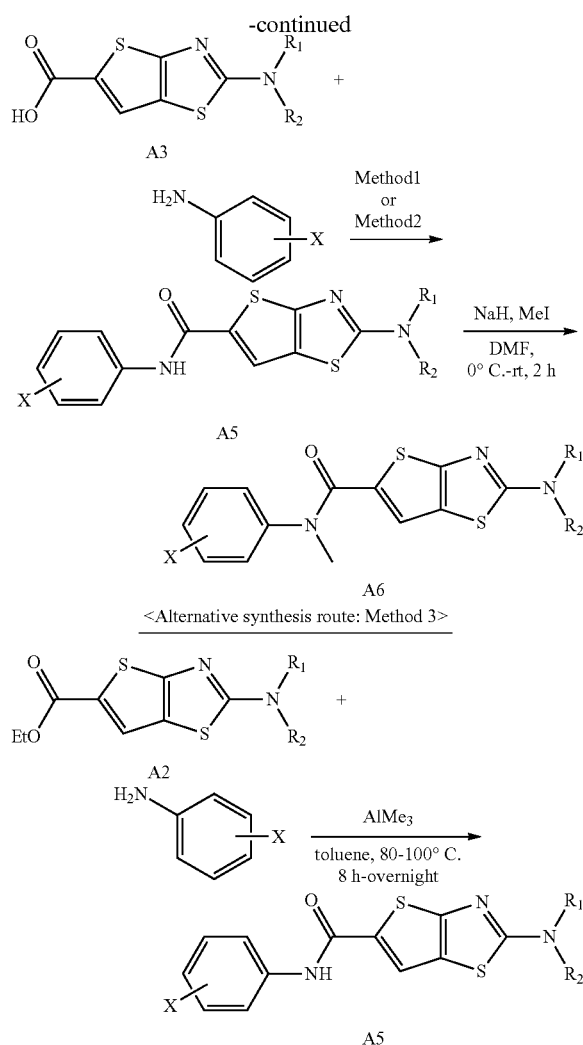

General Procedure for the Synthesis of A1

To a stirred solution of 2,4-dichlorothiazole-5-carbaldehyde (2.19 mmol) in MeCN (10 mL) were added adequate amine (2.64 mmol) and triethylamine (11.0 mmol) and the mixture was stirred for 2 hours at room temperature. After the reaction completion, the reaction mixture was poured to the cold water and then a resulting solid was collected. The crude compound was used for next reaction without further purification or was purified by column chromatography as necessary to give A1.

General Procedure for the Synthesis of A2

A mixture of A1 (1.61 mmol), ethylthioglycolate (1.93 mmol) and triethylamine (3.22 mmol) in DMSO (3.0 mL) was heated to 100° C. for 3 hours. The reaction mixture was diluted with EtOAc (15 mL), washed with water (10 mL), dried over $MgSO_4$ and concentrated. The resulting residue was dissolved in EtOH (5.0 mL) and sodium ethoxide solution (21% in EtOH, 2.42 mmol) was added. The reaction mixture was stirred for an hour at room temperature. After the reaction completion, the reaction was quenched with water (2.0 mL) and the organic solvent was evaporated. The generated precipitates was filtered, washed with water and dried in vacuo to give A2.

General Procedure for the Synthesis of A3

To a stirred suspension of A2 (1.26 mmol) in MeOH (6.0 mL) was added an aqueous solution of lithium hydroxide (6.32 mmol in 2.0 mL of water) and the mixture was heated to 50° C. for 3 hours. The organic solvent was evaporated and 1N HCl was added until pH was reached to 4. The residual white solid was collected by filtration, washed with water and dried in vacuo to give A3 as a white solid.

General Procedure for the Synthesis of A5

Method 1: To a stirred solution of A3 (0.16 mmol) in anhydrous DMF or methylene chloride (2.0 mL) were added 1-(3-dimethylaminopropyl)-3-ethylcarbodiimide hydrochloride (0.24 mmol), 1-hydroxybenzotriazole (0.082 mmol), triethylamine (0.33 mmol) and adequate amine A4 (0.15 mmol) at room temperature, then the resulting solution was stirred for 4 hours at room temperature. The reaction mixture was concentrated and the resulting crude residue was purified by flash column chromatography to give A5.

Method 2: To a stirred suspension of A3 (1.0 mmol) in methylene chloride (10.0 mL) were added oxalyl chloride (0.50 mL) and 2-drops of N, N-dimethylformamide at room temperature and the reaction mixture was stirred for 2 hours. After reaction completion, the mixture was concentrated and the resulting residue was washed with diethyl ether (20 mL×3) and dried to give a acyl chloride. The resulting acyl chloride (0.15 mmol) was dissolved in methylene chloride (3.0 mL) and then A4 (0.15 mmol) and triethylamine (0.45 mmol) were added to the solution. The resulting mixture was stirred at room temperature for 3 hours. After reaction completion, the mixture was diluted with methylene chloride (10 mL), washed with brine (10 mL), dried over $MgSO_4$ and concentrated in vacuo. The crude residue was purified by flash column chromatography togive A5.

Method 3 (from A2): To a stirred solution of A2 (0.15 mmol) and A4 (0.15 mmol) in toluene (2.0 mL) was added trimethyl aluminum (2.0 M in hexane, 0.23 mmol) under ice bath. The resulting mixture was allowed room temperature and then heated to 80-100° C. After reaction completion, the reaction mixture was cooled to room temperature, quenched with water and then resulting aluminum slurry was filtered off using cellite. The filtrate was extracted with methylene chloride several times, washed with water and brine and organic layer was dried over $MgSO_4$. The crude residue was purified by flash column chromatography to give A5.

General Procedure for the Synthesis of A6

To a stirred solution of A5 (0.021 mmol) in N,N-dimethylformamide (0.5 mL) was added sodium hydride (0.025 mmol) at 0° C. After 20 min of pre-stirring, iodomethane (0.042 mmol) was added to the solution and the mixture was further stirred at room temperature for 2 hours. After reaction completion, the reaction mixture was poured to the water (5 mL) and extracted with methylene chloride (10 mL×3). The organic layer was washed with brine (5 mL), dried over anhydrous $Na_2SO_4$ and concentrated in vacuo. The resulting crude residue was purified by flash column chromatography to give A6.

Scheme 1

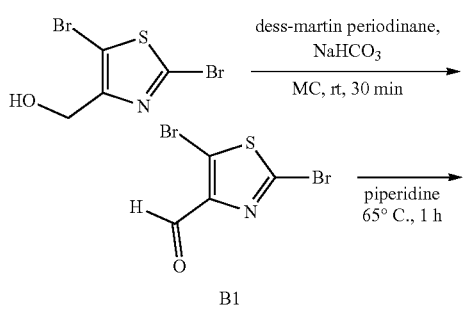

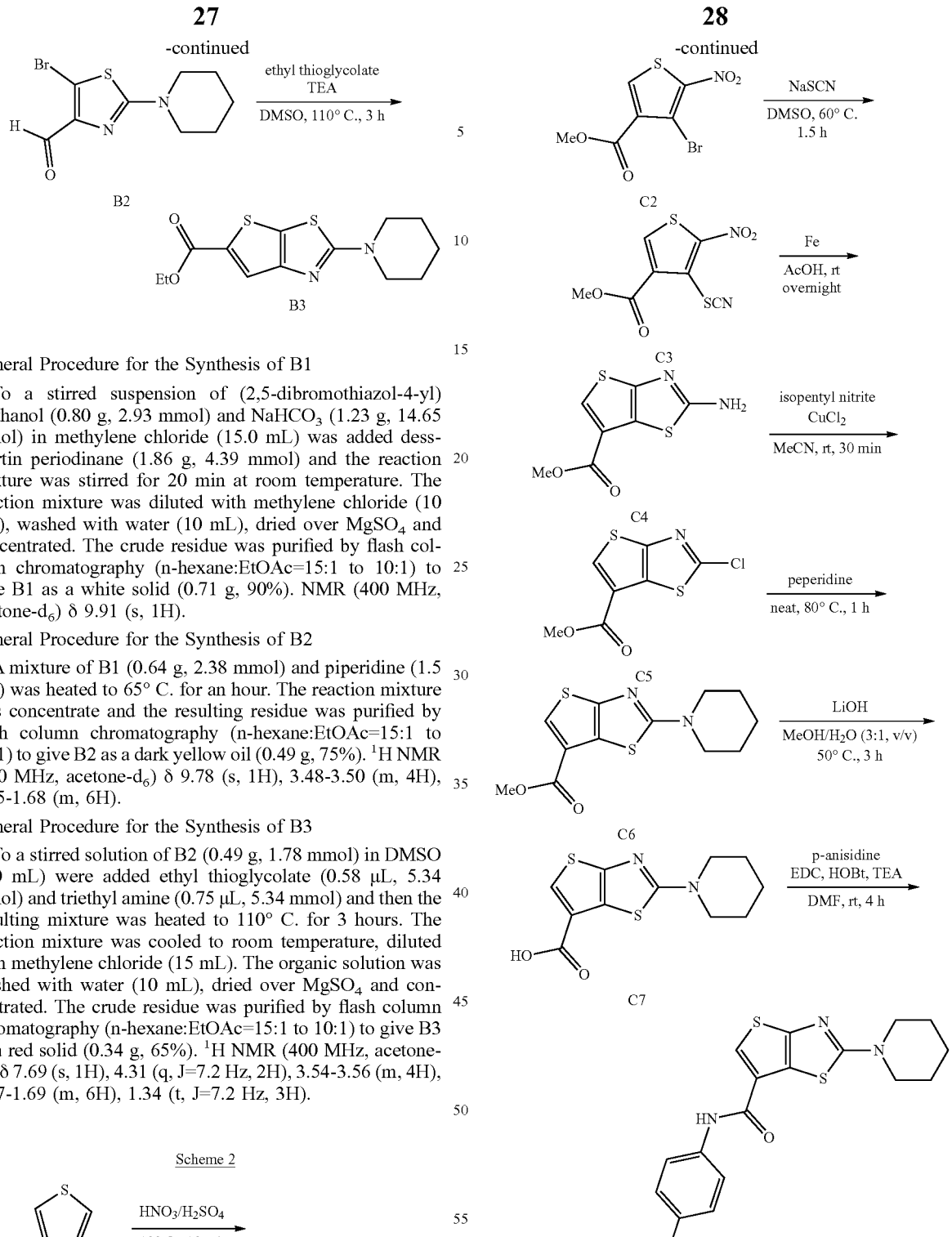

General Procedure for the Synthesis of B1

To a stirred suspension of (2,5-dibromothiazol-4-yl)methanol (0.80 g, 2.93 mmol) and $NaHCO_3$ (1.23 g, 14.65 mmol) in methylene chloride (15.0 mL) was added dess-martin periodinane (1.86 g, 4.39 mmol) and the reaction mixture was stirred for 20 min at room temperature. The reaction mixture was diluted with methylene chloride (10 mL), washed with water (10 mL), dried over $MgSO_4$ and concentrated. The crude residue was purified by flash column chromatography (n-hexane:EtOAc=15:1 to 10:1) to give B1 as a white solid (0.71 g, 90%). NMR (400 MHz, acetone-$d_6$) δ 9.91 (s, 1H).

General Procedure for the Synthesis of B2

A mixture of B1 (0.64 g, 2.38 mmol) and piperidine (1.5 mL) was heated to 65° C. for an hour. The reaction mixture was concentrate and the resulting residue was purified by flash column chromatography (n-hexane:EtOAc=15:1 to 10:1) to give B2 as a dark yellow oil (0.49 g, 75%). $^1$H NMR (400 MHz, acetone-$d_6$) δ 9.78 (s, 1H), 3.48-3.50 (m, 4H), 1.65-1.68 (m, 6H).

General Procedure for the Synthesis of B3

To a stirred solution of B2 (0.49 g, 1.78 mmol) in DMSO (5.0 mL) were added ethyl thioglycolate (0.58 μL, 5.34 mmol) and triethyl amine (0.75 μL, 5.34 mmol) and then the resulting mixture was heated to 110° C. for 3 hours. The reaction mixture was cooled to room temperature, diluted with methylene chloride (15 mL). The organic solution was washed with water (10 mL), dried over $MgSO_4$ and concentrated. The crude residue was purified by flash column chromatography (n-hexane:EtOAc=15:1 to 10:1) to give B3 as a red solid (0.34 g, 65%). $^1$H NMR (400 MHz, acetone-$d_6$) δ 7.69 (s, 1H), 4.31 (q, J=7.2 Hz, 2H), 3.54-3.56 (m, 4H), 1.67-1.69 (m, 6H), 1.34 (t, J=7.2 Hz, 3H).

sGeneral Procedure for the Synthesis of C1

A mixture of fuming nitric acid (0.5 mL) and $H_2SO_4$ (0.4 mL) was added slowly to a solution of 4-bromothiophene-3-carboxylic acid (1.0 g, 4.83 mmol) in $H_2SO_4$ (2.0 mL) at −10° C. and the resulting mixture was stirred for 10 min. The reaction mixture was poured to the ice and stirred for 5 min. The resulting precipitates was filtered, washed with water and dried in vacuo to give a target compound as a pale yellow solid (1.13 g, 93%). $^1$H NMR (400 MHz, CDCl$_3$) δ 8.67 (s, 1H).

General Procedure for the Synthesis of C2

To a solution of C1 (1.10 g, 4.36 mmol) in MeOH (20.0 mL) was added thionyl chloride (1.6 mL, 22.0 mmol) slowly under ice bath. After the addition, the ice-bath was removed and the reaction was allowed to warm up to room temperature and further stirred for overnight. The reaction mixture was concentrated and then dissolved in methylene chloride (20 mL). The organic solution was washed with aqueous Na$_2$CO$_3$ (sat. 20 mL) and brine (20 mL), dried over MgSO$_4$ and concentrated in vacuo. The resulting crude residue was purified by flash column chromatography (n-hexane:EtOAc=5:1 to methylene chloride:EtOAc=5:1) to give C2 as a pale yellow solid (0.93 g, 80%). $^1$H NMR (400 MHz, CDCl$_3$) δ 8.29 (s, 1H), 3.94 (s, 3H).

General Procedure for the Synthesis of C3

A mixture of C2 (0.50 g, 1.88 mmol) and dried NaSCN (0.46 g, 5.63 mmol) in DMSO (4.0 mL) was heated to 60° C. for 1.5 h. The reaction mixture was cooled to room temperature, poured to cold water and then the resulting precipitates was filtered and dried in vacuo to give a target compound C3 as a pale yellow solid (0.44 g, 96%).

General Procedure for the Synthesis of C4

To a stirred solution of C3 (0.39 g, 1.60 mmol) in AcOH (5.0 mL) was added a small portion of Fe. The resulting mixture was stirred for overnight at room temperature. After the reaction completion, the solution was basified with sat. Na$_2$CO$_3$ (aq. 20 mL) and then extracted with EtOAc (15 mL) several times. The combined organic layer was washed with brine (10 mL), dried over MgSO$_4$ and concentrated. The resulting crude residue was purified by flash column chromatography (n-hexane:EtOAc=2:1) to give C4 as a brown solid (0.10 g, 29%). $^1$H NMR (400 MHz, DMSO-d$_6$) δ 7.91 (s, 1H), 7.52 (s, 2H), 3.82 (s, 3H).

General Procedure for the Synthesis of C5

To a stirred suspension of copper (II) chloride (0.075 g, 0.56 mmol) in acetonitrile (3.0 mL) was added isopentyl nitrite (0.094 μL, 0.70 mmol). After 10 min of stirring, a solution of C4 (0.10 g, 0.46 mmol) in acetonitrile (2.0 mL) was added and the resulting mixture was further stirred for 30 min at room temperature. The insoluble residue was filtered off by cellite and the filtrate was concentrated in vacuo. The crude residue was purified by flash column chromatography (n-hexane:EtOAc=10:1) to give C5 as a yellow solid (0.050 g, 46%).

General Procedure for the Synthesis of C6

A mixture of C5 (0.050 g, 0.21 mmol) and piperidine (1.5 mL) was heated to 80° C. for an hour. The mixture was diluted with methylene chloride (5 mL), washed with water (5 mL) and brine (5 mL), dried MgSO$_4$ and concentrated in vacuo. The crude residue was purified by flash column chromatography (n-hexane:EtOAc=10:1) to give C6 as a pale yellow solid (0.045 g, 74%). $^1$H NMR (400 MHz, acetone-d$_6$) δ 7.85 (s, 1H), 3.87 (s, 3H), 3.54-3.57 (m, 4H), 1.67-1.70 (m, 6H).

General Procedure for the Synthesis of C7

To a stirred suspension of C6 (0.045 g, 0.16 mmol) in MeOH (3.0 mL) was added an aqueous solution of lithium hydroxide (0.019 g, 0.80 mmol in 1.0 mL of water) and the mixture was heated to 50° C. for 3 hours. The organic solvent was evaporated and aqueous 1N HCl was added until pH was reached to 4. The residual white solid was collected by filtration, washed with water and dried in vacuo to give C7 as a white solid (0.039 g, 91%).

General Procedure for the Synthesis of C8

To a stirred solution of C7 (0.039 g, 0.14 mmol) in anhydrous DMF (1.5 mL) were added 1-(3-dimethylaminopropyl)-3-ethylcarbodiimide hydrochloride (0.042 g, 0.21 mmol), 1-hydroxybenzotriazole (0.0098 mg, 0.073 mmol), triethylamine (40 μL, 0.29 mmol) and p-anisidine (0.015 g, 0.12 mmol) at room temperature, then the resulting solution was stirred for 4 hours at room temperature. The reaction mixture was concentrated and the resulting crude residue was purified by flash column chromatography (n-hexane:EtOAc=3:1 to 2:1) to give C8 as a pale pink solid (0.039 g, 85%).

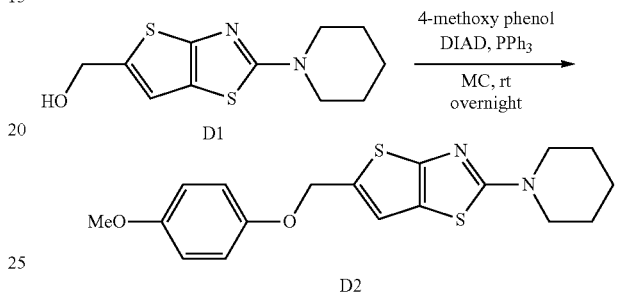

Scheme 3

General Procedure for the Synthesis of D2

To a stirred solution of D1 (0.050 g, 0.20 mmol) in methylene chloride (2.0 mL) were added diisopropyl axodicarboclate (43 μL, 0.12 mmol), triphenylphospine (0.062 g, 0.24 mmol) and 4-methoxy phenol (0.015 g, 0.12 mmol). The reaction mixture was stirred at room temperature for overnight. After reaction completion, the mixture was concentrated and purified by flash column chromatography (n-hexane:EtOAc=10:1) to give D2 as a white solid (0.011 g, 26%).

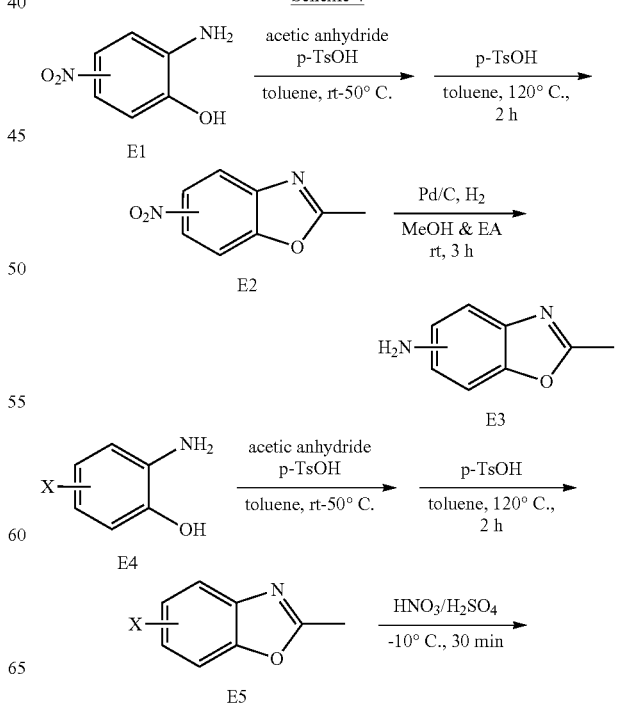

Scheme 4

-continued

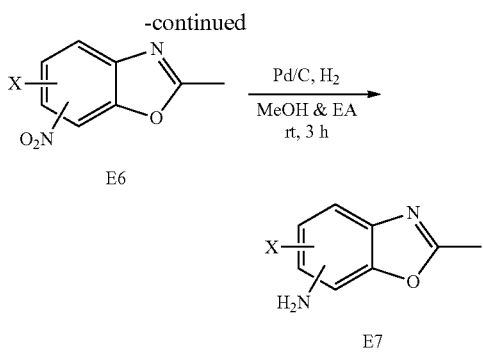

General Procedure for the Synthesis of E2 & E5

To a stirred solution of E1 or E4 (6.49 mmol) in toluene (5.0 mL) were added acetic anhydride (32.0 mmol) andp-toluene sulfonic acid monohydrate (0.65 mmol) and the resulting mixture was heated to 50° C. After an hour, additional p-toluenesulfonic acid monohydrate (7.14 mmol) was added and the reaction mixture was heated to 120° C. for 2 h. The resulting mixture was cooled to room temperature, poured to cooled water and then a resulting solid was collected and dried. The crude product was purified by flash column chromatography to give E2 or E5.

2-Methyl-5-nitrobenzo[d]oxazole

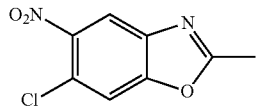

Pale yellow solid; $^1$H NMR (400 MHz, CDCl$_3$) δ 8.54 (d, J=2.4 Hz, 1H), 8.26 (dd, J=8.8, 2.4 Hz, 1 H), 7.56 (d, J=8.8 Hz, 1H), 2.71 (s, 3H).

2-Methyl-4-nitrobenzo[d]oxazole

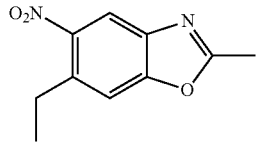

Pale yellow solid; $^1$H NMR (400 MHz, CDCl$_3$) δ 8.15 (dd, J=8.0, 0.8 Hz, 1H), 7.80 (dd, J=8.4, 0.8 Hz, 1H), 7.44 (dd, J=8.0, 8.4 Hz, 1H), 2.77 (s, 3H).

General Procedure for the Synthesis of E6

A mixture of fuming nitric acid (0.50 mL) and sulfuric acid (0.40 mL) were added to a solution of E5 (2.39 mmol) in sulfuric acid (2.0 mL) at −10° C. The resulting mixture was stirred for 30 min at the same temperature. Once starting material was disappeared, the reaction mixture was poured to the ice with stirring and then the generated white precipitates were filtered and dried invacuo to give a target compound E6.

6-Chloro-2-methyl-5-nitrobenzo[d]oxazole

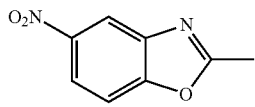

White solid; $^1$H NMR (400 MHz, acetone-d$_6$) δ 8.28 (s, 1H). 8.01 (s, 1H), 2.05 (s, 3H).

6-Ethyl-2-methyl-5-nitrobenzo[d]oxazole

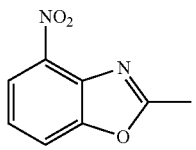

White solid; $^1$H NMR (400 MHz, acetone-d$_6$); δ 8.16 (s, 1H), 7.71 (s, IH), 2.95 (q, J=7.2 Hz, 2H), 2.66 (s, 3H), 1.28 (t, J=7.2 Hz, 3H).

General Procedure for the Synthesis of E3 & E7

To a stirred solution of E2 or E6 (1.68 mmol) in a mixture of ethyl acetate and methanol (3:1 ratio, 5.0 mL) was added palladium on activated carbon (30 mg) and the resulting solution was stirred under H$_2$ for 2 hours. The palladium was filtered off by cellite and the filtrate was concentrated in vacuo to give E3 or E7.

Scheme 5

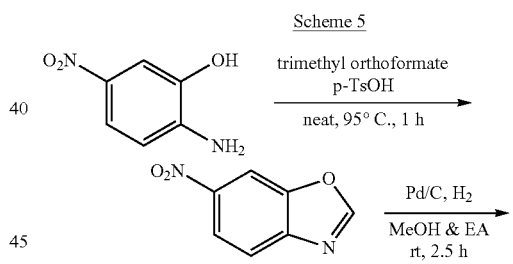

General Procedure for the Synthesis of F1

A mixture of 2-amino-4-nitrophenol (1.00 g, 6.49 mmol), trimethyl orthoformate (3.98 mL, 36.0 mmol) and p-toluenesulfonic acid (62.0 mg, 0.32 mmol) was stirred at 95° C. for an hour. The reaction mixture was cooled to room temperature and then the cold water was poured to the reaction mixture (10.0 mL). The generated solid was filtered, washed with water and dried to give F1 as a brown needle shape solid (0.54 g, 51%). $^1$H NMR (400 MHz, CDCl$_3$) δ 8.52 (d, J=2.0 Hz, IH), 8.33-8.36 (m, 2H), 7.91 (d, J=9.2 Hz, 1H).

General Procedure for the Synthesis of F2

Target compound F2 was synthesized according to general procedure for the synthesis of E3 & E7.

Scheme 6

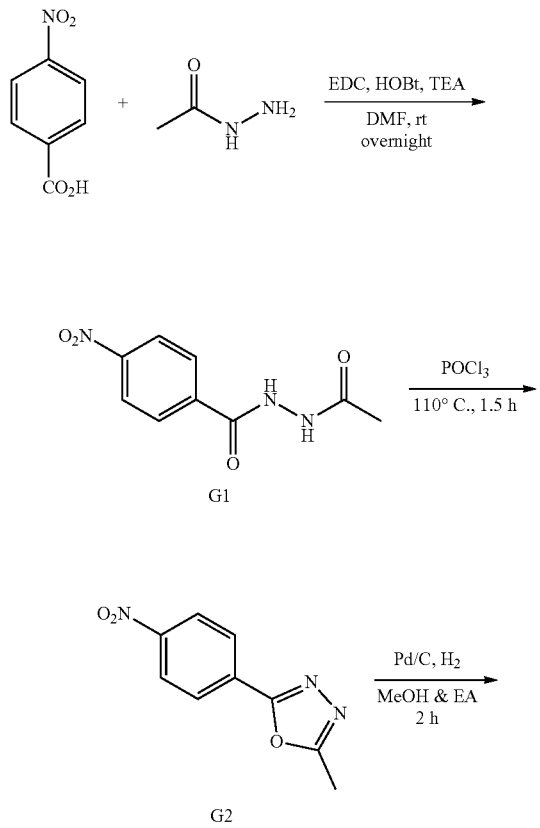

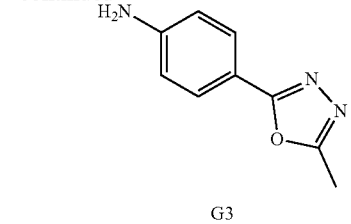

G3

General Procedure for the Synthesis of G1

To a stirred solution of 4-nitrobenzoic acid (1.0 g, 5.98 mmol) in anhydrous DMF (10.0 mL) were added acethydrazide (0.53 g, 7.18 mmol), 1-ethyl-3-(3-dimethylaminopropyl) carbodiimide (1.72 g, 8.97 mmol), 1-hydroxybenzotriazole (0.40 g, 2.99 mmol) and triethylamine (1.70 mL, 2.99 mmol) and the reaction mixture was stirred at room temperature for overnight. After the concentration of the reaction mixture, the resulting residue was dissolved in methylene chloride (20 mL) and washed with water (10 mL). At that time, the pale yellow precipitates were generated and it was filtered and dried to give G1 as a pale yellow solid. $^1$H NMR (400 MHz, DMSO-d6) δ 10.61 (s, 1H), 9.89 (s, 1H), 8.32 (d, J=8.4 Hz, 2H), 8.06 (d, J=8.4 Hz, 2H), 1.91 (s, 3H).

General Procedure for the Synthesis of G2

A mixture of G1 (0.50 g, 2.24 mmol) and POCl$_3$ (3.0 mL) was heated to 110° C. for 1.5 h. After reaction completion, the reaction mixture was basified with 3N NaOH (aq.) and then a generated solid was filtered and dried to give G2 (0.44 g, 96%) as a pale yellow solid. $^1$H NMR (400 MHz, DMSO-d$_6$) δ 8.42 (d, J=9.2 Hz, 2H), 8.23 (d, J=9.2 Hz, 2H), 2.62 (s, 3H).

General Procedure for the Synthesis of G3

Target compound G3 was synthesized according to general procedure for the synthesis of E3&E7.

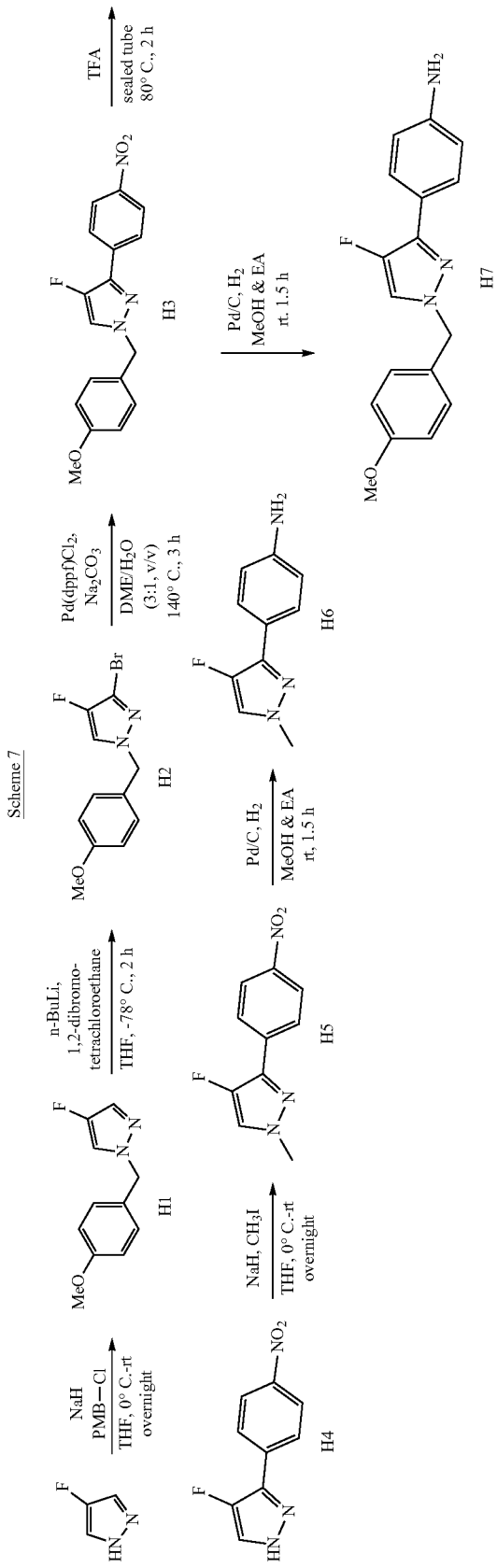
Scheme 7

General Procedure for the Synthesis of H1

To a stirred solution of 4-fluoropyrazole (0.40 g, 4.65 mmol) in THF (15.0 mL) was added NaH (60% dispersion in paraffin, 0.28 g, 6.97 mmol) under ice bath. After 10 min of stirring, p-methoxybenzyl chloride (0.76 mL, 5.58 mmol) was added slowly to the reaction mixture. The resulting solution was allowed to room temperature and stirred for overnight. The reaction was quenched with water and extracted with EtOAc (20 mL×2). The organic phase was washed with brine (15 mL), dried over MgSO$_4$ and concentrated in vacuo to give H1. $^1$H NMR (400 MHz, acetone-d$_6$) δ 7.65 (d, J=4.8 Hz, 1H), 7.34 (d, J=4.8 Hz, 1H), 7.23-7.26 (m, 2H), 6.88-6.91 (m, 2H), 5.18 (s, 2H).

General Procedure for the Synthesis of H2

To a stirred solution of H1 (0.52 g, 2.52 mmol) in THF (10.0 mL) at −78° C. was added a solution of n-BuLi (2.5 M in n-hexane, 1.5 mL, 3.78 mmol) slowly and the mixture was stirred for 15 min while maintaining the temperature below −60° C. A solution of 1,2-dibromo-tetrachloroethane (0.98 g, 3.02 mmol) in THF (3.0 mL) was added to the reaction mixture and the resulting solution was continuously stirred for an additional 2 hours. The reaction was quenched with water and extracted with EtOAc (20 mL×2). The organic phase was washed with brine (10 mL), dried over MgSO$_4$ and concentrated in vacuo. The crude residue was purified by flash column chromatography (n-hexane:EtOAc=15:1) to give 112 as a white solid (0.49 g, 69%). $^1$H NMR (400 MHz, acetone-d$_6$) δ 7.55 (d, J=4.8 Hz, 1H), 7.19-7.21 (m, 2H), 6.89-6.91 (m, 2H), 5.28 (s, 2H).

General Procedure for the Synthesis of H3

To a solution of H2 (0.21 g, 0.73 mmol) in dimethoxyethane (3.0 mL) were added 4-nitrophenylboronic acid (0.14 g, 0.81 mmol), 1,1'-bis(diphenylphosphino)ferrocene)-dichloropalladium(II) (0.027 g, 0.037 mmol) and Na$_2$CO$_3$ (0.16 g, 1.47 mmol in 1 mL of water) and the mixture was stirred at 140° C. After 3 hours, the mixture was cooled to room temperature, then the mixture was extracted with EtOAc (10 mL), washed with sat. NaHCO$_3$(aq. 10 mL) and brine (10 mL) and dried over MgSO$_4$ and concentrated. The resulting residue was purified by flash column chromatography (n-hexane:EtOAc=4:1) to give H3 as a pale yellow solid (0.14 g, 58%). $^1$H NMR (400 MHz, acetone-d$_6$) δ 8.35-8.37 (m, 2H), 7.72-7.74 (m, 2H), 7.61 (d, J=4.4 Hz, 1H), 6.97-6.99 (m, 2H), 6.80-6.82 (m, 2H), 5.37 (s, 2H).

General Procedure for the Synthesis of H4

A mixture of H3 (0.14 g, 0.43 mmol) and trifluoroacetic acid (3.0 mL) was placed in sealed tube and heated to 80° C. with stirring. After 2 hours, the mixture was concentrated and then resulting residue was dissolved in methylene chloride (5 mL), washed with saturated Na$_2$CO$_3$ (aq. 5.0 mL), dried over MgSO$_4$ and concentrated to give H4. The crude residue was used for next reaction without further purification.

General Procedure for the Synthesis of H5

To a stirred solution of H4 (0.095 g, 0.46 mmol) in THF (5.0 mL) was added NaH (60% dispersion in paraffin, 0.028 g, 0.69 mmol) under ice bath. After 10 min of stirring, iodomethane (34 μL, 0.55 mmol) was added slowly to the reaction mixture. The resulting solution was allowed to room temperature and stirred for overnight. The reaction was quenched with water and extracted with EtOAc (5 mL×2). The organic phase was washed with brine (5 mL), dried over MgSO$_4$ and concentrated. The crude residue was purified by flash column chromatography (n-hexane:EtOAc=5:1) to give H5 as a white solid (0.078 g, 78%). $^1$H NMR (400 MHz, acetone-d$_6$) δ 8.31-8.33 (m, 2H), 8.06-8.09 (m, 2H), 7.83 (d, J=4.8 Hz, 1H), 3.94 (s, 3H).

General Procedure for the Synthesis of H6 & H7

Target compounds H6 & H7 were synthesized according to general procedure for the synthesis of E3&E7.

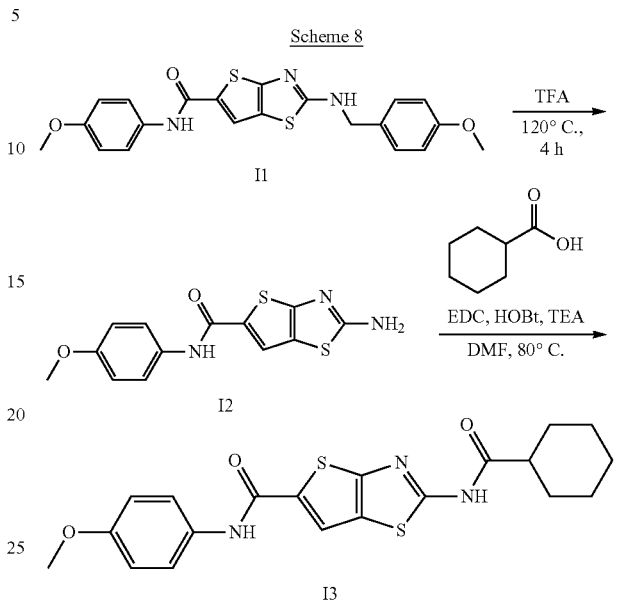

Scheme 8

General Procedure for the Synthesis of I2

A mixture of I1 (0.28 mmol) and trifluoroacetic acid (3.0 mL) was placed in sealed tube and heated to 120° C. for 4 hours with stirring. After reaction completion, the reaction mixture was concentrated and dissolved with methylene chloride (10.0 mL) again. The organic solution was washed with saturated Na$_2$CO$_3$ (aq. 10.0 mL), dried over MgSO$_4$ and concentrated in vacuo. The resulting crude residue was purified by flash column chromatography (methylene chloride:MeOH=99:1) to give I2. $^1$H NMR (400 MHz, acetone-d$_6$) δ 9.28 (s, 1H, NH), 7.89 (s, 1H), 7.66 (d, J=8.8 Hz, 2H), 7.08 (s, 2H, NH$_2$), 6.90 (d, J=8.8 Hz, 2H), 3.78 (s, 3H); LCMS (electrospray) m/z 306 (M+H)$^+$.

General Procedure for the Synthesis of I3

To a stirred solution of 12 (0.10 mmol) in N,N-dimethylformamide (3.0 mL) were added cyclohexanecarboxylic acid (0.10 mmol), 1-ethyl-3-(3-dimethylaminopropyl) carbodiimide hydrochloride (0.12 mmol), 1-hydroxybenzotriazole (0.03 mmol) and triethylamine (0.20 mmol) at room temperature. The reaction mixture was stirred at 80° C. for 4 hours, diluted with EtOAc (20 mL) and washed with brine (20 mL×3). The organic layer was dried over anhydrous MgSO$_4$ and concentrated invacuo. The crude product was purified by flash column chromatography (n-hexane:EtOAc=2:1) to give I3. $^1$H NMR (400 MHz, acetone-d$_6$) δ 9.47 (s, 1H, NH), 8.09 (s, 1H), 7.69 (d, J=8.8 Hz, 2H), 6.92 (d, J=8.8 Hz, 2H), 3.79 (s, 3H), 2.63-2.68 (m, 1H), 1.96-2.01 (m, 2H), 1.81-1.84 (m, 2H), 1.69-1.72 (m, 1H), 1.51-1.60 (m, 2H), 1.26-1.40 (m, 3H); LCMS (electrospray) m/z 416 (M+H)$^+$.

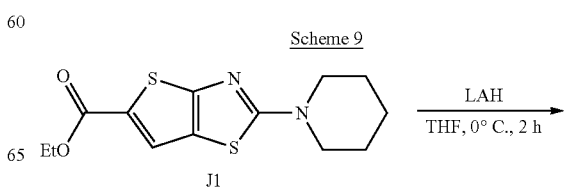

Scheme 9

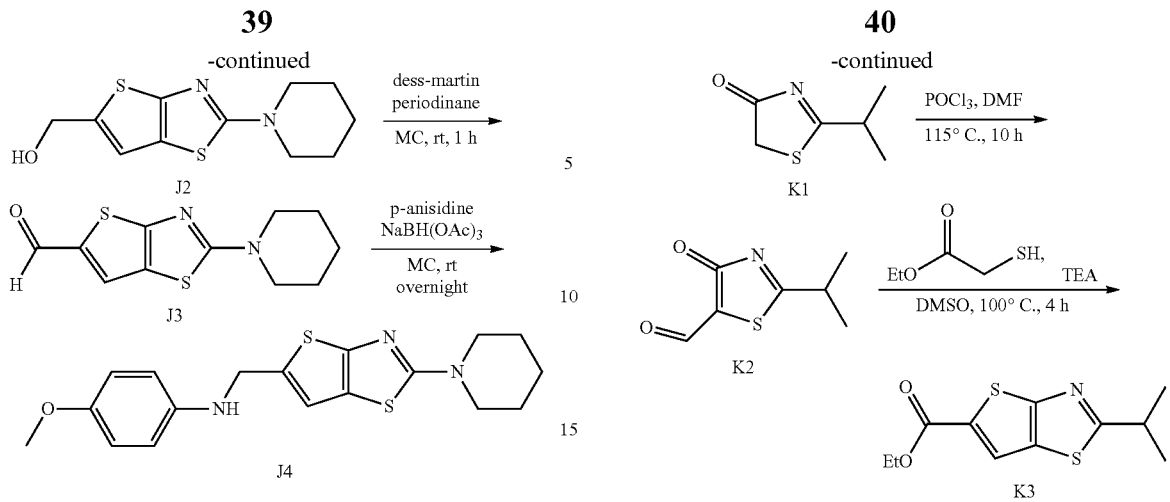

General Procedure for the Synthesis of J2

To a stirred solution of J1 (3.4 mmol) in tetrahydrofuran (20 mL) was added lithium aluminum hydride (5.1 mmol) at 0° C. and the reaction mixture was stirred for 2 hours while maintaining the temperature below 4° C. The reaction mixture was quenched by water with stirring and the insoluble solid was filtered off. The filtrate was extracted with methylene chloride (50 mL×2), dried over anhydrous $MgSO_4$ and concentrated invacuo. The crude product was purified by flash column chromatography (n-hexane:EtOAc=3:1) to give J2. $^1$H NMR (400 MHz, DMSO-$d_6$) 7.02 (s, 1H), 5.39 (t, J=5.6 Hz, 1H, OH), 4.56 (d, J=5.6 Hz, 2H), 3.42-3.45 (m, 4H), 1.58-1.60 (m, 6H); LCMS (electrospray) m/z 255 (M+H)$^+$.

General Procedure for the Synthesis of J3

To a stirred solution of J2 (0.87 mmol) in methylene chloride (20.0 mL) was added dess-martin periodinane (0.95 mmol) and the resulting mixture was stirred at room temperature for an hour. The reaction mixture was diluted with methylene chloride (10.0 mL), washed with brine (20 ml×2), dried over anhydrous $MgSO_4$ and concentrated invacuo. The crude product was purified by flash column chromatography (n-hexane:EtOAc=5:1) to give J3.

General Procedure for the Synthesis of J4

To a stirred solution of J3 (0.20 mmol) in methylene chloride (10.0 ml) were added p-anisidine (0.22 mmol) and sodium triacetoxyborohydride (0.40 mmol) and the resulting mixture was stirred at room temperature for overnight. After reaction completion, the mixture was diluted with methylene chloride (10 mL), washed with brine (10 ml×2), dried over anhydrous $MgSO_4$ and concentrated invacuo. The crude residue was purified by flash column chromatography (n-hexane:EtOAc=4:1) to give J4. $^1$H NMR (400 MHz, acetone-$d_6$) δ 7.07 (s, 1H), 6.72 (d, J=8.8 Hz, 2H), 6.69 (d, J=8.8 Hz, 2H), 5.09 (brs, 1H, NH), 4.47 (d, J=5.6 Hz, 2H), 3.67 (s, 3H), 3.48-3.50 (m, 4H), 1.65-1.68 (m, 6H); LCMS (electrospray) m/z 360 (M+H)$^+$.

Scheme 10

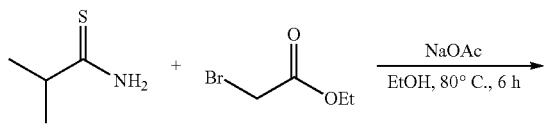

General Procedure for the Synthesis of K1

To a stirred solution of 2-methylpropanethioamide (5.0 mmol) in ethanol (5.0 mL) were added ethyl 2-bromoacetate (6.0 mmol) and sodium acetate (7.5 mmol) and the reaction mixture was heated to 80° C. for 6 hours with stirring. The reaction mixture was evaporated, diluted with methylene chloride (30 mL), washed with brine (30 mL), dried over anhydrous $MgSO_4$ and concentrated invacuo. The crude product was recrystallized by ether to give K1.

General Procedure for the Synthesis of K2

To a stirred solution of K1 (1.0 mmol) in phosphoryl chloride (1.0 mL) was added N,N-dimethylformamide (1.1 mmol) at room temperature. The reaction mixture was stirred at 115° C. for 10 hours. The mixture was poured to the ice and stirred for 30 min and extracted with methylene chloride (20 mL), washed with brine (20 mL), dried over anhydrous $MgSO_4$ and concentrated invacuo. The crude product was purified by flash column chromatography (n-hexane:EtOAc=8:1) to give K2.

General Procedure for the Synthesis of K3

To a stirred solution of K2 (0.90 mmol) in dimethyl sulfoxide (3.0 mL) were added ethyl 2-mercaptoacetate (1.08 mmol) and triethylamine (1.80 mmol) and the reaction mixture was stirred at 110° C. for 4 hours. The reaction mixture was diluted with EtOAc (30 mL) and washed with brine (30 ml×3). The organic layer was dried over anhydrous $MgSO_4$ and concentrated invacuo. The crude product was purified by flash column chromatography (n-hexane:EtOAc=10:1) to give K3. $^1$H NMR (400 MHz, acetone-$d_6$) δ 8.09 (s, 1H), 4.37 (q, J=7.2 Hz, 2H), 3.39-3.47 (m, 1H), 1.44 (d, J=6.8 Hz, 6H), 1.37 (t, J=7.2 Hz, 3H); LCMS (electrospray) m/z 256 (M+H)$^+$.

Scheme 11

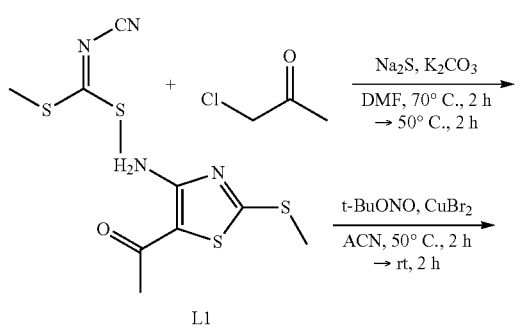

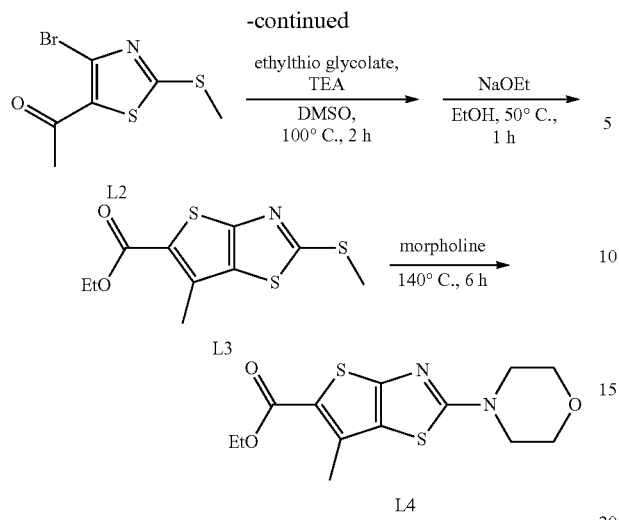

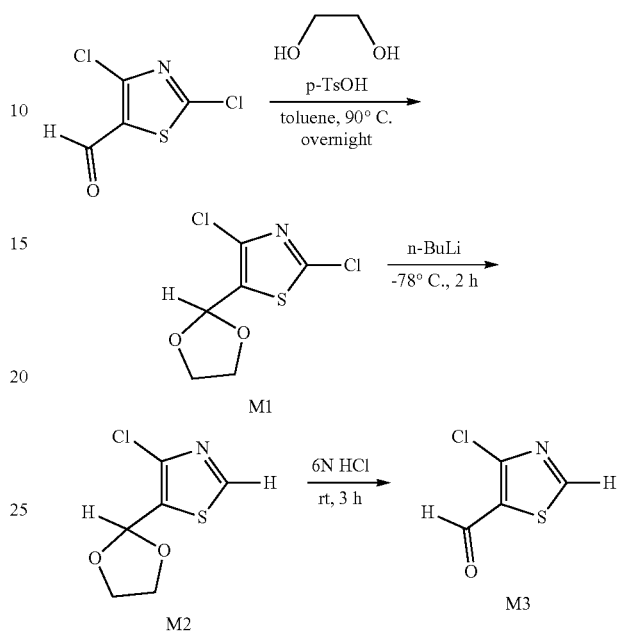

Scheme 12

General Procedure for the Synthesis of L1

To a stirred solution of dimethyl cyanocarbonimidodithioate (5.0 mmol) in N,N-dimethylformamide (10.0 mL) was added sodium sulfide (5.5 mmol) at room temperature. The reaction mixture was stirred at 70° C. for 2 hr. To the mixture were added 1-chloropropan-2-one (10.0 mmol) and potassium carbonate (10.0 mmol) and the resulting mixture was stirred at 50° C. for 2 hr. After reaction completion, the reaction mixture was added to water (50.0 mL) and the resulting solid was filtered and dried to give L1.

General Procedure for the Synthesis of L2

To a stirred solution of copper (II) bromide (3.44 mmol) in acetonitrile (20.0 mL) was added tert-butyl nitrite (4.30 mmol) at room temperature and then the resulting solution was heated to 50° C. After an hour, the reaction mixture was cooled to room temperature, L1 (2.87 mmol) was added to the solution and the resulting mixture was further stirred for 2 hours. After reaction completion, the mixture was diluted with methylene chloride (50.0 mL) and washed with brine (30 mL×2). The organic layer was dried over anhydrous MgSO$_4$ and concentrated invacuo. The crude product was purified by flash column chromatography (n-hexane:EtOAc=10:1) to give L2.

General Procedure for the Synthesis of L3

To a stirred solution of L2 (2.42 mmol) in dimethyl sulfoxide (5.0 mL) were added ethyl 2-mercaptoacetate (2.66 mmol) and triethylamine (4.84 mmol) at room temperature and the reaction mixture was stirred at 100° C. for 2 hr. The reaction mixture was diluted with EtOAc (30 mL) and the organic solution was washed with brine (30 mL×2), dried over anhydrous MgSO$_4$ and concentrated in vacuo. The crude residue was dissolved in ethanol (10.0 mL) and sodium ethoxide (21% in EtOH, 4.84 mmol) was added to the solution at 0° C. The reaction mixture was stirred at 50° C. for 1 hr. After reaction completion, the reaction mixture was diluted with methylene chloride (50 mL) and the organic solution was washed with brine (50 m), dried over anhydrous MgSO$_4$ and concentrated in vacuo. The crude residue was purified by flash column chromatography (n-hexane:EtOAc=5:1) to give L3.

General Procedure for the Synthesis of L4

A mixture of L3 (1.76 mmol) and morpholine (5.0 mL) was heated to 140° C. for 6 hours with stirring. After reaction completion, the mixture was diluted with EtOAc (30.0 mL) and washed with brine (30 mL×2). The organic layer was dried over anhydrous MgSO$_4$ and concentrated invacuo. The crude product was purified by flash column chromatography (n-hexane:EtOAc=2:1) to give L4.

General Procedure for the Synthesis of M1

To a stirred solution of 2,4-dichlorothiazole-5-carbaldehyde (0.50 g, 2.75 mmol) and ethane-1,2-diol (0.51 g, 8.24 mmol) in toluene (2.5 mL) was added p-toluenesulfonic acid monohydrate (0.042 g, 0.22 mmol) at room temperature. The mixture was stirred at 90° C. for overnight. After reaction completion, the reaction mixture was poured to the water (20 mL) and extracted by ethyl acetate (30 mL×3). The organic layer was dried over anhydrous Na$_2$SO$_4$ and concentrated in vacuo. The resulting crude residue was purified by flash column chromatography (n-hexane:EtOAc=30:1) to give M1.

General Procedure for the Synthesis of M2

To a stirred solution of M1(0.60 g, 2.65 mmol) in tetrahydrofuran (13.0 mL) was added n-butyllithium (2.5M in n-hexane, 2.1 mL, 5.30 mmol) at −78° C. and the reaction mixture was stirred for 2 hours while maintaining temperature below −60° C. After reaction completion, the reaction was quenched with water (10 mL) and extracted with ethyl acetate (30 mL×3). The organic layer was washed with brine (30 mL), dried over anhydrous Na$_2$SO$_4$ and concentrated in vacuo to give M2.

General Procedure for the Synthesis of M3

To a stirred solution of M2 (0.53 g, 2.74 mmol) in tetrahydrofuran (6.0 mL) was added 6 N HCl (1.2 m) and the mixture was stirred at room temperaturefor 3 h. The reaction mixture was diluted with water (10 mL) and extracted with ethyl acetate (30 mL×3). The organic layer was dried over anhydrous Na$_2$SO$_4$ and concentrated in vacuo to give M3.

Scheme 13

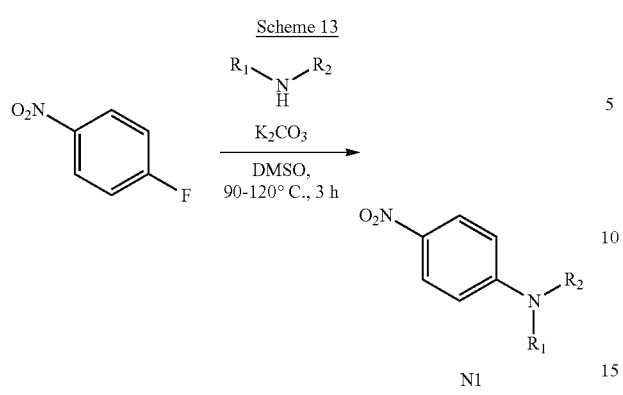

General Procedure for the Synthesis of N1

A mixture of 1-fluoro-4-nitrobenzene (2.0 mmol), adequate amine (2.0 mmol) and $K_2CO_3$ (6.0 mmol) in DMSO (5 mL) was heated to 120° C. for 4 hours. After the cooling, the mixture was poured to the water and then generating solid was filtered, washed with water and dried to give N1.

Scheme 14

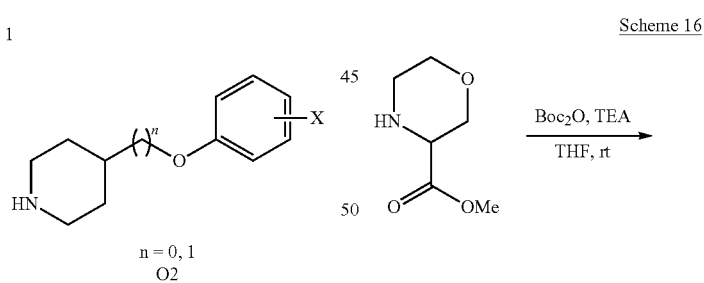

General Procedure for the Synthesis of O1

To a stirred solution of alcohol as starting material (2.55 mmol), adequate phenol (2.13 mmol) and triphenylphosphane (2.55 mmol) in N,N-dimethylformamide or methylene chloride (7.0 mL) was added diisopropyl azodicarboxylate (2.55 mmol) at 0° C. The mixture was allowed to room temperature and stirred for overnight. After reaction completion, the reaction mixture was concentrated in vacuo and then the resulting crude residue was purified by flash column chromatography (n-hexane:EtOAc=20:1) to give O1.

General Procedure for the Synthesis of O2

To a stirred solution of O1 (1.88 mmol) in methylene chloride (4.0 mL) was added trifluoroacetic acid (2.0 ml) at room temperature. The mixture was stirred at room temperature for an hour. The reaction mixture was quenched by Sat. $Na_2CO_3$ aqueous solution (4.0 ml) and extracted by methylene chloride (20 mL×3). The organic layer was dried over anhydrous $Na_2SO_4$ and concentrated in vacuo to give O2.

Scheme 15

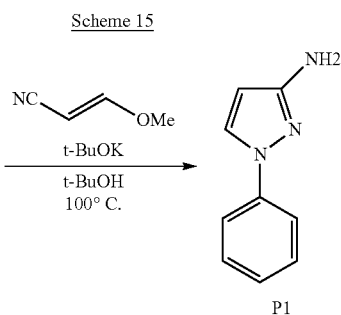

General Procedure for the Synthesis of P1

To a stirred solution of potassium tert-butoxide (2.30 g, 20.30 mmol) in tert-butyl alcohol (15 mL) were added phenylhydrazine (1.0 g, 9.25 mmol) and (E)-3-methoxyacrylonitrile (0.77 g, 9.25 mmol) at room temperature. The mixture was stirred at room temperature for overnight. After reaction completion, the reaction mixture was added to $H_2O$ (15 mL) and extracted by methylene chloride (45 mL×3). The organic layer was dried over anhydrous $Na_2SO_4$ and concentrated in vacuo. The resulting crude residue was purified by silica gel flash column chromatography (n-hexane:EtOAc=5:1) to give P1.

Scheme 16

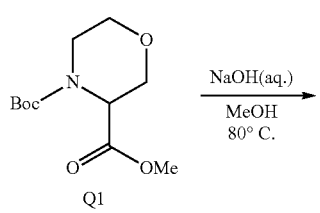

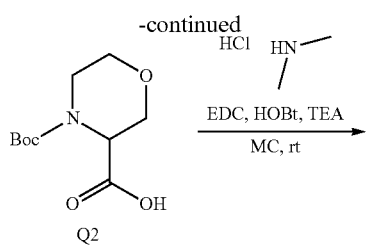

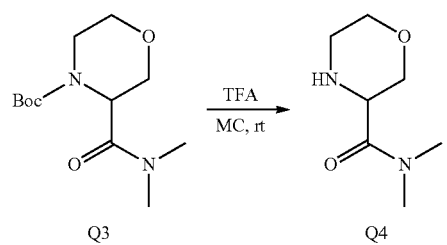

General Procedure for the Synthesis of Q1

To a stirred solution of methyl morpholine-3-carboxylate (0.050 g, 0.34 mmol) in tetrahydrofuran (2.0 mL) were added triethylamine (0.042 g, 0.41 mmol) and di-tert-butyl dicarbonate (0.075 g, 0.34 mmol) at room temperature. The mixture was stirred at room temperature for overnight. The reaction mixture was added to H₂O (5 mL) and extracted by methylene chloride (15 mL×3). The organic layer was dried over anhydrous Na₂SO₄ and concentrated in vacuo. The resulting crude residue was purified by flash column chromatography (n-hexane:EtOAc=10:1) to give Q1.

General Procedure for the Synthesis of Q2

To a stirred solution of Q1 (0.090 g, 0.37 mmol) in methanol (1.5 mL) was added sodium hydroxide (0.044 g, 1.10 mmol) in water (0.5 mL) at room temperature. The mixture was stirred at 75° C. for 3 h. After reaction completion, the reaction mixture was acidified with 6 N HCl aqueous solution until pH 4. The white precipitate was filtered and concentrated in vacuo to give Q2.

General Procedure for the Synthesis of Q3

To a stirred solution of Q2 (0.079 g, 0.34 mmol) in methylene chloride (1.7 mL) were added dimethylamine hydrochloride (0.030 g, 0.37 mmol), 1-ethyl-3-(3-dimethylaminopropyl)carbodiimide (0.078 g, 0.41 mmol) and 4-dimethylamino pyridine(0.042 g, 0.34 mmol) and triethylamine (0.10 g, 1.02 mmol) at room temperature. The mixture was stirred at room temperature for overnight. The reaction mixture was diluted with methylene chloride (10 mL) and washed with water (5 mL). The organic layer was dried over anhydrous Na₂SO₄ and concentrated in vacuo. The resulting crude residue was purified by flash column chromatography (n-hexane:EtOAc=10:1) to give Q3.

General Procedure for the Synthesis of Q4

To a stirred solution of Q3 (0.60 g, 2.3 mmol) in methylene chloride (3.0 mL) was added trifluoroacetic acid (1.5 mL) at room temperature. The mixture was stirred at room temperature for 4 hr. The reaction mixture was quenched by sat. Na₂CO₃ aqueous solution (5 mL) and extracted by methylene chloride (15 mL×3). The organic layer was dried over anhydrous Na₂SO₄ and concentrated in vacua to give Q4.

Scheme 17

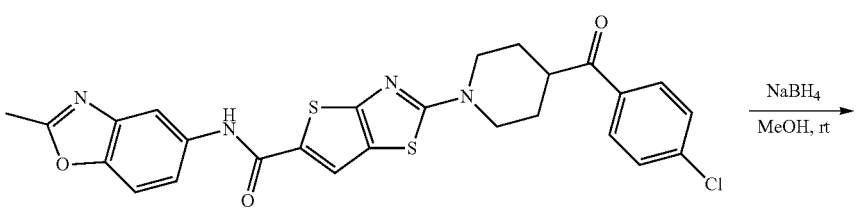

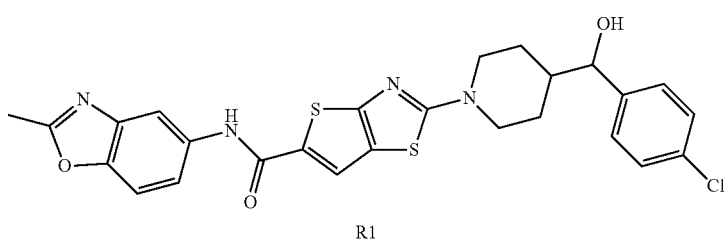

R1

General Procedure for the Synthesis of R1

To a stirred solution of 2-(4-(4-chlorobenzoyl)piperidin-1-yl)-N-(2-methylbenzo[d]oxazol-5-yl)thieno[2,3-d]thiazole-5-carboxamide (0.010 g, 0.019 mmol) in methanol (0.1 mL) was added sodium borohydride (0.0010 g, 0.022 mmol) at room temperature. The mixture was stirred at room temperature for overnight. After reaction was completed, the reaction mixture was added to H₂O (5 ml) and concentrated in vacua. The resulting crude residue was purified by silica gel flash column chromatography (n-hexane:EtOAc=1:1) to give R1.

Scheme 19

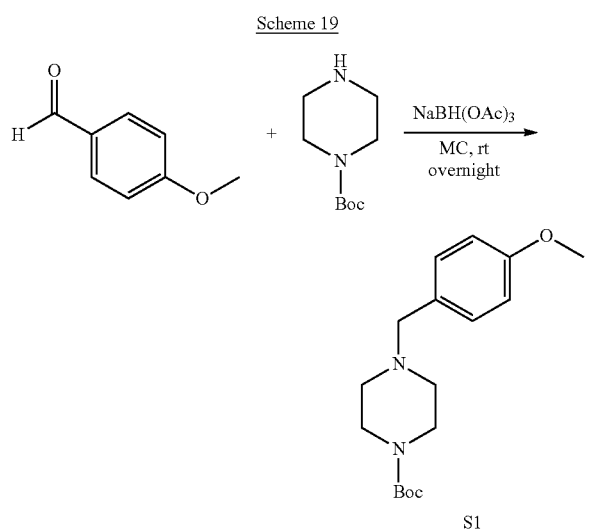

S1

General Procedure for the Synthesis of S1

To a solution of 4-methoxybenzaldehyde (0.30 g, 2.21 mmol) and tert-butyl piperazine-1-carboxylate (0.49 g, 2.64 mmol) in dichloromethane (8.0 mL) was added NaBH(OAc)₃ (0.93 g, 4.41 mmol). The resulting mixture was stirred at room temperature for overnight. After reaction completion, the reaction mixture was diluted with methylene chloride (30 mL) and washed with water (20 mL). The organic layer was dried over MgSO₄ and concentrated invacuo. The resulting crude residue was purified by flash column chromatography (n-hexane:EtOAc=2:1) to give S1.

Scheme 20

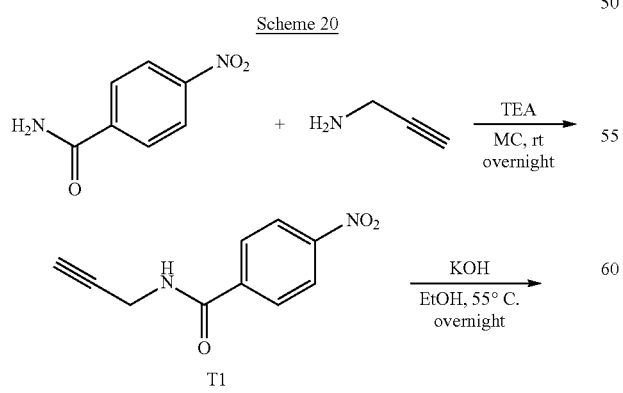

T1

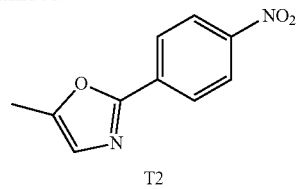

T2

General Procedure for the Synthesis of T1

To a stirred solution of 4-nitrobenzamide (0.50 g, 2.69 mmol) in methylene chloride (15.0 mL) were added triethylamine (0.545 g, 4.04 mmol) and propargylamine (0.107 g, 3.23 mmol) at 0° C. The mixture was allowed to room temperature and stirred for overnight. The reaction mixture was diluted with methylene chloride (15 mL) and washed with water (20 mL). The organic layer was dried over MgSO₄ and concentrated in vacuo. The resulting crude residue was purified by flash column chromatography (n-hexane:EtOAc=1:1) to give T1.

General Procedure for the Synthesis of T2

To a stirred solution of T1 (0.142 g, 0.69 mmol) in ethanol (2.8 mL) was added a solution of potassium hydroxide (0.078 g, 1.39 mmol) in ethanol (1.9 mL) at room temperature and then the mixture was heated to 50° C. and stirred for overnight. After reaction completion, the reaction mixture was concentrated. The resulting residue was dissolved with methylene chloride (30 mL) and washed with water (20 mL) and brine (20 mL). The organic layer was dried over MgSO₄ and concentrated in vacuo and the resulting crude residue was purified by flash column chromatography (n-hexane:EtOAc=5:1) to give T2.

Scheme 21

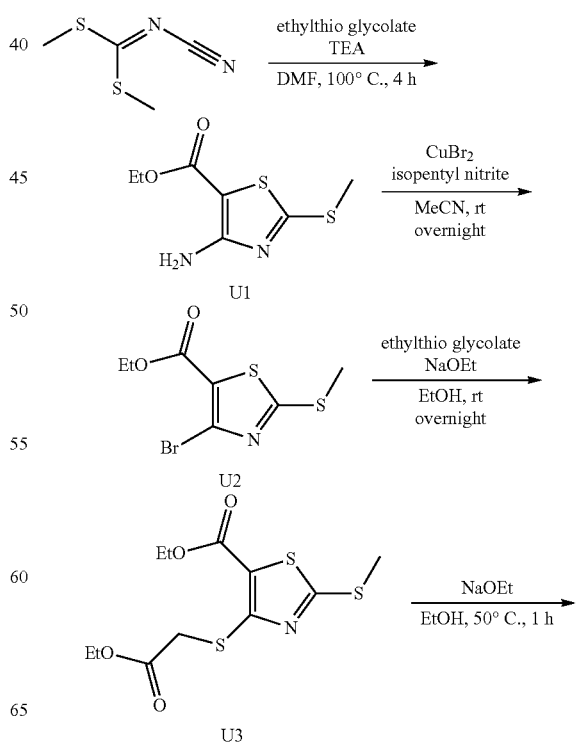

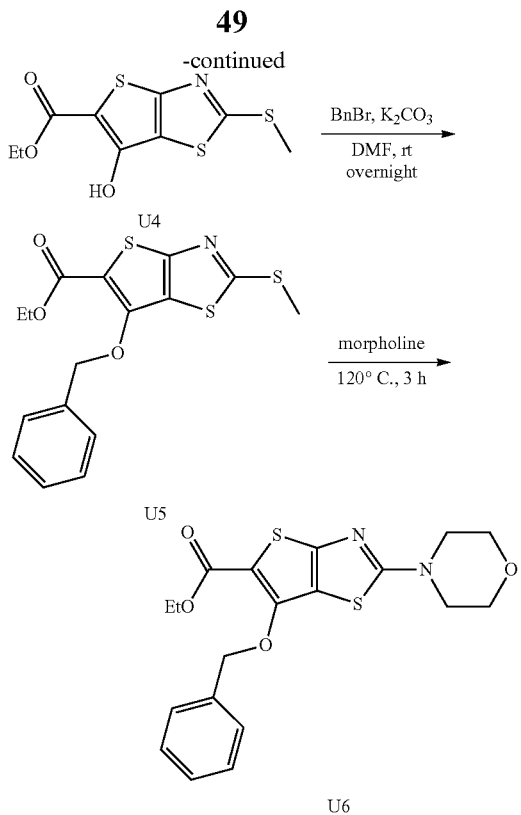

General Procedure for the Synthesis of U1

To a stirred solution of ethyl 2-mercaptoacetate (0.82 g, 6.80 mol) in N,N-dimethylformamide (8.5 mL) were added triethylamine (1.5 mL, 10.0 mmol) and dimethyl cyanocarbonimidodithioate (1.0 g, 6.80 mol) and the mixture was stirred at 100° C. for 2 h. The reaction mixture was cooled to room temperature, diluted with EtOAc (30 mL) and washed with water (30 mL). The organic layer was dried over $MgSO_4$ and concentrated invacuoand the resulting crude residue was purified by flash column chromatography (n-hexane:EtOAc=20:1) to give U1. $^1$H NMR (400 MHz, acetone-$d_6$) δ 6.56 (brs, 2H), 4.19 (q, J=7.2 Hz, 2H), 2.67 (s, 3H), 1.27 (t, J=7.2 Hz, 3H).

General Procedure for the Synthesis of U2

To a stirred solution of isopentyl nitrite (3.1 mL, 0.023 mmol) in acetonitrile(36.0 mL) was added $CuBr_2$ (5.1 g, 0.023 mol) at room temperature and the resulting solution was heated to 50° C. After an hour, the solution was cooled to room temperature and U1 (2.0 g, 9.0 mol) was added slowly. The reaction mixture was further stirred at room temperature for overnight. After reaction completion, the solution was diluted with water (50 mL) and extracted by EtOAc (30 mL×2). The organic layer was dried over $MgSO_4$ and concentrated invacuo. The resulting crude residue was purified by flash column chromatography (n-hexane: EtOAc=10:1) to give U2.

General Procedure for the Synthesis of U3

To a stirred solution of U2 (0.89 g, 3.16 mmol) in ethanol (12.0 mL) were added ethyl 2-mercaptoacetate (0.57 mg, 4.75 mmol) and NaOEt (1.8 mL, 4.75 mmol) and the resulting mixture was stirred at room temperature for overnight. The reaction mixture was diluted with water (20 mL) and extracted by EtOAc (30 mL×2). The organic layer was dried over $MgSO_4$ and concentrated in vacuo. The resulting crude residue was purified by flash column chromatography (n-hexane:EtOAc=20:1) to give U3.

General Procedure for the Synthesis of U4

To a stirred solution of U3 (1.11 g, 3.40 mol) in ethanol (13.7 mL) was added NaOEt (2.5 mL, 6.90 mol) at room temperature and the mixture was stirred at 50° C. for an hour. After reaction completion, the reaction mixture was quenched with water (50 mL) and extracted by EtOAc (30 mL×2). The organic layer was dried over $MgSO_4$ and concentrated in vacuo. The resulting crude residue was purified by flash column chromatography (n-hexane: EtOAc=20:1) to give U4.

General Procedure for the Synthesis of U5

To a stirred solution of U4 (0.050 mg, 0.18 mmol) in N, N-dimethylformamide (0.75 mL) were added potassium carbonate (0.038 mg, 0.27 mmol) and benzyl bromide (0.032 mg, 0.19 mmol) at room temperature and the resulting mixture was stirred for overnight. The reaction mixture was diluted with water (10 mL) and extracted by EtOAc (10 mL×2). The organic layer was dried over $MgSO_4$ and concentrated in vacuo. The resulting crude residue was purified by flash column chromatography (n-hexane: EtOAc=20:1) to give U5. $^1$H NMR (400 MHz, DMSO-$d_6$) δ 7.46-7.48 (m, 2H), 7.32-7.40 (m, 3H), 5.44 (s, 2H), 4.24 (q, J=7.2 Hz, 2H), 2.77 (s, 3H), 1.26 (t, J=7.2 Hz, 3H).

General Procedure for the Synthesis of U6

A mixture of U5 (0.26 g, 0.73 mmol) and morpholine (1.5 mL) was heated to 130° C. with stirring for 3 h. The reaction mixture was diluted with water (20 mL) and extracted with EtOAc (20 mL×2). The organic layer was dried over $MgSO_4$ and concentrated in vacuo. The resulting crude residue was purified by flash column chromatography (n-hexane: EtOAc=10:1) to give U6. $^1$H NMR (400 MHz, DMSO-$d_6$) δ 7.45-7.47 (m, 2H), 7.30-7.39 (m, 3H), 5.37 (s, 2H), 4.18 (q, J=6.8 Hz, 2H), 3.69-3.71 (m, 4H), 3.48-3.53 (m, 4H), 1.21 (t, J=6.8 Hz, 3H).

Scheme 22

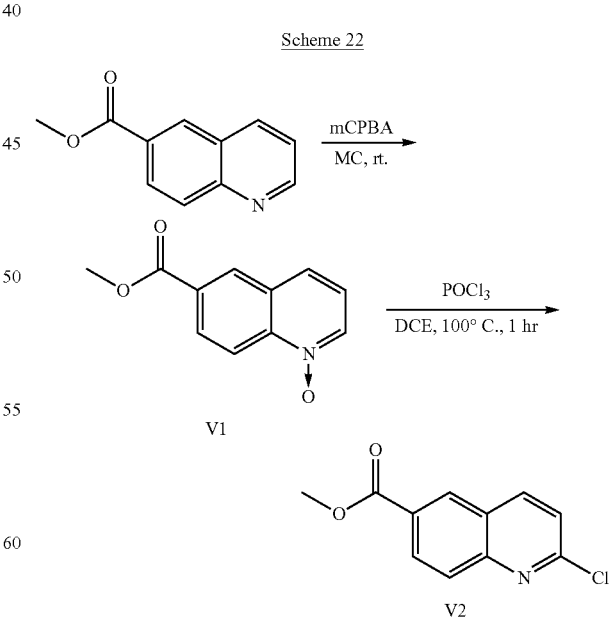

General Procedure for the Synthesis of V1

To a stirred solution of methyl quinoline-6-carboxylate (5.34 mmol) in methylene chloride (20 mL) was added 3-chloroperbenzoic acid (13.35 mmol). The reaction mixture was stirred at room temperature for overnight. After reaction completion, the reaction mixture was diluted methylene chloride (5 mL) and washed with brine (5 mL). The organic layer was dried over anhydrous MgSO₄ and concentrated in vacuo. The crude product was purified by flash column chromatography (5% MeOH in methylene chloride) to give V1.

General Procedure for the Synthesis of V2

To a stirred solution of 6-(methoxycarbonyl) quinoline 1-oxide (0.98 mmol) in dichloroethane (3 mL) was added phosphorus(V) oxychloride (3 mL) at 0° C. The reaction mixture was stirred at reflux temperature for an hour. The reaction mixture was poured into the ice water and extracted bymethylene chloride (10 mL) twice. The organic layer was dried over anhydrous MgSO₄ and concentrated in vacuo. The crude product was purified by flash column chromatography (n-hexane:EtOAc=6:1) to give V2. $^1$H NMR (400 MHz, CDCl₃) δ 8.58 (d, J=2.0 Hz, IH), 8.33 (dd, J=8.8 2.0 Hz, 1H), 8.21 (d, J=8.8 Hz, 1H), 8.07 (d, J=8.8 Hz, 1H), 7.46 (d, J=8.8 Hz, 1H), 4.00 (s, 3H).

Scheme 23

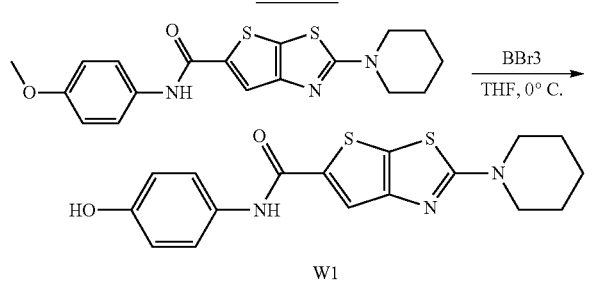

General Procedure for the Synthesis of W1

To a stirred solution of N-(4-methoxyphenyl)-2-(piperidin-1-yl)thieno[3,2-d]thiazole-5-carboxamide (0.24 mmol) in methylene chloride (3 mL) was added borontribromide (1.0 M in methylene chloride, 4 mL) at 0° C. The reaction mixture was stirred at room temperature for 2 hours. After reaction completion, the reaction mixture was quenched with cold water (5 mL) and extracted with methylene chloride (10 mL×2). The organic layer was dried over anhydrous MgSO₄ and concentrated in vacuo. The crude product was purified by flash column chromatography (2% MeOH in methylene chloride) to give W1.

Scheme 24

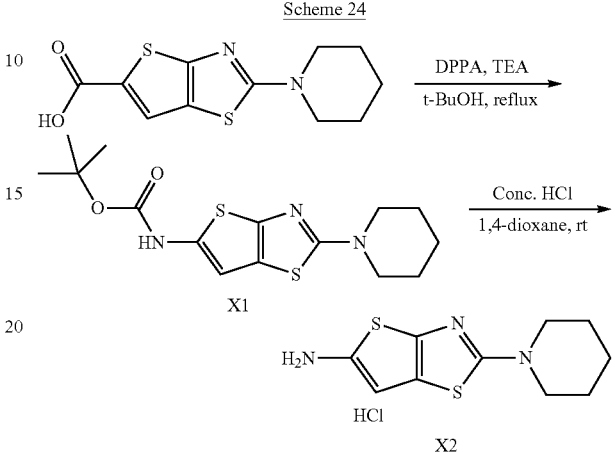

General Procedure for the Synthesis of X1

To a stirred solution of 2-(piperidin-1-yl) thieno[2,3-d]thiazole-5-carboxylic acid (1.11 mmol) in tert-buthanol (8 mL) was added diphenylphosphorylazide (1.34 mmol). The reaction mixture was stirred at 95° C. for 4 hours. The reaction mixture was diluted methylene chloride (5 mL) and washed with brine (5 mL). The organic layer was dried over anhydrous MgSO₄ and concentrated in vacuo. The crude product was purified by flash column chromatography (n-hexane:EtOAc=10:1) to give X1.

General Procedure for the Synthesis of X2

To a stirred solution of X1 (0.58 mmol) in 1,4-dioxane (4 mL) was added 35% hydrogenchloride (0.7 mL). The reaction mixture was stirred at room temperature. After 2 hours, the reaction mixture was concentrated in vacuo and the crude product was used for next reaction without further purification to give X2.

Scheme 25

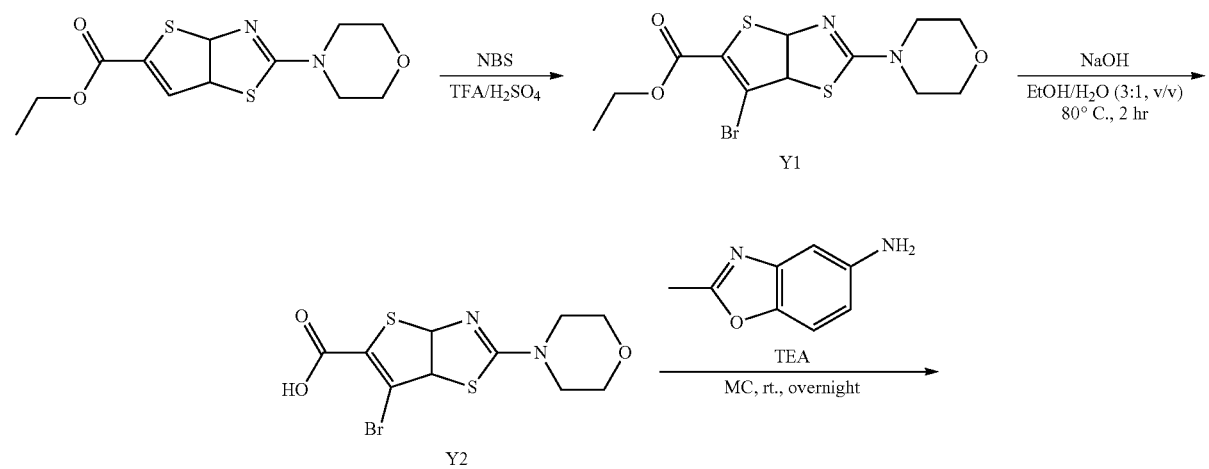

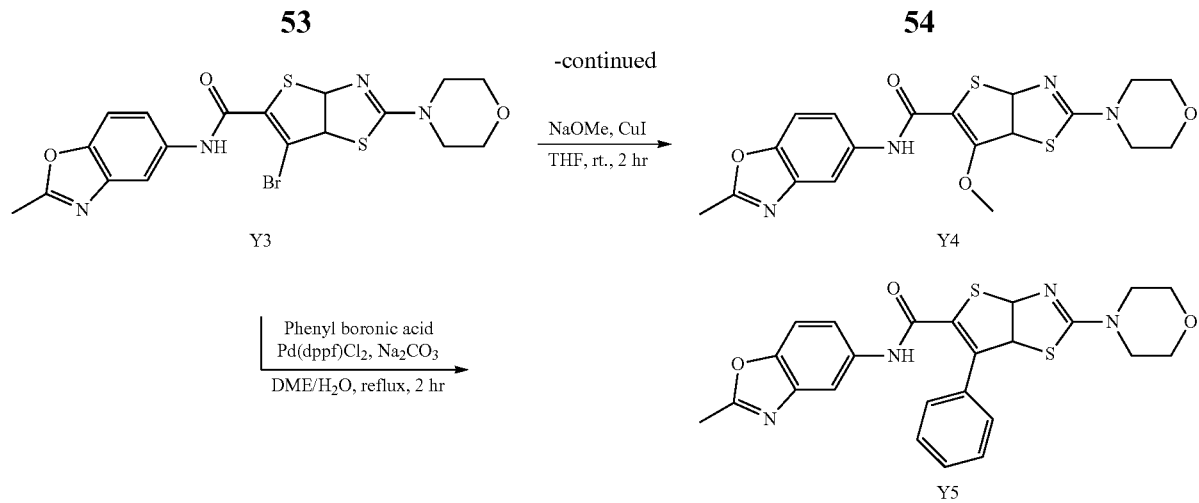

General Procedure for the Synthesis of Y1

To a stirred solution of ethyl 2-morpholino-3a,6a-dihydrothieno[2,3-d]thiazole-5-carboxylate (0.67 mmol) in trifluoroacetic acid/sulfuric acid (2:1 v/v, 3.0 mL) was added N-bromosuccinimide (1.34 mmol) at 0° C. The reaction mixture was stirred at room temperature for 2 days. The reaction mixture was poured into the ice water and extracted with methylene chloride (10 mL×2). The organic layer was dried over anhydrous MgSO$_4$ and concentrated in vacuo. The crude product was purified by flash column chromatography (n-hexane:EtOAc=6:1) to give Y1.

General Procedure for the Synthesis of Y2

Target compound Y2 was synthesized according to general procedure for the synthesis of A3.

General Procedure for the Synthesis of Y3

Target compound Y3 was synthesized according to general procedure for the synthesis of A5-method 2.

General Procedure for the Synthesis of Y4

To a stirred solution of Y3 (0.94 mmol) in tetrahydrofuran (2.0 mL) were added sodium methoxide (0.14 mmol) and copper iodide (0.94 mmol) at 0° C. and the reaction mixture was stirred at room temperature for overnight. After reaction completion, the mixture was diluted with methylene chloride (10 mL) and washed with brine (10 mL). The organic layer was dried over anhydrous MgSO$_4$ and concentrated in vacuo. The resulting crude residue was purified by flash column chromatography to give Y4.

General Procedure for the Synthesis of Y5

Target compound Y5 was synthesized according to general procedure for the synthesis of H3.

Scheme 26

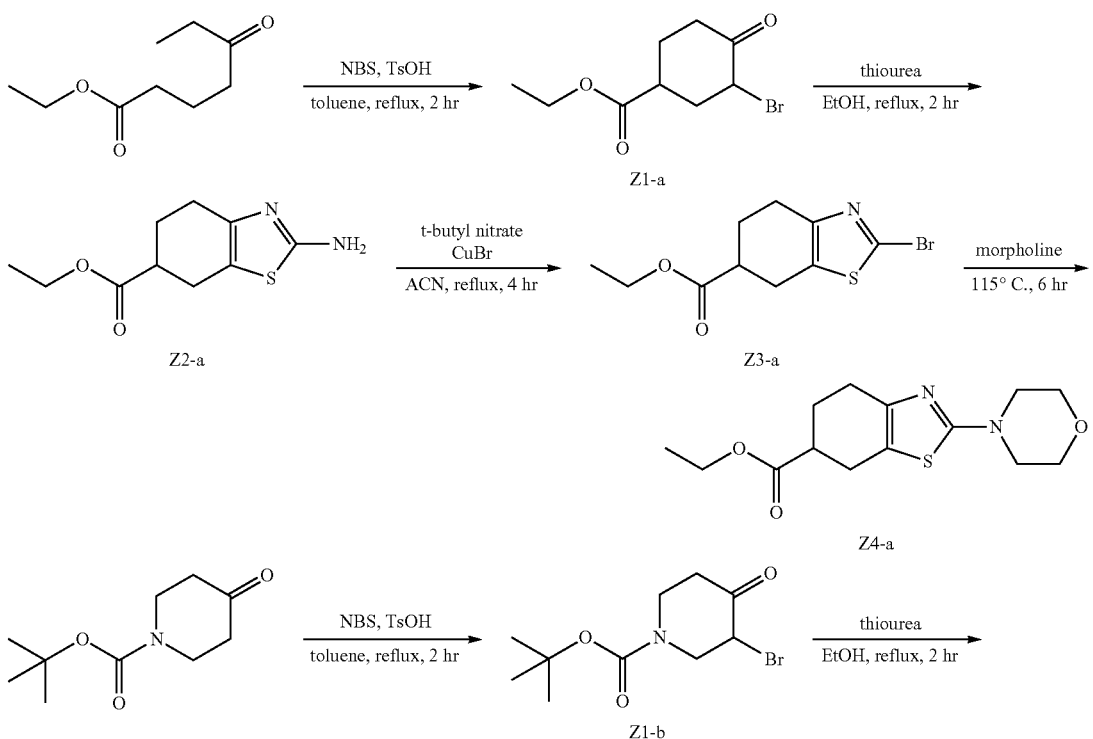

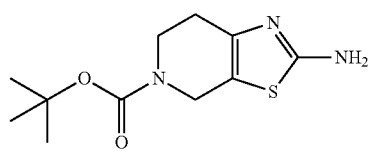 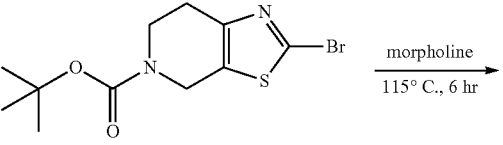

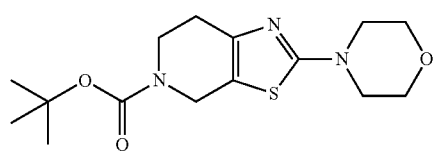 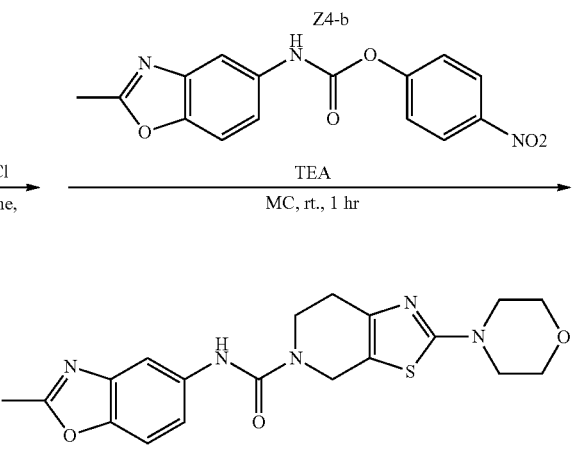

General Procedure for the Synthesis of Z1-a and Z1-b

To a stirred solution of starting material (8.81 mmol) in toluene (20 mL) were added N-bromosuccinimide (8.81 mmol) and p-toluenesulfonic acid monohydrate (0.88 mmol) and then the resulting mixture was stirred at 115° C. for 2 hours. The reaction mixture was diluted with methylene chloride (20 mL) and washed with brine (20 mL). The organic layer was dried over anhydrous MgSO₄ and concentrated in vacuo. The crude product was purified by flash column chromatography to give Z1-a or Z1-b.

General Procedure for the Synthesis of Z2-a and Z2-b

To a stirred solution of Z1-a or Z1-b (5.98 mmol) in EtOH (20 mL) was added thiourea (6.28 mmol) and the mixture was stirred at reflux temperature for 2 hours. After reaction completion, the reaction mixture was diluted with methylene chloride (20 mL) and washed with brine (20 mL). The organic layer was dried over anhydrous MgSO₄ and concentrated in vacuo to give Z2-a or Z2-b.

Z2-a; $^1$H NMR (400 MHz, DMSO-$d_6$) δ 8.62 (brs, 2H, NH₂), 4.03-4.10 (m, 2H), 2.59-2.72 (m, 2H), 2.39-2.44 (m, 2H), 1.99-2.03 (m, 1H), 1.69-1.79 (m, 1H), 1.49-1.18 (m, 3H).

Z2-b; $^1$H NMR (400 MHz, CDCl₃) δ 4.77 (brs, 2H, NH₂), 4.42 (s, 2H), 3.67-3.71 (m, 2H), 2.61-2.65 (m, 2H), 1.46 (s, 9H).

General Procedure for the Synthesis of Z3-a and Z3-b

To a stirred solution of Z2-a or Z2-b (5.87 mmol) in acetonitrile (20 mL) were added copper(II)bromide (7.04 mmol) and tert-butyl nitrate (14.67 mmol). The reaction mixture was stirred at reflux temperature for 3 hours. The reaction mixture was diluted with methylene chloride (20 mL) and washed with brine (20 mL). The organic layer was dried over anhydrous MgSO₄ and concentrated in vacuo. The crude product was purified by flash column chromatography to give Z3-a or Z3-b.

Z3-a; $^1$H NMR (400 MHz, CDCl₃) δ 4.16-4.21(m, 2H), 2.72-3.01 (m, 5H), 2.21-2.27 (m, 1H), 1.95-2.01 (m, 1H), 1.22-1.28 (m, 3H).

Z3-b; $^1$H NMR (400 MHz, CDCl₃) δ 4.17-4.21 (m, 2H), 3.77-4.01 (m, 4H), 3.39-3.42 (m, 4H), 2.85-2.89 (m, 2H), 2.59-2.79 (m, 3H), 2.18-2.24 (m, 1H), 1.90-1.98 (m, 1H), 1.25-1.30 (m, 3H).

General Procedure for the Synthesis of Z4-a and Z4-b

Target compound Z4-a and Z4-b were synthesized according to general procedure for the synthesis of U6.

Z4-a; $^1$H NMR (400 MHz, CDCl₃) δ 4.17-4.21 (m, 2H), 3.77-4.01 (m, 4H), 3.39-3.42 (m, 4H), 2.85-2.89 (m, 2H), 2.59-2.79 (m, 31-1), 2.18-2.24 (m, 1H), 1.90-1.98 (m, 1H), 1.25-1.30 (m, 3H).

Z4-b; $^1$H NMR (400 MHz, CDCl₃) δ 4.44 (s, 2H), 3.78-3.80 (m, 4H), 3.67-3.70 (m, 2H), 3.38-3.43 (m, 4H), 2.64-2.67 (m, 2H), 1.47 (m, 9H).

General Procedure for the Synthesis of Z5

To a stirred solution of Z4-b (0.020 g, 0.076 mmol) in 1,4-dioxane (2.0 mL) was added conc. HCl (10 μL) and the reaction mixture was stirred for 3 hours. The solution was concentrated and dried under reduced pressure. The resulting residue was dissolved in methylene chloride (2.0 mL) and triethylamine (32 μL, 0.23 mmol) and carbamate (0.026 g, 0.084 mmol) were added to the solution. After that, the resulting solution was stirred for an hour at room temperature. After reaction completion, the solution was diluted with methylene chloride (5 mL) and washed with water (5 mL). The organic layer was dried over anhydrous MgSO₄ and concentrated in vacuo to give Z5.

Scheme 27

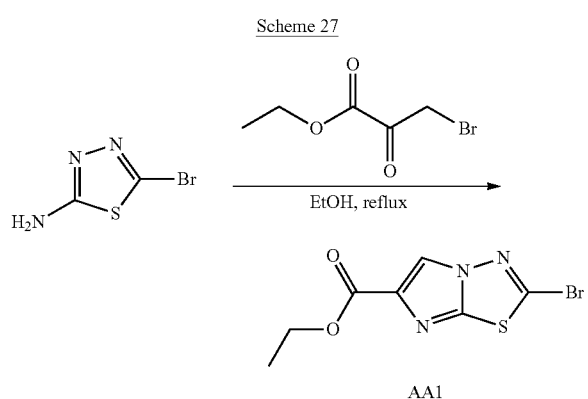

General Procedure for the Synthesis of AA1

To a stirred solution of 5-bromo-1,3,4-thiadiazol-2-amine (8.33 mmol) in ethanol (20 mL) was added ethyl bromopyruvate (9.16 mmol). The reaction mixture was stirred at reflux temperature for 8 hours. After reaction completion, the reaction mixture was diluted with methylene chloride (20 mL) and washed with brine (20 mL). The organic layer was dried over anhydrous MgSO4 and concentrated in vacuo. The crude product was purified by flash column chromatography to give AA1.

AA1; $^1$H NMR (400 MHz, CDCl$_3$) δ 8.34 (s, 1H), 4.38-4.43 (m, 2H), 1.38-1.44 (m, 3H).

Scheme 28

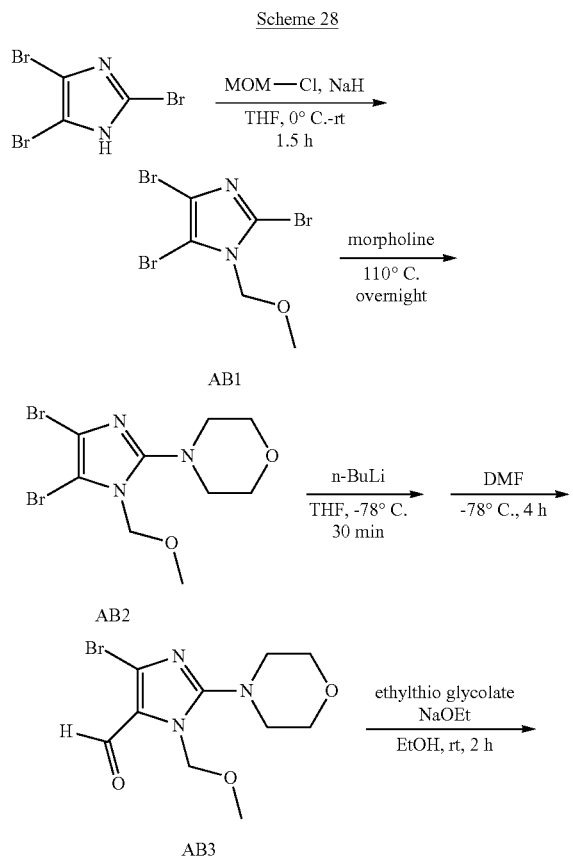

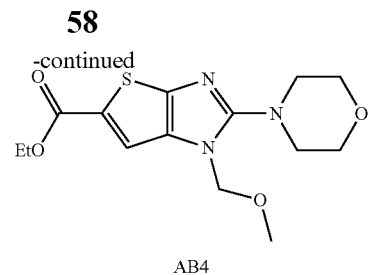

General Procedure for the Synthesis of AB1

To a stirred solution of 2,4,5-tribromoimidazole (1.0 g, 3.28 mmol) in tetrahydrofuran (15.0 mL) was added NaH (60% dispersion in paraffin, 0.20 g, 4.92 mmol) under ice-bath. After 10 min, chloromethyl methyleter (0.30 mL, 3.94 mmol) was added slowly. The reaction mixture was allowed to room temperature and further stirred for 1.5 hours. The reaction mixture was quenched with water (20 mL) and extracted with EtOAc (20 mL×2). The organic layer was dried over anhydrous MgSO4 and concentrated in vacuo to give AB1.

General Procedure for the Synthesis of AB2

Target compound AB2 was synthesized according to general procedure for the synthesis of U6. $^1$H NMR (400 MHz, acetone-d$_6$) δ 5.23 (s, 2H), 3.74-3.76 (m, 4H), 3.38 (s, 3H), 3.08-3.11 (m, 4H).

General Procedure for the synthesis of AB3

To a stirred solution of AB2 (0.21 g, 0.59 mmol) in tetrahydrofuran (5.0 mL) was added n-BuLi (2.5 M in n-hexane, 0.26 mL, 0.65 mmol) at −78° C. After 30 min, N,N-dimethylformamide (46 μL, 0.59 mmol) was added and the resulting mixture was stirred for 4 hours while maintaining temperature below −60° C. The reaction mixture was quenched with water (5 mL) and extracted with EtOAc (5 mL×2). The organic solution was washed with brine (5 mL), dried over anhydrous MgSO4 and concentrated in vacuo. The crude residue was purified by flash column chromatography (n-hexane:EtOAc=3:1) to give AB3.

General Procedure for the Synthesis of AB4

To a stirred solution of AB3 (0.056 g, 0.18 mmol) in ethanol (3.0 mL) were added sodium ethoxide (20% in EtOH, 0.19 mL, 0.055 mmol) and ethylthio glycolate (0.027 g, 0.22 mmol) and the reaction mixture was stirred at room temperature for 2 hours. The reaction was quenched with water (2 mL) and the resulting mixture was concentrated under reduced pressure. The crude residue was purified by flash column chromatography (n-hexane:EtOAc=3:1) to give AB4.

Scheme 29

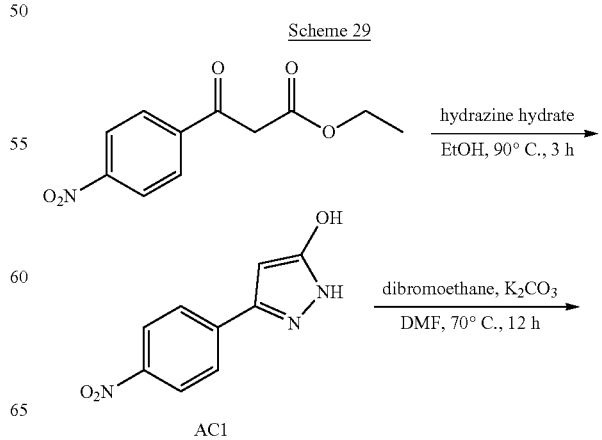

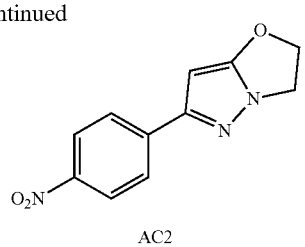

AC2

General Procedure for the Synthesis of AC1

To a stirred solution of ethyl 3-(4-nitrophenyl)-3-oxopropanoate (0.50 g, 2.11 mmol) in EtOH (7.0 mL) was added hydrazine hydrate (0.12 mL, 2.53 mmol). The reaction mixture was stirred at 90° C. for 3 hours. After reaction completion, the mixture was evaporated and $H_2O$ (10 mL) was added. The residual pale solid was collected by filtration, washed with water and dried in vacuo to give AC1 (165 mg, yield=38%).

General Procedure for the Synthesis of AC2

To a stirred solution AC1 (165 mg, 0.80 mmol) in anhydrous DMF (5.0 mL) were added dibromoethane (0.076 mL, 0.88 mmol) and $K_2CO_3$ (445 mg, 3.22 mmol). The reaction mixture was stirred at 70° C. for 12 hours. The reaction mixture was cooled to room temperature and then water (10 mL) was poured. The residual pale solid was collected by filtration and dried in vacuo to give AC2 (163 mg, yield=88%).

Scheme 30

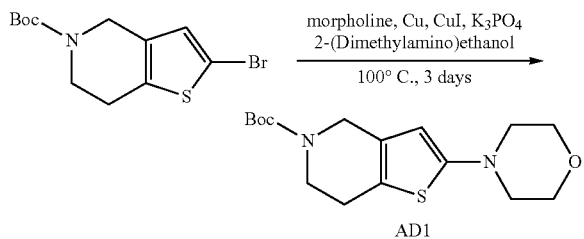

AD1

General Procedure for the Synthesis of AD1

To a stirredsolution of tert-butyl 2-bromo-6,7-dihydrothieno[3,2-c]pyridine-5(4H)-carboxylate (0.070 g, 0.22 mmol) in 2-(dimethylamino)ethanol (1.0 mL) were added morpholine (0.095 mL, 1.10 mmol), CuI (0.0042 g, 0.022 mmol), Cu (0.0014 g, 0.022 mmol) and $K_3PO_4$ (0.12 g, 0.55 mmol). The reaction mixture was stirred at 100° C. for 3 days. After reaction completion, the reaction mixture was diluted with dichloromethane (5 mL) and washed with brine (5 mL). The organic layer was dried over anhydrous $MgSO_4$ and concentrated in vacuo. The crude product was purified by flash column chromatography to give AD1 (33.4 mg, yield=47%).

Scheme 31

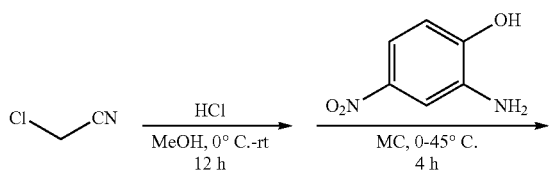

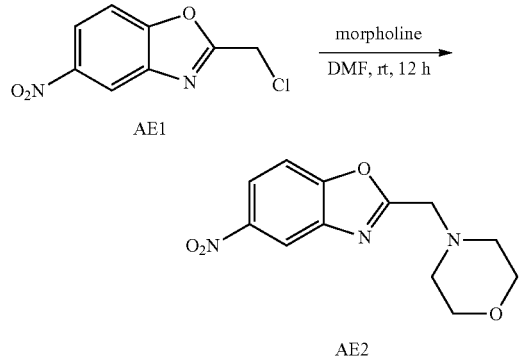

AE2

General Procedure for the Synthesis of AE1

To a stirred solution of 2N HCl in diethylether:MeOH=1:1 (8.0 mL) was added 2-chloroacetonitrile (0.17 ml, 2.65 mmol) at 0° C. The reaction mixture was stirred at room temperature for 12 hours. After reaction completion, the reaction mixture was concentrated. The resulting residue was dissolved in methylene chloride (3.0 mL) and 2-amino-4-nitrophenol (20 mg, 0.13 mmol) was added at 0° C. The reaction mixture was stirred at room temperature for 2 hours and then the reaction temperature was raised to 45° C. After 4 hours, the mixture was evaporated and methanol was added to the resulting residue. The insoluble solid was filtered off and the filtrate was concentrated and purified by flash column chromatography to give AE1.

General Procedure for the synthesis of AE2

To a stirred solution of AE1 (29 mg, 0.14 mmol) in N,N-dimethylformamide (0.3 mL) was added morpholine (0.18 ml, 2.05 mmol). The reaction mixture was stirred at room temperaturefor 12 h. The reaction mixture was diluted with EtOAC (5 mL) and washed with brine (5 mL). The organic layer was dried over anhydrous $MgSO_4$ and concentrated in vacuo. The crude product was purified by flash column chromatography to give AE2 (19 mg, yield=53%).

Scheme 32

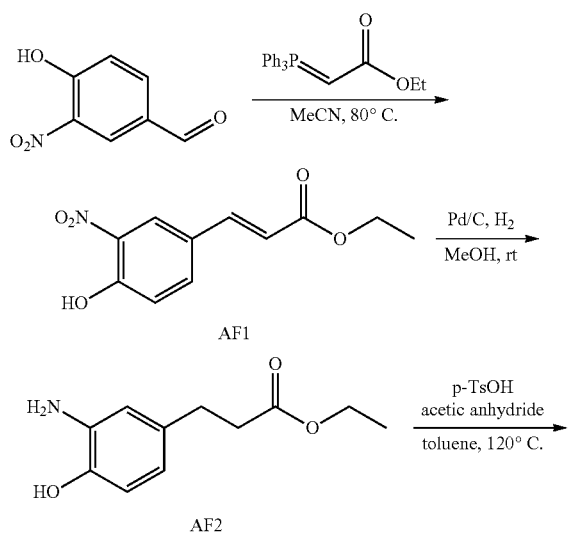

AF2

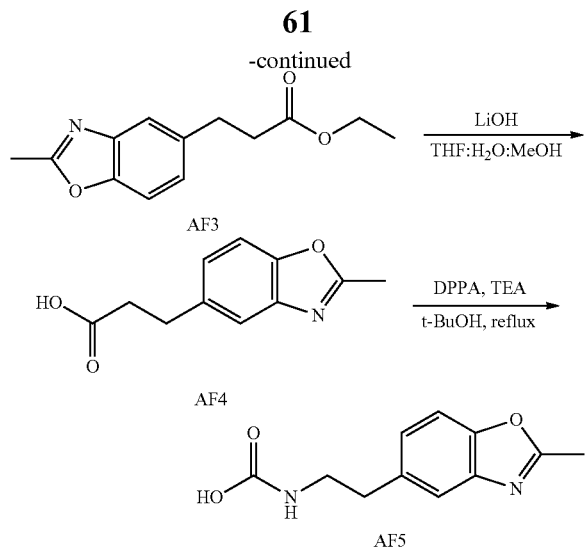

General Procedure for the Synthesis of AF1

To a stirred solution of 4-hydroxy-3-nitrobenzaldehyde (0.50 mg, 2.99 mmol) in acetonitrile (15 mL) was added (carbethoxymethylene)triphenylphosphorane (1.15 mg, 3.29 mmol). The reaction mixture was stirred at 80° C. for 5 h. After reaction was completed, the reaction mixture was diluted with EtOAC (20 mL) and washed with brine (15 mL). The organic layer was dried over anhydrous MgSO$_4$ and concentrated in vacuo. The crude product was purified by flash column chromatography to give AF1 (488 mg, yield=69%).

General Procedure for the Synthesis of AF2

Target compound AF2 was synthesized according to general procedure for the synthesis of E3&E7.

General Procedure for the Synthesis of AF3

Target compound AF3 was synthesized according to general procedure for the synthesis of E2&E5.

General Procedure for the Synthesis of AF4

To a stirred solution of AF3 (0.15 g, 0.64 mmol) in THF (2.0 mL) and MeOH (0.2 mL) and H$_2$O (1.0 ml) was added lithium hydroxide (77 mg, 3.22 mmol). The mixture was stirred at room temperature for overnight. After reaction completion, the mixture was evaporated and 1 N HCl (10 mL) was added until pH was reached to 5. The residual pale solid was collected by filtration, washed with water and dried in vacuo to give AF4 (67 mg, yield=51%).

General Procedure for the Synthesis of AF5

Target compound AF5 was synthesized according to general procedure for the synthesis of X1.

Scheme 33

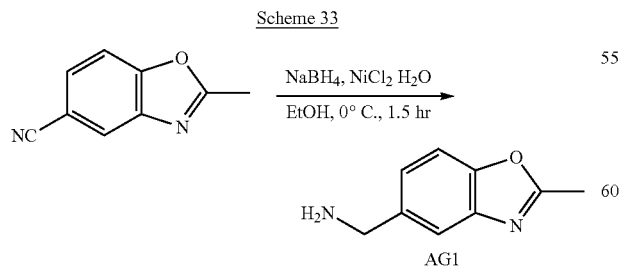

General Procedure for the Synthesis of AG1

To a solution of nitrile starting material (60 mg, 0.38 mmol) and nickel(II) chloride hexahydrate (135 mg, 0.57 mmol) in EtOH (4.8 ml) was added sodium borohydride (43 mg, 1.14 mmol) portionwise under ice bath. The reaction mixture was warmed to room temperature slowly and the further stirred for 1.5 h. After reaction completion, the mixture was quenched with water, diluted with dichloromethane, dried over MgSO$_4$ and concentrated to give mixture of desired amine AG1 and dimer (2:1 ratio, 42%). The resulting crude residue was used for next reaction without further purification.

Scheme 34

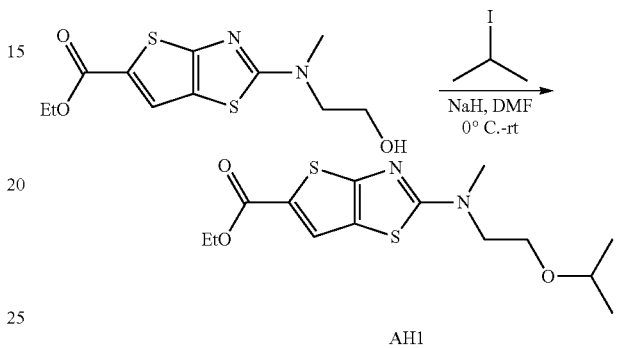

General Procedure for the Synthesis of AH1

To a stirred solution of ethyl 2-((2-hydroxyethyl)(methyl)amino)thieno[2,3-d]thiazole-5-carboxylate (0.50 g, 1.7 mmol) in DMF (5 mL) was added sodium hydride (0.084 g, 2.1 mmol) at 0° C. After 15 min, 2-iodopropane (0.89 g, 5.2 mmol) was added and then the resulting mixture was further stirred for 3 h at room temperature. The reaction mixture was quenched with water (10 ml) and extracted with dichloromethane (30 mL×3). The organic layer was dried over anhydrous Na$_2$SO$_4$ and concentrated in vacuo. The resulting crude residue was purified by flash column chromatography (n-hexane:EtOAc=3:1) to give AH1.

Scheme 35

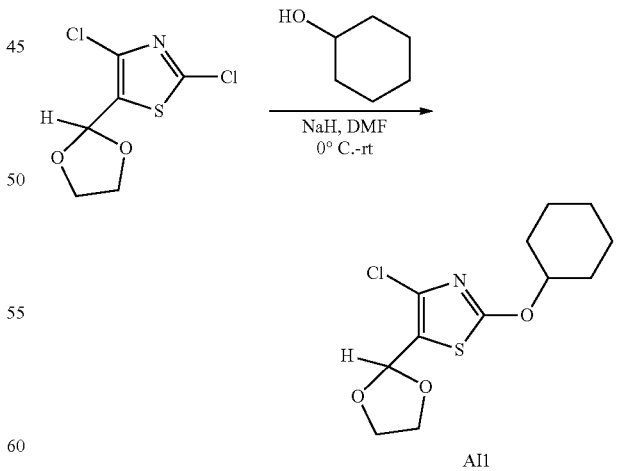

General Procedure for the Synthesis of AI1

To a stirred solution of 2,4-dichloro-5-(1,3-dioxolan-2-yl)thiazole (0.91 g, 4.0 mmol) in DMF (15 mL) was added sodium hydride (0.20 g, 5.0 mmol) under ice bath. After stirring for 5 min, cyclohexanol (0.34 g, 3.4 mmol) was slowly added and then the reaction mixture was further stirred for overnight at room temperature. After reaction completion, the mixture was quenched with water (10 ml) and extracted with dichloromethane (30 mL×3). The organic layer was dried over anhydrous $Na_2SO_4$ and concentrated in vacuo. The resulting crude residue was purified by flash column chromatography (n-hexane:EtOAc=10:1) to give AI1.

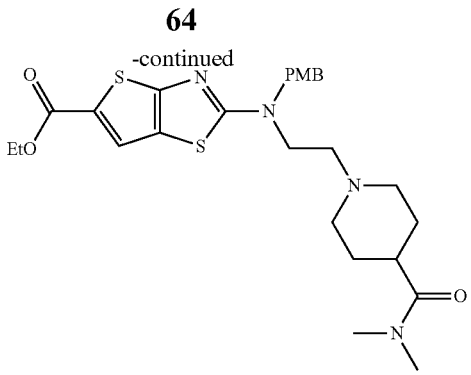

AJ2

General Procedure for the Synthesis of AJ2

To a stirred solution of N,N-dimethylpiperidine-4-carboxamide trifluoroacetic acid (0.085 mg, 0.55 mmol) in acetonitrile (1.2 mL) was added potassium carbonate (0.22 g, 1.56 mmol) at room temperature. After stirring for 10 min, AJ1 (0.146 g, 0.31 mmol) was added and then the mixture was further stirred at 50° C. for for overnight. The reaction mixture was quenched with water (20 mL) and extracted with ethylacetate (20 mL×2). The organic layer was dried over $MgSO_4$ and concentrated in vacuo. The resulting crude residue was purified by flash column chromatography (dichloromethane:methanol=50:1 ratio) to give AJ2.

The invention is now further described by reference to Tables 1-3.

TABLE 1

Structures and Characteristics of Compounds 1-360

| No. | Structure | NMR Characterization |
|---|---|---|
| 1 | 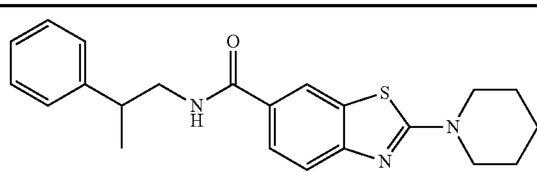 | White solid; mp = 196° C.; $^1$H NMR (400 MHz, acetone-$d_6$) δ 8.16 (d, J = 1.6 Hz, 1H), 7.74 (dd, J = 8.4 Hz, 1.6 Hz, 1H), 7.61 (brs, 1H), 7.39 (d, J = 8.4 Hz, 1H), 7.28-7.31 (m, 4H), 7.18-7.21 (m, 1H), 3.62-3.65 (m, 4H), 3.54-3.58 (m, 2H), 3.13-3.18 (m, 1H), 1.66-1.70 (m, 6H), 1.30 (d, J = 6.8 Hz, 3H); LCMS (electrospray) m/z 380 (M + H)$^+$. |
| 2 | 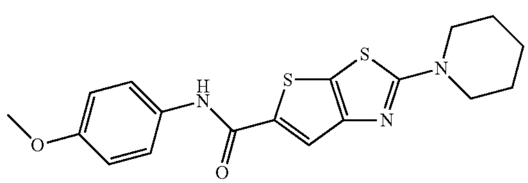 [SMILES: COc1ccc(NC(=O)c2cc3nc(N4CCCCC4)sc3s2)cc1] | Pale yellow solid; $^1$H NMR (400 MHz, acetone-$d_6$) δ 9.36 (brs, 1H), 7.89 (s, 1H), 7.66-7.68 (m, 2H), 6.90-6.94 (m, 2H), 3.79 (s, 3H), 3.52-3.57 (m, 4H), 1.66-1.72 (m, 6H); LCMS (electrospray) m/z 374 (M + H)$^+$. |
| 3 | 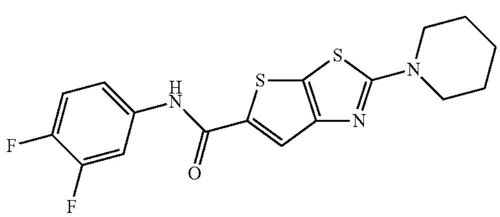 | Yellow solid; mp = 246.3° C.; $^1$H NMR (400 MHz, acetone-$d_6$) δ (9.65 (brs, 1H), 7.93-7.97 (m, 1H), 7.91 (s, 1H), 7.46-7.51 (m, 1H), 7.27-7.34 (m, 1H), 3.50-3.60 (m, 4H), 1.64-1.74 (m, 6H); LCMS (electrospray) m/z 380 (M + H)$^+$. |
| 4 | 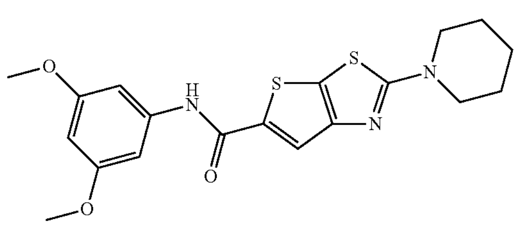 [SMILES: COc1cc(NC(=O)c2cc3nc(N4CCCCC4)sc3s2)cc(OC)c1] | Yellow solid; mp = 231.2° C.; $^1$H NMR (400 MHz, acetone-$d_6$) δ 9.38 (brs, 1H), 7.91 (s, 1H), 7.06-7.07 (m, 2H), 6.26-6.27 (m, 1H), 3.78 (s, 6H), 3.52-3.58 (m, 4H), 1.68-1.72 (m, 6H); LCMS (electrospray) m/z 404 (M + H)$^+$. |

TABLE 1-continued

Structures and Characteristics of Compounds 1-360

| No. | Structure | NMR Characterization |
|---|---|---|
| 5 | 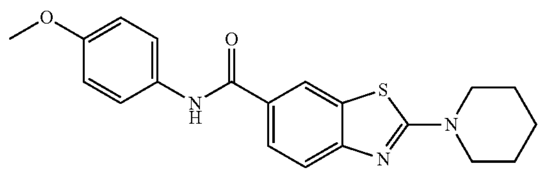 [SMILES: COc1ccc(NC(=O)c2ccc3nc(N4CCCCC4)sc3c2)cc1] | White solid; mp 214° C.; $^1$H NMR (400 MHz, acetone-d$_6$) δ 0.32 (s, 1H, NH), 8.33 (d, J = 2.0 Hz, 1H), 7.93 (dd, J = 8.4 Hz, 2.0 Hz, 1H), 7.75 (d, J = 9.2 Hz, 2H), 7.46 (d, J = 8.4 Hz, 1H), 6.92 (d, J = 9.2 Hz, 2H), 3.79 (s, 3H), 3.66-3.68 (m, 4H), 1.69-1.74 (m, 6H); LCMS (electrospray) m/z 368 (M + H)$^+$. |
| 6 | 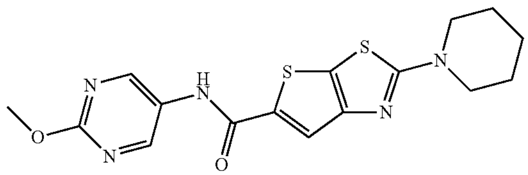 [SMILES: COc1ncc(NC(=O)c2cc3nc(N4CCCCC4)sc3s2)cn1] | Pale yellow solid; mp = 274° C.; $^1$H NMR (400 MHz. acetone-d$_6$) δ 9.64 (s, 1H, NH), 8.89 (s, 2H), 7.90 (s, 1H), 3.95 (s, 3H), 3.54-3.56 (m, 4H), 1.68-1.72 (m, 6H); LCMS (electrospray) m/z 376 (M + H)$^+$. |
| 7 | 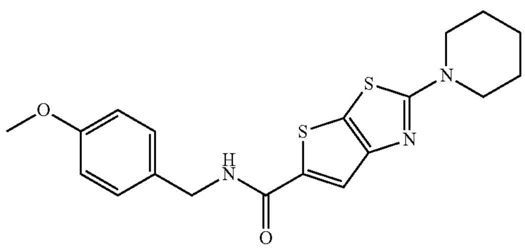 [SMILES: COc1ccc(CNC(=O)c2cc3nc(N4CCCCC4)sc3s2)cc1] | Ivory solid; mp = 179° C.; $^1$H NMR (400 MHz, acetone-d$_6$) δ 8.10 (brs, 1H, NH), 7.74 (s, 1H), 7.29 (d, J = 8.4 Hz, 2H), 6.88 (d, J = 8.4 Hz, 2H), 4.49 (d, J = 6.0 Hz, 2H), 3.77 (s, 3H), 3.52-3.54 (m, 4H), 1.66-1.70 (m, 6H); LCMS (electrospray) m/z 388 (M + H)$^+$. |
| 8 | 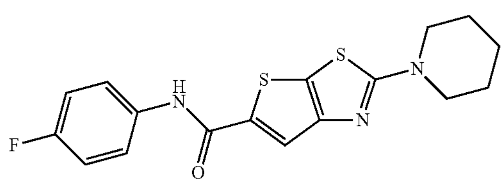 [SMILES: O=C(Nc1ccc(F)cc1)c1cc2nc(N3CCCCC3)sc2s1] | Yellow solid; mp = 218° C.; $^1$H NMR (400 MHz, acetone-d$_6$) δ 9.53 (s, 1H, NH), 7.90 (s, 1H), 7.79 (dd, J = 8.8 Hz, 5.2 Hz, 2H). 7.12 (dd, J = 8.8 Hz, 8.8 Hz, 2H), 3.54-3.56 (m, 4H), 1.68-1.71 (m, 6H); LCMS (electrospray) m/z 362 (M + H)$^+$. |
| 9 | 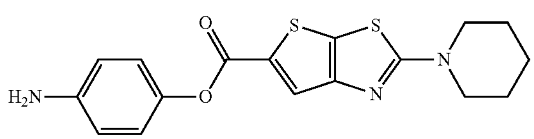 [SMILES: Nc1ccc(OC(=O)c2cc3nc(N4CCCCC4)sc3s2)cc1] | Ivory solid; mp = 153° C.; $^1$H NMR (400 MHz, CDCl$_3$) δ 7.96 (s, 1H), 7.01 (d, J = 8.8 Hz, 2H). 6.70 (d, J = 8.8 Hz, 2H), (brs, 2H, NH2), 3.52-3.55 (m, 4H), 1.66-1.71 (m, 6H); LCMS (electrospray) m/z 359 (M + H)$^+$. |
| 10 | 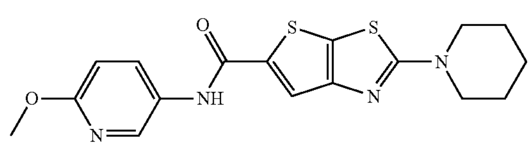 [SMILES: COc1ccc(NC(=O)c2cc3nc(N4CCCCC4)sc3s2)cn1] | Orange solid; mp = 270° C.; $^1$H NMR (400 MHz. acetone-d$_6$) δ 9.51 (s, 1H, NH), 8.48 (d, J = 2.4 Hz, 1H), 8.04 (dd, J = 8.0, 2.4 Hz, 1H), 7.88 (s, 1H), 6.77 (d, J = 8.8 Hz, 1H), 3.87 (s, 3H), 3.52-3.56 (m, 4H), 1.67-1.71 (m, 6H); LCMS (electrospray) m/z 374 (M + H)$^+$. |
| 11 | 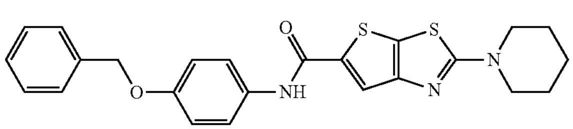 [SMILES: O=C(Nc1ccc(OCc2ccccc2)cc1)c1cc2nc(N3CCCCC3)sc2s1] | Ivory solid; mp = 223° C.; $^1$H NMR (400 MHz, acetone-d$_6$) δ 9.38 (s, 1H, NH), 7.88 (s, 1H), 7.68 (d, J = 9.2 Hz, 2H), 7.45-7.51 (m, 2H), 7.30-7.41 (m, 3H), 7.02 (d, J = 9.2 Hz, 2H), 5.12 (s, 2H), 3.52-3.56 (m, 4H), 1.67-1.71 (m, 6H); LCMS (electrospray) m/z 449 (M + H)$^+$. |
| 12 | 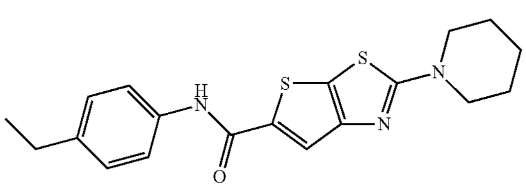 [SMILES: CCc1ccc(NC(=O)c2cc3nc(N4CCCCC4)sc3s2)cc1] | $^1$H NMR (400 MHz, acetone-d$_6$) δ 9.40 (s, 1H, NH), 7.90 (s, 1H), 7.67 (d, J = 8.8 Hz, 2H), 7.19 (d, J = 8.8 Hz, 2H), 3.52-3.56 (m, 4H), 2.60 (q, J = 7.6 Hz, 2H), 1.67-1.71 (m, 6H), 1.20 (t, J = 7.6 Hz, 3H); LCMS (electrospray) m/z 371 (M + H)$^+$. |

TABLE 1-continued

Structures and Characteristics of Compounds 1-360

| No. | Structure | NMR Characterization |
|---|---|---|
| 13 | 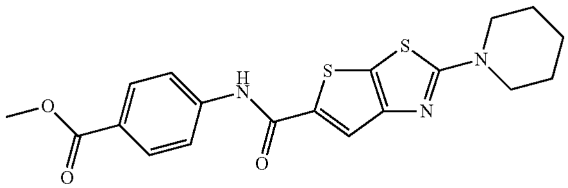 [SMILES: COC(=O)c1ccc(NC(=O)c2cc3nc(N4CCCCC4)sc3s2)cc1] | $^1$H NMR (400 MHz, acetone-d$_6$) δ 9.76 (s, 1H, NH), 8.00 (d, J = 8.8 Hz, 2H), 7.97 (s, 1H), 7.91 (d, J = 8.8 Hz, 2H), 3.86 (s, 3H), 3.53-3.58 (m, 4H), 1.66-1.71 (m, 6H); LCMS (electrospray) m/z 401 (M + H)$^+$. |
| 14 | 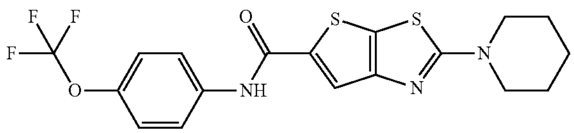 [SMILES: O=C(Nc1ccc(OC(F)(F)F)cc1)c1cc2nc(N3CCCCC3)sc2s1] | Pale yellow solid; mp = 238.0° C.; $^1$H NMR (400 MHz, CDCl$_3$) δ 7.97 (brs, 1H), 7.75 (s, 1H), 7.67 (d, J = 8.8 Hz, 2H), 7.21 (d, J = 8.8 Hz, 2H), 3.58-3.61 (m, 4H), 1.71-1.74 (m, 6H); LCMS (electrospray) m/z 428 (M + H)$^+$. |
| 15 | 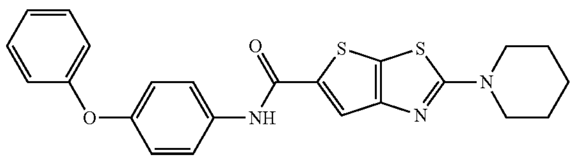 [SMILES: O=C(Nc1ccc(Oc2ccccc2)cc1)c1cc2nc(N3CCCCC3)sc2s1] | Pale yellow solid; mp = 225.8° C.; $^1$H NMR (400 MHz, acetone-d$_6$) δ 9.51 (s, 1H), 7.91 (s, 1H), 7.77-7.79 (m, 2H), 7.35-7.39 (m, 2H), 7.09-7.13 (m, 1H), 7.00-7.02 (m, 4H), 3.53-3.55 (m, 4H), 1.68-1.70 (m, 6H); LCMS (electrospray) m/z 436 (M + H)$^+$. |
| 16 | 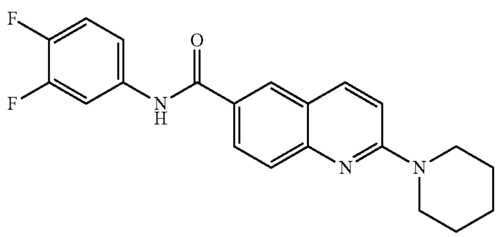 [SMILES: O=C(Nc1ccc(F)c(F)c1)c1ccc2nc(N3CCCCC3)ccc2c1] | Ivory solid; mp = 194° C.; $^1$H NMR (400 MHz, acetone-d$_6$) δ 9.73 (s, 1H, NH), 8.32 (s, 1H), 8.03-8.09 (m, 3H), 7.57-7.62 (m, 2H), 7.24-7.32 (m, 2H), 3.80-3.84 (m, 4H), 1.63-1.73 (m, 6H); LCMS (electrospray) m/z 368 (M + H)$^+$. |
| 17 | 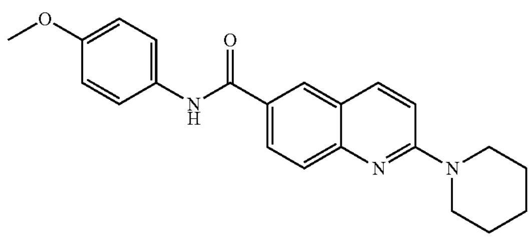 [SMILES: COc1ccc(NC(=O)c2ccc3nc(N4CCCCC4)ccc3c2)cc1] | White solid; mp = 209° C.; $^1$H NMR (400 MHz, acetone-d$_6$) δ 9.42 (s, 1H, NH), 8.31 (s, 1H), 8.10 (d, J = 9.6 Hz, 1H), 8.05 (d, J = 9.2 Hz, 1H), 7.79 (d, J = 8.8 Hz, 2H), 7.62 (d, J = 9.2 Hz, 1H), 7.25 (d, J = 9.6 Hz, 1H), 6.94 (d, J = 8.8 Hz, 2H), 3.81 (s, 3H), 3.79-3.84 (m, 4H), 1.64-1.74 (m, 6H); LCMS (electrospray) m/z 362 (M + H)$^+$. |
| 18 | 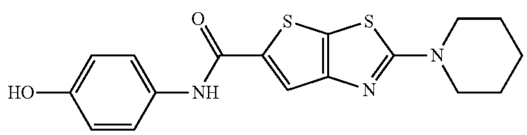 [SMILES: O=C(Nc1ccc(O)cc1)c1cc2nc(N3CCCCC3)sc2s1] | Ivory solid; mp = 266° C.; $^1$H NMR (400 MHz, acetone-d$_6$) δ 9.31 (s, 1H, NH), 8.20 (s, 1H, OH), 7.87 (s, 1 H), 7.57 (d, J = 8.8 Hz, 2H), 6.82 (d, J = 8.8 Hz, 2H), 3.53-3.56 (m, 4H), 1.67-1.71 (m, 6H); LCMS (clectrospray) m/z 359 (M + H)$^+$. |
| 19 | 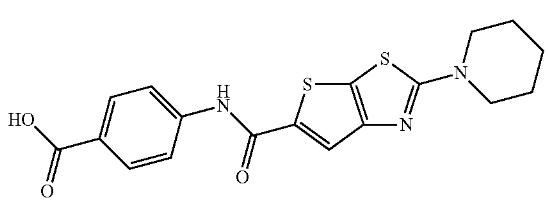 [SMILES: O=C(O)c1ccc(NC(=O)c2cc3nc(N4CCCCC4)sc3s2)cc1] | $^1$H NMR (400 MHz, DMSO-d$_6$) δ 10.40 (s, 1H, NH), 8.17 (s, 1H), 7.95 (d, J = 8.0 Hz, 2H), 7.79 (d, J = 8.8 Hz, 2H), 3.50-3.54 (m, 4H), 1.62-1.67 (m, 6H); LCMS (electrospray) m/z 387 (M + H)$^+$. |
| 20 | 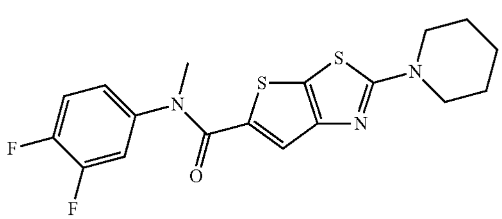 [SMILES: CN(C(=O)c1cc2nc(N3CCCCC3)sc2s1)c1ccc(F)c(F)c1] | Pale yellow solid; mp = 170.1° C.; $^1$H NMR (400 MHz, acetone-d$_6$) δ 7.50-7.56 (m, 1H), 7.43-7.48 (m, 1H), 7.29-7.31 (m, 1H), 6.51 (s, 1H), 3.42-3.48 (m, 4H), 3.38 (s, 3H), 1.58-1.68 (m, 6H); LCMS (electrospray) m/z 394 (M + H)$^+$. |

TABLE 1-continued

Structures and Characteristics of Compounds 1-360

| No. | Structure | NMR Characterization |
|---|---|---|
| 21 | 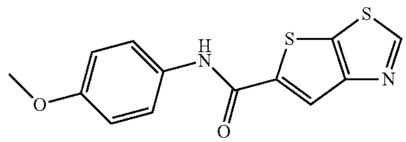 [SMILES: COc1ccc(NC(=O)c2cc3ncsc3s2)cc1] | White solid; mp = 236.0° C.; $^1$H NMR (400 MHz, acetone-$d_6$) δ 9.60 (brs, 1H, NH), 9.20 (s, 1H), 8.32 (s, 1H), 7.70 (d, J = 8.8 Hz, 2H), 6.94 (d, J = 8.8 Hz, 2H), 3.80 (s, 3H); LCMS (electrospray) m/z 291 (M + H)$^+$. |
| 22 | 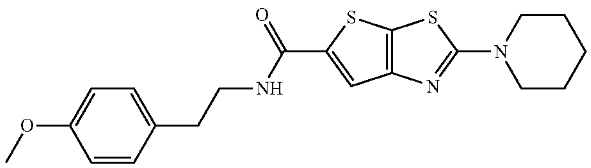 [SMILES: COc1ccc(CCNC(=O)c2cc3nc(N4CCCCC4)sc3s2)cc1] | White solid; mp = 188.0° C.; $^1$H NMR (400 MHz, acetone-$d_6$) δ 7.77 (s, 1H), 7.65 (s, 1H), 7.16-7.65 (m, 2H), 6.84-6.87 (m, 2H), 3.76 (s, 3H), 3.56-3.57 (m, 2H), 3.52-3.54 (m, 4H), 2.78-2.85 (m, 2H), 1.68-1.69 (s, 6H); LCMS (electrospray) m/z 401 (M + H)$^-$. |
| 23 | 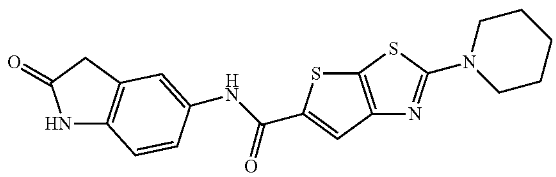 [SMILES: O=C1Cc2cc(NC(=O)c3cc4nc(N5CCCCC5)sc4s3)ccc2N1] | Yellow solid; mp = 260° C.; $^1$H NMR (400 MHz, DMSO-$d_6$) δ 10.32 (s, 1H, NH), 10.05 (s, 1H, NH), 8.00 (s, 1H), 7.58 (s, 1H), 7.43 (d, J = 8.4 Hz, 1H), 6.77 (d, J = 8.4 Hz, 1H), 3.46-3.49 (m, 6H), 1.58-1.61 (m, 6H); LCMS (electrospray) m/z 399 (M + H)$^+$. |
| 24 | 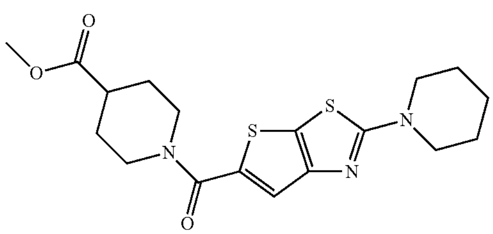 [SMILES: COC(=O)C1CCN(C(=O)c2cc3nc(N4CCCCC4)sc3s2)CC1] | Colorless oil; $^1$H NMR (400 MHz, acetone-$d_6$) δ 7.36 (s, 1H), 4.33-4.36 (m, 2H), 3.67 (s, 3H), 3.52-3.54 (m, 4H), 3.20-3.25 (m, 2H), 2.69-2.75 (m, 1H), 1.98-2.01 (m, 2H), 1.67-1.70 (m, 8H); LCMS (electrospray) m/z 394 (M + H)$^+$. |
| 25 | 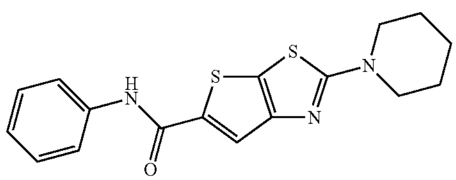 [SMILES: O=C(Nc1ccccc1)c1cc2nc(N3CCCCC3)sc2s1] | Pale yellow solid; mp = 222.6° C.; $^1$H NMR (400 MHz, acetone-$d_6$) δ 9.48 (brs, 1H, NH), 7.93 (s, 1H), 7.77-7.79 (m, 2H), 7.33-7.37 (m, 2H), 7.09-7.12 (m, 1H), 3.52-3.58 (m, 4H), 1.66-1.76 (m, 6H); LCMS (electrospray) m/z 344 (M + H)$^+$. |
| 26 | 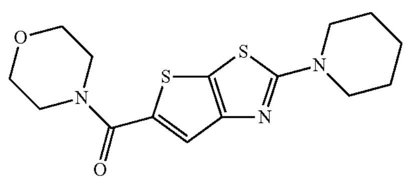 [SMILES: O=C(c1cc2nc(N3CCCCC3)sc2s1)N1CCOCC1] | Pale yellow solid: mp = 188.0° C.; $^1$H NMR (400 MHz, acetone-$d_6$) δ 7.39 (s, 1H, NH), 3.74-3.80 (m, 4H), 3.68-3.73 (m, 4H), 3.48-3.57 (m, 4H), 1.64-1.72 (m, 6H): LCMS (electrospray), m/z 338 (M + H)$^+$. |
| 27 | 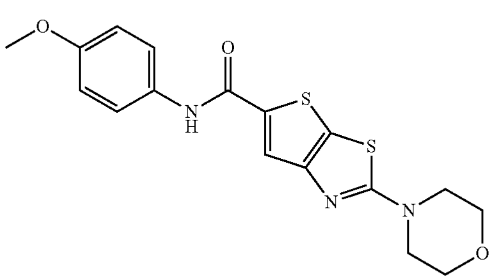 [SMILES: COc1ccc(NC(=O)c2cc3nc(N4CCOCC4)sc3s2)cc1] | Pale yellow solid; $^1$H NMR (400 MHz, acetone-$d_6$) δ 9.41 (s, 1H), 7.93 (s, 1H), 7.67 (d, J = 8.8 Hz, 2H), 6.92 (d, J = 8.8 Hz, 2H), 3.77-3.79 (m, 7H), 3.52-3.58 (m, 4H); LCMS (electrospray) m/z 375 (M + H)$^+$. |
| 28 | 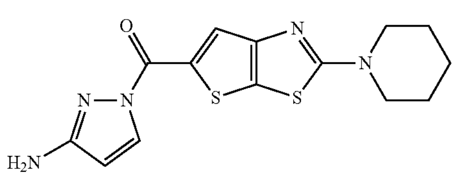 [SMILES: Nc1ccn(C(=O)c2cc3nc(N4CCCCC4)sc3s2)n1] | Yellow solid; mp = 289° C.; $^1$H NMR (400 MHz, DMSO-$d_6$) δ 10.33 (s, 1H, NH), 8.35 (q, J = 4.4 Hz, 1H, NH), 8.20 (s, 1H), 7.86 (d, J = 9.2 Hz, 2H), 7.81 (d, J = 9.2 Hz, 2H), 3.59-3.61 (m, 4H), 2.81 (d, J = 4.4 Hz, 3H), 1.67-1.69 (m, 6H); LCMS (electrospray) m/z 401 (M + H)$^+$. |

TABLE 1-continued

Structures and Characteristics of Compounds 1-360

| No. | Structure | NMR Characterization |
|---|---|---|
| 29 | 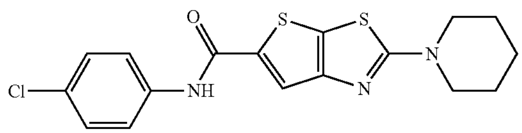 [SMILES: O=C(Nc1ccc(Cl)cc1)c1cc2nc(N3CCCCC3)sc2s1] | Yellow solid; mp = 230° C.; $^1$H NMR (400 MHz, acetone-d$_6$) δ 9.58 (s, 1H, NH), 7.91 (s, 1H), 7.81 (d, J = 8.8 Hz, 2H), 7.37 (d, J = 8.8 Hz, 2H), 3.53-3.57 (m, 4H), 1.67-1.71 (m, 6H); LCMS (electrospray) m/z 377 (M + H)$^+$. |
| 30 | 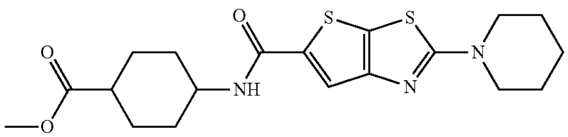 [SMILES: COC(=O)C1CCC(NC(=O)c2cc3nc(N4CCCCC4)sc3s2)CC1] | White solid; mp = 191° C.; $^1$H NMR (400 MHz, CDCl$_3$) δ 7.42 (s, 1H), 5.85 (brs, 1H, NH), 4.06-4.12 (m, 1H), 3.70 (s, 3H), 3.48-3.52 (m, 4H), 2.52-2.58 (m, 1H), 1.86-1.96 (m, 2H), 1.80-1.85 (m, 2H), 1.73-1.78 (m, 2H), 1.66-1.70 (m, 6H), 1.61-1.64 (m, 2H); LCMS (electrospray) m/z 408 (M + H)$^+$. |
| 31 | 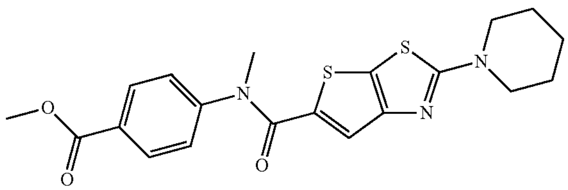 [SMILES: COC(=O)c1ccc(N(C)C(=O)c2cc3nc(N4CCCCC4)sc3s2)cc1] | Pale yellow solid; mp = 178.5° C.; $^1$H NMR (400 MHz, acetone-d$_6$) δ 8.10 (d, J = 8.4 Hz, 2H), 7.53 (d, J = 8.4 Hz, 2H), 6.41 (s, 1H), 3.91 (s, 3H), 3.42-3.47 (m, 7H), 1.58-1.67 (m, 6H); LCMS (electrospray) m/z 416 (M + H)$^+$. |
| 32 | 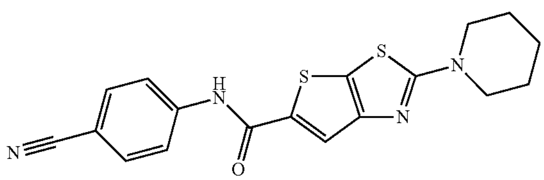 [SMILES: N#Cc1ccc(NC(=O)c2cc3nc(N4CCCCC4)sc3s2)cc1] | Orange solid; mp = 163° C.; $^1$H NMR (400 MHz, DMSO-d$_6$) δ 10.50 (s, 1H, NH), 8.08 (s, 1H), 7.92 (d, J = 8.8 Hz, 2H), 7.80 (d, J = 8.8 Hz, 2H), 3.46-3.49 (m, 4H), 1.59-1.62 (m, 6H); LCMS (electrospray) m/z 369 (M + H)$^+$. |
| 33 | 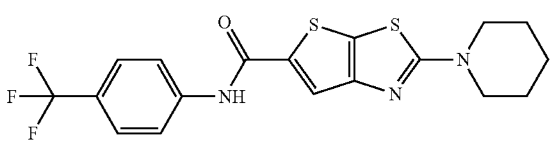 [SMILES: O=C(Nc1ccc(C(F)(F)F)cc1)c1cc2nc(N3CCCCC3)sc2s1] | Pale yellow solid; mp = 228.6° C.; $^1$H NMR (400 MHz, acetone-d$_6$) δ 9.78 (s, 1H), 8.01 (d, J = 8.8 Hz, 2H), 7.97 (s, 1H), 7.70 (d, J = 8.8 Hz, 2H), 3.54-3.56 (m, 4H), 1.68-1.69 (m, 6H); LCMS (electrospray) m/z 411 (M + H)$^+$. |
| 34 | 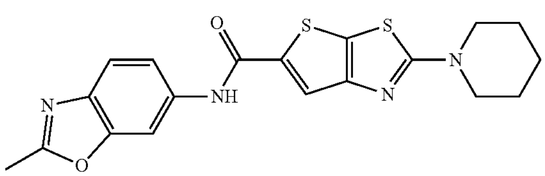 [SMILES: Cc1nc2ccc(NC(=O)c3cc4nc(N5CCCCC5)sc4s3)cc2o1] | Dark yellow solid; mp = 213.0° C.; $^1$H NMR (400 MHz, acetone-d$_6$) δ 9.68 (brs, 1H, NH), 8.27-8.28 (m, 1H), 7.95 (s, 1H), 7.53-7.54 (m, 2H), 3.52-3.58 (m, 4H), 2.59 (s, 3H), 1.68-1.73 (m, 6H); LCMS (electrospray) m/z 399 (M + H)$^+$. |
| 35 | 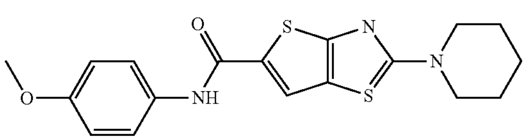 | Ivory solid; mp = 23° C.; $^1$H NMR (400 MHz, DMSO-d$_6$) δ 10.01 (s, 1H, NH), 8.08 (s, 1H), 7.59 (d, J = 8.8 Hz, 2H), 6.91 (d, J = 8.8 Hz, 2H), 3.73 (s, 3H), 3.52-3.56 (m, 4H), 1.61-1.65 (m, 6H); LCMS (electrospray) m/z 373 (M + H)$^+$. |
| 36 | 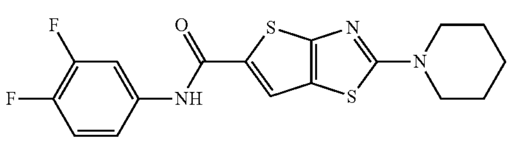 [SMILES: O=C(Nc1ccc(F)c(F)c1)c1cc2sc(N3CCCCC3)nc2s1] | Yellow solid; mp = 218° C.; $^1$H NMR (400 MHz, DMSO-d$_6$) δ 10.31 (s, 1H, NH), 8.16 (s, 1H), 7.82-7.89 (m, 1H), 7.37-7.49 (m, 2H), 3.50-3.58 (m, 4H), 1.59-1.68 (m, 6H); LCMS (electrospray) m/z 379 (M + H)$^+$. |
| 37 | 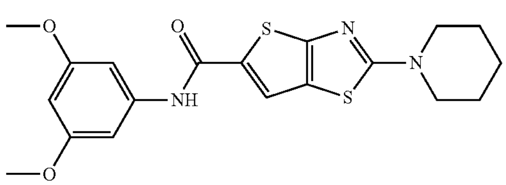 [SMILES: COc1cc(NC(=O)c2cc3sc(N4CCCCC4)nc3s2)cc(OC)c1] | Yellow solid; mp = 148° C.; $^1$H NMR (400 MHz, DMSO-d$_6$) δ 10.02 (s, 1H, NH), 8.11 (s, 1H), 6.99 (s, 1H), 6.98 (s, 1H), 6.23 (s, 1H), 3.73 (s, 6H), 3.52-3.56 (m, 4H), 1.61-1.65 (m, 6H); LCMS (electrospray) m/z 403 (M + H)$^+$. |

TABLE 1-continued

Structures and Characteristics of Compounds 1-360

| No. | Structure | NMR Characterization |
|---|---|---|
| 38 | 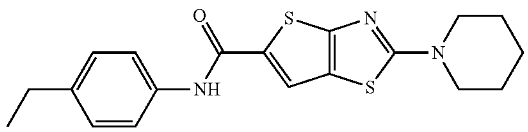 | Brown solid; mp = 198.0° C.; $^1$H NMR (400 MHz, CDCl$_3$) δ 7.68-7.70 (m, 2H), 7.52 (d, J = 8.0 Hz, 2H), 7.16 (d, J = 8.0 Hz, 2H), 3.57-3.61 (m, 4H), 2.60 (q, J = 7.2 Hz, 2H), 1.69-1.71 (m, 6H), 1.20 (t, J = 12 Hz, 3H); LCMS (electrospray) m/z 372 (M + H)$^+$. |
| 39 | 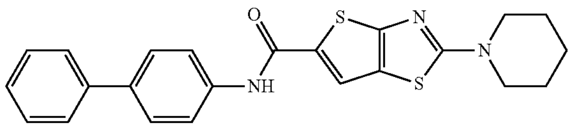 [SMILES: O=C(Nc1ccc(-c2ccccc2)cc1)c1cc2sc(N3CCCCC3)nc2s1] | Orange solid; mp = 231.1° C.; $^1$H NMR (400 MHz, DMSO-d$_6$) δ 10.21 (s, 1H), 8.16 (s, 1H), 7.80 (d, J = 8.8 Hz, 2H), 7.65-7.67 (m, 4H), 7.43-7.47 (m, 2H), 7.31-7.35 (m, 1H), 3.54-3.56 (m, 4H), 1.62-1.64 (m, 6H); LCMS (electrospray) m/z 420 (M + H)$^+$. |
| 40 | 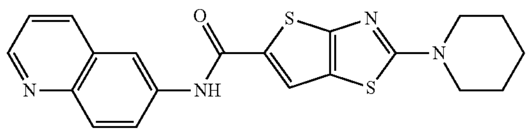 [SMILES: O=C(Nc1ccc2ncccc2c1)c1cc2sc(N3CCCCC3)nc2s1] | Pale yellow solid; mp = 279.5° C.; $^1$H NMR (400 MHz, DMSO-d$_6$) δ 10.44 (s, 1H), 8.78 (dd, J = 4.0, 1.6 Hz, 1H), 8.41 (s, 1H), 18.28 (dd, J = 8.4, 1.6 Hz, 1H), 8.21 (s, 1H), 8.00-8.01 (m, 2H), 7.47 (dd, J = 8.4, 4.0 Hz, 1H), 3.55-3.57 (m, 4H), 1.63-1.65 (m, 6H); LCMS (electrospray) m/z 395 (M + H)$^+$. |
| 41 | 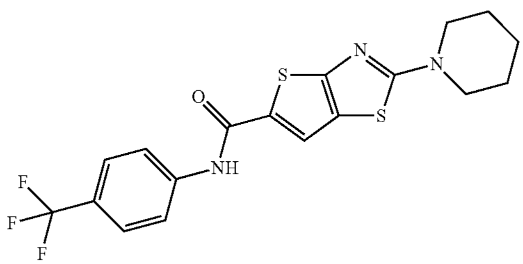 [SMILES: O=C(Nc1ccc(C(F)(F)F)cc1)c1cc2sc(N3CCCCC3)nc2s1] | Pale green solid; mp = 289.2° C.; $^1$H NMR (400 MHz, acetone-d$_6$) δ 9.68 (s, 1H), 8.00-8.01 (m, 3H), 7.68-7.69 (m, 2H), 3.61-3.62 (m, 4H), 2.77-2.81 (m, 2H), 1.71-1.72 (m, 4H); LCMS (electrospray) m/z 411 (M + H)$^+$. |
| 42 | 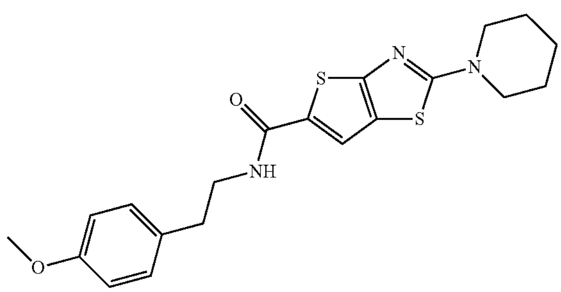 [SMILES: COc1ccc(CCNC(=O)c2cc3sc(N4CCCCC4)nc3s2)cc1] | Pale yellow solid; mp = 177.2° C.; $^1$H NMR (400 MHz, acetone-d$_6$) δ 7.69 (s, 1H), 7.59 (s, 1H), 7.17 (d, J = 8.4 Hz, 2H), 6.85 (d, J = 8.4 Hz, 2H), 3.76 (s, 3H), 3.55-3.58 (m, 4H), 3.51-3.53 (m, 2H), 2.81-2.84 (m, 2H), 1.67-1.69 (m, 6H); LCMS (electrospray) m/z 401 (M + H)$^+$. |
| 43 | 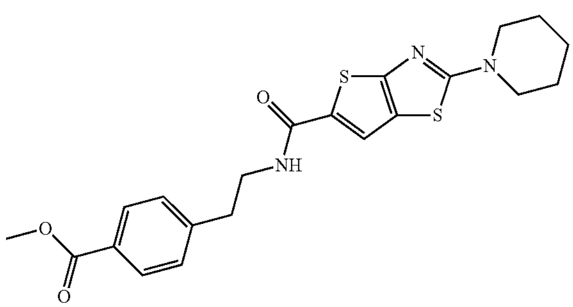 [SMILES: COC(=O)c1ccc(CCNC(=O)c2cc3sc(N4CCCCC4)nc3s2)cc1] | Pale yellow solid; mp = 212.9° C.; $^1$H NMR (400 MHz, acetone-d$_6$) δ 7.93 (d, J = 8.0 Hz, 2H), 7.68 (s, 1H), 7.67 (s, 1H), 7.40 (d, J = 8.0 Hz, 2H), 3.86 (s, 3H), 3.62-3.65 (m, 2H), 3.57-3.60 (m, 4H), 2.97-3.01 (m, 2H), 1.67-1.69 (m, 6H); LCMS (electrospray) m/z 429 (M + H)$^+$. |
| 44 | 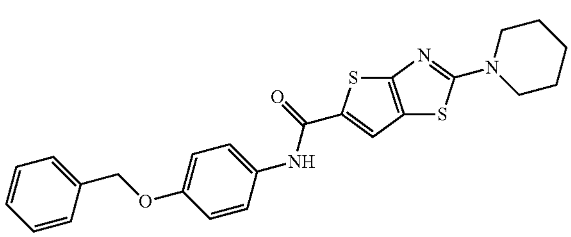 [SMILES: O=C(Nc1ccc(OCc2ccccc2)cc1)c1cc2sc(N3CCCCC3)nc2s1] | Pale yellow solid; $^1$H NMR (400 MHz, acetone-d$_6$) δ 9.28 (s, 1H), 7.93 (s, 1H), 7.67 (d, J = 8.8 Hz, 2H), 7.48-7.49 (m, 2H), 7.38-7.41 (m, 2H), 7.31-7.34 (m, 1H), 6.99 (d, J = 8.8 Hz, 2H), 5.12 (s, 2H), 3.60-3.61 (m, 4H), 1.71-1.72 (m, 6H); LCMS (electrospray) m/z 449 (M + H)$^+$. |

TABLE 1-continued

Structures and Characteristics of Compounds 1-360

| No. | Structure | NMR Characterization |
|---|---|---|
| 45 | 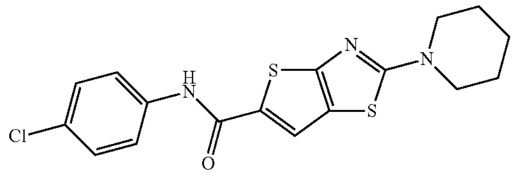 [SMILES: O=C(Nc1ccc(Cl)cc1)c1cc2sc(N3CCCCC3)nc2s1] | Pale yellow solid; mp = 275.2° C.; $^1$H NMR (400 MHz, acetone-d$_6$) δ 9.48 (brs, 1H, NH), 7.96 (s, 1H), 7.79 (d, J = 8.0 Hz, 2H), 7.35 (d, J = 8.0 Hz, 2H), 3.58-3.63 (m, 4H), 1.68-1.74 (m, 6H); LCMS (electrospray) m/z 378, 380 (M + H)$^-$ (Cl$^-$ isotope pattern). |
| 46 | 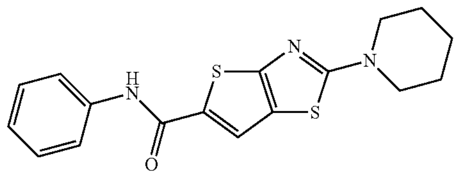 [SMILES: O=C(Nc1ccccc1)c1cc2sc(N3CCCCC3)nc2s1] | Pale yellow solid; mp = 259.1° C.; $^1$H NMR (400 MHz, acetone-d$_6$) δ 9.36 (brs, 1H, NH), 7.97 (s, 1H), 7.75-7.77 (m, 2H), 7.31-7.35 (m, 2H), 7.06-7.10 (m, 1H), 3.58-3.63 (m, 4H), 1.68-1.73 (m, 6H); LCMS (electrospray) m/z 344 (M + H)$^+$. |
| 47 | 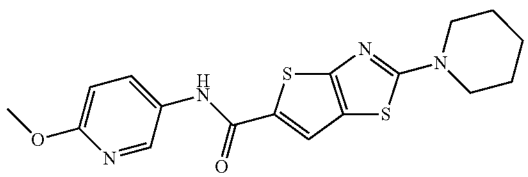 [SMILES: COc1ccc(NC(=O)c2cc3sc(N4CCCCC4)nc3s2)cn1] | Pale yellow solid; mp = 232.4° C.; $^1$H NMR (400 MHz, acetone-d$_6$) δ 9.41 (brs, 1H, NH), 8.47 (s, 1H), 8.05 (d, J = 8.8 Hz, 1H), 7.94 (s, 1H), 6.76 (d, J = 8.8 Hz, 1H), 3.87 (s, 3H), 3.58-3.63 (m, 4H), 1.66-1.74 (m, 6H); LCMS (electrospray) m/z 375 (M + H)$^+$. |
| 48 | 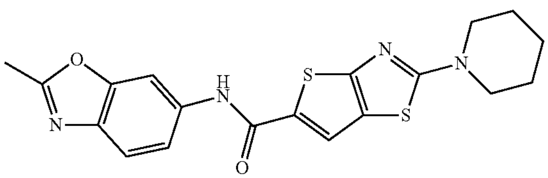 [SMILES: Cc1nc2ccc(NC(=O)c3cc4sc(N5CCCCC5)nc4s3)cc2o1] | Pale yellow solid; mp = 259.2° C.; $^1$H NMR (400 MHz, acetone-d$_6$) δ 9.58 (brs, 1H, NH), 8.26 (s, 1H), 8.00 (s, 1H), 7.51-7.54 (m, 2H), 3.58-3.63 (m, 4H), 2.58 (s, 3H), 1.66-1.74 (m, 6H); LCMS (electrospray) m/z 399 (M + H)$^+$. |
| 49 | 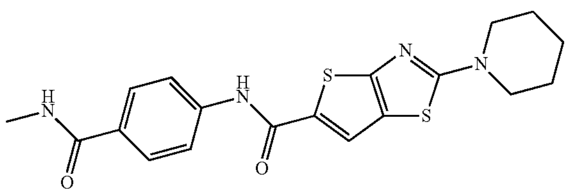 [SMILES: CNC(=O)c1ccc(NC(=O)c2cc3sc(N4CCCCC4)nc3s2)cc1] | Yellow solid; mp = 243° C.; $^1$H NMR (400 MHz, DMSO-d$_6$) δ 10.46 (s, 1H, NH), 8.23 (s, 1H), 7.99 (d, J = 8.8 Hz, 2H), 7.91 (d, J = 8.8 Hz, 2H), 3.87 (s, 3H), 3.59-3.61 (m, 4H), 1.67-1.69 (m, 6H); LCMS (electrospray) m/z 402 (M + H)$^+$. |
| 50 | 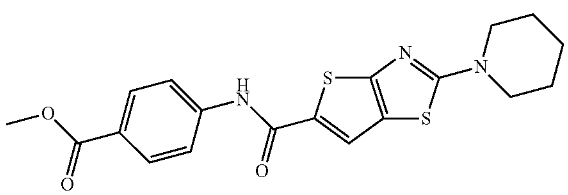 | Pale yellow solid; mp = 326° C.; $^1$H NMR (400 MHz, acetone-d$_6$) δ 9.68 (s, 1H), 7.97 (s, 1H), 7.84-7.91 (m, 4H), 7.63 (s, 1H), 3.56-3.57 (m, 4H), 2.94-3.31 (m, 2H), 1.94-2.01 (m, 4H), 1.70 (s, 3H); LCMS (electrospray) m/z 400 (M + H)$^+$. |
| 51 | 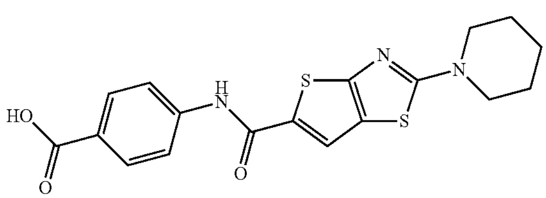 [SMILES: O=C(O)c1ccc(NC(=O)c2cc3sc(N4CCCCC4)nc3s2)cc1] | $^1$H NMR (400 MHz, DMSO-d$_6$) δ 10.34 (s, 1H), 8.23 (s, 1H), 7.90 (d, J = 8.0 Hz, 2H), 7.75 (d, J = 8.0 Hz, 2H), 3.53-3.54 (m, 4H), 1.61-1.62 (m, 6H); LCMS (electrospray) m/z 387 (M + H)$^+$. |
| 52 | 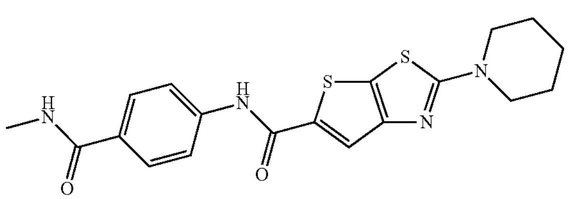 | Pale brown solid; mp = 202° C.; $^1$H NMR (400 MHz, DMSO-d$_6$) δ 10.04 (s, 1H), 8.12 (s, 1H), 7.63 (d, J = 8.8 Hz, 2H), 6.96 (d, J = 8.8 Hz, 2H), 3.78 (s, 3H), 3.18 (s, 6H); LCMS (electrospray) m/z 333 (M + H)$^+$. |

TABLE 1-continued

Structures and Characteristics of Compounds 1-360

| No. | Structure | NMR Characterization |
|---|---|---|
| 53 | 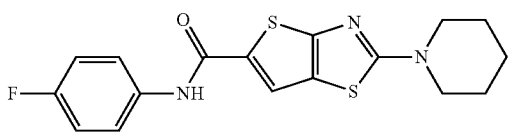 [SMILES: O=C(Nc1ccc(F)cc1)c1cc2sc(N3CCCCC3)nc2s1] | Yellow solid; mp = 233° C.; $^1$H NMR (400 MHz, acetone-d$_6$) δ 9.43 (s, 1H, NH), 7.95 (s, 1H), 7.76-7.80 (m, 2H), 7.11 (dd, J = 8.8 Hz, 8.8 Hz, 2H), 3.58-3.62 (m, 4H), 1.69-1.72 (m, 6H); LCMS (electrospray) m/z 362 (M + H)$^+$. |
| 54 | 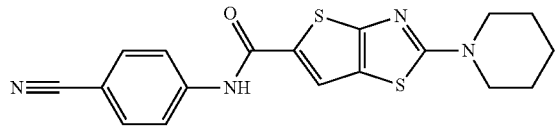 | Yellow solid; mp = 177° C.; $^1$H NMR (400 MHz, acetone-d$_6$) δ 9.74 (s, 1H, NH), 8.02 (s, 1H), 7.99 (d, J = 8.8 Hz, 2H), 7.73 (d, J = 8.8 Hz, 2H), 3.60-3.63 (m, 4H), 1.70-1.73 (m, 6H); LCMS (electrospray) m/z 369 (M + H)$^+$. |
| 55 | 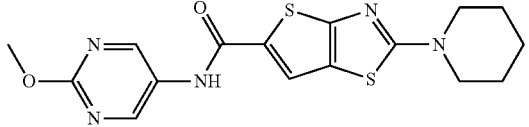 [SMILES: COc1ncc(NC(=O)c2cc3sc(N4CCCCC4)nc3s2)cn1] | Yellow solid; mp = 219° C.; $^1$H NMR (400 MHz, acetone-d$_6$) δ 9.56 (s, 1H, NH), 8.88 (s, 2H), 7.96 (s, 1H), 3.94 (s, 3H), 3.60-3.63 (m, 4H), 1.70-1.72 (m, 6H); LCMS (electrospray) m/z 376 (M + H)$^+$. |
| 56 | 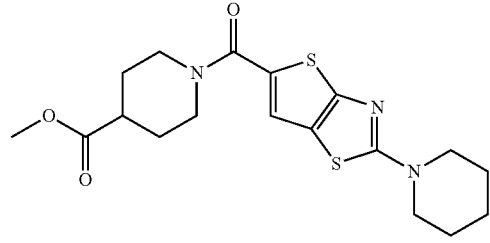 [SMILES: COC(=O)C1CCN(C(=O)c2cc3sc(N4CCCCC4)nc3s2)CC1] | Yellow solid; mp = 136° C.; $^1$H NMR (400 MHz, acetone-d$_6$) δ 7.51 (s, 1H), 4.32-4.36 (m, 2H), 3.66 (s, 3H), 3.56-3.59 (m, 4H), 3.16-3.23 (m, 2H), 2.68-2.73 (m, 1H), 1.98-2.00 (m, 2H), 1.64-1.74 (m, 8H); LCMS (electrospray) m/z 394 (M + H)$^+$. |
| 57 | 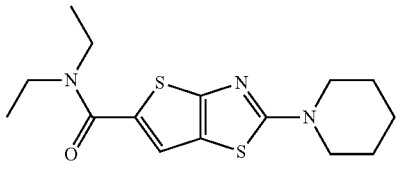 [SMILES: CCN(CC)C(=O)c1cc2sc(N3CCCCC3)nc2s1] | Ivory solid; mp = 84° C.; $^1$H NMR (400 MHz, acetone-d$_6$) δ 7.52 (s, 1H), 3.55-3.62 (m, 8H), 1.65-1.69 (m, 6H), 1.24 (t, J = 7.2 Hz, 6H); LCMS (electrospray) m/z 323 (M + H)$^+$. |
| 58 | 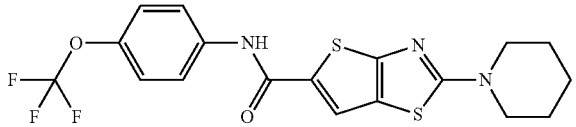 [SMILES: O=C(Nc1ccc(OC(F)(F)F)cc1)c1cc2sc(N3CCCCC3)nc2s1] | Yellow solid; mp = 239° C.; $^1$H NMR (400 MHz, DMSO-d$_6$) δ 10.32 (s, 1H, NH), 8.13 (s, 1H), 7.82 (d, J = 8.4 Hz, 2H), 7.36 (d, J = 8.4 Hz, 2H), 3.53-3.57 (m, 4H), 1.61-1.65 (m, 6H); LCMS (electrospray) m/z 427 (M + H)$^+$. |
| 59 | 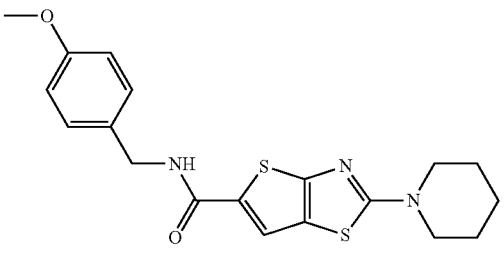 [SMILES: COc1ccc(CNC(=O)c2cc3sc(N4CCCCC4)nc3s2)cc1] | Yellow solid; mp = 142° C.; $^1$H NMR (400 MHz, DMSO-d$_6$) 8.84 (t, J = 8.0 Hz, 1H, NH), 7.87 (s, 1H), 7.24 (d, J = 8.8 Hz, 2H), 6.89 (d, J = 8.8 Hz, 2H), 4.36 (d, J = 8.8 Hz, 2H), 3.72 (s, 3H), 3.49-3.55 (m, 4H), 1.60-1.65 (m, 6H); LCMS (electrospray) m/z 387 (M + H)$^+$. |
| 60 | 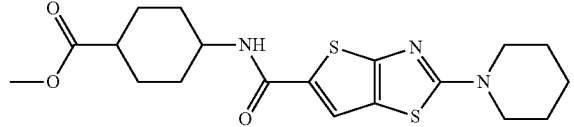 [SMILES: COC(=O)C1CCC(NC(=O)c2cc3sc(N4CCCCC4)nc3s2)CC1] | Yellow solid; mp = 74° C.; $^1$H NMR (400 MHz, acetone-d$_6$) δ 7.78 (s, 1H), 7.29 (brs, 1H, NH), 3.95-3.99 (m, 1H), 3.64 (s, 3H), 3.54-3.60 (m, 4H), 2.57-2.59 (m, 1H), 1.57-1.77 (m, 14H); LCMS (electrospray) m/z 408 (M + H)$^+$. |

TABLE 1-continued

Structures and Characteristics of Compounds 1-360

| No. | Structure | NMR Characterization |
|---|---|---|
| 61 | 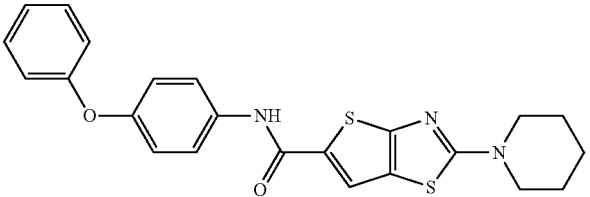 [SMILES: O=C(Nc1ccc(Oc2ccccc2)cc1)c1cc2sc(N3CCCCC3)nc2s1] | Orange solid; mp = 201° C.; $^1$H NMR (400 MHz, DMSO-d$_6$) δ 10.15 (s, 1H, NH), 8.11 (s, 1H), 7.71 (d, J = 9.2 Hz, 2H), 7.35-7.39 (m, 2H), 6.98-7.04 (m, 5H), 3.52-3.57 (m, 4H), 1.61-1.65 (m, 6H); LCMS (electrospray) m/z 435 (M + H)$^+$. |
| 62 | 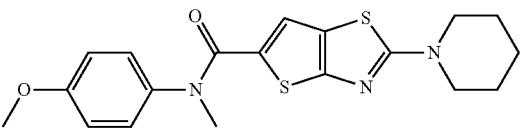 [SMILES: COc1ccc(N(C)C(=O)c2cc3sc(N4CCCCC4)nc3s2)cc1] | Ivory solid; mp = 195° C.; $^1$H NMR (400 MHz, acetone-d$_6$) δ 7.29 (d, J = 7.6 Hz, 2H), 7.02 (d, J = 7.6 Hz, 2H), 6.72 (s, 1H), 3.85 (s, 3H), 3.46-3.52 (m, 4H), 3.18 (s, 3H), 1.61-1.69 (m, 6H); LCMS (electrospray) m/z 387 (M + H)$^+$. |
| 63 | 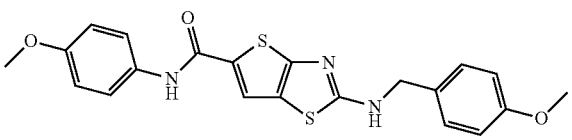 | White solid; mp = 243° C.; $^1$H NMR (400 MHz, DMSO-d$_6$) δ 9.96 (s, 1H, NH), 8.76 (t, J = 5.6 Hz, 1H, NH), 8.00 (s, 1H), 7.57 (d, J = 8.8 Hz, 2H), 7.29 (d, J = 8.8 Hz, 2H), 6.88-6.91 (m, 4H), 4.47 (d, J = 5.6 Hz, 2H), 3.72 (s, 6H); LCMS (electrospray) m/z 426 (M + H)$^+$. |
| 64 | 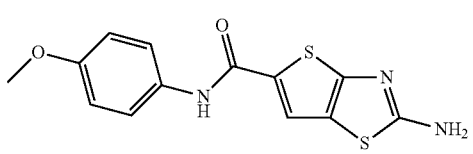 [SMILES: COc1ccc(NC(=O)c2cc3sc(N)nc3s2)cc1] | Gray solid; mp = 260° C.; $^1$H NMR (400 MHz, acetone-d$_6$) δ 9.28 (s, 1H, NH), 7.89 (s, 1H), 7.66 (d, J = 8.8 Hz, 2H), 7.08 (s, 2H, NH$_2$), 6.90 (d, J = 8.8 Hz, 2H), 3.78 (s, 3H); LCMS (electrospray) m/z 306 (M + H)$^+$. |
| 65 | 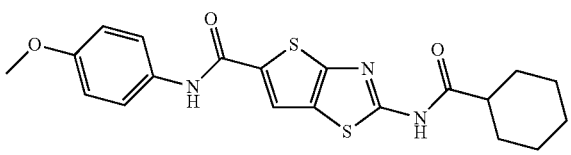 [SMILES: COc1ccc(NC(=O)c2cc3sc(NC(=O)C4CCCCC4)nc3s2)cc1] | Ivory solid; mp = 271° C.; $^1$H NMR (400 MHz, acetone-d$_6$) δ 9.47 (s, 1H, NH), 8.09 (s, 1H), 7.69 (d, J = 8.8 Hz, 2H), 6.92 (d, J = 8.8 Hz, 2H), 3.79 (s, 3H), 2.63-2.68 (m, 1H), 1.96-2.01 (m, 2H), 1.81-1.84 (m, 2H), 1.69-1.72 (m, 1H), 1.51-1.60 (m, 2H), 1.26-1.40 (m, 3H); LCMS (electrospray) m/z 416 (M + H)$^+$. |
| 66 | 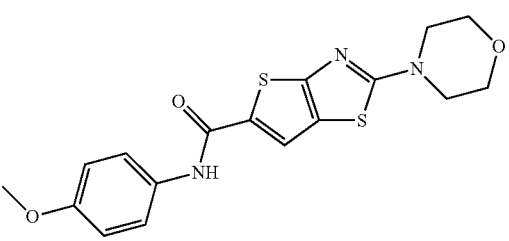 [SMILES: COc1ccc(NC(=O)c2cc3sc(N4CCOCC4)nc3s2)cc1] | Pale brown solid; trip = 248.8° C.; $^1$H NMR (400 MHz, acetone-d$_6$) δ 9.32 (s, 1H), 7.96 (s, 1H), 7.66 (d, J = 8.8 Hz, 2H), 6.91 (d, J = 8.8 Hz, 2H), 3.79-3.81 (m, 4H), 3.78 (s, 3H), 3.57-3.59 (m, 4H); LCMS (electrospray) m/z 375 (M + H)$^+$. |
| 67 | 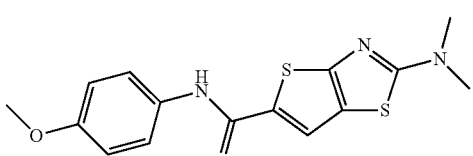 | Pale yellow solid; mp = 105° C.; $^1$H NMR (400 MHz, DMSO-d$_6$) δ 10.24 (brs, 1H, NH), 8.14 (s, 1H), 7.75 (d, J = 8.8 Hz, 2H), 7.39 (d, J = 8.8 Hz, 2H) 3.52-3.56 (m, 4H), 2.95 (s, 6H), 1.58-1.64 (m, 6H); LCMS (electrospray) m/z 415 (M + H)$^+$. |
| 68 | 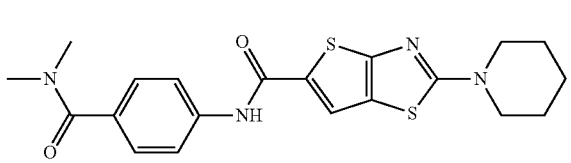 | Pale yellow solid; mp = 175° C.; $^1$H NMR (400 MHz, CDCl$_3$) δ 7.66 (s, 1H), 7.58 (brs, 1H, NH), 7.52 (d, J = 8.8 Hz, 2H), 6.88 (d, J = 8.8 Hz, 2H), 4.37-4.40 (m, 1H), 3.80 (s, 3H), 3.02 (s, 3H), 1.28 (s, 6H); LCMS (electrospray) m/z 362 (M + H)$^+$. |
| 69 | 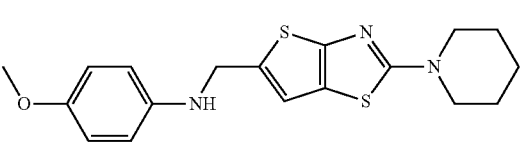 | Yellow solid; mp = 105° C.; $^1$H NMR (400 MHz, acetone-d$_6$) δ 7.07 (s, 1H), 6.72 (d, J = 8.8 Hz, 2H), 6.69 (d, J = 8.8 Hz, 2H), 5.09 (brs, 1H, NH), 4.47 (d, J = 5.6 Hz, 2H), 3.67 (s, 3H), 3.48-3.50 (m, 4H), 1.65-1.68 (m, 6H); LCMS (electrospray) m/z 360 (M + H)$^+$. |

TABLE 1-continued

Structures and Characteristics of Compounds 1-360

| No. | Structure | NMR Characterization |
|---|---|---|
| 70 | 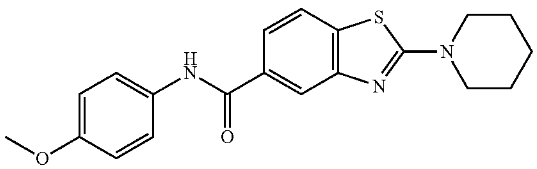 [SMILES: COc1ccc(NC(=O)c2ccc3sc(N4CCCCC4)nc3c2)cc1] | White solid; mp = 222° C.; ¹H NMR (400 MHz, acetone-$d_6$) δ 9.38 (s, 1H, NH), 8.04 (d, J = 2.0 Hz, 1H), 7.79-7.82 (m, 3H), 7.69 (dd, J = 8.8 Hz, 2.0 Hz, 1H), 6.93 (d, J = 8.8 Hz, 2H), 3.80 (s, 3H), 3.64-3.67 (m, 4H), 1.70-1.73 (m, 6H); LCMS (electrospray) m/z 368 (M + H)⁺. |
| 71 | 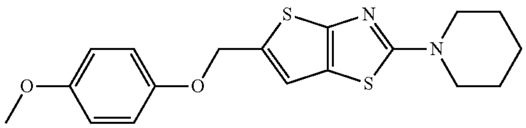 [SMILES: COc1ccc(OCc2cc3sc(N4CCCCC4)nc3s2)cc1] | Green solid; mp = 127.5° C.; ¹H NMR (400 MHz, CDCl₃) δ 6.99 (s, 1H), 6.90 (d, J = 8.8 Hz, 2H), 6.81 (d, J = 8.8 Hz, 2H), 5.11 (s, 2H), 3.76 (s, 3H), 3.50-3.52 (m, 4H), 1.67-1.69 (m, 6H); LCMS (electrospray) m/z 361 (M + H)⁺. |
| 72 | 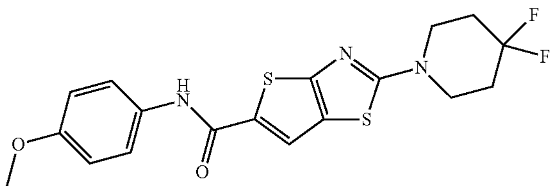 [SMILES: COc1ccc(NC(=O)c2cc3sc(N4CCC(F)(F)CC4)nc3s2)cc1] | Pale yellow solid; mp = 263.5° C.; ¹H NMR (400 MHz, DMSO-$d_6$) δ 10.06 (s, 1H), 8.11 (s, 1H), 7.58 (d, J = 8.8 Hz, 2H), 6.91 (d, J = 8.8 Hz, 2H), 3.74 (s, 3H), 3.69-3.72 (m, 4H), 2.09-2.19 (m, 4H); LCMS (electrospray) m/z 410 (M + H)⁺. |
| 73 | 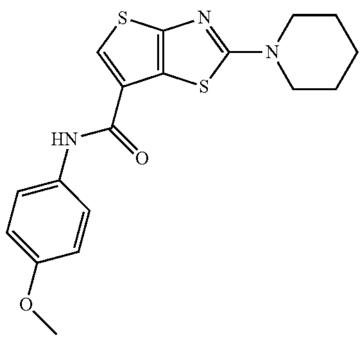 [SMILES: COc1ccc(NC(=O)c2csc3nc(N4CCCCC4)sc23)cc1] | Pale pink solid; mp = 209.8° C.; ¹H NMR (400 MHz, DMSO-$d_6$) δ 10.12 (s, 1H), 8.08 (s, 1H), 7.62 (d, J = 8.8 Hz, 2H), 6.92 (d, J = 8.8 Hz, 2H), 3.74 (s, 3H), 3.49-3.51 (m, 4H), 1.60-1.63 (m, 6H); LCMS (electrospray) m/z 374 (M + H)⁺. |
| 74 | 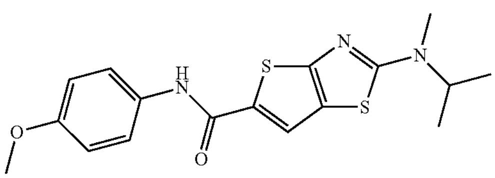 | ¹H NMR (400 MHz, DMSO-$d_6$) δ 8.57 (s, 1H), 8.20-8.22 (m, 1H), 7.94 (brs, 1H, NH), 7.70-7.74 (m, 1H), 7.57-7.60 (m, 1H), 3.80-3.81 (m, 4H), 3.69-3.70 (m, 4H); LCMS (electrospray) m/z 403 (M + H)⁺. |
| 75 | 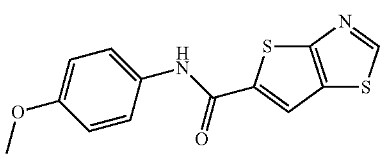 [SMILES: COc1ccc(NC(=O)c2cc3scnc3s2)cc1] | Pale yellow solid; mp = 212.0° C.; ¹H NMR (400 MHz, acetone-$d_6$) δ 9.62 (brs, 1H, NH), 9.28 (s, 1H), 8.24 (s, 1H), 7.69 (d, J = 8.8 Hz, 2H), 6.94 (d, J = 8.8 Hz, 2H), 3.80 (s, 3H); LCMS (electrospray) m/z 291 (M + H)⁺. |
| 76 | 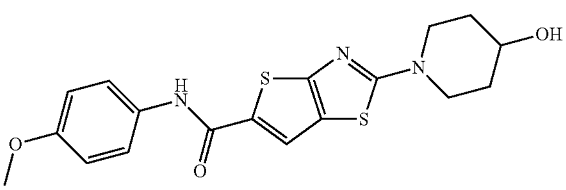 | Pale yellow solid; mp = 216.3° C.; ¹H NMR (400 MHz, acetone-$d_6$) δ 9.31 (brs, 1H, NH), 7.93 (s, 1H), 7.66 (d, J = 8.8 Hz, 2H), 6.90 (d, J = 8.8 Hz, 2H), 3.86-3.96 (m, 3H), 3.78 (s, 3H), 3.40-3.46 (m, 2H), 1.94-1.99 (m, 2H), 1.61-1.65 (m, 2H); LCMS (electrospray) m/z 399 (M + H)⁺. |
| 77 | 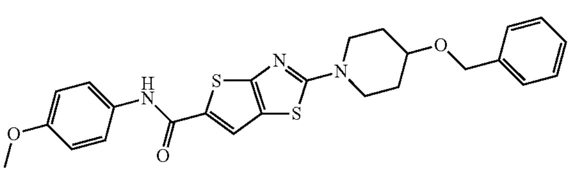 [SMILES: COc1ccc(NC(=O)c2cc3sc(N4CCC(OCc5ccccc5)CC4)nc3s2)cc1] | Pale yellow solid; mp = 190.3° C.; ¹H NMR (400 MHz, acetone-$d_6$) δ 9.28 (brs, 1H, NH), 7.93 (s, 1H), 7.66 (d, J = 8.4 Hz, 2H), 7.32-7.43 (m, 4H), 7.25-7.31 (m, 1H), 6.90 (d, J = 8.4 Hz, 2H), 4.64 (s, 2H), 3.80-3.90 (m, 3H), 3.78 (s, 3H), 3.48-3.57 (m, 2H), 2.10-2.18 (m, 2H), 1.75-1.85 (m, 2H); LCMS (electrospray) m/z 480 (M + H)⁺. |

TABLE 1-continued

Structures and Characteristics of Compounds 1-360

| No. | Structure | NMR Characterization |
|---|---|---|
| 78 | 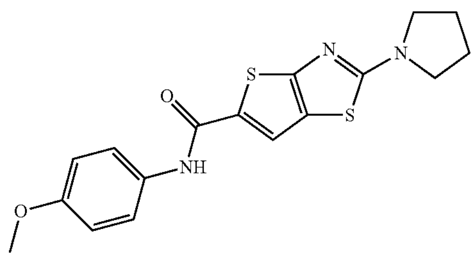 [SMILES: COc1ccc(NC(=O)c2cc3sc(N4CCCC4)nc3s2)cc1] | Pale yellow solid; mp = 274.4° C.; $^1$H NMR (400 MHz, acetone-$d_6$) δ 9.24 (s, 1H), 7.92 (s, 1H), 7.66 (d, J = 8.4 Hz, 2H), 6.90 (d, J = 8.4 Hz, 2H), 3.79 (s, 3H), 3.51-3.54 (m, 4H), 2.09-2.13 (m, 4H); LCMS (electrospray) m/z 359 (M + H)$^+$. |
| 79 | 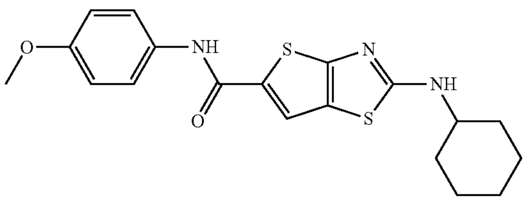 [SMILES: COc1ccc(NC(=O)c2cc3sc(NC4CCCCC4)nc3s2)cc1] | Ivory solid; mp = 231° C.; $^1$H NMR (400 MHz, DMSO-$d_6$) δ 9.96 (s, 1H, NH), 8.31 (brs, 1H, NH), 8.00 (s, 1H), 7.58 (d, J = 9.2 Hz, 2H), 6.92 (d, J = 9.2 Hz, 2H), 3.75 (s, 3H), 3.61-3.65 (m, 1H), 1.94-1.99 (m, 2H), 1.69-1.73 (m, 2H), 1.55-1.60 (m, 1H), 1.15-1.36 (m, 5H); LCMS (electrospray) m/z 387 (M + H)$^+$. |
| 80 | 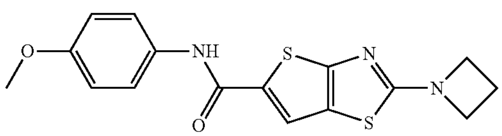 [SMILES: COc1ccc(NC(=O)c2cc3sc(N4CCC4)nc3s2)cc1] | Brown solid; mp = 256° C.; $^1$H NMR (400 MHz, DMSO-$d_6$) δ 10.02 (s, 1H, NH), 8.08 (s, 1H), 7.59 (d, J = 8.8 Hz, 2H), 6.92 (d, J = 8.8 Hz, 2H), 4.09-4.15 (m, 4H), 3.73 (s, 3H), 2.43-2.46 (m, 2H); LCMS (electrospray) m/z 345 (M + H)$^+$. |
| 81 | 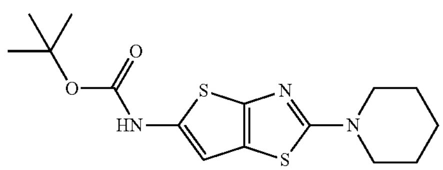 [SMILES: CC(C)(C)OC(=O)Nc1cc2sc(N3CCCCC3)nc2s1] | Ivory solid; mp = 157° C.; $^1$H NMR (400 MHz, CDCl$_3$) δ 6.62 (s, 1H), 6.61 (brs, 1H, NH), 3.45-3.49 (m, 4H), 1.66-1.71 (m, 6H), 1.50 (s, 9H); LCMS (electrospray) m/z 339 (M + H)$^+$. |
| 82 | 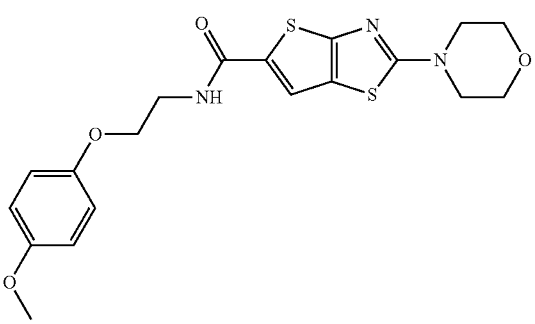 [SMILES: COc1ccc(OCCNC(=O)c2cc3sc(N4CCOCC4)nc3s2)cc1] | Yellow solid; mp = 172.1° C.; $^1$H NMR (400 MHz, CDCl$_3$) δ 7.52 (s, 1H), 6.82-6.87 (m, 4H), 6.30 (brt, 1H), 4.07 (t, J = 4.8 Hz, 2H), 3.80-3.86 (m, 6H), 3.58-3.61 (m, 4H); LCMS (electrospray) m/z 420 (M + H)$^+$. |
| 83 | 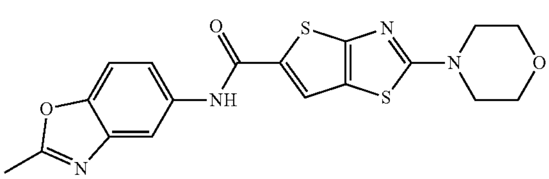 [SMILES: Cc1nc2cc(NC(=O)c3cc4sc(N5CCOCC5)nc4s3)ccc2o1] | Pale yellow solid; mp = 268.3° C.; $^1$H NMR (400 MHz, CDCl$_3$ + MeOH-$d_4$) δ 7.79 (s, 1H), 7.69-7.73 (m, 2H), 7.38 (d, J = 8.8 Hz, 1H), 3.76-3.78 (m, 4H), 3.51-3.53 (m, 4H), 2.59 (s, 3H); LCMS (electrospray) m/z 401 (M + H)$^+$. |
| 84 | 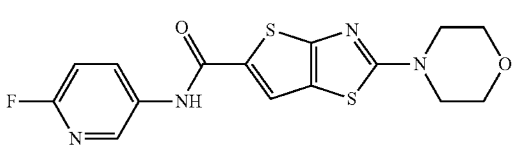 [SMILES: O=C(Nc1ccc(F)nc1)c1cc2sc(N3CCOCC3)nc2s1] | Pale yellow solid; mp = 262.3° C.; $^1$H NMR (400 MHz, DMSO-$d_6$) δ 10.44 (s, 1H), 8.51 (s, 1H), 8.22-8.27 (m, 1H), 8.15 (s, 1H), 7.19 (dd, J = 8.8, 2.8 Hz, 1H), 3.72-3.75 (m, 4H), 3.53-3.55 (m, 4H); LCMS (electrospray) m/z 365 (M + H)$^+$. |

TABLE 1-continued

Structures and Characteristics of Compounds 1-360

| No. | Structure | NMR Characterization |
| --- | --- | --- |
| 85 | 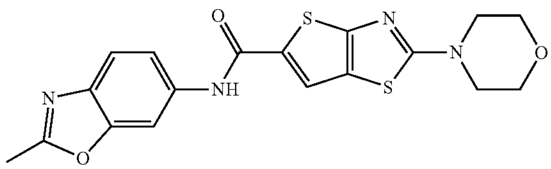 | Pale yellow solid; mp = 273.6° C.; $^1$H NMR (400 MHz, DMSO-$d_6$) δ 10.34 (s, 1H), 8.13-8.16 (m, 2H), 7.58-7.60 (m, 1H), 7.52-7.54 (m, 1H), 3.70-3.74 (m, 4H), 3.51-3.54 (m, 4H), 2.58 (s, 3H); LCMS (electrospray) m/z 401 (M + H)$^+$. |
| 86 | 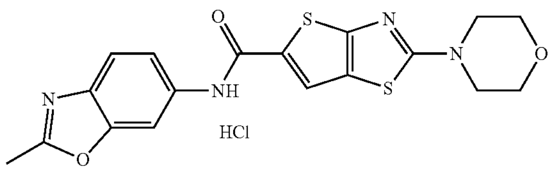 [SMILES: Cc1nc2ccc(NC(=O)c3cc4sc(N5CCOCC5)nc4s3)cc2o1 ; Cl] | White solid; mp = 272.2° C.; $^1$H NMR (400 MHz, DMSO-$d_6$) δ 10.47 (s, 1H), 8.28 (s, 1H), 8.15 (s, 1H), 7.58-7.59 (m, 2H), 3.72-3.74 (m, 4H), 3.52-3.54 (m, 4H), 2.58 (s, 3H). |
| 87 | 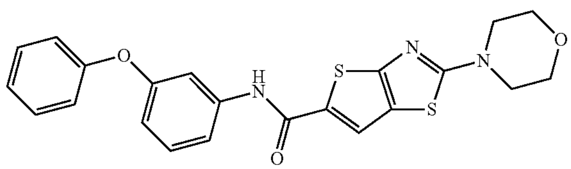 [SMILES: O=C(Nc1cccc(Oc2ccccc2)c1)c1cc2sc(N3CCOCC3)nc2s1] | Pale yellow solid; mp = 169.5° C.; $^1$H NMR (400 MHz, acetone-$d_6$) δ 9.48 (brs, 1H, NH), 7.97 (s, 1H), 7.53-7.55 (m, 2H), 7.38-7.42 (m, 2H), 7.31-7.35 (m, 1H), 7.13-7.17 (m, 1H), 7.05 (d, J = 8.8 Hz, 2H), 6.74 (dd, J = 8.8, 2.2 Hz, 1H), 3.78-3.83 (m, 4H), 3.56-3.62 (m, 4H); LCMS (electrospray) m/z 438 (M + H)$^+$. |
| 88 | 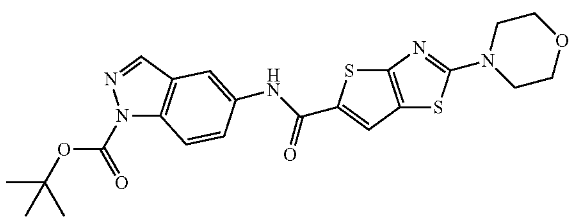 [SMILES: CC(C)(C)OC(=O)n1ncc2cc(NC(=O)c3cc4sc(N5CCOCC5)nc4s3)ccc21] | Pale yellow solid; mp = 331.7° C.; $^1$H NMR (400 MHz, DMSO-$d_6$) δ 10.40 (brs, 1H, NH), 8.42 (s, 1H), 8.30 (s, 1H), 8.19 (s, 1H), 8.05 (d, J = 8.8 Hz, 1 H). 7.83 (d, J = 8.8 Hz, 1H), 3.72-3.78 (m, 4H), 3.52-3.57 (m, 4H), 1.66 (s, 9H); LCMS (electrospray) m/z 486 (M + H)$^+$. |
| 89 | 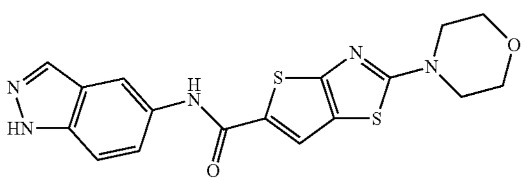 [SMILES: O=C(Nc1ccc2[nH]ncc2c1)c1cc2sc(N3CCOCC3)nc2s1] | Pale yellow solid; mp = 329.8° C.; $^1$H NMR (400 MHz, acetone-$d_6$) δ 12.20 (brs, 1H, NH), 9.48 (brs, 1H, NH), 8.27 (s, 1H), 8.01-8.04 (m, 2H), 7.65 (d, J = 8.0 Hz, 1H), 7.55 (d, J = 8.0 Hz, 1H), 3.78-3.84 (m, 4H), 3.57-3.62 (m, 4H); LCMS (electrospray) m/z 386 (M + H)$^+$. |
| 90 | 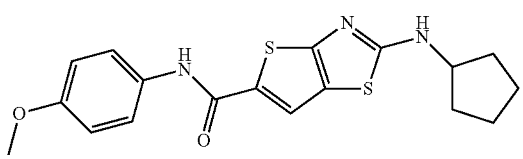 [SMILES: COc1ccc(NC(=O)c2cc3sc(NC4CCCC4)nc3s2)cc1] | Pale yellow solid; mp = 239.3° C.; $^1$H NMR (400 MHz, DMSO-$d_6$) δ 9.97 (brs, 1H, NH), 8.39 (brs, 1H, NH), 8.01 (s, 1H), 7.58 (d, J = 8.8 Hz, 2H), 6.91 (d, J = 8.8 Hz, 2H), 4.04-4.14 (m, 1H), 3.74 (s, 3H), 1.90-2.00 (m, 2H), 1.62-1.74 (m, 2H), 1.50-1.62 (m, 4H); LCMS (electrospray) m/z 374 (M + H)$^+$. |
| 91 | 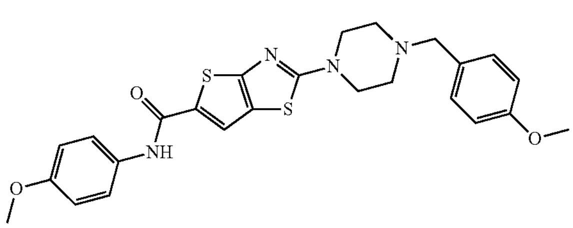 | Pale yellow solid: $^1$H NMR (400 MHz, acetone-$d_6$) δ 9.29 (s, 1H), 7.94 (s, 1H), 7.66 (d, J = 8.8 Hz, 2H), 7.28 (d, J = 8.8 Hz, 2H), 6.90 (d, J = 8.8 Hz, 4H), 3.79 (s, 6H), 3.59-3.62 (m, 4H), 3.52 (s, 2H), 2.56-2.58 (m, 4H): LCMS (electrospray) m/z 494 (M + H)$^+$. |

TABLE 1-continued

Structures and Characteristics of Compounds 1-360

| No. | Structure | NMR Characterization |
|---|---|---|
| 92 | 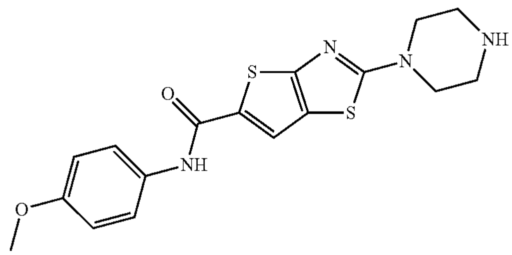 [SMILES: COc1ccc(NC(=O)c2cc3sc(N4CCNCC4)nc3s2)cc1] | Pale yellow solid; $^1$H NMR (400 MHz, acetont-d$_6$) δ 9.32 (s, 1H), 7.96 (s, 1H), 7.67 (d, J = 8.8 Hz, 2H), 6.91 (d, J = 8.8 Hz, 2H), 3.79 (s, 3H), 3.58-3.59 (m, 4H), 3.00-3.01 (m, 4H); LCMS (electrospray) m/z 374 (M + H)$^+$. |
| 93 | 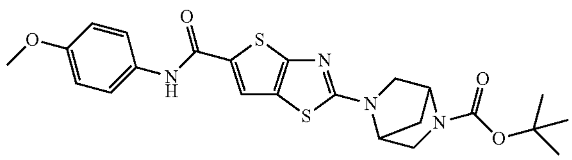 [SMILES: COc1ccc(NC(=O)c2cc3sc(N4CC5CC4CN5C(=O)OC(C)(C)C)nc3s2)cc1] | Pale yellow solid; mp = 249° C.; $^1$H NMK (400 MHz, acetone-d$_6$) δ 9.29 (s, 1H, NH), 7.94 (s, 1H), 7.67 (d, J = 9.2 Hz, 2H), 6.90 (d, J = 9.2 Hz, 2H), 4.73-4.76 (m, 1H), 4.62-4.63 (m, 1H), 3.79 (s, 3H), 3.67-3.69 (m, 1H), 3.44-3.50 (m, 3H), 1.89-1.93 (m, 2H), 1.40-1.46 (m, 9H); LCMS (electrospray) m/z 487 (M + H)$^+$. |
| 94 | 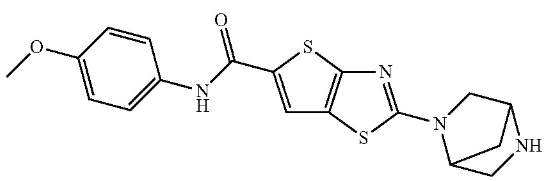 [SMILES: COc1ccc(NC(=O)c2cc3sc(N4CC5CC4CN5)nc3s2)cc1] | Pale yellow solid; mp = 161° C.; $^1$H NMR (400 MHz, acetone-d$_6$) δ 9.30 (s, 1H, NH), 7.93 (s, 1H), 7.67 (d, J = 8.8 Hz, 2H), 6.90 (d, J = 8.8 Hz, 2H), 4.73-4.75 (m, 1H), 4.40-4.44 (m, 1H), 3.78 (s, 3H), 3.49-3.62 (m, 4H), 1.85-1.96 (m, 2H); LCMS (electrospray) m/z 387 (M + H)$^+$. |
| 95 | 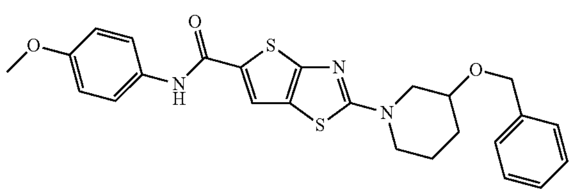 [SMILES: COc1ccc(NC(=O)c2cc3sc(N4CCCC(OCc5ccccc5)C4)nc3s2)cc1] | Yellow solid; mp = 169° C.; $^1$H NMR (400 MHz, acetone-d$_6$) δ 9.28 (s, 1H, NH), 7.92 (s, 1H), 7.66 (d, J = 8.8 Hz, 2H), 7.26-7.37 (m, 5H), 6.90 (d, J = 8.8 Hz, 2H), 4.61-4.70 (m, 2H), 3.87-3.91 (m, 1H), 3.78 (s, 3H), 3.56-3.70 (m, 4H), 2.02-2.05 (m, 2H), 1.77-1.79 (m, 1H), 1.63-1.65 (m, 1H); LCMS (electrospray) m/z 480 (M + H)$^+$. |
| 96 | 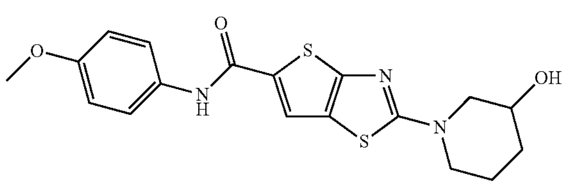 [SMILES: COc1ccc(NC(=O)c2cc3sc(N4CCCC(O)C4)nc3s2)cc1] | Beige solid; mp = 238° C.; $^1$H NMR (400 MHz, acetone-d$_6$) δ 9.27 (s, 1H, NH), 7.92 (s, 1H), 7.66 (d, J = 8.4 Hz, 2H), 6.90 (d, J = 8.4 Hz, 2H), 4.15 (d, J = 4.0 Hz, 1H, OH), 3.90-3.94 (m, 1H), 3.73-3.83 (m, 5H), 3.36-3.40 (m, 1H), 3.20-3.25 (m, 1H), 1.92-2.02 (m, 2H), 1.59-1.65 (m, 2H); LCMS (electrospray) m/z 390 (M + H)$^+$. |
| 97 | 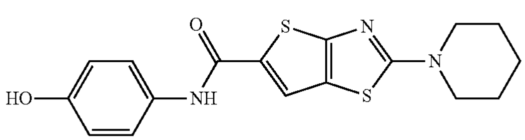 [SMILES: O=C(Nc1ccc(O)cc1)c1cc2sc(N3CCCCC3)nc2s1] | Yellow solid; mp = 246° C.; $^1$H NMR (400 MHz, DMSO-d$_6$) δ 9.91 (s, 1H, NH), 8.05 (s, 1H), 7.44 (d, J = 8.8 Hz, 2H), 6.72 (d, J = 8.8 Hz, 2H), 3.51-3.55 (m, 4H), 1.60-1.64 (m, 6H); LCMS (electrospray) m/z 359 (M + H)$^+$. |
| 98 | 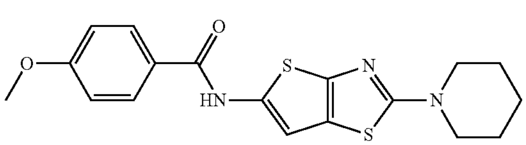 [SMILES: COc1ccc(C(=O)Nc2cc3sc(N4CCCCC4)nc3s2)cc1] | Green solid; mp = 92° C.; $^1$H NMR (400 MHz, DMSO-d$_6$) δ 11.33 (s, 1H, NH), 7.96 (d, J = 8.8 Hz, 2H), 7.08 (d, J = 8.8 Hz, 2H), 6.97 (s, 1H), 3.84 (s, 3H), 3.41-3.44 (m, 4H), 1.59-1.63 (m, 6H); LCMS (electrospray) m/z 373 (M + H)$^+$. |
| 99 | 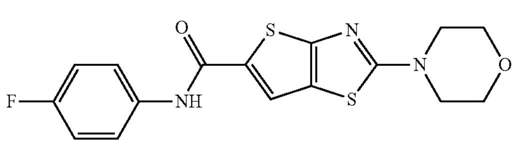 [SMILES: O=C(Nc1ccc(F)cc1)c1cc2sc(N3CCOCC3)nc2s1] | Ivory solid; mp = 240° C.; $^1$H NMR (400 MHz, DMSO-d$_6$) δ 10.22 (s, 1H, NH), 8.13 (s, 1H), 7.68-7.72 (m, 2H), 7.16-7.20 (m, 2H), 3.72-3.74 (m, 4H) 3.52-3.55 (m, 4H); LCMS (electrospray) m/z 363 (M + H)$^+$. |

TABLE 1-continued

Structures and Characteristics of Compounds 1-360

| No. | Structure | NMR Characterization |
|---|---|---|
| 100 | 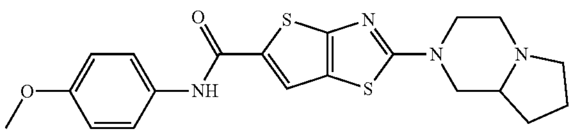 [SMILES: COc1ccc(NC(=O)c2cc3sc(N4CCN5CCCC5C4)nc3s2)cc1] | Ivory solid; mp = 195° C.; $^1$H NMR (400 MHz, DMSO-$d_6$) δ 10.03 (s, 1H, NH), 8.09 (s, 1H), 7.59 (d, J = 8.4 Hz, 2H), 6.91 (d, J = 8.4 Hz, 2H), 4.04-4.09 (m, 1H), 3.87-3.92 (m, 1H), 3.47-3.50 (m, 1H), 3.19-3.26 (m, 1H), 3.00-3.08 (m, 2H), 2.84-2.93 (m, 1H), 2.17-2.23 (m, 1H), 1.99-2.12 (m, 2H), 1.81-1.89 (m, 1H), 1.68-1.75 (m, 2H), 1.34-1.42 (m, 1H), 1.15-2.00 (m, 2H); LCMS (electrospray) m/z 414 (M + H)$^+$. |
| 101 | 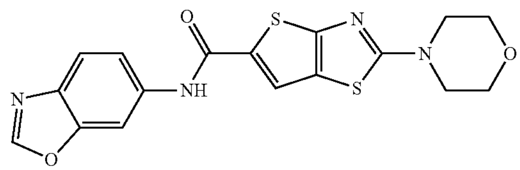 [SMILES: O=C(Nc1ccc2ncoc2c1)c1cc2sc(N3CCOCC3)nc2s1] | Pale yellow solid; mp = 281.8° C.; $^1$H NMR (400 MHz, DMSO-$d_6$) δ 10.41 (s, 1H), 8.67 (s, 1H), 8.27 (s, 1H), 8.19 (s, 1H), 7.75 (d, J = 8.4 Hz, 1H), 7.60-7.62 (m, 1H), 3.73-3.75 (m, 4H), 3.53-3.55 (m, 4H); LCMS (electrospray) m/z 387 (M + H)$^+$. |
| 102 | 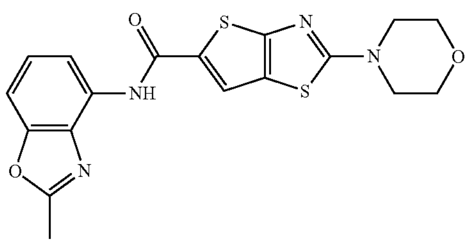 [SMILES: Cc1nc2c(NC(=O)c3cc4sc(N5CCOCC5)nc4s3)cccc2o1] | Pale yellow solid; mp = 209.3° C.; $^1$H NMR (400 MHz, DMSO-$d_6$, ~30% mixture of conformational isomers) δ 10.22 (s, 1H), 8.25 & 8.27 (s, 1H), 7.66 (d, J = 8.0 Hz, 1H), 7.45 (d, J = 8.0 Hz, 1H), 7.33 (dd, J = 8.0, 8.0 Hz, 1H), 3.73-3.76 (m, 4H), 3.53-3.61 (m, 4H), 2.63 (s, 3H); LCMS (electrospray) m/z 401 (M + H)$^+$. |
| 103 | 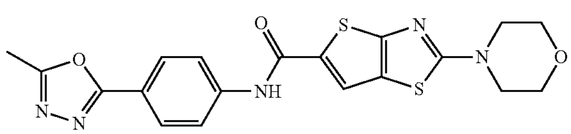 [SMILES: Cc1nnc(-c2ccc(NC(=O)c3cc4sc(N5CCOCC5)nc4s3)cc2)o1] | White solid; mp = 319.1° C.; $^1$H NMR (400 MHz, DMSO-$d_6$) δ 10.46 (s, 1H), 8.21 (s, 1H), 7.92-7.94 (m, 4H), 3.73-3.75 (m, 4H), 3.53-3.56 (m, 4H), 2.57 (s, 3H); LCMS (electrospray) m/z 428 (M + H)$^+$. |
| 104 | 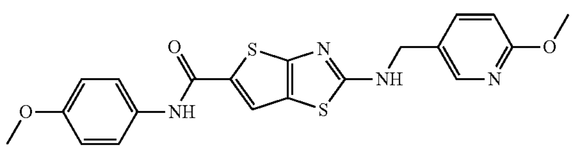 | White solid; mp = 230.9° C.; $^1$H NMR (400 MHz, DMSO-$d_6$) δ 9.99 (s, 1H), 8.79 (brs, 1H), 8.18 (s, 1H), 8.02 (d, J = 1.6 Hz, 1H), 7.71 (d, J = 8.4 Hz, 1H), 7.57-7.60 (m, 2H), 6.90-6.92 (m, 2H), 6.81 (dd, J = 8.4, 1.6 Hz, 1H), 4.49 (d, J = 3.6 Hz, 2H), 3.83 (s, 3H), 3.74 (s, 3H); LCMS (electrospray) m/z 427 (M + H)$^+$. |
| 105 | 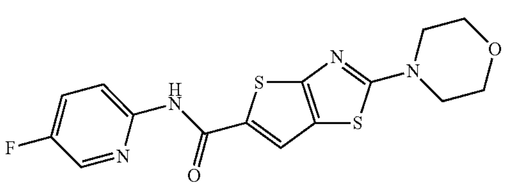 [SMILES: O=C(Nc1ccc(F)cn1)c1cc2sc(N3CCOCC3)nc2s1] | Pale yellow solid; $^1$H NMR (400 MHz, acetone-$d_6$) δ 9.66 (brs, 1H, NH), 8.30-8.35 (m, 2H), 8.24 (s, 1H), 7.63-7.71 (m, 1H), 3.78-3.83 (m, 4H), 3.58-3.63 (m, 4H); LCMS (electrospray) m/z 365 (M + H)$^+$. |
| 106 | 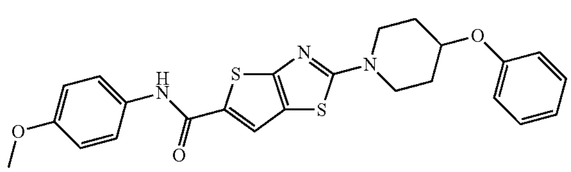 [SMILES: COc1ccc(NC(=O)c2cc3sc(N4CCC(Oc5ccccc5)CC4)nc3s2)cc1] | Pale yellow solid; mp = 225.0° C.; $^1$H NMR (400 MHz, DMSO-$d_6$) δ 10.01 (brs, 1H, NH), 8.08 (s, 1H), 7.57 (d, J = 8.0 Hz, 2H), 7.27-7.32 (m, 2H), 7.00 (d, J = 8.0 Hz, 2H), 6.89-6.98 (m, 3H), 4.65-4.72 (m, 1H), 3.78-3.87 (m, 2H), 3.72 (s, 3H), 3.48-3.57 (m, 2H), 2.02-2.11 (m, 2H), 1.70-1.80 (m, 2H); LCMS (electrospray) m/z 466 (M + H)$^+$. |
| 107 | 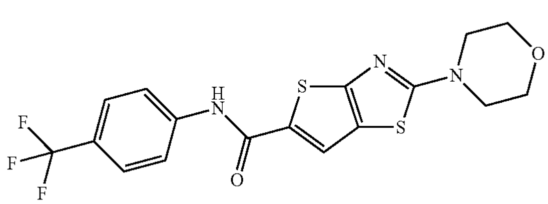 [SMILES: O=C(Nc1ccc(C(F)(F)F)cc1)c1cc2sc(N3CCOCC3)nc2s1] | Pale yellow solid: mp = 259.3° C.; $^1$H NMR (400 MHz, DMSO-$d_6$) δ 10.48 (brs, 1H, NH), 8.21 (s, H1), 7.94 (d, J = 7.6 Hz, 2H), 7.71 (d, J = 1.6 Hz, 2H), 3.72-3.77 (m, 4H), 3.53-3.58 (m, 4H); LCMS (electrospray) m/z 414 (M + H)$^+$. |

TABLE 1-continued

Structures and Characteristics of Compounds 1-360

| No. | Structure | NMR Characterization |
|---|---|---|
| 108 | 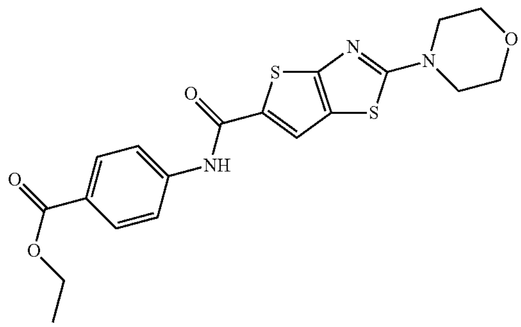 [SMILES: CCOC(=O)c1ccc(NC(=O)c2cc3sc(N4CCOCC4)nc3s2)cc1] | Pale yellow solid; mp = 274.0° C.; $^1$H NMR (400 MHz, DMSO-$d_6$) δ 10.44 (s, 1H), 8.20 (s, 1H), 7.93 (d, J = 8.4 Hz, 2H), 7.85 (d, J = 8.4 Hz, 2H), 4.28 (q, J = 6.8 Hz, 2H), 3.71-3.78 (m, 4H), 3.52-3.54 (m, 4H), 1.30 (t, J = 6.8 Hz. 3H); LCMS (electrospray) m/z 417 (M + H)$^+$. |
| 109 | 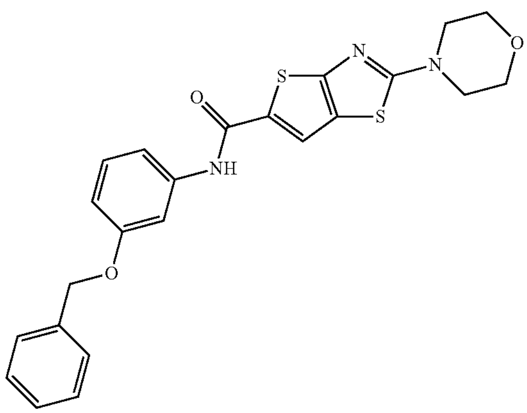 [SMILES: O=C(Nc1cccc(OCc2ccccc2)c1)c1cc2sc(N3CCOCC3)nc2s1] | White solid; mp = 223.4° C.; $^1$H NMR (400 MHz, DMSO-$d_6$) δ 10.11 (s, 1H), 8.13 (s, 1H), 7.43-7.47 (m, 2H), 7.36-7.40 (m, 3H), 7.27-7.33 (m, 1H), 7.20-7.25 (m, 2H), 6.72-6.74 (m, 1H), 5.08 (s, 2H), 3.71-3.72 (m, 4H), 3.51-3.52 (m, 4H); LCMS (electrospray) m/z 451 (M + H)$^+$. |
| 110 | 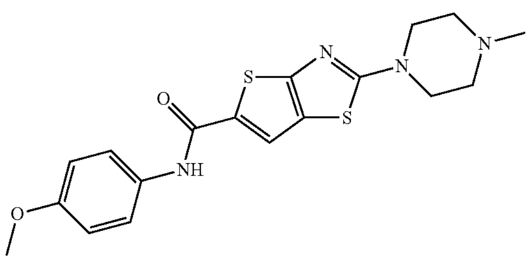 | White solid; mp = 219.8° C.; $^1$H NMR (400 MHz, DMSO-$d_6$) δ 10.03 (s, 1H), 8.11 (s, 1H), 7.63 (d, J = 8.8 Hz, 2H), 6.96 (d, J = 8.8 Hz, 2H), 3.73-3.78 (m, 4H), 3.58 (s, 3H), 3.53 (s, 3H), 2.23-2.78 (s, 4H); LCMS (electrospray) m/z 388 (M + H)$^+$. |
| 111 | 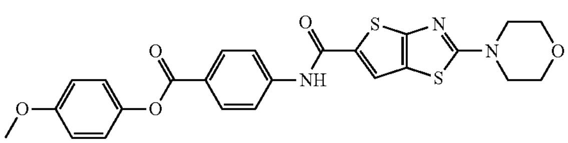 [SMILES: COc1ccc(OC(=O)c2ccc(NC(=O)c3cc4sc(N5CCOCC5)nc4s3)cc2)cc1] | Pale yellow solid; mp = 302.6° C.; $^1$H NMR (400 MHz, DMSO-$d_6$) δ 10.53 (s, 1H), 8.24 (s, 1H), 8.12 (d, J = 8.0 Hz, 2H), 7.95 (d, J = 8.0 Hz, 2H), 7.19 (d, J = 7.6 Hz, 2H), 6.99 (d, J = 7.6 Hz, 2H), 3.78 (s, 3H), 3.73-3.74 (m, 4H), 3.54-3.55 (m, 4H); LCMS (electrospray) m/z 495 (M + H)$^+$. |
| 112 | 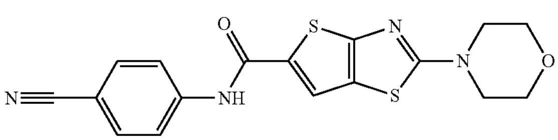 [SMILES: N#Cc1ccc(NC(=O)c2cc3sc(N4CCOCC4)nc3s2)cc1] | Pale yellow solid: mp = 212° C.; $^1$H NMR (400 MHz, acetone-$d_6$) δ 9.78 (s, 1H, NH), 8.05 (s, 1H), 7.99 (d, J = 7.6 Hz, 2H), 7.74 (d, J = 7.6 Hz, 2H), 3.79-3.82 (m, 4H), 3.59-3.62 (m, 4H); LCMS (electrospray) m/z 371 (M + H)$^+$. |
| 113 | 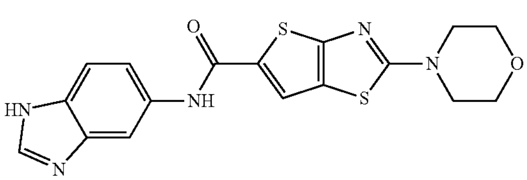 [SMILES: O=C(Nc1ccc2[nH]cnc2c1)c1cc2sc(N3CCOCC3)nc2s1] | Yellow solid; $^1$H NMR (400 MHz, DMSO-$d_6$) δ 12.48 (s, 1H, NH), 10.25 (s, 1H, NH), 8.15-8.25 (m, 2H), 7.50-7.58 (m, 3H), 3.81-3.84 (m, 4H), 3.61-3.63 (m, 4H); LCMS (electrospray) m/z 386 (M + H)$^+$. |

TABLE 1-continued

Structures and Characteristics of Compounds 1-360

| No. | Structure | NMR Characterization |
|---|---|---|
| 114 | 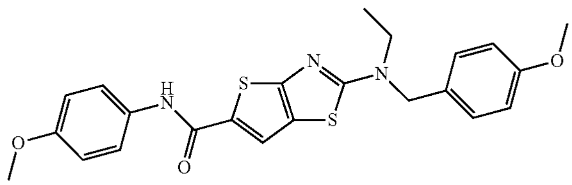 | Orange solid; mp = 112° C.; $^1$H NMR (400 MHz, acetone-d$_6$) δ 9.26 (s, 1H, NH), 7.93 (s, t H), 7.67 (d, J = 6.8 Hz, 2H), 7.33 (d, J = 6.8 Hz, 2H), 6.89-6.94 (m, 4H), 4.75 (s, 2H), 3.79 (s, 3H), 3.78 (s, 3H), 3.59 (q, J = 7.2 Hz, 2H), 1.23 (t, J = 7.2 Hz, 3H); LCMS (electrospray) m/z 454 (M + H)$^+$. |
| 115 | 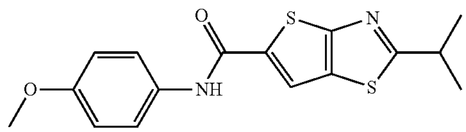 [SMILES: COc1ccc(NC(=O)c2cc3sc(C(C)C)nc3s2)cc1] | White solid; mp = 149° C.; $^1$H NMR (400 MHz, acetone-d$_6$) δ 9.54 (s, 1H, NH), 8.15 (s, 1H), 7.69 (d, J = 8.8 Hz. 2H), 6.93 (d, J = 8.8 Hz, 2H), 3.98 (s, 3H), 3.40-3.47 (m, 1H), 1.45 (d, J = 6.8 Hz, 6H); LCMS (electrospray) m/z 333 (M + H)$^+$. |
| 116 | 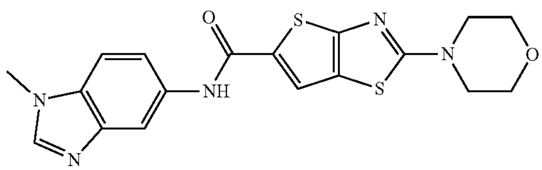 | White solid; mp = 291° C.; $^1$H NMR (400 MHz, DMSO-d$_6$) δ 10.16 (s, 1H,NH), 8.13-8.14 (m, 2H), 8.01 (s, 1H), 7.51-7.52 (m, 2H), 3.81 (s, 3H), 3.69-3.73 (m, 4H), 3.48-3.53 (m, 4H); LCMS (electrospray) m/z 400 (M + H)$^+$. |
| 117 | 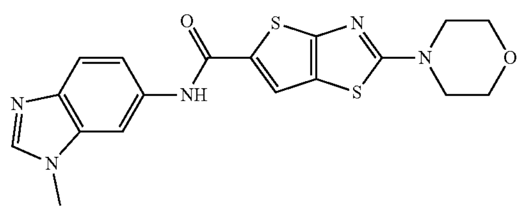 | White solid; mp = 314° C.; $^1$H NMR (400 MHz, DMSO-d$_6$) δ 10.25 (s, 1H, NH), 8.17 (s, 1H), 8.11 (s, 1H), 8.05 (d, J = 2.0 Hz, 1H), 7.58 (d, J = 8.8 Hz, 1H), 7.39 (dd, 8.8 Hz, 2.0 Hz, 1H), 3.79 (s, 3H), 3.71-3.74 (m, 4H), 3.51-3.54 (m, 4H); LCMS (electrospray) m/z 400 (M + H)$^+$. |
| 118 | 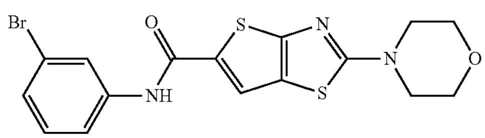 [SMILES: O=C(Nc1cccc(Br)c1)c1cc2sc(N3CCOCC3)nc2s1] | Orange solid; mp = 199° C.; $^1$H NMR (400 MHz, acetone-d$_6$) δ 9.52 (s, 1H, NH), 8.11 (s, 1H), 8.01 (s, 1 H), 7.71-7.73 (m, 1H), 7.26-7.29 (m, 2H), 3.78-3.81 (m, 4H), 3.57-3.60 (m, 4H); LCMS (electrospray) m/z 425 (M + H)$^+$. |
| 119 | 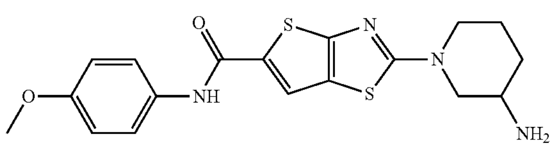 [SMILES: COc1ccc(NC(=O)c2cc3sc(N4CCCC(N)C4)nc3s2)cc1] | White solid; mp = 232° C.; $^1$H NMR (400 MHz, DMSO-d$_6$) δ 9.96 (s, 1H, NH), 8.23 (brs, 1H, NH), 8.00 (s, 1H), 7.59 (d, J = 8.8 Hz, 2H), 6.91 (d, J = 8.8 Hz, 2H), 3.73 (s, 3H), 3.61-3.64 (m, 1H), 1.94-1.99 (m, 2H), 1.69-1.74 (m, 2H), 1.55-1.60 (m, 1H), 1.17-1.35 (m, 3H); LCMS (electrospray) m/z 389 (M + H)$^+$. |
| 120 | 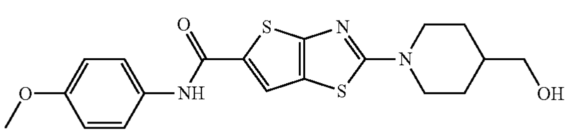 [SMILES: COc1ccc(NC(=O)c2cc3sc(N4CCC(CO)CC4)nc3s2)cc1] | Pale yellow solid; $^1$H NMR (400 MHz, MeOH-d$_4$) δ 7.87 (s, 1H), 7.85 (d, J = 8.8 Hz, 2H), 6.91 (d, J = 8.8 Hz, 2H), 4.10 (m, 2H), 3.79 (s, 3H), 3.14-3.22 (m, 3H), 1.86-1.89 (m, 2H), 1.78-1.79 (m, 1H), 1.33-1.39 (m, 3H); LCMS (electrospray) m/z 403 (M + H)$^+$. |
| 121 | 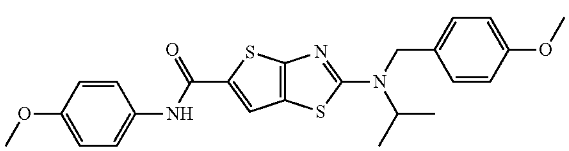 | Ivory solid; mp = 131° C.; $^1$H NMR (400 MHz, acetone-d$_6$) δ 9.27 (s, 1H, NH), 7.91 (s, 1H), 7.65 (d, J = 8.8 Hz, 2H), 7.32 (d, J = 8.8 Hz, 2H), 6.89-6.92 (m, 4H), 4.71 (s, 2H), 4.49-4.53 (m, 1H), 3.78 (s, 6H), 1.31 (d, J = 6.8 Hz, 6H); LCMS (electrospray) m/z 468 (M + H)$^-$. |
| 122 | 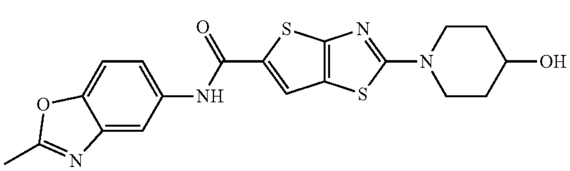 [SMILES: Cc1nc2cc(NC(=O)c3cc4sc(N5CCC(O)CC5)nc4s3)ccc2o1] | Pale yellow solid; mp = 238.5° C.; $^1$H NMR (400 MHz, DMSO-d$_6$) δ 10.23 (s, 1H), 8.13 (s, 1H), 8.05 (s, 1H), 7.60-7.63 (m, 2H), 4.85 (d, J = 4.0 Hz, 1H), 3.79-3.82 (m, 3H), 3.36-3.39 (m, 2H), 2.60 (s, 3H), 1.84-1.87 (m, 2H), 1.46-1.51 (m, 2H); LCMS (electrospray) m/z 415 (M + H)$^+$. |

TABLE 1-continued

Structures and Characteristics of Compounds 1-360

| No. | Structure | NMR Characterization |
|---|---|---|
| 123 | 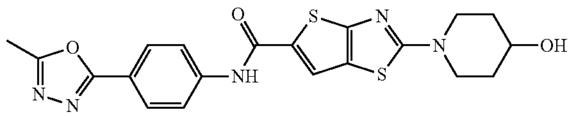 [SMILES: Cc1nnc(-c2ccc(NC(=O)c3cc4sc(N5CCC(O)CC5)nc4s3)cc2)o1] | Pale yellow solid; mp = 334.4° C.; $^1$H NMR (400 MHz, DMSO-d$_6$) δ 10.41 (s, 1H), 8.16 (s, 1H), 7.92-7.94 (m, 4H), 4.84 (brs, 1H), 3.75-3.78 (m, 3H), 3.34-3.36 (m, 2H), 2.55 (s, 3H), 1.80-1.83 (m, 2H), 1.46-1.49 (m, 2H); LCMS (electrospray) m/z 442 (M + H)$^+$. |
| 124 | 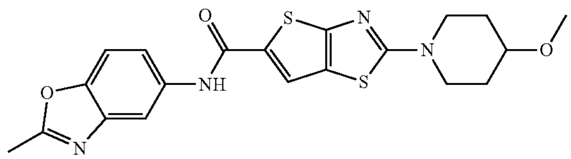 | Yellow solid; mp = 237.9° C.; $^1$H NMR (400 MHz, DMSO-d$_6$) δ 10.23 (s, 1H), 8.13 (s, 1H), 8.05 (s, 1H), 7.60-7.63 (m, 2H), 3.72-3.78 (m, 2H), 3.37-3.51 (m, 3H), 3.29 (s, 3H), 2.59 (s, 3H), 1.92-1.97 (m, 2H), 1.55-1.60 (m, 2H); LCMS (electrospray) m/z 429 (M + H)$^+$. |
| 125 | 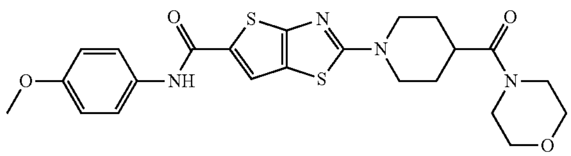 [SMILES: COc1ccc(NC(=O)c2cc3sc(N4CCC(C(=O)N5CCOCC5)CC4)nc3s2)cc1] | Ivory solid; mp = 268° C.; $^1$H NMR (400 MHz, DMSO-d$_6$) δ 10.01 (s, 1H, NH), 8.07 (s, 1H), 7.58 (d, J = 8.8 Hz, 2H), 6.90 (d, J = 8.8 Hz, 2H), 3.96-3.99 (m, 2H), 3.72 (s, 3H), 3.54-3.57 (m, 6H), 3.41-3.44 (m, 2H), 3.21-3.27 (m, 2H), 2.93-2.99 (m, 1H), 1.73-1.76 (m, 2H), 1.58-1.67 (m, 2H); LCMS (electrospray) m/z 487 (M + H)$^+$. |
| 126 | 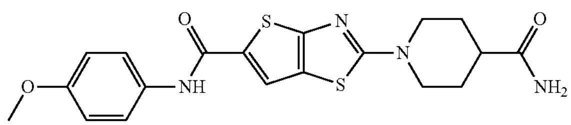 [SMILES: COc1ccc(NC(=O)c2cc3sc(N4CCC(C(N)=O)CC4)nc3s2)cc1] | White solid; mp = 276.1° C.; $^1$H NMR (400 MHz, DMSO-d$_6$) δ 9.99 (s, 1H), 8.07 (s, 1H), 7.57 (d, J = 8.8 Hz, 2H), 7.32 (s, 1 H), 6.90 (d, J = 8.8 Hz, 2H), 6.83 (s, 1H), 3.94-3.98 (m, 2H), 3.72 (s, 3H), 3.14-3.18 (m, 3H), 1.80-1.83 (m, 2H), 1.57-1.61 (m, 2H); LCMS (electrospray) m/z 416 (M + H)$^+$. |
| 127 | 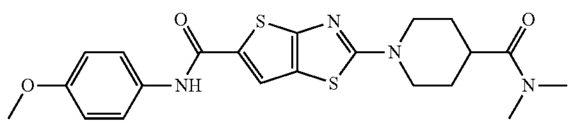 | White solid; mp = 273.4° C.; $^1$H NMR (400 MHz, DMSO-d$_6$) δ 10.01 (s, 1H), 8.07 (s, 1H), 7.57 (d, J = 8.8 Hz, 2H), 6.90 (d, J = 8.8 Hz, 2H), 3.96-3.99 (m, 2H), 3.72 (s, 3H), 3.05 (s, 3H), 2.87-2.99 (m, 2H), 2.80 (s, 3H), 1.73-1.76 (m, 2H), 1.57-1.63 (m, 3H); LCMS (electrospray) m/z 444 (M + H)$^+$. |
| 128 | 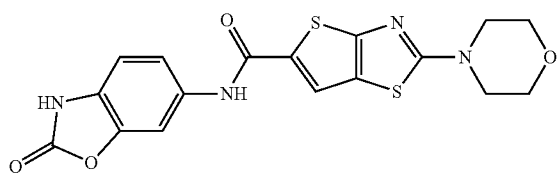 [SMILES: O=C(Nc1ccc2[nH]c(=O)oc2c1)c1cc2sc(N3CCOCC3)nc2s1] | Ivory solid; mp = 354° C.; $^1$H NMR (400 MHz, DMSO-d$_6$) δ 10.48 (s, 1H), 8.25 (s, 1H), 7.86-7.93 (m, 4H), 3.76-3.79 (m, 4H), 3.57-3.59 (m, 4H), 1.58 (s, 9H); LCMS (electrospray) m/z 426 (M + H)$^+$. |
| 129 | 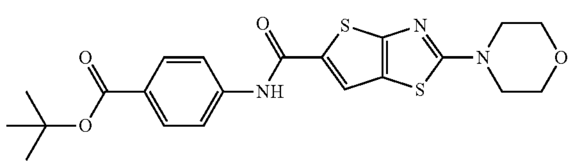 [SMILES: CC(C)(C)OC(=O)c1ccc(NC(=O)c2cc3sc(N4CCOCC4)nc3s2)cc1] | Pale yellow solid; mp = 244° C.; $^1$H NMR (400 MHz, DMSO-d$_6$) δ 10.00 (s, 1H), 8.14 (s, 1H), 7.66-7.68 (m, 2H), 6.93-6.95 (m, 2H), 5.16 (s, 1H), 4.50-4.51 (m, 1H), 3.78 (s, 3H), 3.38-3.66 (m, 4H), 2.01-2.16 (m, 2H). |
| 130 | 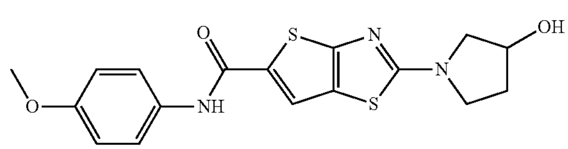 [SMILES: COc1ccc(NC(=O)c2cc3sc(N4CCC(O)C4)nc3s2)cc1] | $^1$H NMR (400 MHz, DMSO-d$_6$) δ 10.00 (s, 1H), 8.14 (s, 1H), 7.66-7.68 (m, 2H), 6.93-6.95 (m, 2H), 5.16 (s, 1H), 4.50-4.51 (m, 1H), 3.78 (s, 3H), 3.38-3.66 (m, 4H), 2.01-2.16 (m, 2H). |
| 131 | 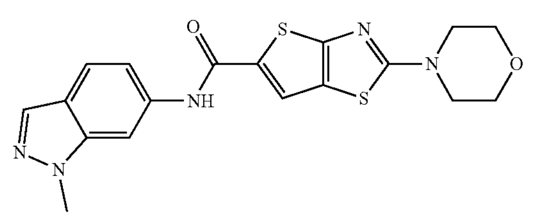 | White solid; mp = 288.0° C.; $^1$H NMR (400 MHz, DMSO-d$_6$) δ 10.12 (brs, 1H, NH), 8.28 (s, 1H), 8.15 (s, 1H), 8.11 (s, 1H), 7.57 (d, J = 9.2 Hz, 1H), 7.43 (d, J = 9.2 Hz, 1H), 4.14 (s, 3H), 3.72-3.77 (m, 4H), 3.52-3.56 (m, 4H); LCMS (electrospray) m/z 400 (M + H)$^+$. |

TABLE 1-continued

Structures and Characteristics of Compounds 1-360

| No. | Structure | NMR Characterization |
|---|---|---|
| 132 | 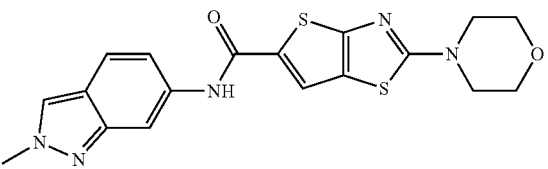 | White solid; mp = 313.7° C.; $^1$H NMR (400 MHz, DMSO-d$_6$) δ 10.22 (brs, 1H, NH), 8.15 (s, 1H), 8.13 (s, 1H), 8.02 (s, 1H), 7.61-7.63 (m, 2H), 4.03 (s, 3H), 3.72-3.76 (m, 4H), 3.52-3.56 (m, 4H); LCMS (electrospray) m/z 400 (M + H)$^+$. |
| 133 | 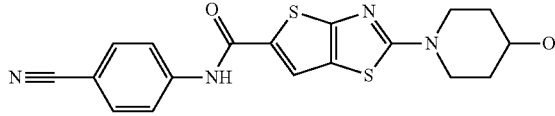 | White solid; $^1$H NMR (400 MHz, acetone-d$_6$) δ 9.77 (brs, 1H, NH), 8.04 (s, 1H), 7.99 (d, J = 8.8 Hz, 2H), 7.73 (d, J = 8.8 Hz, 2H), 3.88-3.99 (m, 3H), 3.43-3.49 (m, 2H), 1.92-2.02 (m, 2H), 1.59-1.69 (m, 2H); LCMS (electrospray) m/z 385 (M + H)$^+$. |
| 134 | 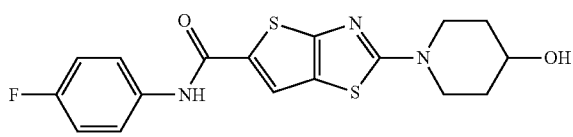 | White solid; mp = 241.7° C.; $^1$H NMR (400 MHz, acetone-d$_6$) δ 9.46 (brs, 1H, NH), 7.96 (s, 1H), 7.74-7.82 (m, 2H), 7.07-7.14 (m, 2H), 3.94-4.02 (m, 1H), 3.83-3.93 (m, 2H). 3.40-3.49 (m, 2H), 1.92-2.02 (m, 2H). 1.56-1.69 (m, 2H); LCMS (electrospray) m/z 378 (M + H)$^+$. |
| 135 | 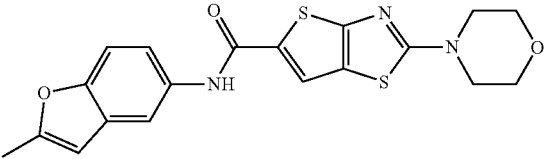 | Yellow solid; mp = 231.3° C.; $^1$H NMR (400 MHz, DMSO-d$_6$) δ 10.14 (s, 1H), 8.15 (s, 1H), 7.89 (s, 1H), 7.44 (s, 2H), 6.57 (s, 1H), 3.73-3.75 (m, 4H), 3.52-3.55 (m, 4H), 2.43 (s, 3H); LCMS (electrospray) m/z 400 (M + H)$^+$. |
| 136 | 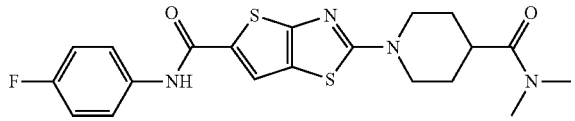 [SMILES: CN(C)C(=O)C1CCN(c2nc3sc(C(=O)Nc4ccc(F)cc4)cc3s2)CC1] | White solid; mp = 296.2° C.; $^1$H NMR (400 MHz, DMSO-d$_6$) δ 10.19 (s, 1H), 8.12 (s, 1H), 7.72 (d, J = 8.8 Hz, 2H), 7.18 (d, J = 8.8 Hz, 2H), 3.98-4.01 (m, 2H), 3.06 (s, 3 H), 2.96-3.01 (m, 2H), 2.82 (s, 3H), 1.75-1.78 (m, 2H), 1.59-1.62 (m, 3H); LCMS (electrospray) m/z 432 (M + H)$^+$. |
| 137 | 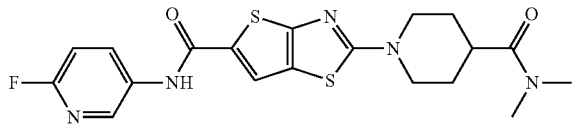 [SMILES: CN(C)C(=O)C1CCN(c2nc3sc(C(=O)Nc4ccc(F)nc4)cc3s2)CC1] | Pale yellow solid: mp = 295.9° C.; $^1$H NMR (400 MHz, DMSO-d$_6$) δ 10.43 (s, 1H), 8.51 (s, 1H), 8.23-8.27 (m, 1H), 8.13 (s, 1H), 7.18-7.21 (m, 1H), 3.99-4.02 (m, 2H), 3.11 (s, 3H), 2.96-3.06 (m, 2H), 2.89 (s, 3H), 1.75-1.79 (m, 2H), 1.57-1.65 (m, 3H); LCMS (electrospray) m/z 433 (M + H)$^+$. |
| 138 | 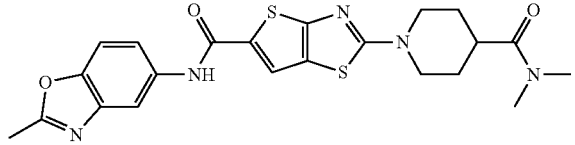 | White solid; mp = 284.2° C.; $^1$H NMR (400 MHz, DMSO-d$_6$) δ 10.25 (s, 1H), 8.15 (s, 1H), 8.05 (s, 1H), 7.60-7.61 (m, 2H) 3.99-4.02 (m, 2H), 3.06 (s, 3H), 2.97-2.99 (m, 2H), 2.82 (s 3H), 2.60 (s, 3H), 1.75-1.78 (m, 2H), 1.59-1.63 (m, 3H);: LCMS (electrospray) m/z 469 (M + H)$^+$. |
| 139 | 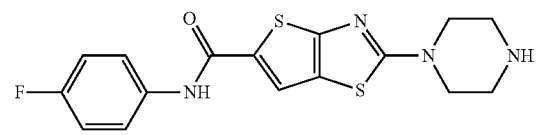 | Pale yellow solid; mp = 247.5° C.; $^1$H NMR (400 MHz, DMSO-d$_6$) δ 9.73 (s, 1H), 7.67 (s, 1H), 7.26 (d, J = 8.4 Hz, 2H), 6.73 (d, J = 8.4 Hz, 2H), 3.00-3.01 (m, 4H), 2.35-2.36 (m, 4H); LCMS (electrospray) m/z 362 (M + H)$^+$. |
| 140 | 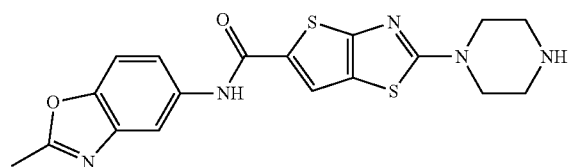 [SMILES: Cc1nc2cc(NC(=O)c3cc4sc(N5CCNCC5)nc4s3)ccc2o1] | Pale yellow solid; mp = 235.3° C.; $^1$H NMR (400 MHz, DMSO-d$_6$) δ 9.79 (s, 1H), 7.69 (s, 1H), 7.60 (s, 1H), 7.15-7.16 (m, 2H), 2.88-3.03 (m, 4H), 2.35-2.38 (m, 4H), 2.15 (s, 3H); LCMS (electrospray) m/z 399 (M + H)$^+$. |
| 141 | 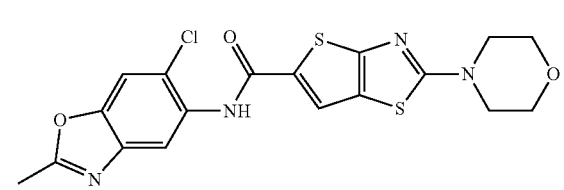 [SMILES: Cc1nc2cc(NC(=O)c3cc4sc(N5CCOCC5)nc4s3)c(Cl)cc2o1] | Pale yellow solid; mp = 277.0° C.; $^1$H NMR (400 MHz, DMSO-d$_6$) δ 10.10 (s, 1H), 8.14 (s, 1H), 8.00 (s, 1H), 7.81 (s, 1H), 3.73-3.75 (m, 4H), 3.53-3.55 (m, 4H), 2.63 (s, 3H); LCMS (electrospray) m/z 435 (M + H)$^+$. |

TABLE 1-continued

Structures and Characteristics of Compounds 1-360

| No. | Structure | NMR Characterization |
|---|---|---|
| 142 | 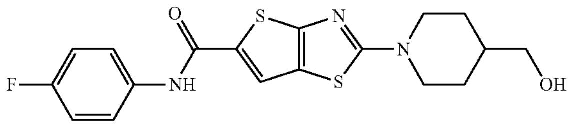 [SMILES: O=C(Nc1ccc(F)cc1)c1cc2sc(N3CCC(CO)CC3)nc2s1] | Pale yellow solid; mp = 246.3° C.; ¹H NMR (400 MHz, DMSO-d₆) δ 10.17 (brs, 1H, NH), 8.11 (s, 1H), 7.69-7.75 (m, 2H), 7.16-7.20 (m, 2H), 6.55 (brs, 1H, OH), 4.52-4.58 (m, 1H), 3.98-4.01 (m, 2H), 3.42 (s, 2H), 3.13-3.22 (m, 2H), 1.68-1.80 (m, 2H), 1.22-1.24 (m 2H); LCMS (electrospray) m/z 392 (M + H)⁺. |
| 143 | 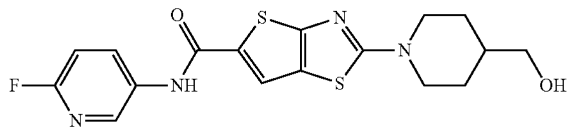 [SMILES: O=C(Nc1ccc(F)nc1)c1cc2sc(N3CCC(CO)CC3)nc2s1] | Pale yellow solid; mp = 240.8° C.; ¹H NMR (400 MHz, acetone-d₆) δ 9.77 (brs, 1H, NH), 8.52 (s, 1H), 8.32-8.38 (m, 1H), 8.00 (s, 1H), 7.06-7.08 (m, 1H), 4.09-4.12 (m, 2H), 3.78-4.82 (m, 1H), 3.46 (s, 2H), 3.16-3.23 (m, 2H), 1.80-1.90 (m, 2H), 1.30-1.40 (m, 2H); LCMS (electrospray) m/z 393 (M + H)⁺. |
| 144 | 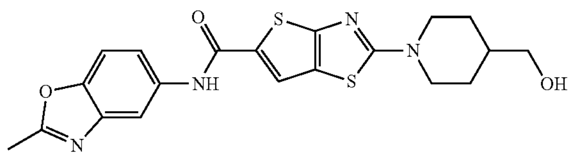 [SMILES: Cc1nc2cc(NC(=O)c3cc4sc(N5CCC(CO)CC5)nc4s3)ccc2o1] | White solid; mp = 196.4° C.; ¹H NMR (400 MHz, acetone-d₆) δ 9.61 (brs, 1H, NH), 8.13 (s, 1H), 8.00 (s, 1H), 7.65 (d, J = 9.2 Hz, 1H), 7.49 (d, J-9.2 Hz, 1H), 4.08-4.11 (m, 2H), 3.80-4.90 (m, 1H), 3.46 (s, 2H), 3.15-3.21 (m, 2H), 2.59 (s, 3H), 1.79-1.90 (m, 2H), 1.28-1.39 (m, 2H); LCMS (electrospray) m/z 429 (M + H)⁺. |
| 145 | 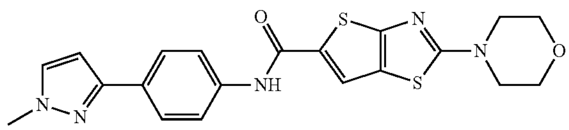 [SMILES: Cn1ccc(-c2ccc(NC(=O)c3cc4sc(N5CCOCC5)nc4s3)cc2)n1] | Ivory solid; mp = 314° C.; ¹H NMR (400 MHz, DMSO-d₆) δ 10.21 (s, 1H, NH), 8.17 (s, 1H), 7.69-7.75 (m, 5H), 6.64 (s, 1H), 3.87 (s, 3H), 3.72-3.76 (m, 4H), 3.52-3.56 (m, 4H); LCMS (electrospray) m/z 425 (M + H)⁺. |
| 146 | 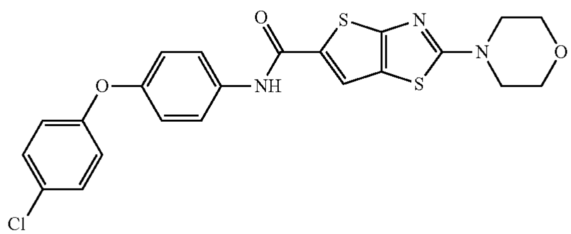 [SMILES: O=C(Nc1ccc(Oc2ccc(Cl)cc2)cc1)c1cc2sc(N3CCOCC3)nc2s1] | White solid; mp = 225° C.; ¹H NMR (400 MHz, DMSO-d₆) δ 10.22 (s, 1H, NH), 8.15 (s, 1H), 7.75 (d, J = 8.0 Hz, 2H), 7.41 (d, J = 8.0 Hz, 2H), 7.05 (d, J = 8.0 Hz, 2H), 7.02 (d, J = 8.0 Hz, 2H), 3.72-3.76 (m, 4H), 3.52-3.55 (m, 4H); LCMS (electrospray) m/z 472 (M + H)⁺. |
| 147 | 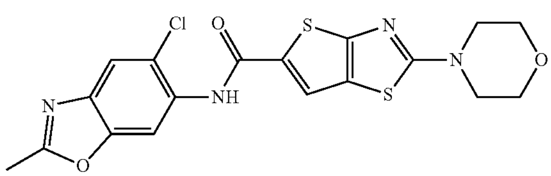 [SMILES: Cc1nc2cc(Cl)c(NC(=O)c3cc4sc(N5CCOCC5)nc4s3)cc2o1] | Pale yellow solid; mp = 275.3° C.; ¹H NMR (400 MHz, DMSO-d₆) δ 10.08 (s, 1H), 8.14 (s, 1H), 7.92 (s, 1H), 7.87 (s, 1H), 3.71-3.73 (m, 4H), 3.51-3.353 (m, 4H), 2.61 (s, 3H); LCMS (electrospray) m/z 435 (M + H)⁺. |
| 148 | 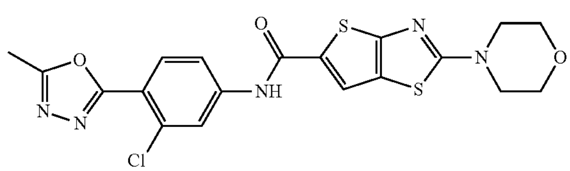 [SMILES: Cc1nnc(-c2ccc(NC(=O)c3cc4sc(N5CCOCC5)nc4s3)cc2Cl)o1] | Yellow solid: mp = 248° C.; ¹H NMR (400 MHz, acetone-d₆) δ 9.85 (s, 1H, NH), 8.21 (s, 1H), 8.10 (s, 1H), 7.89-7.95 (m, 2H), 3.79-3.81 (m, 4H), 3.58-3.61 (m, 4H), 2.59 (s, 3H); LCMS (electrospray) m/z 462 (M + H)⁺. |
| 149 | 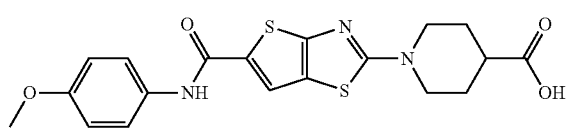 [SMILES: COc1ccc(NC(=O)c2cc3sc(N4CCC(C(=O)O)CC4)nc3s2)cc1] | Pale yellow solid; ¹H NMR (400 MHz, DMSO-d₆) δ 10.04 (s, 1H), 8.09 (s, 1H), 7.59 (d, J = 8.0 Hz, 2H), 6.92 (d, J = 8.0 Hz, 2H), 3.89-3.92 (m, 2H), 3.74 (s, 3H), 1.93-1.96 (m, 3H), 1.61-1.64 (m, 2H), 1.19-1.23 (m, 2H); LCMS (electrospray) m/z 417 (M + H)⁺. |
| 150 | 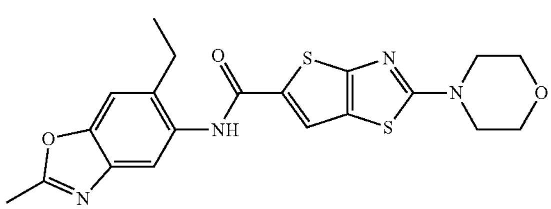 [SMILES: CCc1cc2oc(C)nc2cc1NC(=O)c1cc2sc(N3CCOCC3)nc2s1] | Pale yellow solid; mp = 244.0° C.; ¹H NMR (400 MHz, DMSO-d₆) δ 9.93 (s, 1H), 8.11 (s, 1H), 7.57 (s, 1H), 7.53 (s, 1H), 3.73-3.75 (m, 4H), 3.52-3.54 (m, 4H), 2.67 (q, J = 7.2 Hz, 2H), 2.60 (s, 3H), 1.14 (t, J = 7.2 Hz, 3H); LCMS (electrospray) m/z 429 (M + H)⁺. |

TABLE 1-continued

Structures and Characteristics of Compounds 1-360

| No. | Structure | NMR Characterization |
|---|---|---|
| 151 | 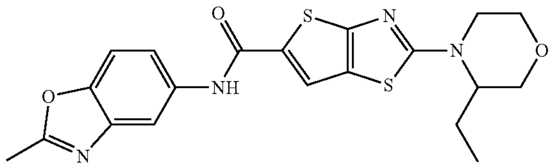 | Ivory solid; mp = 176° C.; ¹H NMR (400 MHz, acetone-d₆) δ 9.52 (s, 1H, NH), 8.14 (s, 1H), 8.00 (s, 1H), 7.63-7.66 (m, 1H), 7.51 (d, J = 8.8 Hz, 1H), 3.75-3.99 (m, 4H), 3.45-3.73 (m, 3H), 2.58 (s, 3H), 1.82-2.02 (m, 2H), 0.99 (t, J = 7.6 Hz, 3H); LCMS (electrospray) m/z 429 (M + H)⁺. |
| 152 | 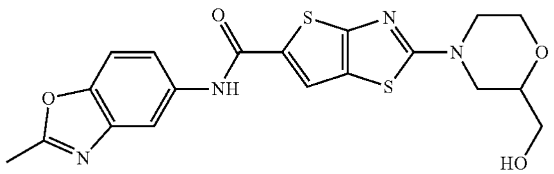 [SMILES: Cc1nc2cc(NC(=O)c3cc4sc(N5CCOC(CO)C5)nc4s3)ccc2o1] | Ivory solid; ¹H NMR (400 MHz, DMSO-d₆) δ 10.28 (s, 1H, NH), 8.17 (s, 1H), 8.04 (s, 1H), 7.57-7.60 (m, 2H), 4.88 (s, 1H, OH), 3.89-3.97 (m, 2H), 3.77-3.80 (m, 1H), 3.50-3.68 (m, 3H), 3.41-3.44 (m, 1H), 3.15-3.20 (m, 1H), 2.98-3.04 (m, 1H), 2.59 (s, 3H); LCMS (electrospray) m/z 431 (M + H)⁺. |
| 153 | 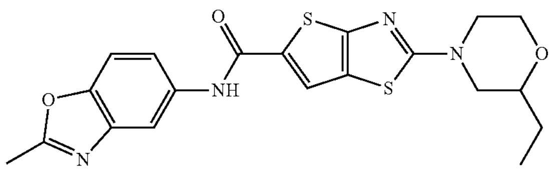 [SMILES: CCC1CN(c2nc3sc(C(=O)Nc4ccc5oc(C)nc5c4)cc3s2)CCO1] | White solid; mp = 214° C.; ¹H NMR (400 MHz, acetone-d₆) δ 9.54 (s, 1H, NH), 8.14 (s, 1H), 8.01 (d, J = 2.0 Hz, 1H), 7.65 (dd, J = 8.8 Hz, 2.0 Hz, 1H), 7.51 (d, J = 8.8 Hz, 1H), 4.00-4.03 (m, 1H), 3.91-3.94 (m, 1H), 3.82-3.85 (m, 1H), 3.66-3.72 (m, 1H), 3.47-3.51 (m, 1H), 3.24-3.31 (m, 1H), 2.92-2.98 (m, 1H), 2.49 (s, 3H), 1.56-1.61 (m, 2H), 1.00 (t, J = 7.6 Hz, 3H); LCMS (electrospray) m/z 429 (M + H)⁺. |
| 154 | 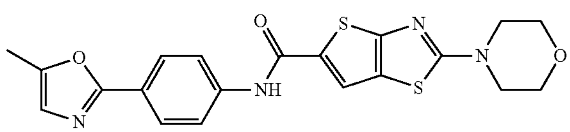 [SMILES: Cc1cnc(-c2ccc(NC(=O)c3cc4sc(N5CCOCC5)nc4s3)cc2)o1] | Pale yellow solid; mp = 287.3° C.; ¹H NMR (400 MHz, DMSO-d₆) δ 10.38 (s, 1H), 8.20 (s, 1H), 7.85-7.92 (m, 4H), 6.56 (s, 1H), 3.73-3.76 (m, 4H), 3.54-3.56 (m, 4H), 2.38 (s, 3H); LCMS (electrospray) m/z 426 (M + H)⁺ 426. |
| 155 | 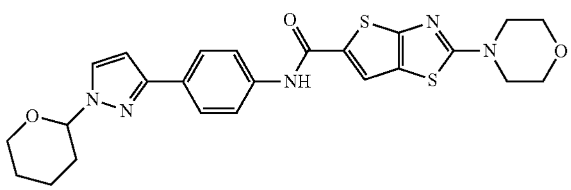 [SMILES: O=C(Nc1ccc(-c2ccn(C3CCCCO3)n2)cc1)c1cc2sc(N3CCOCC3)nc2s1] | Ivory solid; mp = 293° C.; ¹H NMR (400 MHz, DMSO-d₆) δ 10.29 (s, 1H, NH), 8.17 (s, 1H), 7.91 (d, J = 2.8 Hz, 1H), 7.74-7.80 (m, 4H), 6.73 (d, J = 2.8 Hz, 1H), 5.40-5.43 (m, 1H), 3.92-3.97 (m, 1H), 3.67-3.75 (m, 4H), 3.58-3.66 (m, 1H), 3.54-3.58 (m, 4H), 2.11-2.15 (m, 1H), 1.92-1.98 (m, 2H), 1.61-1.68 (m, 1H), 1.54-1.57 (m, 2H); LCMS (electrospray) m/z 496 (M + H)⁺. |
| 156 | 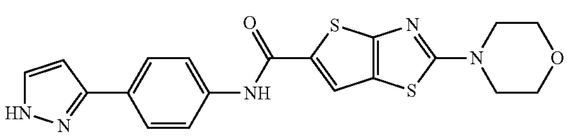 [SMILES: O=C(Nc1ccc(-c2cc[nH]n2)cc1)c1cc2sc(N3CCOCC3)nc2s1] | White solid; mp = 319° C.; ¹H NMR (400 MHz, DMSO-d₆) δ 12.85 (brs, 1H, NH), 10.23 (s, 1H, NH), 8.17 (s, 1H), 7.76 (s, 4H), 7.68 (d, J = 2.0 Hz, 1H), 6.66 (d, J = 2.0 Hz, 1H), 3.72-3.76 (m, 4H), 3.51-3.56 (m, 4H); LCMS (electrospray) m/z 411 (M + H)⁺. |
| 157 | 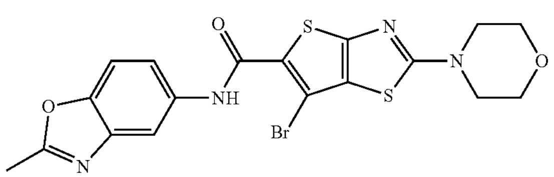 [SMILES: Cc1nc2cc(NC(=O)c3sc4nc(N5CCOCC5)sc4c3Br)ccc2o1] | Ivory solid; mp = 269° C.; ¹H NMR (400 MHz, DMSO-d₆) δ 10.13 (s, 1H, NH), 8.00 (s, 1H), 7.64 (d, J = 8.8 Hz, 1H), 7.56 (d, J = 8.8 Hz, 1H), 3.72-3.76 (m, 4H), 3.54-3.58 (m, 4H), 2.60 (s, 3H); LCMS (electrospray) m/z 478 (M + H)⁺. |
| 158 | 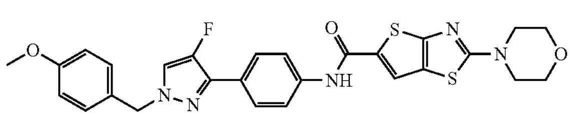 [SMILES: COc1ccc(Cn2cc(F)c(-c3ccc(NC(=O)c4cc5sc(N6CCOCC6)nc5s4)cc3)n2)cc1] | Pale yellow solid; ¹H NMR (400 MHz, acetone-d₆) δ 9.59 (s, 1H), 8.02 (d, J = 1.6 Hz, 1H), 7.90-7.92 (m, 2H), 7.50 (dd, J = 4.8, 1.6 Hz, 1H), 7.37 (d, J = 7.6 Hz, 2H), 6.99 (d, J = 7.6 Hz, 2H), 6.82-6.84 (m, 2H), 5.27 (s, 2H), 3.79-3.82 (m, 4H), 3.75 (s, 3H), 3.58-3.61 (m, 4H); LCMS (electrospray) m/z 550 (M + H)⁺. |
| 159 | 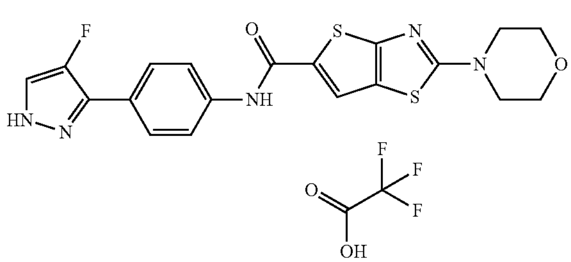 [SMILES: O=C(Nc1ccc(-c2n[nH]cc2F)cc1)c1cc2sc(N3CCOCC3)nc2s1 ; O=C(O)C(F)(F)F] | White solid; mp = 287.2° C.; ¹H NMR (400 MHz, DMSO-d₆) δ 10.26 (s, 1H), 8.16 (s, 1H), 7.78-7.80 (m, 3H), 7.68 (d, J = 8.8 Hz, 2H), 3.71-3.73 (m, 4H), 3.51-3.53 (m, 4H); LCMS (electrospray) m/z 430 (M + H)⁺. |

TABLE 1-continued

Structures and Characteristics of Compounds 1-360

| No. | Structure | NMR Characterization |
|---|---|---|
| 160 | 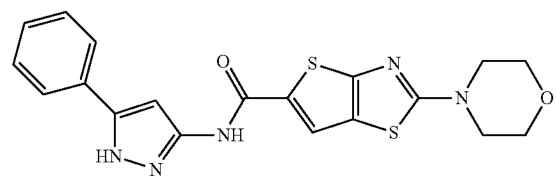 [SMILES: O=C(Nc1cc(-c2ccccc2)[nH]n1)c1cc2sc(N3CCOCC3)nc2s1] | Pale yellow solid; mp = 305° C.; $^1$H NMR (400 MHz, DMSO-d$_6$) δ 12.92 (s, 1H, NH), 10.89 (s, 1H, NH), 8.23 (s, 1H), 7.72-7.73 (m, 2H), 7.33-7.46 (m, 3H), 6.94 (s, 1H), 3.71-3.73 (m, 4H), 3.51-3.53 (m, 4H); LCMS (electrospray) m/z 412 (M + H)$^+$. |
| 161 | 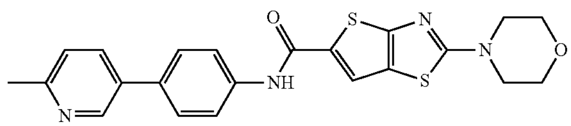 [SMILES: Cc1ccc(-c2ccc(NC(=O)c3cc4sc(N5CCOCC5)nc4s3)cc2)cn1] | Pale yellow solid; mp = 292° C.; $^1$H NMR (400 MHz, DMSO-d$_6$) δ 10.29 (s, 1H, NH), 8.74 (d, J = 2.4 Hz, 1H), 8.18 (s, 1H), 7.94 (dd, J = 8.0 Hz, 2.4 Hz, 1H), 7.82 (d, J = 8.4 Hz, 2H), 7.68 (d, J = 8.4 Hz, 2H), 7.31 (d, J = 8.0 Hz, 1H), 3.71-3.74 (m, 4H), 3.51-3.54 (m, 4H), 3.15 (s, 3H); LCMS (electrospray) m/z 437 (M + H)$^+$. |
| 162 | 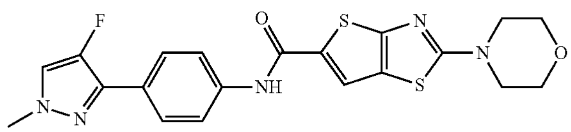 [SMILES: Cn1cc(F)c(-c2ccc(NC(=O)c3cc4sc(N5CCOCC5)nc4s3)cc2)n1] | Bright yellow solid; mp = 280.5° C.; $^1$H NMR (400 MHz, DMSO-d$_6$) δ 10.26 (s, 1H), 8.18 (s, 1H), 7.92 (d, J = 4.8 Hz, 1H), 7.78 (d, J = 8.8 Hz, 2H), 7.69 (d, J = 8.8 Hz, 2H), 3.81 (s, 3H), 3.73-3.75 (m, 4H), 3.53-3.55 (m, 4H); LCMS (electrospray) m/z 444 (M + H)$^+$. |
| 163 | 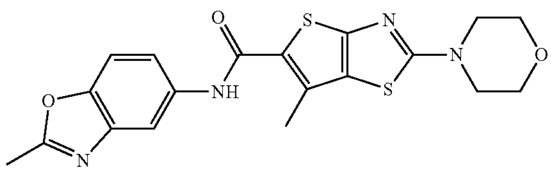 [SMILES: Cc1nc2cc(NC(=O)c3sc4nc(N5CCOCC5)sc4c3C)ccc2o1] | Ivory solid; mp = 226° C.; $^1$H NMR (400 MHz, DMSO-d$_6$) δ 9.91 (s, 1H, NH), 7.97 (s, 1H), 7.59 (d, J = 8.8 Hz, 1H), 7.54 (d, J = 8.8 Hz, 1H), 3.71-3.74 (m, 4H), 3.50-3.53 (m, 4H), 2.58 (s, 3H), 2.54 (s, 3H); LCMS (electrospray) m/z 415 (M + H)$^+$. |
| 164 | 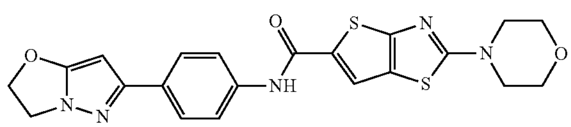 [SMILES: O=C(Nc1ccc(-c2cc3n(n2)CCO3)cc1)c1cc2sc(N3CCOCC3)nc2s1] | Yellow solid; mp = 361.2° C.; $^1$H NMR (400 MHz, DMSO-d$_6$) δ 1H), 8.17 (s, 1H), 7.75-7.67 (m, 4H), 5.88 (s, 1H), 5.07 (t, J = 8.0 Hz, 2H), 4.29 (t, J = 8.0 Hz, 2H), 3.76-3.71 (m, 4H), 3.56-3.51 (m, 4H); LCMS (electrospray) m/z 454 (M + H)$^+$. |
| 165 | 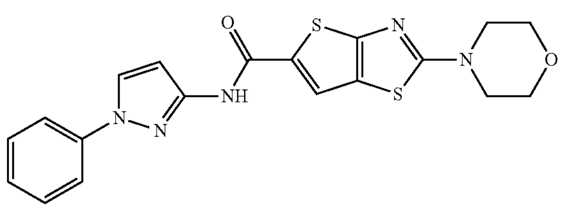 [SMILES: O=C(Nc1ccn(-c2ccccc2)n1)c1cc2sc(N3CCOCC3)nc2s1] | Pale yellow solid; mp = 257.8° C.; $^1$H NMR (400 MHz, acetone-d$_6$) δ 10.01 (brs, 1H, NH), 8.25 (d, J = 1.6 Hz, 1H), 8.22 (s, 1H) 7.77-7.79 (m, 2H), 7.47-7.50 (m, 2H), 7.27-7.29 (m, 1H) 7.00 (d, J = 1.6 Hz, 1H), 3.80-3.82 (m, 4H), 3.59-3.61 (m, 4H); LCMS (electrospray) m/z 412 (M + H)$^+$. |
| 166 | 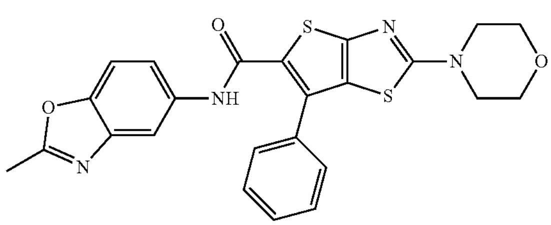 [SMILES: Cc1nc2cc(NC(=O)c3sc4nc(N5CCOCC5)sc4c3-c3ccccc3)ccc2o1] | Ivory solid; mp = 285° C.; $^1$H NMR (400 MHz, CDCl$_3$) δ 7.57-7.62 (m, 5H), 7.34 (brs, 1H, NH), 7.33 (d, J = 2.0 Hz, 1H), 7.30 (d, J = 8.8 Hz, 1H), 7.22 (dd, J = 8.8, 2.0 Hz, 1H), 3.80-3.84 (m, 4H), 3.55-3.59 (m, 4H), 2.59 (s, 3H); LCMS (electrospray) m/z 476 (M + H)$^+$. |
| 167 | 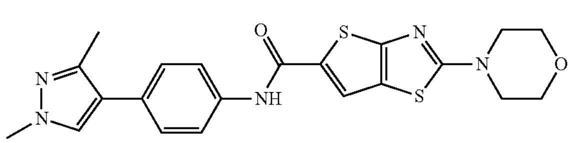 [SMILES: Cc1nn(C)cc1-c1ccc(NC(=O)c2cc3sc(N4CCOCC4)nc3s2)cc1] | Ivory solid; mp = 245° C.; $^1$H NMR (400 MHz, DMSO-d$_6$) δ 10.19 (s, 1H, NH), 8.16 (s, 1H), 7.84 & 7.54 (s, 1H), 7.70-7.74 (m, 2H), 7.35-7.40 (m, 2H), 3.77 (s, 3H), 3.71-3.75 (m, 4H), 3.51-3.55 (m, 4H), 2.36 (s, 3H); LCMS (electrospray) m/z 440 (M + H)$^+$. |
| 168 | 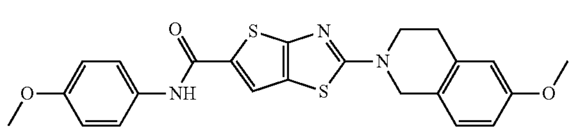 | Pale yellow solid; $^1$H NMR (400 MHz, DMSO-d$_6$) δ 10.02 (s, 1H), 8.10 (s, 1H), 7.58 (d, J = 8.8 Hz, 2H), 7.20 (d, J = 8.8 Hz, 1H), 6.90 (d, J = 8.8 Hz, 2H), 6.80 (d, J = 8.8 Hz, 2H), 4.65 (s, 2H), 3.72-3.77 (m, 2H), 3.72 (s, 6H), 2.94-2.97 (m, 2H); LCMS (electrospray) m/z 451 (M + H)$^+$. |

TABLE 1-continued

Structures and Characteristics of Compounds 1-360

| No. | Structure | NMR Characterization |
|---|---|---|
| 169 | 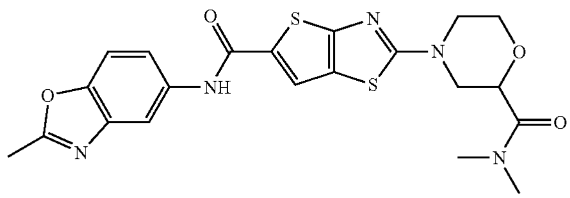 [SMILES: Cc1nc2cc(NC(=O)c3cc4sc(N5CCOC(C(=O)N(C)C)C5)nc4s3)ccc2o1] | White solid; mp = 247.5° C.; $^1$H NMR (400 MHz, DMSO-d$_6$) δ 10.26 (s, 1H), 8.15 (s, 1H), 8.03 (s, 1H), 7.59-7.62 (m, 2H), 4.23-4.45 (m, 1H), 3.93-3.96 (m, 2H), 3.73-3.82 (m, 4H), 3.03 (s, 3H), 2.83 (s, 3H), 2.58 (s, 3H); LCMS (electrospray) m/z 471 (M + H)$^+$. |
| 170 | 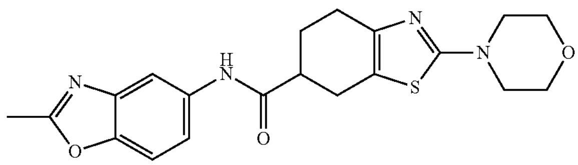 | White solid; mp = 239° C.; $^1$H NMR (400 MHz, CDCl$_3$) δ 7.79 (d, J = 1.6 Hz, 1H), 7.48 (dd, J = 8.8, 1.6 Hz, 1H), 7.46 (brs, 1H, NH), 7.39 (d, J = 8.8 Hz, 1H), 3.77-3.82 (m, 4H), 3.38-3.42 (m, 4H), 2.91-3.07 (m, 1H), 2.86-2.92 (m, 1H), 2.66-2.80 (m, 3H), 2.62 (s, 3H), 2.20-2.25 (m, 1H), 2.02-2.11 (m, 1H); LCMS (electrospray) m/z 399 (M + H)$^+$. |
| 171 | 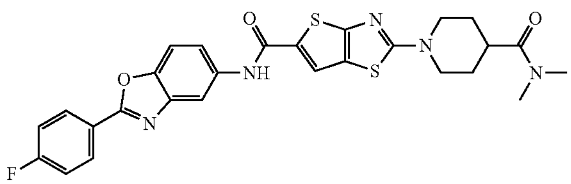 [SMILES: CN(C)C(=O)C1CCN(c2nc3sc(C(=O)Nc4ccc5oc(-c6ccc(F)cc6)nc5c4)cc3s2)CC1] | Ivory solid; mp = 323° C.; $^1$H NMR (400 MHz, DMSO-d$_6$) δ 10.33 (s, 1H, NH), 8.24-8.29 (m, 2H), 8.20 (d, J = 2.0 Hz, 1H), 8.16 (s, 1H), 7.77 (d, J = 8.8 Hz, 1H), 7.69 (dd, J = 8.8 2.0 Hz, 1H), 7.44-7.48 (m, 2H), 3.97-4.03 (m, 2H), 3.21-3.24 (m, 2H), 3.06 (s, 3H), 2.95-3.01 (m, 1H), 2.82 (s, 3H), 1.74-1.79 (m, 2H), 1.60-1.66 (m, 2H); LCMS (electrospray) m/z 549 (M + H)$^+$. |
| 172 | 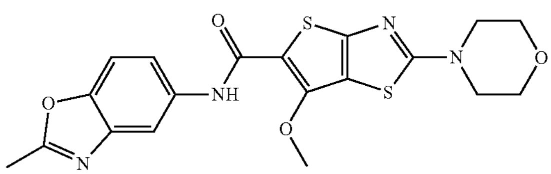 [SMILES: COc1c(C(=O)Nc2ccc3oc(C)nc3c2)sc2nc(N3CCOCC3)sc12] | Ivory solid; mp = 269° C.; $^1$H NMR (400 MHz, CDCl$_3$) δ 8.95 (s, 1H, NH), 7.88 (d, J = 2.0 Hz, 1H), 7.56 (dd, J = 8.8, 2.0 Hz, 1H), 7.40 (d, J = 8.8 Hz, 1H), 4.23 (s, 3H), 3.81-3.86 (m, 4H), 3.56-3.61 (m, 4H), 2.62 (s, 3H); LCMS (electrospray) m/z 430 (M + H)$^+$. |
| 173 | 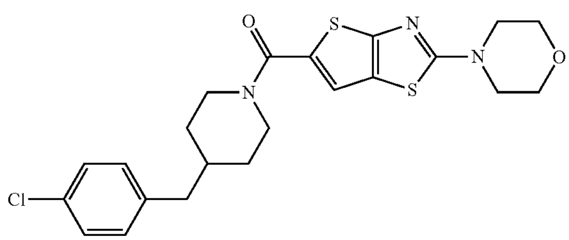 [SMILES: O=C(c1cc2sc(N3CCOCC3)nc2s1)N1CCC(Cc2ccc(Cl)cc2)CC1] | Ivory solid; mp = 167.2° C.; $^1$H NMR (400 MHz, acetone-d$_6$) δ 7.50 (s, 1H), 7.30-7.33 (m, 2H), 7.23-7.26 (m, 2H), 4.42-4.45 (m, 2H), 3.77-3.80 (m, 4H), 3.53-3.56 (m, 4H), 2.93-2.99 (m, 2H), 2.60 (d, J = 7.2 Hz, 2H), 1.92-3.87 (m, 1H), 1.70-1.72 (m, 2H), 1.25-1.32 (m, 2H); LCMS (electrospray) m/z 462 (M + H)$^+$. |
| 174 | 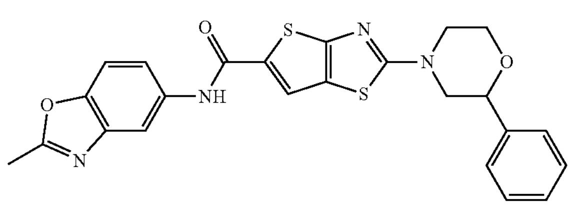 [SMILES: Cc1nc2cc(NC(=O)c3cc4sc(N5CCOC(c6ccccc6)C5)nc4s3)ccc2o1] | Pale yellow solid; mp = 223.5° C.; $^1$H NMR (400 MHz, DMSO-d$_6$) δ 10.29 (brs, 1H, NH), 8.19 (s, 1H), 8.05 (s, 1H), 7.61-7.64 (m, 2H), 7.35-7.48 (m, 5H), 4.67-4.70 (m, 1H), 4.11-4.15 (m, 1H), 4.00-4.04 (m, 1H), 3.80-3.90 (m, 2H), 3.17-3.23 (m, 2H), 2.60 (s, 3H); LCMS (electrospray) m/z 477 (M + H)$^+$. |
| 175 | 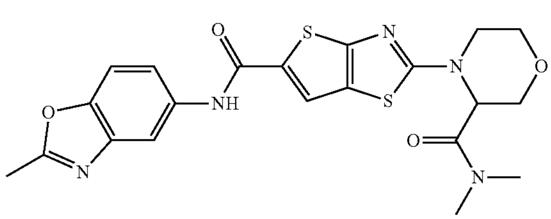 [SMILES: Cc1nc2cc(NC(=O)c3cc4sc(N5CCOCC5C(=O)N(C)C)nc4s3)ccc2o1] | Pale yellow solid, mp = 288.6° C.; $^1$H NMR (400 MHz, DMSO-d$_6$) δ 10.30 (brs, 1H, NH), 8.17 (s, 1H), 8.05 (s, 1H), 7.60-7.63 (m, 2H), 5.13-5.14 (m, 1H), 4.14-4.17 (m, 1H), 3.92-4.00 (m, 2H), 3.82-3.86 (m, 1H), 3.62-3.63 (m, 1H), 3.46-3.50 (m, 1H), 3.10 (s, 3H), 2.84 (s, 3H), 2.60 (s, 3H); LCMS (electrospray) m/z 472 (M + H)$^+$. |

TABLE 1-continued

Structures and Characteristics of Compounds 1-360

| No. | Structure | NMR Characterization |
|---|---|---|
| 176 | 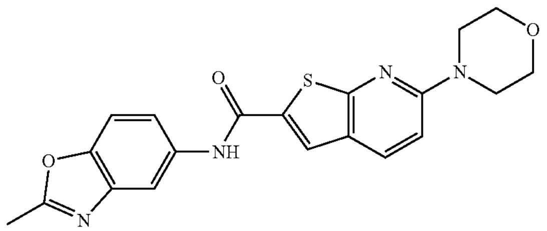 [SMILES: Cc1nc2cc(NC(=O)c3cc4ccc(N5CCOCC5)nc4s3)ccc2o1] | Pale yellow solid; $^1$H NMR (400 MHz, acetone-$d_6$) δ 9.80 (brs, 1H, NH), 8.23-8.25 (m, 1H), 8.17-8.20 (m, 1H), 8.09 (s, 1H), 7.73-7.76 (m, 1H), 7.55 (d, J = 8.8 Hz, 1H), 7.09 (d, J = 8.8 Hz, 1H), 3.77-3.79 (m, 4H), 3.59-3.61 (m, 4H), 2.60 (s, 3H); LCMS (electrospray) m/z 395 (M + H)$^+$. |
| 177 | 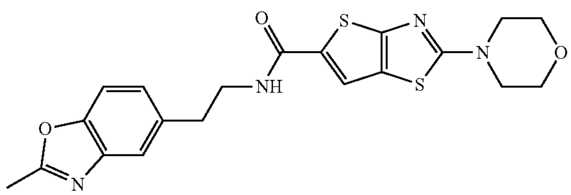 [SMILES: Cc1nc2cc(CCNC(=O)c3cc4sc(N5CCOCC5)nc4s3)ccc2o1] | Gray solid; mp = 219.4° C.; $^1$H NMR (400 MHz, acetone-$d_6$) δ 7.72 (s, 1H), 7.69 (brs, 1H), 7.50 (brs, 1H), 7.46 (d, J = 8.0 Hz, 1H), 7.23 (dd, J = 8.4, 1.6 Hz, 1H), 3.76-3.82 (m, 4H), 3.63 (q, J = 6.8 Hz, 2H), 3.52-3.57 (m, 4H), 3.01 (t, J = 7.6 Hz, 2H), 2.56 (s, 3H); LCMS (electrospray) m/z 429 (M + H)$^+$. |
| 178 | 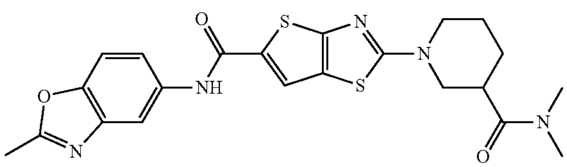 | Yellow solid; mp = 133.6° C.; $^1$H NMR (400 MHz, acetone-$d_6$) δ 9.50 (s, 1H), 8.14 (s, 1H), 7.99 (s, 1H), 7.64 (dd, J = 8.8, 2.0 Hz, 1H), 7.50 (d, J = 8.8 Hz, 1H), 4.01-4.12 (m, 2H), 3.19-3.34 (m, 2H), 3.14 (s, 3H), 2.98-3.04 (m, 1H), 2.82 (s, 3H), 2.59 (s, 3H), 1.98-2.03 (m, 1H), 1.80-1.87 (m, 1H), 1.69-1.78 (m, 2H); LCMS (electrospray) m/z 470 (M + H)$^+$. |
| 179 | 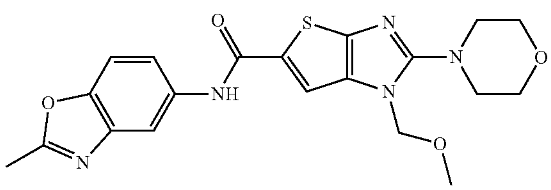 [SMILES: COCn1c(N2CCOCC2)nc2sc(C(=O)Nc3ccc4oc(C)nc4c3)cc21] | Pale brown solid; mp = 117.2° C.; $^1$H NMR (400 MHz, CDCl$_3$) δ 7.90 (d, J = 2.0 Hz, 1H), 7.86 (s, 1H), 7.65 (s, 1H), 7.52 (dd, J = 8.8, 2.0 Hz, 1H), 7.40 (d, J = 8.8 Hz, 1H), 5.25 (s, 2H), 3.84-3.87 (m, 4H), 3.43 (s, 3H), 3.37-3.42 (m, 4H), 2.63 (s, 3H); LCMS (electrospray) m/z 428 (M + H)$^+$. |
| 180 | 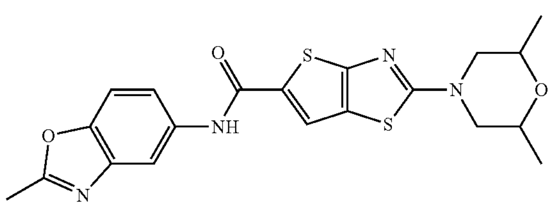 | White solid; mp = 274° C.; $^1$H NMR (400 MHz, DMSO-$d_6$) δ 10.27 (s, 1H, NH), 8.17 (s, 1H), 8.06 (s, 1H), 7.60-7.62 (m, 2H), 3.84-3.87 (m, 2H), 3.70-3.72 (m, 2H), 2.81-2.87 (m, 2H), 2.60 (s, 3H), 1.17 (d, J = 5.6 Hz, 6H); LCMS (electrospray) m/z 429 (M + H)$^+$. |
| 181 | 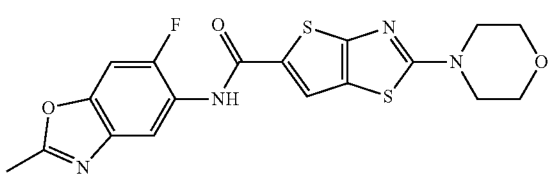 | Pale yellow solid; mp = 287° C.; $^1$H NMR (400 MHz, DMSO-$d_6$) δ 10.12 (s, 1H, NH), 8.13 (s, 1H), 7.76-7.80 (m, 2H), 3.71-3.74 (m, 4H), 3.51-3.54 (m, 4H), 2.59 (s, 3H); LCMS (electrospray) m/z 419 (M + H)$^+$. |
| 182 | 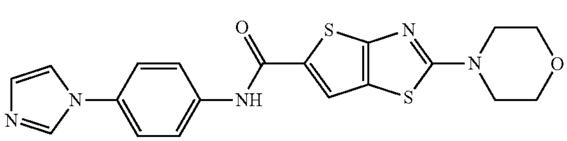 [SMILES: O=C(Nc1ccc(-n2ccnc2)cc1)c1cc2sc(N3CCOCC3)nc2s1] | Ivory solid; mp = 266° C.; $^1$H NMR (400 MHz, DMSO-$d_6$) δ 10.33 (s, 1H), 8.19 (s, 1H), 8.16 (s, 1H), 7.82 (d, J = 8.8 Hz, 2H), 7.68-7.69 (m, 1H), 7.61 (d, J = 8.8 Hz, 2H), 7.07-7.08 (m, 1H), 3.71-3.74 (m, 4H), 3.51-3.54 (m, 4H); LCMS (electrospray) m/z 412 (M + H)$^+$. |
| 183 | 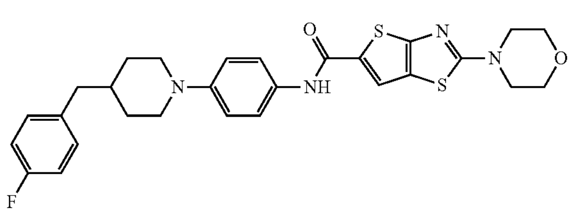 [SMILES: O=C(Nc1ccc(N2CCC(Cc3ccc(F)cc3)CC2)cc1)c1cc2sc(N3CCOCC3)nc2s1] | Pale yellow solid; mp = 246° C.; $^1$H NMR (400 MHz, DMSO-$d_6$) δ 9.96 (s, 1H), 8.09 (s, 1H), 7.50 (d, J = 9.2 Hz, 2H), 7.22 (dd, J = 8.8 Hz, 5.6 Hz, 2H), 7.10 (dd, J = 8.8 Hz, 8.8 Hz, 2H), 6.89 (d, J = 9.2 Hz, 2H), 3.73-3.75 (m, 4H), 3.60-3.63 (m, 2H), 3.51-3.53 (m, 4H), 3.36-3.38 (m, 1H), 2.54-2.59 (m, 3H), 1.61-1.64 (m, 3H), 1.26-1.31 (m, 2H); LCMS (electrospray) m/z 537 (M + H)$^+$. |

TABLE 1-continued

Structures and Characteristics of Compounds 1-360

| No. | Structure | NMR Characterization |
|---|---|---|
| 184 | 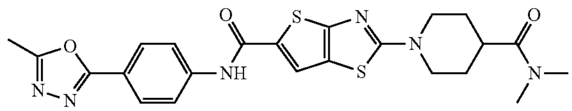 | Pale yellow solid; ¹H NMR (400 MHz, DMSO-$d_6$) δ 10.42 (s 1H), 8.18 (s, 1H), 7.91-7.95 (m, 4H), 3.97-4.01 (m, 2H), 3.05 (s, 3H), 2.94-3.00 (m, 2H), 2.80 (s, 3H), 2.55 (s, 3H), 1.74-1.77 (m, 2H), 1.55-1.65 (m, 3H); LCMS (electrospray) m/z 496 (M + H)⁺. |
| 185 | 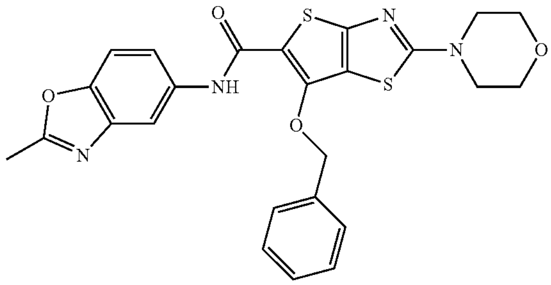 [SMILES: Cc1nc2cc(NC(=O)c3sc4nc(N5CCOCC5)sc4c3OCc3ccccc3)ccc2o1] | Pale yellow solid; ¹H NMR (400 MHz, DMSO-$d_6$) δ 9.29 (s, 1H), 7.82 (s, 1H), 7.54-7.58 (m, 3H), 7.40-7.45 (m, 3H), 7.24-7.26 (m, 1H), 5.53 (s, 2H), 3.71-3.74 (m, 4H), 3.53-3.55 (m, 4H), 2.57 (s, 3H); LCMS (electrospray) m/z 506 (M + H)⁺. |
| 186 | 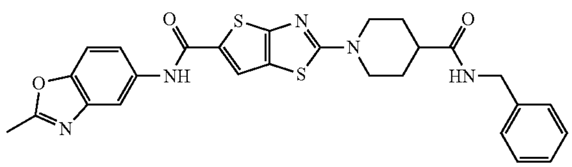 [SMILES: Cc1nc2cc(NC(=O)c3cc4sc(N5CCC(C(=O)NCc6ccccc6)CC5)nc4s3)ccc2o1] | Pale yellow solid; mp = 264.9° C.; ¹H NMR (400 MHz, DMSO-$d_6$) δ 10.23 (s, 1H), 8.38-8.41 (m, 1H), 8.14 (s, 1H), 8.04 (s, 1H), 7.56-7.59 (m, 2H), 7.28-7.32 (m, 2H), 7.21-7.23 (m, 3H), 4.25-4.27 (m, 2H), 3.98-4.02 (m, 2H), 3.18-3.24 (m, 2H), 2.58 (s, 3H), 1.84-1.87 (m, 2H), 1.63-1.72 (m, 3H); LCMS (electrospray) m/z 531 (M + H)⁺. |
| 187 | 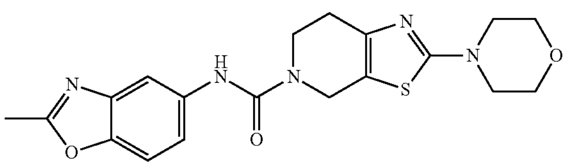 [SMILES: Cc1nc2cc(NC(=O)N3CCc4nc(N5CCOCC5)sc4C3)ccc2o1] | Ivory solid; mp = 104° C.; ¹H NMR (400 MHz, CDCl3) δ 7.58 (d, J = 2.0 Hz, 1H), 7.37 (d, J = 8.8 Hz, 1H), 7.32 (dd, J = 8.8, 2.0 Hz, 1H), 6.48 (s, 1H), 4.58 (s, 2H), 3.77-3.82 (m, 6H), 3.40-3.44 (m, 4H), 2.76-2.81 (m, 2H), 2.61 (s, 3H); LCMS (electrospray) m/z 399 (M + H)⁺. |
| 188 | 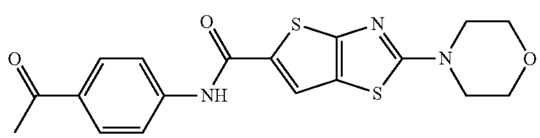 [SMILES: CC(=O)c1ccc(NC(=O)c2cc3sc(N4CCOCC4)nc3s2)cc1] | Ivory solid; mp = 248° C.; ¹H NMR (400 MHz, DMSO-$d_6$) δ 10.48 (s, 1H), 8.22 (s, 1H), 7.96 (d, J = 8.8 Hz, 2H), 7.86 (d, J = 8.8 Hz, 2H), 3.71 (m, 4H), 3.52 3.56 (m, 4H), 2.54 (s, 3H); LCMS (electrospray) m/z 387 (M + H)⁺. |
| 189 | 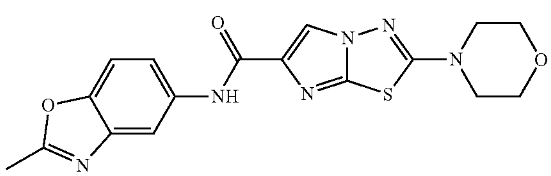 [SMILES: Cc1nc2cc(NC(=O)c3cn4nc(N5CCOCC5)sc4n3)ccc2o1] | Ivory solid; mp = 311° C.; ¹H NMR (400 MHz, DMSO-$d_6$) δ 10.12 (s, 1H), 8.42 (s, 1H), 8.20 (d, J = 2.0 Hz, 1H), 7.76 (dd, J = 8.8 Hz, 1H), 7.59 (d, J = 8.8 Hz, 1H), 3.72-3.76 (m, 4H), 3.46-3.50 (m, 4H), 2.59 (s, 3H); LCMS (electrospray) m/z 384 (M + H)⁺. |
| 190 | 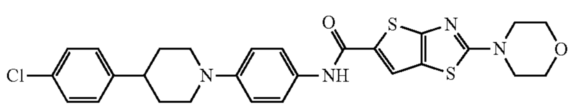 [SMILES: O=C(Nc1ccc(N2CCC(c3ccc(Cl)cc3)CC2)cc1)c1cc2sc(N3CCOCC3)nc2s1] | Pale yellow solid; mp = 281.1° C.; ¹H NMR (400 MHz, DMSO-$d_6$) δ 9.98 (brs, 1H), 8.09 (s, 1H), 7.52 (d, J = 9.2 Hz, 2H), 7.29-7.35 (m, 4H), 6.95 (d, J = 9.2 Hz, 2H), 3.71-3.73 (m, 4H), 3.58-3.60 (m, 1H), 3.50-3.52 (m, 4H), 2.66-2.74 (m, 4H), 1.81-1.89 (m, 2H), 1.70-1.80 (m, 2H); LCMS (electrospray) m/z 539, 541 (M + H)⁺ (Cl⁻ isotope pattern). |
| 191 | 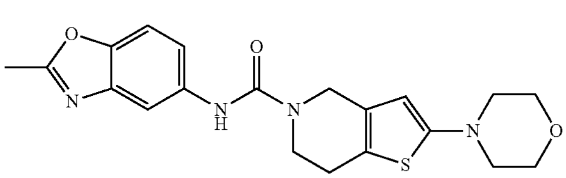 [SMILES: Cc1nc2cc(NC(=O)N3CCc4sc(N5CCOCC5)cc4C3)ccc2o1] | White solid; mp = 171.7° C.; ¹H NMR (400 MHz, acetone-$d_6$) δ 8.10 (s, 1H), 7.88 (d, J = 2.0 Hz, 1H), 7.44-7.37 (m, 2H), 5.90 (s, 1H), 4.49-4.47 (m, 2H), 3.84 (t, J = 5.6 Hz, 2H), 3.72-3.76 (m, 4H), 3.00-3.04 (m, 4H), 2.71-2.76 (m, 2H), 2.55 (s, 3H); LCMS (electrospray) m/z 399 (M + H)⁺. |
| 192 | 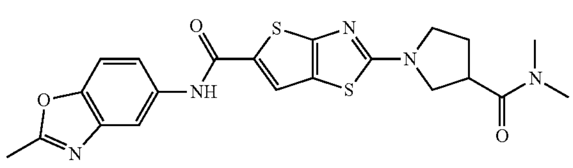 | Ivory solid; mp = 274.0° C.; ¹H NMR (400 MHz, DMSO-$d_6$) δ 10.23 (s, 1H), 8.14 (s, 1H), 8.04 (s, 1H), 7.56-7.63 (m, 2H), 3.59-3.70 (m, 3H), 3.50-3.57 (m, 2H), 3.07 (s, 3H), 2.85 (s, 3H), 2.60 (s, 3H), 2.28-2.34 (m, 1H), 2.08-2.14 (m, 1H); LCMS (electrospray) m/z 456 (M + H)⁺. |

TABLE 1-continued

Structures and Characteristics of Compounds 1-360

| No. | Structure | NMR Characterization |
|---|---|---|
| 193 | 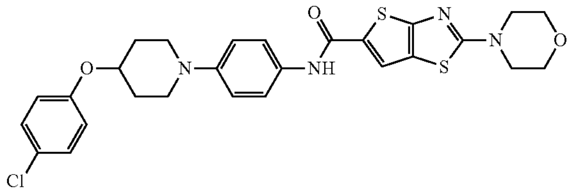 [SMILES: O=C(Nc1ccc(N2CCC(Oc3ccc(Cl)cc3)CC2)cc1)c1cc2sc(N3CCOCC3)nc2s1] | Pale yellow solid; $^1$H NMR (400 MHz, DMSO-d$_6$) δ 9.98 (s, 1H), 8.10 (s, 1H), 7.53 (d, J = 8.8 Hz, 2H), 7.32 (d, J = 8.8 Hz, 2H), 7.02 (d, J = 8.8 Hz, 2H), 6.95 (d, J = 8.8 Hz, 2H), 4.54-4.55 (m, 1H), 3.73-3.75 (m, 4H), 3.59-3.62 (m, 2H), 3.52-3.54 (m, 4H), 2.99-3.04 (m, 2H), 2.02-2.03 (m, 2H), 1.70-1.73 (m, 2H); LCMS (electrospray) m/z 554 (M + H)$^+$. |
| 194 | 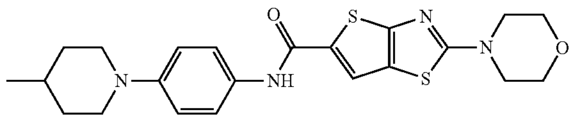 [SMILES: CC1CCN(c2ccc(NC(=O)c3cc4sc(N5CCOCC5)nc4s3)cc2)CC1] | Yellow solid; mp = 278.0° C.; $^1$H NMR (400 MHz, DMSO-d$_6$) δ 9.97 (s, 1H), 8.10 (s, 1H), 7.50-7.52 (m, 2H), 6.90-6.91 (m, 2H), 3.73-3.74 (m, 4H), 3.49-3.61 (m, 6H), 2.58-2.66 (m, 2H), 1.67-1.70 (m, 2H), 1.48-1.50 (m, 1H), 1.17-1.19 (m, 2H), 0.94 (d, J = 6.4 Hz, 3H); LCMS (electrospray) m/z 443 (M + H)$^+$. |
| 195 | 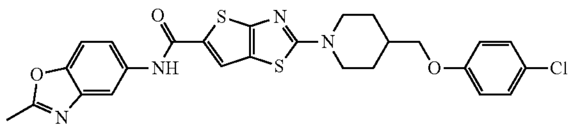 [SMILES: Cc1nc2cc(NC(=O)c3cc4sc(N5CCC(COc6ccc(Cl)cc6)CC5)nc4s3)ccc2o1] | White solid; mp = 256.0° C.; $^1$H NMR (400 MHz, DMSO-d$_6$) δ 10.23 (s, 1H), 8.14 (s, 1H), 8.05 (d, J = 1.6 Hz, 1H), 7.57-7.63 (m, 2H), 7.29-7.33 (m, 2H), 6.96-6.98 (m, 2H), 4.02-4.05 (m, 2H), 3.87 (d, J = 6.4 Hz, 2H), 3.19-3.27 (m, 2H), 2.60 (s, 3H), 2.09-2.10 (m, 1H), 1.88-1.91 (m, 2H), 1.38-1.42 (m, 2H); LCMS (electrospray) m/z 539 (M + H)$^+$. |
| 196 | 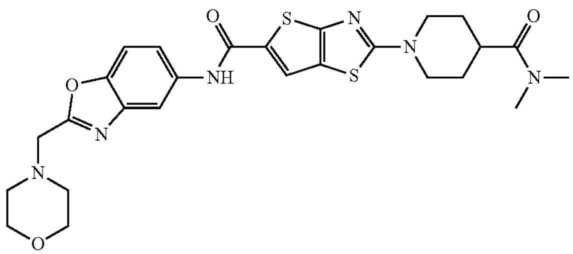 [SMILES: CN(C)C(=O)C1CCN(c2nc3sc(C(=O)Nc4ccc5oc(CN6CCOCC6)nc5c4)cc3s2)CC1] | Yellow solid; mp = 239.0° C.; $^1$H NMR (400 MHz, DMSO-d$_6$) δ 10.29 (s, 1H), 8.15 (s, 1H), 8.12 (d, J = 2.0 Hz, 1H), 7.70-7.62 (m, 2H), 4.04-3.96 (m, 2H), 3.84 (s, 2H), 3.62-3.56 (m, 4H), 3.28-3.22 (m, 2H), 3.06 (s, 3H), 3.02-2.94 (m, 1H), 2.82 (s, 3H), 2.56-2.50 (m, 4H), 1.81-1.74 (m, 2H), 1.67-1.56 (m 2H); LCMS (electrospray) m/z 555 (M + H)$^+$. |
| 197 | 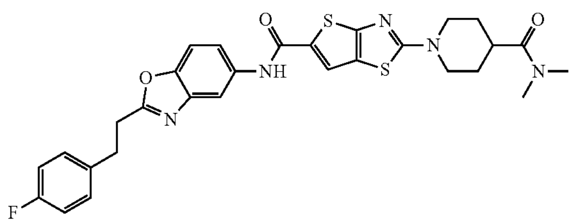 [SMILES: CN(C)C(=O)C1CCN(c2nc3sc(C(=O)Nc4ccc5oc(CCc6ccc(F)cc6)nc5c4)cc3s2)CC1] | White solid; mp = 259° C.; $^1$H NMR (400 MHz, DMSO-d$_6$) δ 10.25 (s, 1H), 8.15 (s, 1H), 8.06 (d, J = 2.0 Hz, 1H), 8.58-7.64 (m, 2H), 7.30-7.34 (m, 2H), 7.07-7.12 (m, 2H), 3.97-4.03 (m, 2H), 3.21-3.28 (m, 4H), 3.11-3.15 (m, 2H), 3.06 (s 3H), 2.95-3.01 (m, 1H), 2.82 (s, 3H), 1.75-1.79 (m, 2H), 1.56-1.66 (m, 2H); LCMS (electrospray) m/z 577 (M + H)$^+$. |
| 198 | 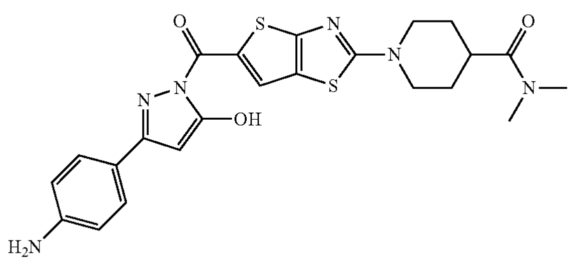 [SMILES: CN(C)C(=O)C1CCN(c2nc3sc(C(=O)n4nc(-c5ccc(N)cc5)cc4O)cc3s2)CC1] | Yellow solid; mp = 269.0° C.; $^1$H NMR (400 MHz, DMSO-d$_6$) δ 12.66 (s, 1H), 8.18 (s, 1H), 7.39 (d, J = 8.4 Hz, 2H), 6.60 (d, J = 8.4 Hz, 2H), 6.32 (s, 1H), 5.36 (s, 2H), 4.02-4.05 (m, 2H), 2.97-3.15 (m, 3H), 3.06 (s, 3H), 2.82 (s, 3H), 1.77-1.80 (m, 2H), 1.59-1.66 (m, 2H); LCMS (electrospray) m/z 497 (M + H)$^+$. |
| 199 | 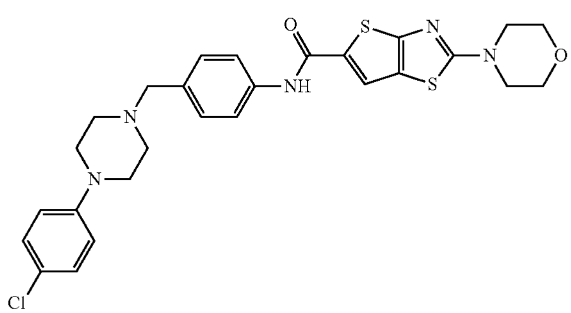 [SMILES: O=C(Nc1ccc(CN2CCN(c3ccc(Cl)cc3)CC2)cc1)c1cc2sc(N3CCOCC3)nc2s1] | Pale yellow solid; mp = 249.9° C.; $^1$H NMR (400 MHz, DMSO-d$_6$) δ 10.14 (brs, 1H), 8.14 (s, 1H), 7.65 (d, J = 8.4 Hz, 2H), 7.27 (d, J = 8.4 Hz, 2H), 7.19 (d, J = 8.8 Hz, 2H), 6.91 (d, J = 8.8 Hz, 2H), 3.71-3.74 (m, 4H), 3.51-3.53 (m, 4H), 3.46 (s, 2H), 3.35-3.37 (m, 4H), 3.10-3.11 (m, 4H); LCMS (electrospray) m/z 554, 556 (M + H)$^+$ (Cl$^-$ isotope pattern). |

TABLE 1-continued

Structures and Characteristics of Compounds 1-360

| No. | Structure | NMR Characterization |
|---|---|---|
| 200 | 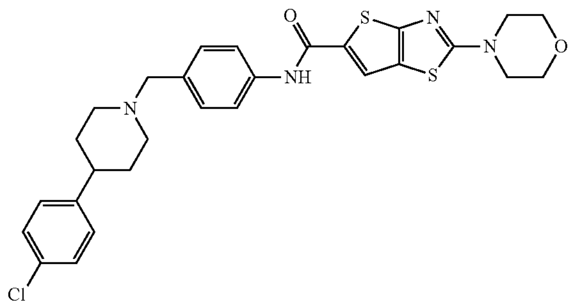 | Pale yellow solid; mp = 254.6° C.; $^1$H NMR (400 MHz, DMSO-d$_6$) δ 10.15 (brs, 1H), 8.16 (s, 1H), 7.65 (d, J = 8.4 Hz, 2H), 7.33 (d, J = 8.4 Hz, 2H), 7.27-7.28 (m, 4H), 3.73-3.75 (m, 4H), 3.52-3.54 (m, 4H), 3.46 (s, 2H), 3.35-3.38 (m, 1H), 2.90-2.92 (m, 2H), 1.99-2.07 (m, 2H), 1.63-1.71 (m, 4H); LCMS (electrospray) m/z 553, 555 (M + H)$^+$ (Cl$^-$ isotope pattern). |
| 201 | 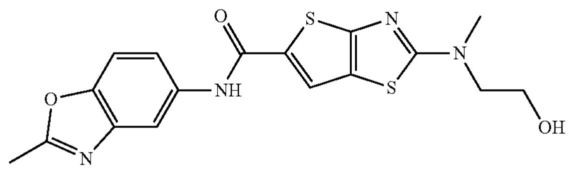 [SMILES: Cc1nc2cc(NC(=O)c3cc4sc(N(C)CCO)nc4s3)ccc2o1] | Yellow solid; mp = 226.3° C.; $^1$H NMR (400 MHz, DMSO-d$_6$) δ 10.22 (s, 1H), 8.14 (s, 1H), 8.06 (s, 1H), 7.57-7.63 (m, 2H), 4.90 (t, J = 5.2 Hz, 1H), 3.64-3.70 (m, 2H), 3.57-3.63 (m, 2H), 3.17 (s, 3H), 2.60 (s, 3H); LCMS (electrospray) m/z 389 (M + H)$^+$. |
| 202 | 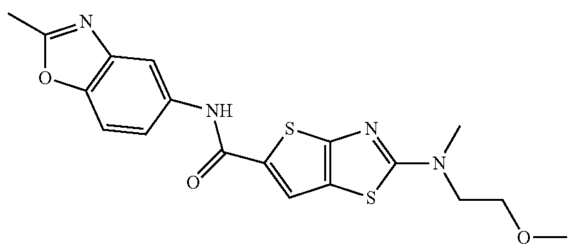 | Yellow solid; $^1$H NMR (400 MHz, DMSO-d$_6$) δ 10.23 (s, 1H), 8.14 (s, 1H), 8.06 (s, 1H), 7.58-7.64 (m, 2H), 3.72 (t, J = 5.6 Hz, 2H), 3.60 (t, J = 5.2 Hz, 2H), 3.28 (s, 3H), 3.15 (s, 3H), 2.60 (s, 3H); LCMS (electrospray) m/z 403 (M + H)$^+$. |
| 203 | 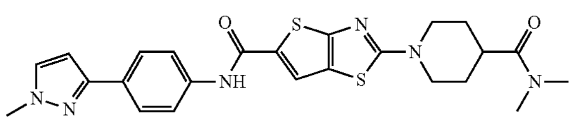 | Ivory solid; $^1$H NMR (400 MHz, DMSO-d$_6$) δ 10.19 (s, 1H), 8.16 (s, 1H), 7.74 (s, 4H), 7.71 (d, J = 2.0 Hz, 1H), 6.64 (d, J = 2.0 Hz, 1H), 3.97-4.03 (m, 2H), 3.87 (s, 3H), 3.27-3.31 (m, 2H), 3.06 (s, 3H), 2.95-3.03 (m, 1H), 2.82 (s, 3H), 1.74-1.81 (m, 2H), 1.58-1.66 (m 2H); LCMS (electrospray) m/z 494 (M + H)$^+$. |
| 204 | 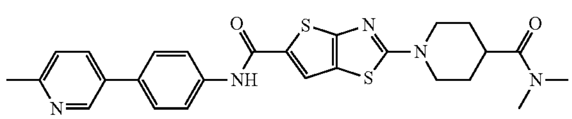 | White solid; $^1$H NMR (400 MHz, DMSO-d$_6$) δ 10.26 (s, 1H), 8.75 (d, J = 2.4 Hz, 1H), 8.18 (s, 1H), 7.95 (dd, J = 8.0, 2.4 Hz, 1H), 7.82-7.85 (m, 2H), 7.68-7.71 (m, 2H), 7.31 (d, J = 8.0 Hz, 1H), 3.99-4.02 (m, 2H), 3.25-3.36 (s, 5H), 3.06 (s, 3H), 2.96-3.06 (m, 1H), 2.82 (s, 3H), 1.76-1.78 (m, 2H), 1.59-1.66 (m, 2H); LCMS (electrospray) m/z 506 (M + H)$^+$. |
| 205 | 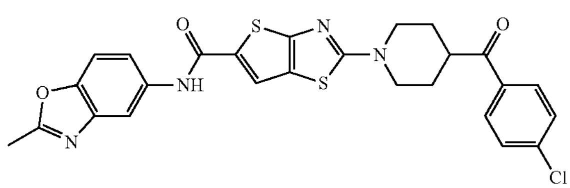 [SMILES: Cc1nc2cc(NC(=O)c3cc4sc(N5CCC(C(=O)c6ccc(Cl)cc6)CC5)nc4s3)ccc2o1] | White solid; $^1$H NMR (400 MHz, DMSO-d$_6$) δ 10.25 (s, 1H), 8.16 (s, 1H), 8.04-8.06 (m, 3H), 7.58-7.65 (m, 4H), 4.03-4.07 (m, 2H), 3.78-3.82 (m, 2H), 3.23-3.39 (m, 1H) 2.60 (s, 3H), 1.93-1.96 (m, 2H), 1.61-1.67 (m, 2H); LCMS (electrospray) m/z 537, 539 (M + H)$^+$ (Cl$^-$ isotope pattern). |
| 206 | 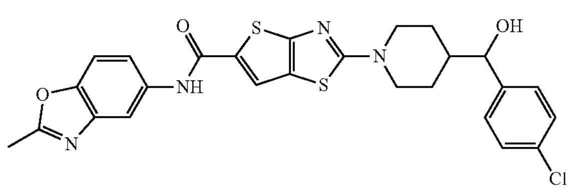 [SMILES: Cc1nc2cc(NC(=O)c3cc4sc(N5CCC(C(O)c6ccc(Cl)cc6)CC5)nc4s3)ccc2o1] | White solid; $^1$H NMR (400 MHz, acetone-d$_6$) δ 9.25 (s, 1H), 8.14-8.15 (m, 1H), 7.99 (s, 1H), 7.65 (dd, J = 8.8, 2.0 Hz, 1H), 7.50 (d, J = 8.4 Hz, 1H), 7.36-7.42 (m, 4H), 4.51-4.54 (m, 2H), 4.06-4.13 (m, 2H), 3.07-3.17 (m, 2H), 2.59 (s, 3H), 1.89-1.94 (m, 1H), 1.45-1.55 (m, 4H); LCMS (electrospray) m/z 539, 541 (M + H)$^+$ (Cl$^-$ isotope pattern). |
| 207 | 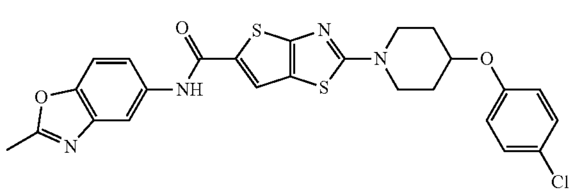 [SMILES: Cc1nc2cc(NC(=O)c3cc4sc(N5CCC(Oc6ccc(Cl)cc6)CC5)nc4s3)ccc2o1] | Pale yellow solid; $^1$H NMR (400 MHz, DMSO-d$_6$) δ 10.24 (s, 1H), 8.14 (s, 1H), 8.04 (s, 1H), 7.56-7.59 (m, 2H), 7.32 (d, J = 8.8 Hz, 2H), 7.04 (d, J = 8.8 Hz, 2H), 4.67-4.69 (m, 1H), 3.79-3.82 (m, 2H), 3.50-3.55 (m, 2H), 2.58 (s, 3H), 2.03-2.05 (m, 2H), 1.73-1.75 (m, 2H); LCMS (electrospray) m/z 524 (M + H)$^+$. |

TABLE 1-continued

Structures and Characteristics of Compounds 1-360

| No. | Structure | NMR Characterization |
|---|---|---|
| 208 | [Structure with HCl] | Yellow solid; ¹H NMR (400 MHz, DMSO-d₆) δ 10.42 (s, 1H), 9.08 (s, 1H), 8.72-8.74 (m, 1H). 8.24 (s, 1H), 7.86-7.95 (m, 4H), 3.99-4.02 (m, 2H), 3.25-3.34 (m, 2H), 3.06 (s, 3H), 2.99-3.02 (m, 1H), 2.82 (s, 3H), 2.73 (s, 3H), 1.76-1.79 (m, 2H), 1.59-1.62 (m, 2H); LCMS (electrospray) m/z 506 (M + H)⁺. |
| 209 | [Structure] | Brown solid; ¹H NMR (400 MHz, DMSO-d₆) δ 10.33 (s, 1H), 9.10 (s, 1H), 8.37 (d, J = 8.4 Hz, 1H), 8.22 (s, 1H), 7.97 (d, J = 8.4 Hz, 1H), 7.92 (d, J = 8.8 Hz, 2H), 7.85 (d, J = 8.8 Hz, 2H), 3.98-4.03 (m, 2H), 3.26-3.11 (m, 2H), 3.06 (s, 3H), 2.96-3.01 (m, 1H), 2.82 (s, 3H), 1.76-1.82 (m, 2H), 1.58-1.67 (m, 2H); LCMS (electrospray) m/z 559 (M + H)⁺. |
| 210 | [Structure] | White solid; ¹H NMR (400 MHz, DMSO-d₆) δ 10.31 (s, 1H), 8.25-8.28 (m, 2H), 8.21 (s, 1H), 8.17 (s, 1H), 7.77 (d, J = 8.8 Hz, 1H), 7.69 (d, J = 8.8 Hz, 1H), 7.45-7.49 (m, 2H), 3.16 (s, 6H); LCMS (electrospray) m/z 439 (M + H)⁺. |
| 211 | [Structure] | Pale yellow solid; ¹H NMR (400 MHz, DMSO-d₆) δ 10.16 (s, 1H), 8.16 (s, 1H), 7.66 (d, J = 8.0 Hz, 2H), 7.29 (d, J = 8.0 Hz, 2H), 7.00-7.05 (m, 2H), 6.92-6.95 (m, 2H), 3.73-3.76 (m, 4H), 3.61 (s, 2H), 3.54-3.57 (m, 4H), 3.48-3.51 (m, 4H), 3.05-3.09 (m, 4H); LCMS (electrospray) m/z 538 (M + H)⁺. |
| 212 | [Structure] | Pale yellow solid; ¹H NMR (400 MHz, DMSO-d₆) δ 10.23 (s, 1H), 8.13 (s, 1H), 8.04 (s, 1H), 7.78-7.79 (m, 1H), 7.56-7.61 (m, 2H), 3.96-3.99 (m, 2H), 3.14-3.22 (m, 2H), 3.58 (s, 3H), 3.56 (s, 3H), 1.92-1.95 (m, 1H), 1.77-1.81 (m, 2H), 1.57-1.66 (m, 2H); LCMS (electrospray) m/z 455 (M + H)⁺. |
| 213 | [Structure] | Pale yellow solid; ¹H NMR (400 MHz, DMSO-d₆) δ 10.21 (s, 1H), 8.47 (s, 1H), 8.15 (s, 1H), 8.00 (d, J = 8.8 Hz, 1H), 7.80 (d, J = 8.4 Hz, 2H), 7.64 (d, J = 8.4 Hz, 2H), 6.88 (d, J = 8.8 Hz, 1H), 3.98-4.01 (m, 2H), 3.88 (s, 3H), 3.23-3.27 (m, 2H), 3.05 (s, 3H), 2.95-3.00 (m, 1H), 2.81 (s, 3H), 1.74-1.77 (m, 2H), 1.58-1.61 (m, 2H); LCMS (electrospray) m/z 521 (M + H)⁺. |
| 214 | [Structure] | Yellow solid; ¹H NMR (400 MHz, DMSO-d₆) δ 10.33 (s, 1H), 8.20-8.22 (m, 3H), 8.17 (s, 1H), 7.78 (d, J = 8.4 Hz, 1H), 7.69-7.72 (m, 3H), 4.02-4.04 (m, 2H), 3.19-3.22 (m, 2H), 3.06 (s, 3H), 2.99-3.01 (m, 1H), 2.82 (s, 3H), 1.75-1.78 (m, 2H), 1.63-1.66 (m, 2H); LCMS (electrospray) m/z 566, 568 (M + H)⁺ (Cl⁻ isotope pattern). |
| 215 | [Structure] | Pale yellow solid; ¹H NMR (400 MHz, DMSO-d₆) δ 10.23 (s, 1H), 8.15 (s, 1H), 8.05 (s, 1H), 7.60-7.61 (m, 2H), 3.60-3.64 (m, 3H), 3.52-3.54 (m, 2H), 3.07 (s, 3H), 2.85 (s, 3H), 2.60 (s, 3H), 2.28-2.32 (m, 1H), 2.09-2.13 (m, 1H); LCMS (electrospray) m/z 566 (M + H)⁺. |

TABLE 1-continued

Structures and Characteristics of Compounds 1-360

| No. | Structure | NMR Characterization |
|---|---|---|
| 216 | 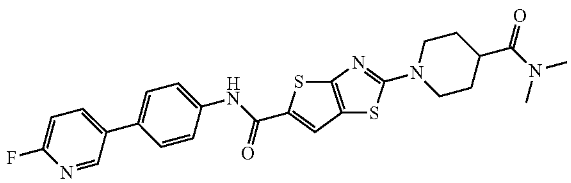 [SMILES: CN(C)C(=O)C1CCN(c2nc3sc(C(=O)Nc4ccc(-c5ccc(F)nc5)cc4)cc3s2)CC1] | Pale yellow solid; $^1$H NMR (400 MHz, DMSO-d$_6$) δ 10.28 (s, 1H), 8.54-8.56 (m, 1H), 8.28-8.29 (m, 1H), 8.17 (s, 1H), 7.85 (d, J = 8.8 Hz, 2H), 7.73 (d, J = 8.8 Hz, 2H), 7.25-7.28 (m, 1H), 3.99-4.02 (m, 2H), 3.22-3.25 (m, 2H), 3.07 (s, 3H), 2.99-3.02 (m, 1H), 2.82 (s, 3H), 1.76-1.79 (m, 2H), 1.59-1.65 (m, 2H); LCMS (electrospray) m/z 510 (M + H)$^+$. |
| 217 | 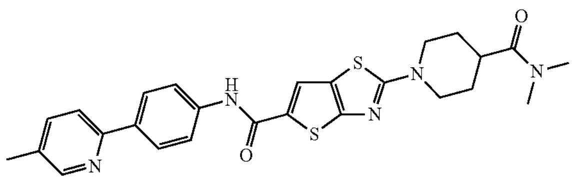 | Pale yellow solid; $^1$H NMR (400 MHz, DMSO-d$_6$) δ 10.26 (s, 1H), 8.46-8.47 (m, 1H), 8.18 (s, 1H), 8.04 (d, J = 8.4 Hz, 2H), 7.81-7.84 (m, 3H), 7.66-7.68 (m, 1H), 3.99-4.02 (m, 2H), 3.24-3.26 (m, 2H), 3.06 (s, 3H), 2.94-3.01 (m, 1H), 2.82 (s, 3H), 2.32 (s, 3H), 1.75-1.79 (m, 2H), 1.57-1.66 (m, 2H); LCMS (electrospray) m/z 506 (M + H)$^+$. |
| 218 | 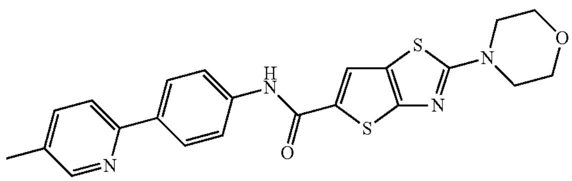 [SMILES: Cc1ccc(-c2ccc(NC(=O)c3cc4sc(N5CCOCC5)nc4s3)cc2)nc1] | White solid; $^1$H NMR (400 MHz, DMSO-d$_6$) δ 10.30 (s, 1H), 8.47 (s, 1H), 8.20 (s, 1H), 8.04 (d, J = 8.4 Hz, 2H), 7.81-7.84 (m, 3H), 7.66-7.68 (m, 1H), 3.73-3.76 (m, 4H), 3.53-3.56 (m, 4H), 2.32 (s, 3H); LCMS (electrospray) m/z 437 (M + H)$^+$. |
| 219 | 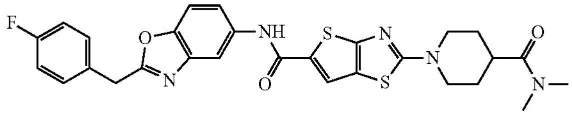 [SMILES: CN(C)C(=O)C1CCN(c2nc3sc(C(=O)Nc4ccc5oc(Cc6ccc(F)cc6)nc5c4)cc3s2)CC1] | Ivory solid; $^1$H NMR (400 MHz, DMSO-d$_6$) δ 10.26 (s, 1H), 8.14 (s, 1H), 8.08 (s, 1H), 7.57-7.64 (m, 2H), 7.40-7.46 (m, 2H), 7.14-7.22 (m, 2H), 4.33 (s, 2H), 3.97-4.02 (m, 2H), 3.25-3.31 (m, 2H), 3.06 (s, 3H), 2.95-3.01 (m, 1H), 2.82 (s, 3H), 1.74-1.79 (m, 2H), 1.55-1.66 (m, 2H); LCMS (electrospray) m/z 563 (M + H)$^+$. |
| 220 | 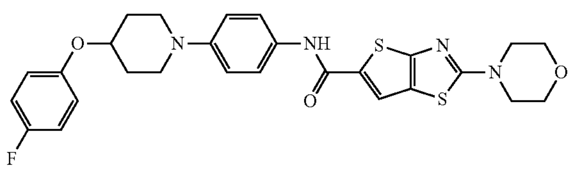 [SMILES: O=C(Nc1ccc(N2CCC(Oc3ccc(F)cc3)CC2)cc1)c1cc2sc(N3CCOCC3)nc2s1] | Ivory solid; $^1$H NMR (400 MHz, DMSO-d$_6$) δ 9.98 (s, 1H), 8.10 (s, 1H), 7.54 (d, J = 8.8 Hz, 2H), 7.08-7.13 (m, 2H), 6.99-7.02 (m, 2H), 6.96 (d, J = 8.8 Hz, 2H), 4.47-4.51 (m, 1H), 3.73-3.76 (m, 4H), 3.59-3.61 (m, 1H), 3.45-3.50 (m, 4H), 3.45-3.49 (m, 1H), 2.97-3.09 (m, 2H), 2.00-2.06 (m, 2H), 1.66-1.75 (m, 2H); LCMS (electrospray) m/z 539 (M + H)$^+$. |
| 221 | 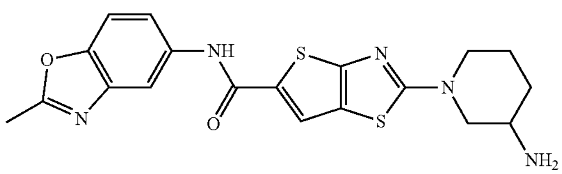 [SMILES: Cc1nc2cc(NC(=O)c3cc4sc(N5CCCC(N)C5)nc4s3)ccc2o1] | White solid; $^1$H NMR (400 MHz, DMSO-d$_6$) δ 10.18 (s, 1H), 8.34-8.36 (m, 1H), 8.04-8.06 (m, 2H), 7.57-7.62 (m, 2H), 3.61-3.65 (m, 1H), 2.59 (s, 3H), 1.95-1.97 (m, 2H), 1.69-1.74 (m, 2H), 1.55-1.61 (m, 1H), 1.17-1.38 (m, 4H); LCMS (electrospray) m/z 413 (M + H)$^+$. |
| 222 | 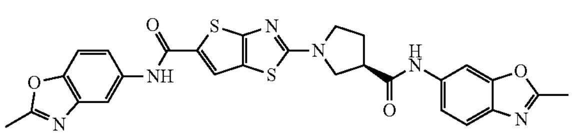 | Yellow solid; $^1$H NMR (400 MHz, DMSO-d$_6$) δ 10.28 (s, 1H), 10.24 (s, 1H), 8.16 (s, 1H), 8.05 (s, 1H), 8.03 (d, J = 2.0 Hz, 1H), 7.58-7.61 (m, 3H), 7.45-7.48 (m, 1H), 3.70-3.82 (m, 3H), 3.51-3.64 (m, 2H), 2.60 (s, 3H), 2.59 (s, 3H), 2.38-2.44 (m, 1H), 2.26-2.33 (m, 1H); LCMS (electrospray) m/z 559 (M + H)$^+$. |
| 223 | 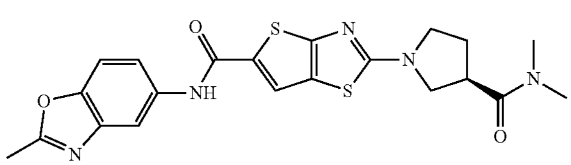 | Yellow solid; $^1$H NMR (400 MHz, DMSO-d$_6$) δ 10.24 (s, 1H), 8.15 (s, 1H), 8.05 (s, 1H), 7.60-7.64 (m, 2H), 3.59-3.72 (m, 3H), 3.48-3.58 (m, 2H), 3.70 (s, 3H), 2.86 (s, 3H), 2.60 (s, 3H), 2.24-2.34 (m, 1H), 2.07-2.16 (m, 1H); LCMS (electrospray) m/z 456 (M + H)$^+$. |
| 224 | 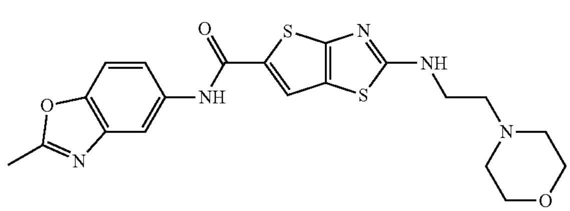 [SMILES: Cc1nc2cc(NC(=O)c3cc4sc(NCCN5CCOCC5)nc4s3)ccc2o1] | Ivory solid; $^1$H NMR (400 MHz, CDCl$_3$) δ 7.86 (d, J = 2.0 Hz, 1H), 7.66 (s, 1H), 7.63 (s, 1H), 7.54 (dd, J = 8.4, 2.0 Hz, 1H), 7.43 (d, J = 8.4 Hz, 1H), 6.09 (brs, 1H), 3.70-3.75 (m, 4H), 3.44-3.49 (m, 2H), 2.64-2.69 (m, 2H), 2.63 (s, 3H), 2.48-2.53 (m, 4H); LCMS (electrospray) m/z 444 (M + H)$^+$. |

TABLE 1-continued

Structures and Characteristics of Compounds 1-360

| No. | Structure | NMR Characterization |
| --- | --- | --- |
| 225 | 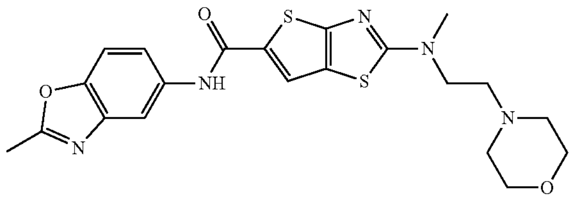 [SMILES: Cc1nc2cc(NC(=O)c3cc4sc(N(C)CCN5CCOCC5)nc4s3)ccc2o1] | White solid; $^1$H NMR (400 MHz, CDCl$_3$) δ 7.87 (d, J = 2.0 Hz, 1H), 7.65 (s, 1H), 7.60 (s, 1H), 7.55 (dd, J = 8.8, 2.0 Hz, 1H), 7.44 (d, J = 8.8 Hz, 1H), 3.66-3.71 (m, 6H), 3.19 (s, 3H), 2.63-2.66 (m, 2H), 2.64 (s, 3H), 2.52-2.54 (m, 4H); LCMS (electrospray) m/z 458 (M + H)$^+$. |
| 226 | 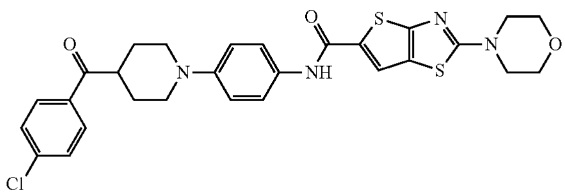 [SMILES: O=C(Nc1ccc(N2CCC(C(=O)c3ccc(Cl)cc3)CC2)cc1)c1cc2sc(N3CCOCC3)nc2s1] | Yellow solid; $^1$H NMR (400 MHz, DMSO-d$_6$) δ 10.00 (s, 1H), 8.10 (s, 1H), 8.03 (d, J = 9.2 Hz, 2H), 7.62 (d, J = 9.2 Hz, 2H), 7.53 (d, J = 8.8 Hz, 2H), 6.95 (d, J = 8.8 Hz, 2H), 3.72-3.74 (m, 4H), 3.68-3.69 (m, 2H), 3.50-3.53 (m, 4H), 2.80-2.87 (m, 3H), 1.94-1.97 (m, 2H), 1.66-1.70 (m, 2H); LCMS (electrospray) m/z 567, 569 (M + H)$^+$ (Cl$^-$ isotope pattern). |
| 227 | 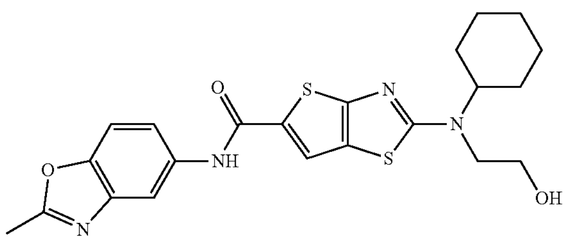 [SMILES: Cc1nc2cc(NC(=O)c3cc4sc(N(CCO)C5CCCCC5)nc4s3)ccc2o1] | Pale yellow solid; $^1$H NMR (400 MHz, acetone-d$_6$) δ 9.51 (s, 1H), 8.15 (s, 1H), 7.98 (s, 1H), 7.64-7.66 (m, 1H), 7.48 (d, J = 8.8 Hz, 1H), 4.03 (brs, 1H), 3.77-3.80 (m, 3H), 3.61-3.64 (m, 2H), 2.58 (s, 3H), 1.86-1.94 (m, 4H), 1.64-1.73 (m, 3H), 1.38-1.48 (m, 2H), 1.24-1.29 (m, 1H); LCMS (electrospray) m/z 457 (M + H)$^+$. |
| 228 | 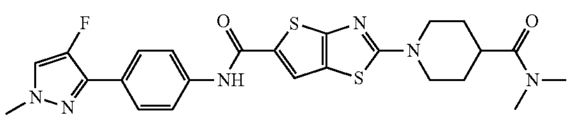 | Pale yellow solid; $^1$H NMR (400 MHz, DMSO-d$_6$) δ 10.23 (s, 1H), 8.15 (s, 1H), 7.92 (m, 1H), 7.78 (d, J = 8.4 Hz, 2H), 7.69 (d, J = 8.4 Hz, 2H), 3.97-4.01 (m, 2H), 3.80 (s, 3H), 3.23-3.26 (m, 2H), 3.05 (s, 3H), 2.94-3.00 (m, 1H), 2.80 (s, 3H), 1.74-1.77 (m, 2H), 1.55-1.65 (m, 2H); LCMS (electrospray) m/z 512 (M + H)$^+$. |
| 229 | 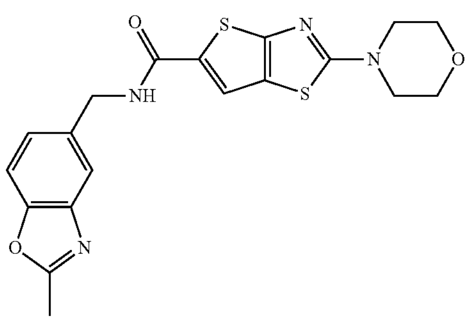 [SMILES: Cc1nc2cc(CNC(=O)c3cc4sc(N5CCOCC5)nc4s3)ccc2o1] | Yellow solid; $^1$H NMR (400 MHz, acetone-d$_6$) δ 8.15 (brs, 1H), 7.83 (s, 1H), 7.62 (d, J = 1.2 Hz, 1H), 7.48 (d, J = 8.0 Hz, 1H), 7.36 (dd, J = 8.0, 1.2 Hz, 1H), 4.65 (d, J = 6.0 Hz, 2H), 3.77-3.80 (m, 4H), 3.54-3.56 (m, 4H), 2.57 (s, 3H); LCMS (electrospray) m/z 415 (M + H)$^+$. |
| 230 | 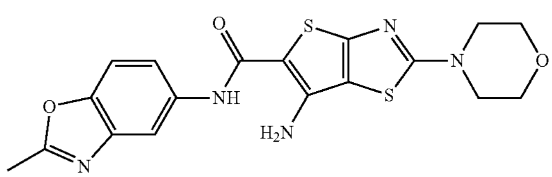 | Pale yellow solid; $^1$H NMR (400 MHz, acetone-d$_6$) δ 8.48 (s, 1H), 8.06 (d, J = 2.0 Hz, 1H), 7.57-7.59 (m, 1H), 7.44 (d, J = 8.8 Hz, 1H), 6.84-6.85 (m, 2H), 3.78-3.81 (m, 4H), 3.56-3.58 (m, 4H), 2.57 (s, 3H); LCMS (electrospray) m/z 416 (M + H)$^+$. |
| 231 | 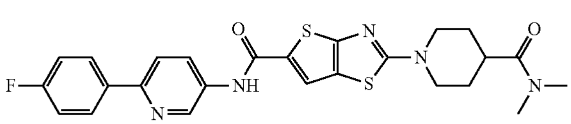 | White solid; $^1$H NMR (400 MHz, DMSO-d$_6$) δ 10.45 (s, 1H), 8.94 (d, J = 2.0 Hz, 1H), 8.21 (dd, J = 8.4, 2.0 Hz, 1H), 8.18 (s, 1H), 8.09-8.13 (m, 2H), 7.95 (d, J = 8.4 Hz, 1H), 7.28-7.32 (m, 2H), 3.98-4.02 (m, 2H), 3.25-3.37 (m, 2H), 3.06 (s, 3H), 2.94-3.02 (m, 1H), 2.82 (s, 3H), 1.75-1.79 (m, 2H), 1.59-1.65 (m, 2H); LCMS (electrospray) m/z 510 (M + H)$^+$. |

TABLE 1-continued

Structures and Characteristics of Compounds 1-360

| No. | Structure | NMR Characterization |
|---|---|---|
| 232 | 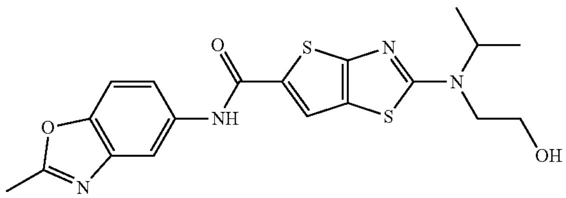 [SMILES: Cc1nc2cc(NC(=O)c3cc4sc(N(CCO)C(C)C)nc4s3)ccc2o1] | Pale yellow solid; ¹H NMR (400 MHz, acetone-d₆) δ 9.49 (s, 1H), 8.15 (s, 1H), 7.98 (s, 1H), 7.65 (d, J = 8.8 Hz, 1H), 7.50 (d, J = 8.8 Hz, 1H), 4.18-4.25 (m, 1H), 4.04-4.07 (m, 1H), 3.79-3.84 (m, 2H), 3.59-3.62 (m, 2H), 2.59 (s, 3H), 1.34 (d, J = 6.8 Hz, 6H); LCMS (electrospray) m/z 416 (M + H)⁺. |
| 233 | 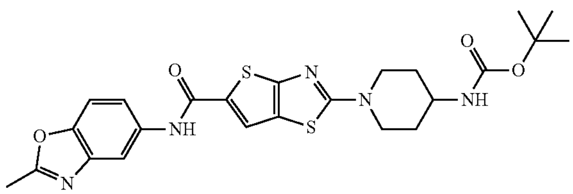 [SMILES: Cc1nc2cc(NC(=O)c3cc4sc(N5CCC(NC(=O)OC(C)(C)C)CC5)nc4s3)ccc2o1] | White solid; ¹H NMR (400 MHz, DMSO-d₆) δ 10.23 (s, 1H), 8.13 (s, 1H), 8.03 (s, 1H), 7.56-7.61 (m, 2H), 6.90-6.92 (m, 1H), 3.89-3.93 (m, 2H), 3.55 (m, 1H), 3.22-3.29 (m, 2H), 2.58 (s, 3H), 1.82-1.85 (m, 2H), 1.43-1.45 (m, 2H), 1.38 (s, 9H); LCMS (electrospray) m/z 513 (M + H)⁺. |
| 234 | 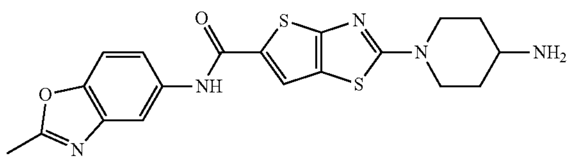 [SMILES: Cc1nc2cc(NC(=O)c3cc4sc(N5CCC(N)CC5)nc4s3)ccc2o1] | Pale yellow solid; ¹H NMR (400 MHz, DMSO-d₆) δ 10.20 (s, 1H), 8.11 (s, 1H), 8.03 (s, 1H), 7.55-7.61 (m, 2H), 3.86-3.90 (m, 2H), 3.18-3.24 (m, 2H), 2.81-2.84 (m, 1H), 2.58 (s, 3H), 1.77-1.80 (m, 2H), 1.68 (s, 2H), 1.25-1.33 (m, 2H); LCMS (electrospray) m/z 413 (M + H)⁺. |
| 235 | 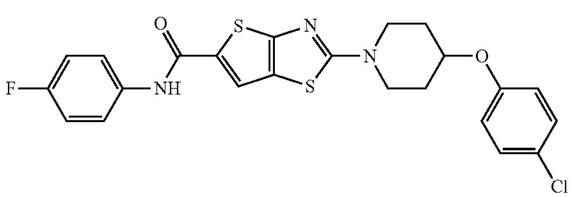 [SMILES: O=C(Nc1ccc(F)cc1)c1cc2sc(N3CCC(Oc4ccc(Cl)cc4)CC3)nc2s1] | Pale pink solid; ¹H NMR (400 MHz, DMSO-d₆) δ 10.20 (s, 1H), 8.13 (s, 1H), 7.69-7.73 (m, 2H), 7.33-7.35 (m, 2H), 7.16-7.20 (m, 2H), 7.04-7.06 (m, 2H), 4.69-4.70 (m, 1H), 3.80-3.83 (m, 2H), 3.54-3.56 (m, 2H), 1.99-2.05 (m, 2H), 1.74-1.77 (m, 2H); LCMS (electrospray) m/z 487 (M + H)⁺. |
| 236 | 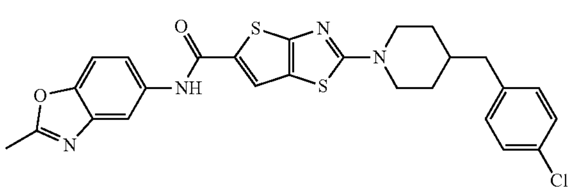 [SMILES: Cc1nc2cc(NC(=O)c3cc4sc(N5CCC(Cc6ccc(Cl)cc6)CC5)nc4s3)ccc2o1] | Ivory solid; ¹H NMR (400 MHz, DMSO-d₆) δ 10.23 (s, 1H), 8.13 (s, 1H), 8.05 (s, 1H), 7.57-7.63 (m, 2H), 7.33 (d, J = 8.0 Hz, 2H), 7.21 (d, J = 8.4 Hz, 2H), 3.95-4.02 (m, 2H), 3.09-3.17 (m, 2H), 2.59 (s, 3H), 2.55 (d, J = 7.2 Hz, 2H), 1.80-1.85 (m, 1H), 1.66-1.69 (m, 2H), 1.23-1.32 (m, 2H); LCMS (electrospray) m/z 523 (M + H)⁺. |
| 237 | 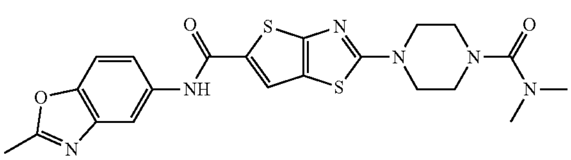 | Ivory solid; ¹H NMR (400 MHz, DMSO-d₆) δ 10.27 (s, 1H), 8.16 (s, 1H), 8.05 (s, 1H), 7.28-7.62 (m, 2H), 3.55-3.60 (m, 4H), 3.24-3.29 (m, 4H), 2.78 (s, 6H), 2.60 (s, 3H); LCMS (electrospray) m/z 470 (M + H)⁺. |
| 238 | 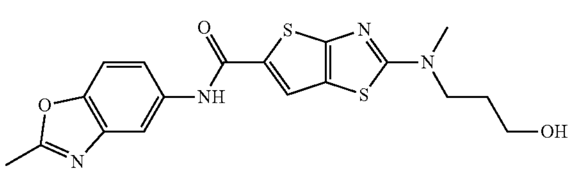 [SMILES: Cc1nc2cc(NC(=O)c3cc4sc(N(C)CCCO)nc4s3)ccc2o1] | White solid; ¹H NMR (400 MHz, DMSO-d₆) δ 10.23 (s, 1H), 8.14 (s, 1H), 8.06 (s, 1H), 7.60-7.61 (m, 2H), 4.58-4.61 (m, 1H), 3.59-3.60 (m, 2H), 3.46-3.50 (m, 2H), 3.13 (s, 3H), 2.60 (s, 3H), 1.78-1.81 (m, 2H); LCMS (electrospray) m/z 403 (M + H)⁺. |
| 239 | 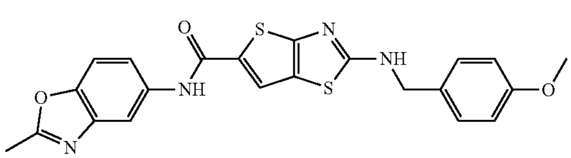 | Pale yellow solid; ¹H NMR (400 MHz, acetone-d₆) δ 9.51 (s, 1H), 8.13 (s, 1H), 7.95-7.96 (m, 1H), 7.78 (brs, 1H), 7.63-7.65 (m, 1H), 7.47-7.51 (m, 1H), 7.36-7.37 (m, 2H), 6.89-6.92 (m, 2H), 4.60 (s, 2H), 3.78 (s, 3H), 2.58 (s, 3H); LCMS (electrospray) m/z 451 (M + H)⁺. |

TABLE 1-continued

Structures and Characteristics of Compounds 1-360

| No. | Structure | NMR Characterization |
|---|---|---|
| 240 | 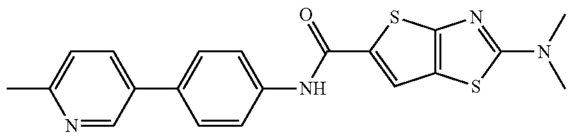 | Beige solid; $^1$H NMR (400 MHz, acetone-d$_6$) δ 9.52 (s, 1H), 8.75 (d, J = 1.6 Hz, 1H), 8.01 (s, 1H), 7.90-7.92 (m, 3H), 7.65-7.67 (m, 2H), 7.30 (d, J = 8.0 Hz, 1H), 3.20 (s, 6H), 2.52 (s, 3H); LCMS (electrospray) m/z 395 (M + H)$^+$. |
| 241 | 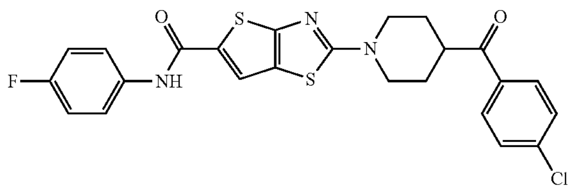 [SMILES: O=C(Nc1ccc(F)cc1)c1cc2sc(N3CCC(C(=O)c4ccc(Cl)cc4)CC3)nc2s1] | Pale yellow solid; $^1$H NMR (400 MHz, acetone-d$_6$) δ 9.47 (s, 1H), 8.08-8.10 (m, 2H), 7.98 (s, 1H), 7.77-7.80 (m, 2H), 7.58-7.60 (m, 2H), 7.08-7.13 (m, 2H), 4.14-4.18 (m, 2H), 3.82-3.88 (m, 1H), 3.40-3.48 (m, 2H), 3.09-3.11 (m, 2H), 1.81-1.89 (m, 2H); LCMS (electrospray) m/z 500, 502 (M + H)$^+$ (Cl$^-$ isotope pattern). |
| 242 | 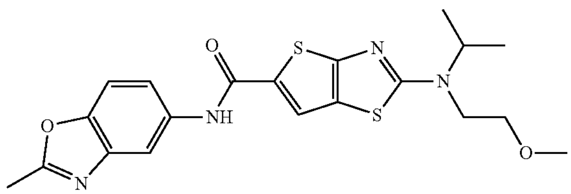 | White solid; $^1$H NMR (400 MHz, acetone-d$_6$) δ 9.52 (s, 1H), 8.15 (s, 1H), 7.99 (s, 1H), 7.64-7.66 (m, 1H), 7.49-7.51 (m, 1H), 4.17-4.23 (m, 1H), 3.63-3.65 (m, 4H), 3.34 (s, 3H), 2.59 (s, 3H), 1.33 (d, J = 6.8 Hz, 6H); LCMS (electrospray) m/z 430 (M + H)$^+$. |
| 243 | 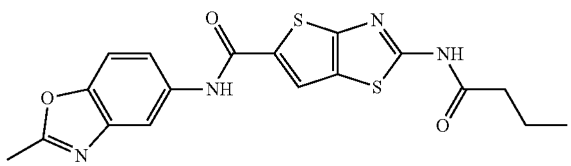 [SMILES: CCCC(=O)Nc1nc2sc(C(=O)Nc3ccc4oc(C)nc4c3)cc2s1] | Pale beige solid; $^1$H NMR (400 MHz, DMSO-d$_6$) δ 12.48 (s, 1H), 10.40 (s, 1H), 8.26 (s, 1H), 8.06 (s, 1H), 7.59-7.64 (m, 2H), 2.59 (s, 3H), 2.44-2.48 (m, 2H), 1.59-1.68 (m, 2H), 0.89-0.93 (m, 3H); LCMS (electrospray) m/z 400 (M + H)$^+$. |
| 244 | 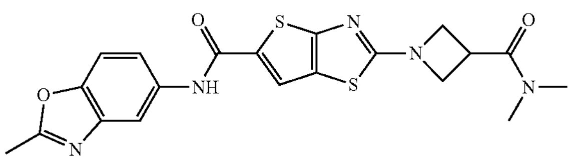 | Pale yellow solid; $^1$H NMR (400 MHz, DMSO-d$_6$) δ 10.28 (s, 1H), 8.16 (s, 1H), 8.05 (s, tH), 7.58-7.63 (m, 2H), 4.31-4.35 (m, 2H), 4.19-4.23 (m, 2H), 3.97-4.02 (m, 1H), 2.89 (s, 3H), 2.86 (s, 3H), 2.60 (s, 3H); LCMS (electrospray) m/z 442 (M + H)$^+$. |
| 245 | 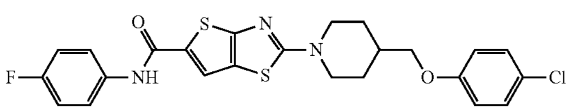 [SMILES: O=C(Nc1ccc(F)cc1)c1cc2sc(N3CCC(COc4ccc(Cl)cc4)CC3)nc2s1] | Pale yellow solid; $^1$H NMR (400 MHz, CDCl$_3$ + MeOD-d$_4$) δ 7.68 (s, 1H), 7.48-7.51 (m, 2H), 7.12 (d, J = 8.8 Hz, 2H), 6.91-6.95 (m, 2H), 6.71 (d, J = 8.8 Hz, 2H), 4.01-4.05 (m, 2H), 3.73 (d, J = 6.0 Hz, 2H), 3.07-3.13 (m, 2H), 1.88-2.03 (m, 3H), 1.37-1.48 (m, 2H); LCMS (electrospray) m/z 502 (M + H)$^+$. |
| 246 | 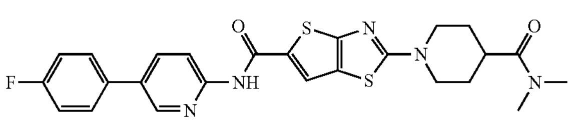 | Pale yellow solid; $^1$H NMR (400 MHz, DMSO-d$_6$) δ 10.93 (s, 1H), 8.69 (s, 1H), 8.39 (s, 1H), 8.21 (d, J = 8.4 Hz, 1H), 8.13 (d, J = 8.4 Hz, 1H), 7.78-7.81 (m, 2H), 7.31-7.35 (m, 2H), 3.99-4.03 (m, 2H), 3.07 (s, 3H), 2.99-3.01 (m, 1H), 2.82 (s, 3H), 1.94-1.97 (m, 2H), 1.76-1.79 (m, 2H), 1.60-1.63 (m, 2H); LCMS (electrospray) m/z 510 (M + H)$^+$. |
| 247 | 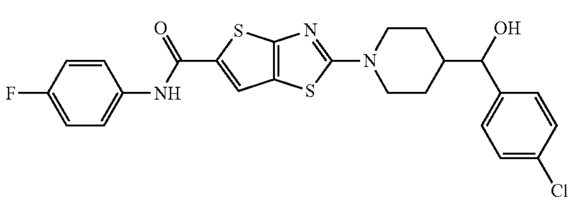 [SMILES: O=C(Nc1ccc(F)cc1)c1cc2sc(N3CCC(C(O)c4ccc(Cl)cc4)CC3)nc2s1] | Pale ivory solid; $^1$H NMR (400 MHz, acetone-d$_6$) δ 9.45 (s, 1H), 7.95 (s, 1H), 7.76-7.80 (m, 2H), 7.35-7.41 (m, 4H), 7.08-7.12 (m, 2H), 4.52-4.53 (m, 2H), 4.07-4.09 (m, 2H), 3.09-3.13 (m, 3H), 1.90-2.05 (m, 2H), 1.47-1.51 (m, 2H); LCMS (electrospray) m/z 502, 504 (M + H)$^+$ (Cl$^-$ isotope pattern). |
| 248 | 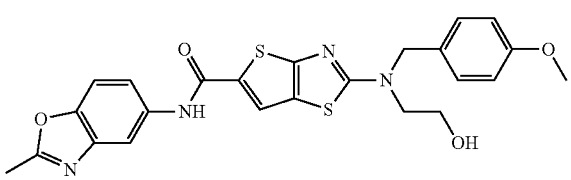 | Yellow solid; $^1$H NMR (400 MHz, acetone-d$_6$) δ 9.54 (s, 1H), 8.15 (s, 1H), 7.99 (s, 1H), 7.65 (d, J = 8.8 Hz, 1H), 7.50 (d, J = 8.8 Hz, 1H), 7.33 (d, J = 7.6 Hz, 2H), 6.93 (d, J = 7.6 Hz, 2H), 4.84 (s, 2H), 4.10 (s, 1H), 3.83-3.86 (m, 2H), 3.79 (s, 3H), 3.67-3.69 (m, 2H), 2.59 (s, 3H); LCMS (electrospray) m/z 495 (M + H)$^+$. |

TABLE 1-continued

Structures and Characteristics of Compounds 1-360

| No. | Structure | NMR Characterization |
|---|---|---|
| 249 | 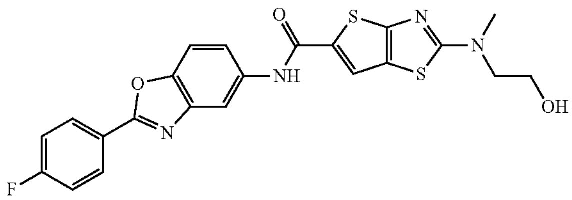 [SMILES: CN(CCO)c1nc2sc(C(=O)Nc3ccc4oc(-c5ccc(F)cc5)nc4c3)cc2s1] | Brown solid; $^1$H NMR (400 MHz, DMSO-d$_6$) δ 10.30 (s, 1H), 8.24-8.28 (m, 2H), 8.21 (d, J = 2.0 Hz, 1H), 8.16 (s, 1H), 7.76 (d, J = 8.8 Hz, 1H), 7.69 (dd, J = 8.8, 2.0 Hz, 1H), 7.43-7.50 (m, 2H), 4.87-4.91 (m, 1H), 3.65-3.69 (m, 2H), 3.57-3.62 (m, 2H), 3.17 (s, 3H); LCMS (electrospray) m/z 468 (M + H)$^+$. |
| 250 | 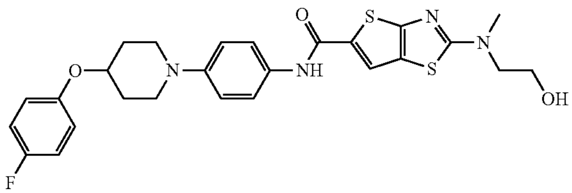 [SMILES: CN(CCO)c1nc2sc(C(=O)Nc3ccc(N4CCC(Oc5ccc(F)cc5)CC4)cc3)cc2s1] | Green solid; $^1$H NMR (400 MHz, DMSO-d$_6$) δ 9.30 (s, 1H), 8.07 (s, 1H), 7.54 (d, J = 9.2 Hz, 2H), 7.08-7.13 (m, 2H), 6.99-7.02 (m, 2H), 6.96 (d, J = 9.2 Hz, 2H), 4.87-4.90 (m, 1H), 4.47-4.51 (m, 1H), 3.64-3.66 (m, 2H), 3.56-3.59 (m, 2H), 3.44-3.49 (m, 2H), 3.16 (s, 3H), 2.97-3.03 (m, 2H), 2.00-2.06 (m, 2H), 1.48-1.57 (m, 2H); LCMS (electrospray) m/z 526 (M + H)$^+$. |
| 251 | 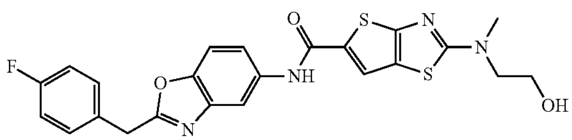 [SMILES: CN(CCO)c1nc2sc(C(=O)Nc3ccc4oc(Cc5ccc(F)cc5)nc4c3)cc2s1] | Ivory solid; $^1$H NMR (400 MHz, DMSO-d$_6$) δ 10.23 (s, 1H), 8.13 (s, 1H), 8.08 (s, 1H), 7.60-7.64 (m, 2H), 7.41-7.43 (m, 2H), 7.15-7.22 (m, 2H), 4.87-4.91 (m, 1H), 4.33 (s, 2H), 3.63-3.67 (m, 2H), 3.57-3.61 (m, 2H), 3.17 (s, 3H); LCMS (electrospray) m/z 482 (M + H)$^+$. |
| 252 | 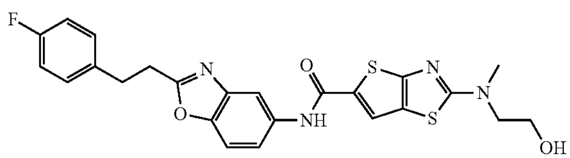 [SMILES: CN(CCO)c1nc2sc(C(=O)Nc3ccc4oc(CCc5ccc(F)cc5)nc4c3)cc2s1] | Ivory solid; $^1$H NMR (400 MHz, DMSO-d$_6$) δ 10.22 (s, 1H), 8.14 (s, 1H), 8.06 (d, J = 2.0 Hz, 1H), 7.63 (d, J = 8.4 Hz, 1H), 7.59 (dd, J = 8.4, 2.0 Hz, 1H), 7.30-7.35 (m, 2H), 7.07-7.12 (m, 2H), 4.87-4.91 (m, 1H), 3.64-3.69 (m, 2H), 3.57-3.61 (m, 2H), 3.22-3.26 (m, 2H), 3.17 (s, 3H), 3.10-3.15 (m, 2H); LCMS (electrospray) m/z 496 (M + H)$^+$. |
| 253 | 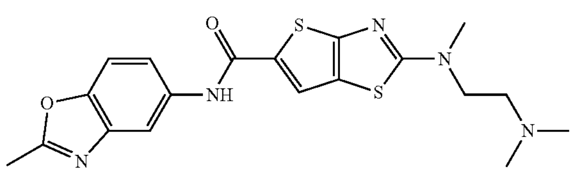 | Pale yellow solid; $^1$H NMR (400 MHz, acetone-d$_6$) δ 9.51 (s, 1H), 8.15 (s, 1H), 7.99 (s, 1H), 7.64-7.66 (m, 1H), 7.48-7.51 (m, 1H), 3.68-3.71 (m, 2H), 3.21 (s, 3H), 2.60 (s, 3H), 2.58-2.84 (m, 2H), 2.25 (s, 6H); LCMS (electrospray) m/z 415 (M + H)$^+$. |
| 254 | 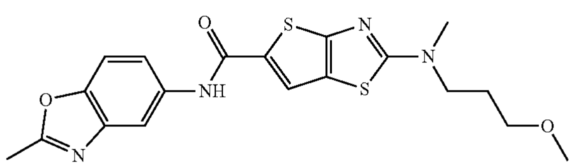 | Pale yellow solid; $^1$H NMR (400 MHz, acetone-d$_6$) δ 9.48 (s, 1H), 8.13-8.14 (m, 1H), 7.97 (s, 1H), 7.63-7.66 (m, 1H), 7.48-7.51 (m, 1H), 3.63-3.67 (m, 2H), 3.42-3.45 (m, 2H), 3.29 (s, 3H), 3.18 (s, 3H), 2.58 (s, 3H), 1.94-1.97 (m, 2H); LCMS (electrospray) m/z 417 (M + H)$^+$. |
| 255 | 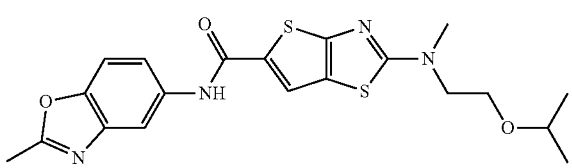 | Pale yellow solid; $^1$H NMR (400 MHz, acetone-d$_6$) δ 9.31 (s, 1H), 8.16-8.17 (m, 1H), 7.64-7.67 (m, 2H), 7.46-7.49 (m, 1H), 4.61 (t, J = 8.0 Hz, 2H), 3.74 (t, J = 8.0 Hz, 2H), 3.47-3.52 (m, 1H), 3.03 (s, 3H), 2.57 (s, 3H), 1.19 (d, J = 6.8 Hz, 6H); LCMS (electrospray) m/z 431 (M + H)$^+$. |
| 256 | 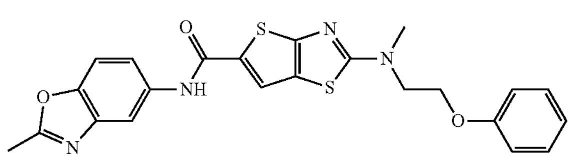 [SMILES: Cc1nc2cc(NC(=O)c3cc4sc(N(C)CCOc5ccccc5)nc4s3)ccc2o1] | Pale yellow solid; $^1$H NMR (400 MHz, acetone-d$_6$) δ 9.51 (s, 1H), 8.14-8.15 (m, 1H), 8.00 (s, 1H), 7.64-7.66 (m, 1H), 7.48 (d, J = 8.8 Hz, 1H), 7.26-7.30 (m, 2H), 6.92-6.98 (m, 3H), 4.33 (t, J = 5.6 Hz, 2H), 4.02 (t, J = 5.6 Hz, 2H), 3.13 (s, 3H), 2.59 (s, 3H); LCMS (electrospray) m/z 465 (M + H)$^+$. |
| 257 | 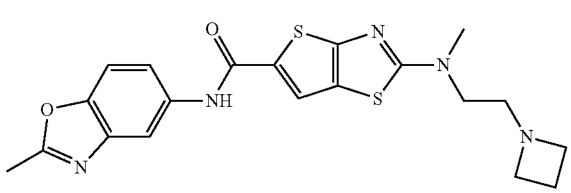 [SMILES: Cc1nc2cc(NC(=O)c3cc4sc(N(C)CCN5CCC5)nc4s3)ccc2o1] | Pale yellow solid; $^1$H NMR (400 MHz, acetone-d$_6$) δ 9.49 (s, 1H), 8.14 (s, 1H), 7.98 (s, 1H), 7.63 (d, J = 8.8 Hz, 1H), 7.48 (d, J = 8.8 Hz, 1H), 3.50 (t, J = 6.4 Hz, 2H), 3.17 (s, 3H), 2.77-2.81 (m, 2H), 2.66 (t, J = 6.4 Hz, 2H), 2.58 (s, 3H), 1.95-1.99 (m, 2H), 1.29 1.32 (m, 2H); LCMS (electrospray) m/z 428 (M + H)$^+$. |

TABLE 1-continued

Structures and Characteristics of Compounds 1-360

| No. | Structure | NMR Characterization |
|---|---|---|
| 258 | 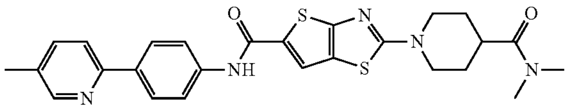 | Orange solid; $^1$H NMR (400 MHz, DMSO-d$_6$) δ 10.42 (s, 1H), 8.59 (s, 1H), 8.23 (s, 1H), 8.04-8.06 (m, 4H), 7.90-7.93 (m, 2H), 3.99-4.02 (m, 2H), 3.25-3.31 (m, 2H), 3.06 (s, 3H), 2.97-3.00 (m, 1H), 2.82 (s, 3H), 2.41 (s, 3H), 1.75-1.79 (m, 2H), 1.60-1.62 (m, 2H). |
| 259 | 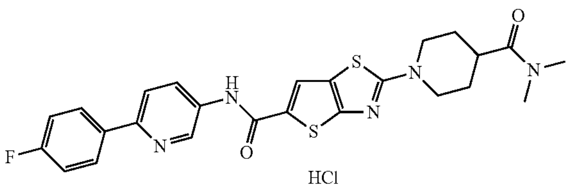 [SMILES: CN(C)C(=O)C1CCN(c2nc3sc(C(=O)Nc4ccc(-c5ccc(F)cc5)nc4)cc3s2)CC1 ; Cl] | Bright yellow solid; $^1$H NMR (400 MHz, DMSO-d$_6$) δ 10.59 (s, 1H), 9.00 (d, J = 2.0 Hz, 1H), 8.59 (dd, J = 8.8, 2.0 Hz, 1H), 8.24 (s, 1H), 8.09-8.12 (m, 2H), 8.01 (d, J = 8.8 Hz, 1H), 7.30-7.35 (m, 2H), 3.99-4.02 (m, 2H), 3.25-3.31 (m, 2H), 3.06 (s, 3H), 2.99-3.06 (m, 1H), 2.82 (s, 3H), 1.76-1.79 (m, 2H), 1.59-1.63 (m, 2H). |
| 260 | 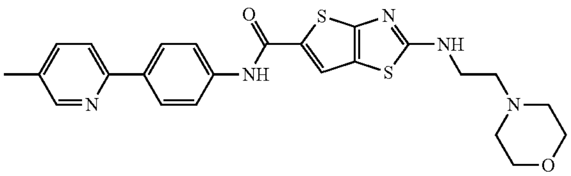 [SMILES: Cc1ccc(-c2ccc(NC(=O)c3cc4sc(NCCN5CCOCC5)nc4s3)cc2)nc1] | Yellow solid; $^1$H NMR (400 MHz, DMSO-d$_6$) δ 10.21 (s, 1H), 8.47 (d, J = 2.0 Hz, 1H), 8.37 (s, 1H), 8.10 (s, 1H), 8.06 (d, J = 8.4 Hz, 2H), 7.84 (d, J = 8.4 Hz, 1H), 7.80 (d, J = 8.4 Hz, 2H), 7.67 (dd, J = 8.4, 2.0 Hz, 1H), 3.56-3.58 (m, 4H), 3.46-3.50 (m, 2H), 2.50-2.55 (m, 2H), 2.40-2.44 (m, 4H), 2.32 (s, 3H); LCMS (electrospray) 479 m/z (M + H)$^+$. |
| 261 | 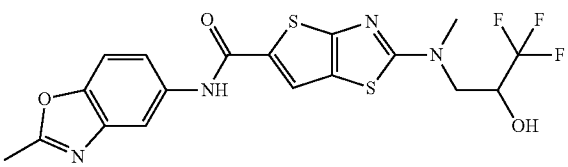 [SMILES: Cc1nc2cc(NC(=O)c3cc4sc(N(C)CC(O)C(F)(F)F)nc4s3)ccc2o1] | White solid; $^1$H NMR (400 MHz, DMSO-d$_6$) δ 10.27 (s, 1H), 8.16 (s, 1H), 8.05 (s, 1H), 7.61-7.63 (m, 2H), 6.67 (s, 1H), 4.42-4.48 (m, 1H), 3.89-3.93 (m, 1H), 3.61-3.67 (m, 1H), 3.19 (s, 3H), 2.60 (s, 3H); LCMS (electrospray) m/z 456 (M + H)$^+$. |
| 262 | 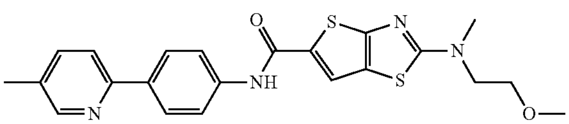 | Ivory solid; $^1$H NMR (400 MHz, DMSO-d$_6$) δ 10.25 (s, 1H), 8.47 (d, J = 2.0 Hz, 1H), 8.17 (s, 1H), 8.06 (d, J = 8.4 Hz, 2H), 7.84 (d, J = 8.4 Hz, 1H), 7.81 (d, J = 8.4 Hz, 2H), 7.68 (dd, J = 8.4, 2.0 Hz, 1H), 3.70-3.74 (m, 2H), 3.58-3.62 (m, 2H), 3.28 (s, 3H), 3.15 (s, 3H), 2.32 (s, 3H); LCMS (electrospray) m/z 438 (M + H)$^+$. |
| 263 | 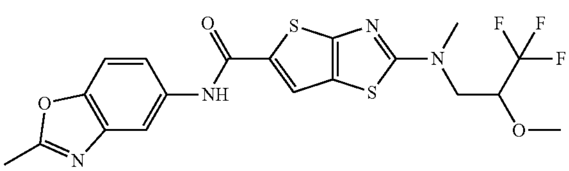 [SMILES: COC(CN(C)c1nc2sc(C(=O)Nc3ccc4oc(C)nc4c3)cc2s1)C(F)(F)F] | Ivory solid; $^1$H NMR (400 MHz, DMSO-d$_6$) δ 10.05 (s, 1H), 8.03 (s, 1H), 7.83 (s, 1H), 7.56-7.62 (m, 2H), 5.63-5.68 (m, 1H), 3.97-4.02 (m, 1H), 3.80-3.84 (m, 1H), 2.97 (s, 3H), 2.59 (s, 3H), 2.43 (s, 3H); LCMS (electrospray) m/z 470 (M + H)$^+$. |
| 264 | 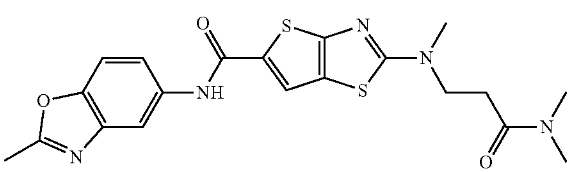 | Pale yellow solid; $^1$H NMR (400 MHz, DMSO-d$_6$) δ 10.21 (s, 1H), 8.13 (s, 1H), 8.04 (s, 1H), 7.56-7.61 (m, 2H), 3.71-3.75 (m, 2H), 3.12 (s, 3H), 2.95 (s, 3H), 2.80 (s, 3H), 2.69-2.72 (m, 2H), 2.58 (s, 3H); LCMS (electrospray) m/z 443 (M + H)$^+$. |
| 265 | 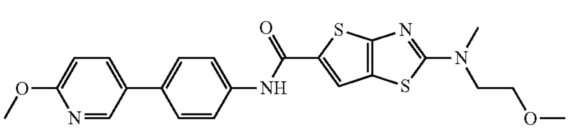 | Yellow solid; $^1$H NMR (400 MHz, acetone-d$_6$) δ 9.48 (s, 1H), 8.44 (s, 1H), 7.99 (s, 1H), 7.96 (d, J = 8.8 Hz, 1H), 7.88 (d, J = 8.8 Hz, 2H), 7.62 (d, J = 8.8 Hz, 2H), 6.84 (d, J = 8.8 Hz, 1H), 3.93 (s, 3H), 3.78 (t, J = 5.2 Hz, 2H), 3.67 (t, J = 5.2 Hz, 2H), 3.33 (s, 3H), 3.22 (s, 3H); LCMS (electrospray) m/z 454 (M + H)$^+$. |
| 266 | 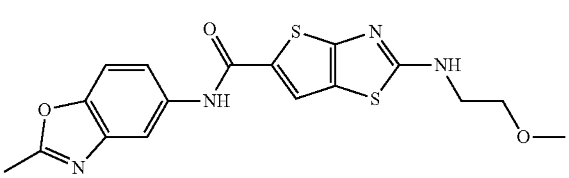 | Pale yellow solid; $^1$H NMR (400 MHz, DMSO-d$_6$) δ 10.20 (brs, 1H), 8.50 (brs, 1H), 8.04-8.07 (m, 2H), 7.59-7.62 (m, 2H), 3.51-3.54 (m, 5H), 3.29-3.31 (m, 2H), 2.60 (s, 3H); LCMS (electrospray) m/z 388 (M + H)$^+$. |

TABLE 1-continued

Structures and Characteristics of Compounds 1-360

| No. | Structure | NMR Characterization |
|---|---|---|
| 267 | 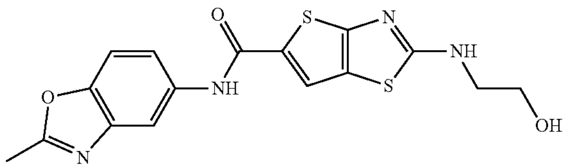 [SMILES: Cc1nc2cc(NC(=O)c3cc4sc(NCCO)nc4s3)ccc2o1] | Pale yellow solid; $^1$H NMR (400 MHz, DMSO-d$_6$) δ 10.19 (s, 1H), 8.46 (brt, J = 5.2 Hz, 1H), 8.05-8.07 (m, 2H), 7.59-7.60 (m, 2H), 4.83 (t, J = 5.2 Hz, 1H), 3.57-3.61 (m, 2H), 3.40-3.44 (m, 2H), 2.59 (s, 3H); LCMS (electrospray) m/z 374 (M + H)$^+$. |
| 268 | 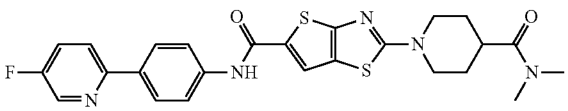 [SMILES: CN(C)C(=O)C1CCN(c2nc3sc(C(=O)Nc4ccc(-c5ccc(F)cn5)cc4)cc3s2)CC1] | solid; $^1$H NMR (400 MHz, DMSO-d$_6$) δ 10.30 (s, 1H), 8.62 (d, J = 2.4 Hz, 1H), 8.18 (s, 1H), 8.00-8.06 (m, 3H), 7.77-7.85 (m, 3H), 3.99-4.02 (m, 2H), 3.25-3.32 (m, 2H), 3.06 (s, 3H), 2.96-3.06 (m, 1H), 2.82 (s, 3H), 1.76-1.79 (m, 2H), 1.56-1.66 (m, 2H); LCMS (electrospray) m/z 510 (M + H)$^+$. |
| 269 | 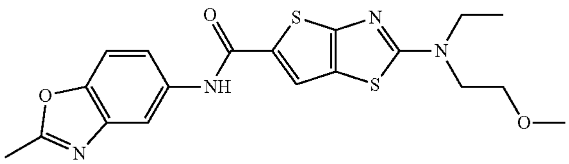 | White solid; $^1$H NMR (400 MHz, DMSO-d$_6$) δ 9.95 (s, 1H), 8.01 (s, 1H), 7.78 (s, 1H), 7.56-7.57 (m, 2H), 4.54 (t, J = 8.0 Hz, 2H), 3.63 (t, J = 8.0 Hz, 2H), 3.36 (q, J = 6.8 Hz, 2H), 2.57 (s, 3H), 2.39 (s, 3H), 1.13 (t, J = 6.8 Hz, 3H); LCMS (electrospray) m/z 417 (M + H)$^+$. |
| 270 | 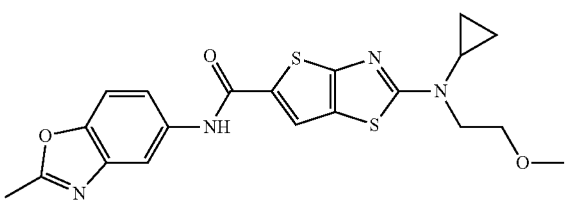 | Pale yellow solid; $^1$H NMR (400 MHz. DMSO-d$_6$) δ 9.98 (s, 1H), 8.03 (s, 1H), 7.80 (s, 1H), 7.57-7.59 (s, 2H), 4.50 (t, J = 7.6 Hz, 2H), 3.61 (t, J = 7.6 Hz, 2H), 2.68-2.72 (m, 1H), 2.59 (s, 3H), 2.45 (s, 3H), 0.74-0.79 (m, 4H). |
| 271 | 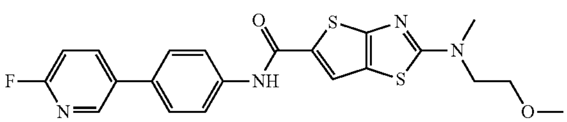 [SMILES: COCCN(C)c1nc2sc(C(=O)Nc3ccc(-c4ccc(F)nc4)cc3)cc2s1] | Pale yellow solid; $^1$H NMR (400 MHz, acetone-d$_6$) δ 9.53 (s, 1H), 8.49-8.50 (m, 1H), 8.20-8.25 (m, 1H), 8.00 (s, 1H), 7.92 (d, J = 9.2 Hz, 2H), 7.68 (d, J = 9.2 Hz, 2H), 7.14-7.17 (m, 1H), 3.77-3.79 (m, 2H), 3.66-3.68 (m, 2H), 3.33 (s, 3H), 2.22 (s, 3H); LCMS (electrospray) m/z 443 (M + H)$^+$. |
| 272 | 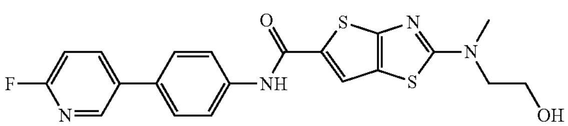 [SMILES: CN(CCO)c1nc2sc(C(=O)Nc3ccc(-c4ccc(F)nc4)cc3)cc2s1] | Pale yellow solid; $^1$H NMR (400 MHz, DMSO-d$_6$) δ 10.26 (s, 1H), 8.54-8.55 (m, 1H), 8.28-8.29 (m, 1H), 8.17 (s, 1H), 7.85 (d, J = 8.8 Hz, 2H), 7.72 (d, J = 8.8 Hz, 2H), 7.25-7.28 (m, 1H), 4.90 (s, 1H), 3.65-3.67 (m, 2H), 3.60-3.61 (m, 2H), 3.18 (s, 3H); LCMS (electrospray) m/z 429 (M + H)$^+$. |
| 273 | 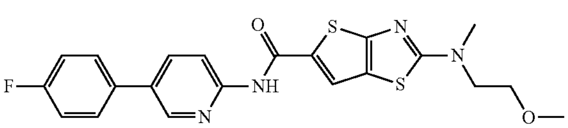 [SMILES: COCCN(C)c1nc2sc(C(=O)Nc3ccc(-c4ccc(F)cc4)cn3)cc2s1] | Pale yellow solid; $^1$H NMR (400 MHz, methanol-d$_6$) δ 8.58-8.59 (m, 1H), 8.21-8.23 (m, 1H), 8.03-8.06 (m, 1H), 8.01 (s, 1H), 7.66-7.70 (m, 2H), 7.19-7.24 (m, 2H), 3.77-3.80 (m, 2H), 3.68-3.70 (m, 2H), 3.38 (s, 3H), 3.23 (s, 3H); LCMS (electrospray) m/z 443 (M + H)$^+$. |
| 274 | 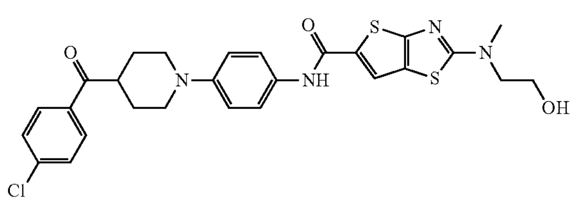 | Yellow solid; $^1$H NMR (400 MHz, DMSO-d$_6$) δ 9.93 (s, 1H), 8.07 (s, 1H), 8.03 (d, J = 8.8 Hz, 2H), 7.62 (d, J = 8.8 Hz, 2H), 7.53 (d, J = 9.2 Hz, 2H), 6.94 (d, J = 9.2 Hz, 2H), 4.89 (s, 1H), 3.71-3.72 (m, 1H), 3.64-3.68 (m, 3H), 3.59-3.60 (m, 3H), 3.16 (s, 3H), 2.81-2.84 (m, 2H), 1.85-1.88 (m, 2H), 1.67-1.69 (m, 2H); LCMS (electrospray) m/z 443, 445 (M + H)$^+$ (Cl– isotope pattern). |
| 275 | 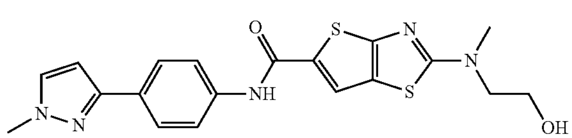 [SMILES: CN(CCO)c1nc2sc(C(=O)Nc3ccc(-c4ccn(C)n4)cc3)cc2s1] | Ivory solid; $^1$H NMR (400 MHz, DMSO-d$_6$) δ 10.15 (s, 1H), 8.14 (s, 1H), 7.70-7.73 (m, 5H), 6.63 (s, 1H), 4.87-4.91 (m, 1H), 3.87 (s, 3H), 3.64-3.69 (m, 2H), 3.58-3.62 (m, 2H), 3.17 (s, 3H); LCMS (electrospray) m/z 413 (M + H)$^+$. |
| 276 | 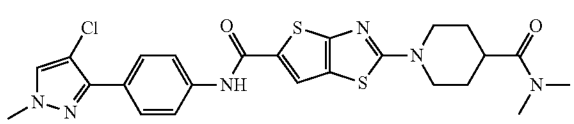 | Pale yellow solid; $^1$H NMR (400 MHz, DMSO-d$_6$) δ 10.25 (s, 1H), 8.16 (s, 1H), 8.01 (s, 1H), 7.78 (s, 4H), 3.97-4.01 (m, 2H), 3.85 (s, 3H), 3.23-3.27 (m, 2H), 3.10 (s, 3H), 2.98-3.05 (m, 1H), 2.81 (s, 3H), 1.74-1.77 (m, 2H), 1.56-1.64 (m, 2H); LCMS (electrospray) m/z 528 (M + H)$^+$. |

TABLE 1-continued

Structures and Characteristics of Compounds 1-360

| No. | Structure | NMR Characterization |
|---|---|---|
| 277 | 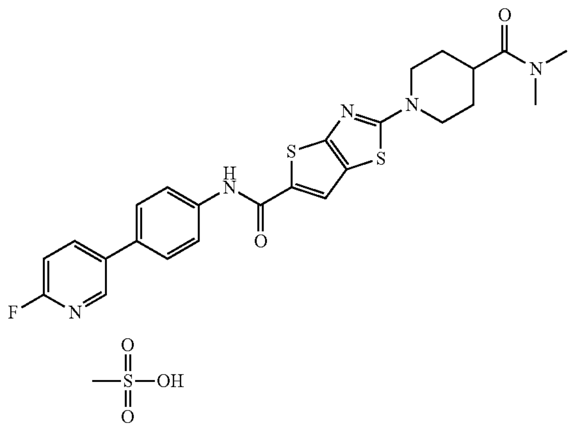 | Pale beige solid; ¹H NMR (400 MHz, DMSO-d$_6$) δ 10.28 (s, 1H), 8.54-8.55 (m, 1H), 8.27-8.28 (m, 1H), 8.17 (s, 1H), 7.85 (d, J = 8.8 Hz, 2H), 7.72 (d, J = 8.8 Hz, 2H), 7.25-7.28 (m, 1H), 3.99-4.02 (m, 2H), 3.25-3.26 (m, 2H), 3.06 (s, 3H), 2.98-2.99 (m, 1H), 2.82 (s, 3H), 2.49 (s, 3H), 1.76-1.79 (m, 2H), 1.60-1.62 (m, 2H); LCMS (electrospray) m/z 510 (M + H)⁺. |
| 278 | 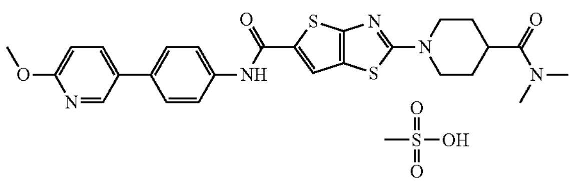 | Pale yellow solid; ¹H NMR (400 MHz, DMSO-d$_6$) δ 10.23 (s, 1H), 8.49 (s, 1H), 8.17 (s, 1H), 8.02 (d, J = 8.4 Hz, 1H), 7.81 (d, J = 8.4 Hz, 2H), 7.66 (d, J = 8.4 Hz, 2H), 6.91 (d, J = 8.4 Hz, 1H), 3.99-4.02 (m, 2H), 3.90 (s, 3H), 3.28-3.31 (m, 2H), 3.07 (s, 3H), 2.99-3.02 (m, 1H), 2.82 (s, 3H), 2.32 (s, 3H), 1.76-1.79 (m, 2H), 1.57-1.67 (m, 2H); LCMS (electrospray) m/z 521 (M + H)⁺. |
| 279 | 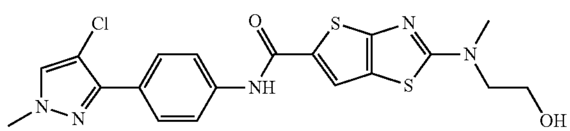 [SMILES: CN(CCO)c1nc2sc(C(=O)Nc3ccc(-c4nn(C)cc4Cl)cc3)cc2s1] | Pale yellow solid; ¹H NMR (400 MHz, acetone-d$_6$) δ 9.49 (s, 1H), 7.99 (s, 1H), 7.84-7.91 (m, 4H), 7.81 (s, 1H), 4.04-4.05 (m, 1H), 3.92 (s, 3H), 3.84-3.87 (m, 2H), 3.69-3.74 (m, 2H), 3.25 (s, 3H); LCMS (electrospray) m/z 447 (M + H)⁺. |
| 280 | 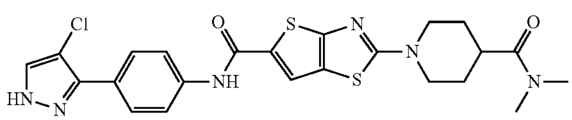 [SMILES: CN(C)C(=O)C1CCN(c2nc3sc(C(=O)Nc4ccc(-c5n[nH]cc5Cl)cc4)cc3s2)CC1] | Pale yellow solid; ¹H NMR (400 MHz, DMSO-d$_6$) δ 13.20 (s, 1H), 10.25 (s, 1H), 8.14 (s, 1H), 7.78 (s, 4H), 3.96-3.99 (m, 2H), 3.21-3.24 (m, 2H), 3.04 (s, 3H), 2.93-2.98 (m, 1H), 2.79 (s, 3H), 1.73-1.76 (m, 2H), 1.54-1.64 (m, 2H); LCMS (electrospray) m/z 514 (M + H)⁺. |
| 281 | 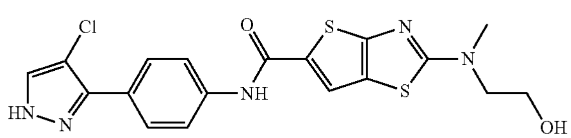 [SMILES: CN(CCO)c1nc2sc(C(=O)Nc3ccc(-c4n[nH]cc4Cl)cc3)cc2s1] | Pale yellow solid; ¹H NMR (400 MHz, acetone-d$_6$) δ 12.19 (s, 1H), 9.55 (s, 1H), 8.01 (s, 1H), 7.85-7.91 (m, 4H), 7.78 (s, 1H), 4.04-4.05 (m, 1H), 3.84-3.88 (m, 2H), 3.70-3.73 (m, 2H), 3.25 (s, 3H); LCMS (electrospray) m/z 433 (M + H)⁺. |
| 282 | 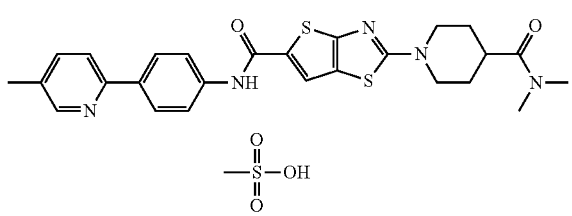 | Pale yellow solid; ¹H NMR (400 MHz, DMSO-d$_6$) δ 10.42 (s, 1H), 8.65 (s, 1H), 8.16-8.24 (m, 3H), 8.01 (d, J = 8.8 Hz, 2H), 7.93 (d, J = 8.8 Hz, 2H), 3.98-4.01 (m, 2H), 3.27-3.30 (m, 2H), 3.05 (s, 3H). 2.95-3.01 (m, 1H), 2.80 (s, 3H), 2.44 (s, 3H), 2.31 (s, 3H), 1.74-1.77 (m, 2H), 1.55-1.64 (m, 2H); LCMS (electrospray) m/z 505 (M + H)⁺. |
| 283 | 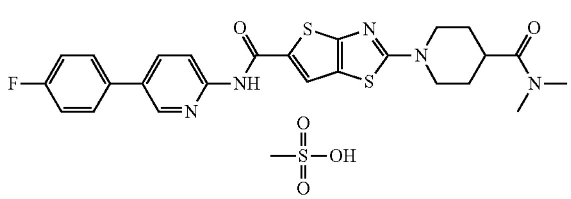 | Yellow solid; ¹H NMR (400 MHz, DMSO-d$_6$) δ 10.98 (s, 1H), 8.69 (s, 1H), 8.39 (s, 1H), 8.14-8.21 (m, 2H), 7.78-7.81 (m, 2H), 7.31-7.35 (m, 2H), 4.00-4.03 (m, 2H), 3.26-3.32 (m, 2H), 3.07 (s, 3H), 2.98-2.99 (m, 1H), 2.82 (s, 3H), 2.32 (s, 3H), 1.76-1.79 (m, 2H), 1.60-1.62 (m, 2H); LCMS (electrospray) m/z 510 (M + H)⁺. |

TABLE 1-continued

Structures and Characteristics of Compounds 1-360

| No. | Structure | NMR Characterization |
|---|---|---|
| 284 | 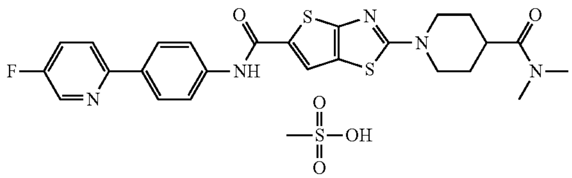 | Yellow solid; $^1$H NMR (400 MHz, DMSO-d$_6$) δ 10.29 (s, 1H), 8.63 (s, 1H), 8.18 (s, 1H), 8.04-8.06 (m, 2H), 8.01-8.03 (m, 1H), 7.84-7.86 (m, 2H), 7.78-7.81 (m, 1H), 3.99-4.03 (m, 2H), 3.25-3.31 (m, 2H), 3.07 (s, 3H), 2.96-3.02 (m, 1H), 2.82 (s, 3H), 2.31 (s, 3H), 1.76-1.79 (m, 2H), 1.58-1.66 (m, 2H); LCMS (electrospray) m/z 509 (M + H)$^+$. |
| 285 | 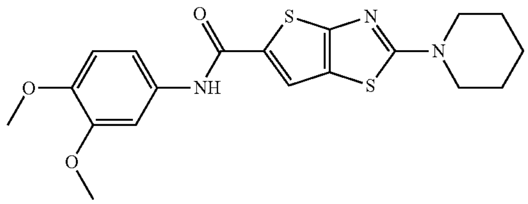 [SMILES: COc1ccc(NC(=O)c2cc3sc(N4CCCCC4)nc3s2)cc1OC] | Pale brown solid; $^1$H NMR (400 MHz, DMSO-d$_6$) δ 9.97 (s, 1H), 8.06 (s, 1H), 7.37 (s, 1H), 7.21 (d, J = 8.8 Hz, 1H), 6.90 (d, J = 8.8 Hz, 1H), 3.73 (s, 3H), 3.71 (s, 3H), 3.52-3.54 (m, 4H), 1.60-1.62 (m, 6H); LCMS (electrospray) m/z 403 (M + H)$^+$. |
| 286 | 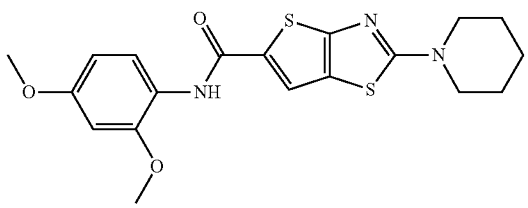 [SMILES: COc1ccc(NC(=O)c2cc3sc(N4CCCCC4)nc3s2)c(OC)c1] | Pale yellow solid; $^1$H NMR (400 MHz, DMSO-d$_6$) δ 9.28 (s, 1H), 8.04 (s, 1H), 7.41 (d, J = 8.8 Hz, 1H), 6.62 (s, 1H), 6.50 (d, J = 8.8 Hz, 1H), 3.78 (s, 3H), 3.75 (s, 3H), 3.51-3.53 (m, 4H), 1.60-1.62 (m, 6H); LCMS (electrospray) m/z 403 (M + H)$^+$. |
| 287 | 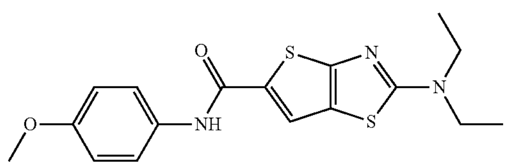 [SMILES: CCN(CC)c1nc2sc(C(=O)Nc3ccc(OC)cc3)cc2s1] | White solid; $^1$H NMR (400 MHz, DMSO-d$_6$) δ 9.99 (s, 1H), 8.08 (s, 1H), 7.58-7.61 (m, 2H), 6.90-6.93 (m, 2H), 3.74 (s, 3H), 3.53 (q, J = 7.2 Hz, 4H), 1.21 (t, J = 7.2 Hz, 6H); LCMS (electrospray) m/z 362 (M + H)$^+$. |
| 288 | 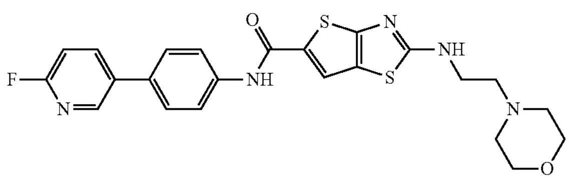 [SMILES: O=C(Nc1ccc(-c2ccc(F)nc2)cc1)c1cc2sc(NCCN3CCOCC3)nc2s1] | Ivory solid; $^1$H NMR (400 MHz, DMSO-d$_6$) δ 10.24 (s, 1H), 8.55 (d, J = 2.8 Hz, 1H), 8.39 (s, 1H), 8.24-8.30 (m, 1H), 8.10 (s, 1H), 7.85 (d, J = 8.4 Hz, 2H), 7.73 (d, J = 8.4 Hz, 2H), 7.27 (dd, J = 8.4, 2.8 Hz, 1H), 3.56-3.60 (m, 4H), 3.46-3.49 (m, 2H), 2.50-2.55 (m, 2H), 2.39-2.46 (m, 4H); LCMS (electrospray) m/z 484 (M + H)$^+$. |
| 289 | 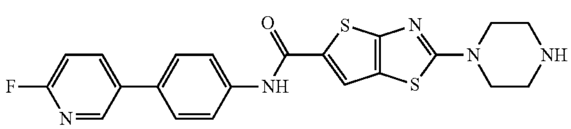 | Pale yellow solid; $^1$H NMR (400 MHz, DMSO-d$_6$) δ 10.26 (s, 1H), 8.54 (s, 1H), 8.24-8.27 (m, 1H), 8.16 (s, 1H), 7.83 (d, J = 8.8 Hz, 2H), 7.71 (d, J = 8.8 Hz, 2H), 7.24-7.27 (m, 1H), 3.44-3.47 (m, 4H), 2.78-2.81 (m, 4H); LCMS (electrospray) m/z 439 (M + H)$^+$. |
| 290 | 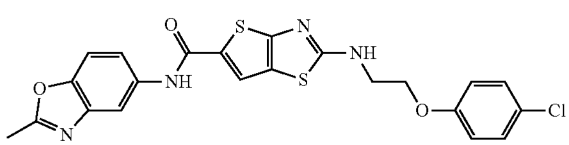 [SMILES: Cc1nc2cc(NC(=O)c3cc4sc(NCCOc5ccc(Cl)cc5)nc4s3)ccc2o1] | Pale yellow solid; $^1$H NMR (400 MHz, DMSO-d$_6$) δ 10.20 (s, 1H), 8.66 (s, 1H), 8.07 (s, 1H), 8.03 (s, 1H), 7.56-7.61 (m, 2H), 7.32 (d, J = 8.4 Hz, 2H), 6.99 (d, J = 8.4 Hz, 2H), 4.15-4.17 (m, 2H), 3.72-3.73 (m, 2H), 2.49 (s, 3H); LCMS (electrospray) m/z 484 (M + H)$^+$. |
| 291 | 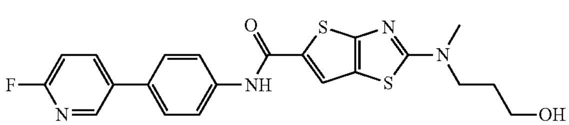 [SMILES: CN(CCCO)c1nc2sc(C(=O)Nc3ccc(-c4ccc(F)nc4)cc3)cc2s1] | White solid; $^1$H NMR (400 MHz, DMSO-d$_6$) δ 10.26 (s, 1H), 8.56 (s, 1H), 8.28-8.29 (m, 1H), 8.17 (s, 1H), 7.85 (d, J = 8.8 Hz, 2H), 7.73 (d, J = 8.8 Hz, 2H), 7.26-7.29 (m, 1H), 4.60 (s, 1H), 3.57-3.60 (m, 2H), 3.47-3.50 (m, 2H), 3.25 (s, 3H), 1.78-1.81 (m, 2H); LCMS (electrospray) m/z 443 (M + H)$^+$. |
| 292 | 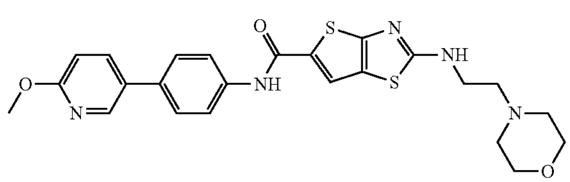 [SMILES: COc1ccc(-c2ccc(NC(=O)c3cc4sc(NCCN5CCOCC5)nc4s3)cc2)cn1] | Ivory solid; $^1$H NMR (400 MHz, DMSO-d$_6$) δ 10.18 (s, 1H), 8.48 (d, J = 2.4 Hz, 1H), 8.37 (brs, 1H), 8.09 (s, 1H), 8.01 (dd, J = 9.2, 2.4 Hz, 1H), 7.81 (d, J = 8.8 Hz, 2H), 7.66 (d, J = 8.8 Hz, 2H), 6.91 (d, J = 9.2 Hz, 1H), 3.89 (s, 3H), 3.56-3.58 (m, 4H), 3.45-3.50 (m, 2H), 2.51-2.54 (m, 2H), 2.39-2.44 (m, 4H); LCMS (electrospray) m/z 496 (M + H)$^+$. |

TABLE 1-continued

Structures and Characteristics of Compounds 1-360

| No. | Structure | NMR Characterization |
|---|---|---|
| 293 | 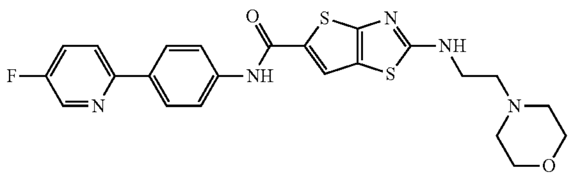 | Ivory solid; $^1$H NMR (400 MHz. DMSO-d$_6$) δ 10.24 (s, 1H), 8.62 (d, J = 2.0 Hz, 1H). 8.39 (brs, 1H), 8.10 (s, 1H), 7.99-8.05 (m, 3H). 7.77-7.84 (m, 3H), 3.56-3.60 (m, 4H), 3.43-3.48 (m, 2H), 2.52-2.55 (m, 2H), 2.39-2.45 (m, 4H); LCMS (electrospray) m/z 483 (M + H)$^+$. |
| 294 | 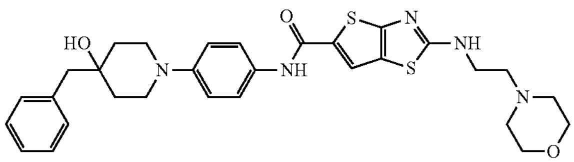 [SMILES: O=C(Nc1ccc(N2CCC(O)(Cc3ccccc3)CC2)cc1)c1cc2sc(NCCN3CCOCC3)nc2s1] | Ivory solid; $^1$H NMR (400 MHz, DMSO-d$_6$) δ 9.87 (s, 1H), 8.31 (brs, 1H), 7.99 (s, 1H), 7.49 (d, J = 8.8 Hz, 2H), 7.16-7.29 (m, 5H), 6.90 (d, J = 8.8 Hz, 2H), 4.31 (s, 1H), 3.55-3.59 (m, 4H), 3.43-3.48 (m, 2H), 3.29-3.36 (m, 2H), 2.93-3.01 (m, 2H), 2.70 (s, 2H), 2.50-2.59 (m, 2H), 2.37-2.43 (m, 4H), 1.55-1.64 (m, 2H), 1.42-1.49 (m, 2H); LCMS (electrospray) m/z 578 (M + H)$^+$. |
| 295 | 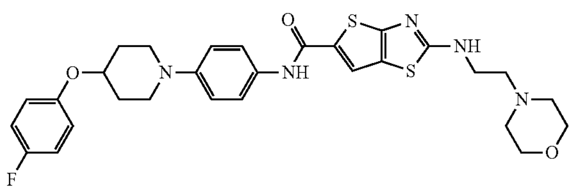 [SMILES: O=C(Nc1ccc(N2CCC(Oc3ccc(F)cc3)CC2)cc1)c1cc2sc(NCCN3CCOCC3)nc2s1] | Pale yellow solid; $^1$H NMR (400 MHz, DMSO-d$_6$) δ 9.91 (s, 1H), 8.32 (brs, 1H), 8.00 (s, 1H), 7.53 (d, J = 8.8 Hz, 2H), 7.07-7.14 (m, 2H), 6.97-7.03 (m, 2H), 6.95 (d, J = 8.8 Hz, 2H), 4.45-4.50 (m, 1H), 3.55-3.60 (m, 4H), 3.43-3.50 (m, 4H), 2.95-3.03 (m, 2H), 2.50-2.55 (m, 2H), 2.39-2.43 (m, 4H), 1.96-2.06 (m, 2H), 1.68-1.75 (m, 2H); LCMS (electrospray) 582 m/z (M + H)$^+$. |
| 296 | 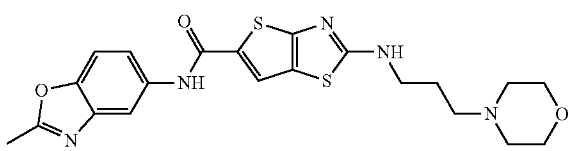 [SMILES: Cc1nc2cc(NC(=O)c3cc4sc(NCCCN5CCOCC5)nc4s3)ccc2o1] | White solid; $^1$H NMR (400 MHz, DMSO-d$_6$) δ 10.20 (s, 1H), 8.42 (brs, 1H), 8.07 (s, 1H), 8.05 (s, 1H), 7.58-7.62 (m, 2H), 3.54-3.60 (m, 4H), 3.34-3.38 (m, 2H), 2.59 (s, 3H), 2.32-2.39 (m, 6H), 1.72-1.77 (m, 2H); LCMS (electrospray) m/z 458 (M + H)$^+$. |
| 297 | 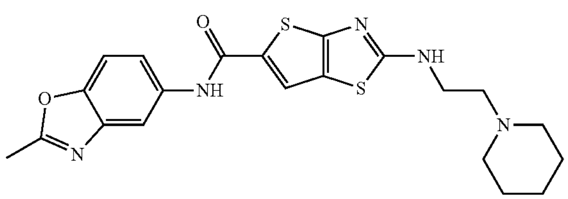 [SMILES: Cc1nc2cc(NC(=O)c3cc4sc(NCCN5CCCCC5)nc4s3)ccc2o1] | Brown solid; $^1$H NMR (400 MHz, DMSO-d$_6$) δ 10.20 (s, 1H), 8.34 (brs, 1H), 8.07 (s, 1H), 8.05 (s, 1H), 7.58-7.61 (m, 2H), 3.41-3.46 (m, 2H), 2.59 (s, 3H), 2.45-2.50 (m, 2H), 2.33-2.40 (m, 4H), 1.46-1.53 (m, 4H), 1.35-1.40 (m, 2H); LCMS (electrospray) m/z 441 (M + H)$^+$. |
| 298 | 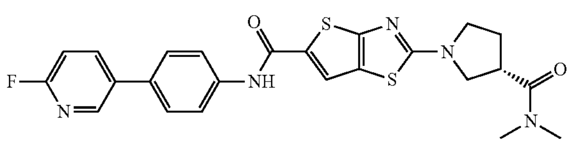 [SMILES: CN(C)C(=O)[C@H]1CCN(c2nc3sc(C(=O)Nc4ccc(-c5ccc(F)nc5)cc4)cc3s2)C1] | Pale yellow solid; $^1$H NMR (400 MHz, acetone-d$_6$) δ 9.54 (s, 1H), 8.50 (s, 1H), 8.21-8.23 (m, 1H), 8.01 (s, 1H), 7.93 (d, J = 8.8 Hz, 2H), 7.68 (d, J = 8.8 Hz, 2H), 7.15-7.18 (m, 1H), 3.65-3.76 (m, 4H), 3.57-3.59 (m, 1H), 3.18 (s, 3H), 2.92 (s, 3H), 2.36-2.39 (m, 1H), 2.26-2.28 (m, 1H); LCMS (electrospray) m/z 496 (M + H)$^+$. |
| 299 | 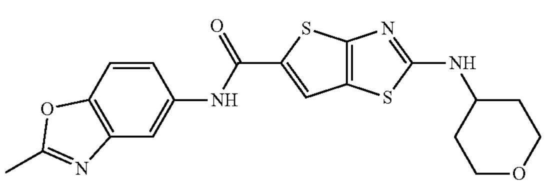 [SMILES: Cc1nc2cc(NC(=O)c3cc4sc(NC5CCOCC5)nc4s3)ccc2o1] | White solid; $^1$H NMR (400 MHz, DMSO-d$_6$) δ 10.22 (s, 1H), 8.45 (d, J = 6.8 Hz, 1H), 8.04-8.06 (m, 2H), 7.59-7.62 (m, 2H), 3.85-3.87 (m, 4H), 3.30-3.35 (m, 1H), 2.59 (s, 3H), 1.93-1.96 (m, 2H), 1.47-1.49 (m, 2H); LCMS (electrospray) m/z 415 (M + H)$^+$. |
| 300 | 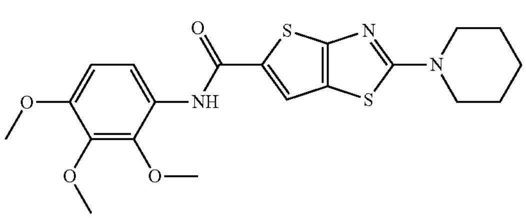 [SMILES: COc1ccc(NC(=O)c2cc3sc(N4CCCCC4)nc3s2)c(OC)c1OC] | Pale yellow solid; $^1$H NMR (400 MHz, DMSO-d$_6$) δ 9.41 (s, 1H), 8.07 (s, 1H), 7.26 (d, J = 8.8 Hz, 1H), 6.78 (d, J = 8.8 Hz, 1H), 3.78 (s, 3H), 3.75 (s, 3H), 3.53 (s, 3H), 3.30-3.32 (m, 4H), 1.60-1.62 (m, 6H); LCMS (electrospray) m/z 433 (M + H)$^+$. |

TABLE 1-continued

Structures and Characteristics of Compounds 1-360

| No. | Structure | NMR Characterization |
|---|---|---|
| 301 | 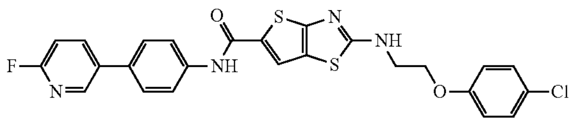 [SMILES: O=C(Nc1ccc(-c2ccc(F)nc2)cc1)c1cc2sc(NCCOc3ccc(Cl)cc3)nc2s1] | Pale yellow solid; $^1$H NMR (400 MHz, DMSO-d$_6$) δ 10.24 (s, 1H), 8.68 (s, 1H), 8.53 (s, 1H), 8.24-8.29 (m, 1H), 8.01 (s, 1H), 7.83 (d, J = 8.8 Hz, 2H), 7.71 (d, J = 8.8 Hz, 2H), 7.32 (d, J = 8.8 Hz, 2H), 7.24-7.27 (m, 1H), 7.99 (d, J = 8.8 Hz, 2H), 4.15-4.17 (m, 2H), 3.73-3.74 (m, 2H); LCMS (electrospray) m/z 524 (M + H)$^+$. |
| 302 | 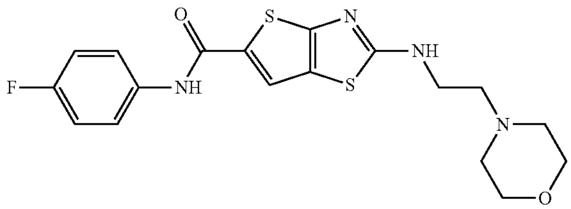 [SMILES: O=C(Nc1ccc(F)cc1)c1cc2sc(NCCN3CCOCC3)nc2s1] | Ivory solid; $^1$H NMR (400 MHz, DMSO-d$_6$) δ 10.14 (s, 1H), 8.36 (s, 1H), 8.04 (s, 1H), 7.68-7.73 (m, 2H), 7.14-7.21 (m, 2H), 3.53-3.61 (m, 4H), 3.44-3.49 (m, 2H), 2.50-2.54 (m, 2H), 2.39-2.45 (m, 4H); LCMS (electrospray) m/z 406 (M + H)$^+$. |
| 303 | 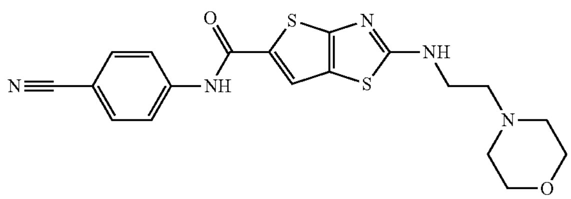 [SMILES: N#Cc1ccc(NC(=O)c2cc3sc(NCCN4CCOCC4)nc3s2)cc1] | Ivory solid; $^1$H NMR (400 MHz, DMSO-d$_6$) δ 10.23 (s, 1H), 8.21 (brs, 1H), 8.10 (s, 1H), 7.90 (d, J = 8.4 Hz, 2H), 7.78 (d, J = 8.4 Hz, 2H), 3.53-3.58 (m, 4H), 3.43-3.48 (m, 2H), 2.49-2.53 (m, 2H), 2.38-2.42 (m, 4H); LCMS (electrospray) m/z 413 (M + H)$^+$. |
| 304 | 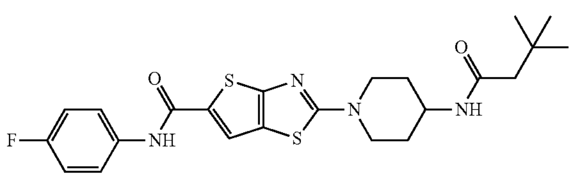 [SMILES: CC(C)(C)CC(=O)NC1CCN(c2nc3sc(C(=O)Nc4ccc(F)cc4)cc3s2)CC1] | Pale yellow solid; $^1$H NMR (400 MHz, DMSO-d$_6$) δ 10.18 (s, 1H), 8.11 (s, 1H), 7.72-7.74 (m, 1H), 7.70 (d, J = 8.8 Hz, 2H), 7.17 (d, J = 8.8 Hz, 2H), 3.84-3.92 (m, 4H), 3.25-3.26 (m, 1H), 1.93 (s, 2H), 1.82-1.86 (m, 2H), 1.40-1.49 (m, 2H), 0.94 (s, 9H); LCMS (electrospray) m/z 474 (M + H)$^+$. |
| 305 | 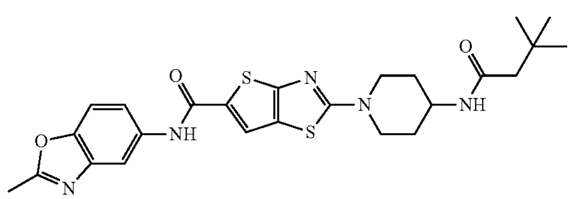 [SMILES: Cc1nc2cc(NC(=O)c3cc4sc(N5CCC(NC(=O)CC(C)(C)C)CC5)nc4s3)ccc2o1] | Pale yellow solid; $^1$H NMR (400 MHz, DMSO-d$_6$) δ 10.24 (s, 1H), 8.15 (s, 1H), 8.05 (s, 1H), 7.73-7.75 (m, 1H), 7.58-7.63 (m, 2H), 3.87-3.93 (m, 3H), 3.28-3.31 (m, 2H), 2.60 (s, 3 H), 1.94 (s, 2H), 1.84-1.87 (m, 2H), 1.43-1.51 (m, 2H), 0.95 (s, 9H); LCMS (electrospray) m/z 511 (M + H)$^+$. |
| 306 | 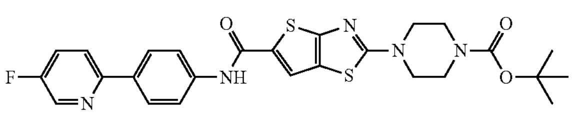 [SMILES: CC(C)(C)OC(=O)N1CCN(c2nc3sc(C(=O)Nc4ccc(-c5ccc(F)cn5)cc4)cc3s2)CC1] | Pale yellow solid; $^1$H NMR (400 MHz, DMSO-d$_6$) δ 10.30 (s, 1H), 8.61 (s, 1H), 8.18 (s, 1H), 8.03 (d, J = 8.8 Hz, 2H), 7.98-8.02 (m, 1H), 7.83 (d, J = 8.8 Hz, 2H), 7.76-7.81 (m, 1H), 3.54-3.56 (m, 4H), 3.48-3.54 (m, 4H), 1.42 (s, 9H); LCMS (electrospray) m/z 539 (M + H)$^+$. |
| 307 | 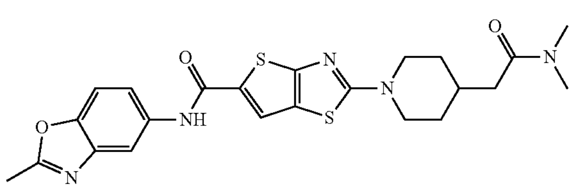 | Pale yellow solid; $^1$H NMR (400 MHz, DMSO-d$_6$) δ 10.23 (s, 1H), 8.13 (s, 1H), 8.04 (s, 1H), 7.56-7.61 (m, 2H), 3.93-3.96 (m, 2H), 3.15-3.20 (m, 2H), 2.94 (s, 3H), 2.80 (s, 3H), 2.58 (s, 3H), 2.26-2.31 (m, 2H), 2.00-2.02 (m, 1H), 1.77-1.80 (m, 2H), 1.22-1.30 (m, 2H); LCMS (electrospray) m/z 484 (M + H)$^+$. |
| 308 | 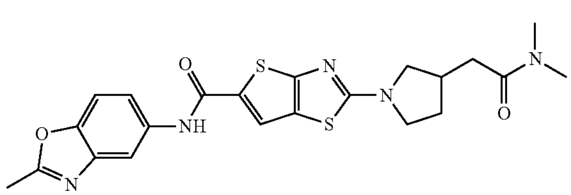 | Pale yellow solid; $^1$H NMR (400 MHz, DMSO-d$_6$) δ 10.22 (s, 1H), 8.14 (s, 1H), 8.05 (s, 1H), 7.58-7.63 (m, 2H), 3.70-3.74 (m, 1H), 3.58-3.60 (m, 1H), 3.44-3.50 (m, 1H), 3.11-3.16 (m, 1H), 2.97 (s, 3H), 2.84 (s, 3H), 2.65-2.73 (m, 1H), 2.60 (s, 3H), 2.50-2.56 (m, 2H), 2.19-2.23 (m, 1H), 1.73-1.78 (m, 1H); LCMS (electrospray) m/z 470 (M + H)$^+$. |

TABLE 1-continued

Structures and Characteristics of Compounds 1-360

| No. | Structure | NMR Characterization |
|---|---|---|
| 309 | 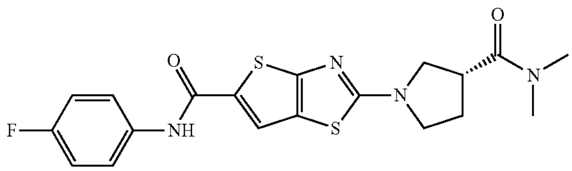 [SMILES: CN(C)C(=O)[C@@H]1CCN(c2nc3sc(C(=O)Nc4ccc(F)cc4)cc3s2)C1] | Pale yellow solid; $^1$H NMR (400 MHz, DMSO-d$_6$) δ 10.18 (s, 1H), 8.12 (s, 1H), 7.69-7.73 (m, 2H), 7.16-7.20 (m, 2H), 3.61-3.69 (m, 3H), 3.51-3.57 (m, 2H), 3.07 (s, 3H), 2.85 (s, 3H), 2.28-2.30 (m, 1H), 2.10-2.12 (m, 1H); LCMS (electrospray) m/z 419 (M + H)$^+$. |
| 310 | 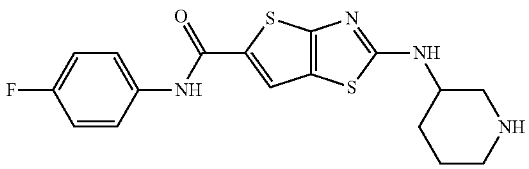 [SMILES: O=C(Nc1ccc(F)cc1)c1cc2sc(NC3CCCNC3)nc2s1] | White solid; $^1$H NMR (400 MHz, DMSO-d$_6$) δ 10.19 (s, 1H), 8.49-8.50 (m, 1H), 8.07 (s, 1H), 7.69-7.72 (m, 2H), 7.15-7.20 (m, 2H), 3.94 (brs, 1H), 3.05-3.08 (m, 2H), 2.69-2.80 (m, 2H), 2.00-2.03 (m, 1H), 1.81-1.90 (m, 1H), 1.51-1.63 (m, 3H); LCMS (electrospray) m/z 377 (M + H)$^+$. |
| 311 | 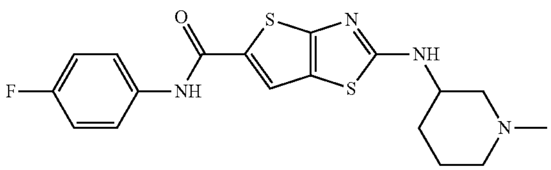 [SMILES: CN1CCCC(Nc2nc3sc(C(=O)Nc4ccc(F)cc4)cc3s2)C1] | White solid; $^1$H NMR (400 MHz, acetone-d$_6$) δ 9.47 (brs, 1H), 7.93 (s, 1H), 7.76-7.80 (m, 2H), 7.46 (brs, 1H), 7.07-7.12 (m, 2H), , 4.01-4.03 (m, 1H), 2.45-2.46 (m, 1H), 2.20-2.32 (m, 4H), 1.58-1.62 (m, 2H), 1.28-1.30 (m, 2H); LCMS (electrospray) m/z 391 (M + H)$^+$. |
| 312 | 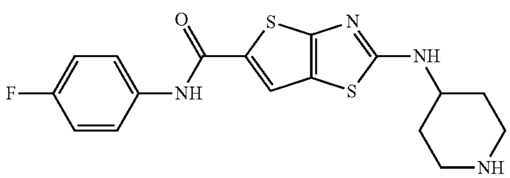 [SMILES: O=C(Nc1ccc(F)cc1)c1cc2sc(NC3CCNCC3)nc2s1] | White solid; $^1$H NMR (400 MHz, DMSO-d$_6$) δ 10.13 (s, 1H), 8.37-8.39 (m, 1H), 8.03 (s, 1H), 7.68-7.72 (m, 2H), 7.15-7.19 (m, 2H), 3.68-3.70 (m, 1H), 2.92-2.95 (m, 2H), 2.50-2.53 (m, 2H), 1.89-1.91 (m, 2H), 1.34-1.37 (m, 2H); LCMS (electrospray) m/z 377 (M + H)$^+$. |
| 313 | 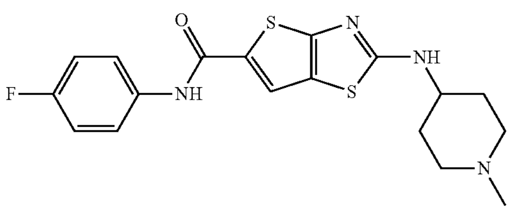 [SMILES: CN1CCC(Nc2nc3sc(C(=O)Nc4ccc(F)cc4)cc3s2)CC1] | White solid; $^1$H NMR (400 MHz, DMSO-d$_6$) δ 10.14 (brs, 1H), 8.36 (d, J = 6.8 Hz, 1H), 8.04 (s, 1H), 7.69-7.72 (m, 2H), 7.15-7.19 (m, 2H), 3.61-3.63 (m, 1H), 2.70-2.73 (m, 2H), 2.16 (s, 3H), 1.88-2.03 (m, 4H), 1.46-1.54 (m, 2H); LCMS (electrospray) m/z 391 (M + H)$^+$. |
| 314 | 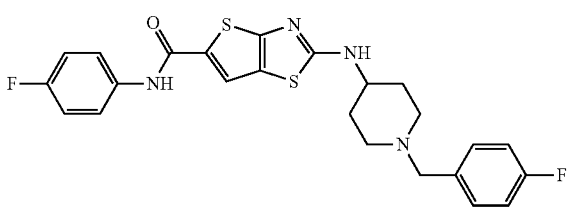 [SMILES: O=C(Nc1ccc(F)cc1)c1cc2sc(NC3CCN(Cc4ccc(F)cc4)CC3)nc2s1] | White solid; $^1$H NMR (400 MHz, DMSO-d$_6$) δ 10.13 (brs, 1H), 8.38 (d, J = 7.2 Hz, 1H), 8.03 (s, 1H), 7.68-7.72 (m, 2H), 7.31-7.35 (m, 2H), 7.12-7.19 (m, 4H), 3.65-3.67 (m, 1H), 3.45 (s, 2H), 2.74-2.77 (m, 2H), 2.05-2.11 (m, 2H), 1.94-1.97 (m, 2H), 1.45-1.53 (m, 2H); LCMS (electrospray) m/z 485 (M + H)$^+$. |
| 315 | 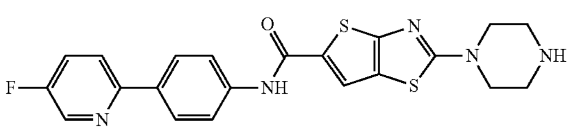 [SMILES: O=C(Nc1ccc(-c2ccc(F)cn2)cc1)c1cc2sc(N3CCNCC3)nc2s1] | Pale yellow solid; $^1$H NMR (400 MHz, DMSO-d$_6$) δ 10.27 (s, 1H), 8.61 (s, 1H), 8.16 (s, 1H), 8.03 (d, J = 8.8 Hz, 2H), 8.00-8.01 (m, 1H), 7.83 (d, J = 8.8 Hz, 2H), 7.78-7.80 (m, 1H), 3.44-3.47 (m, 4H), 2.79-2.81 (m, 4H); LCMS (electrospray) m/z 439 (M + H)$^+$. |
| 316 | 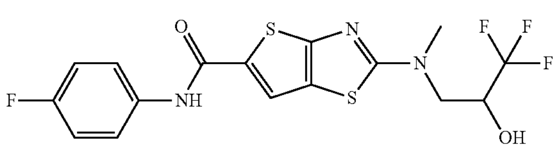 [SMILES: CN(CC(O)C(F)(F)F)c1nc2sc(C(=O)Nc3ccc(F)cc3)cc2s1] | White solid; $^1$H NMR (400 MHz, DMSO-d$_6$) δ 10.19 (brs, 1H), 8.12 (s, 1H), 7.68-7.71 (m, 2H), 7.14-7.18 (m, 2H), 6.65 (brs, 1H), 4.42-4.45 (m, 1H), 3.87-3.90 (m, 1H), 3.59-3.65 (m, 1H), 3.17 (s, 3H); LCMS (electrospray) m/z 420 (M + H)$^-$. |
| 317 | 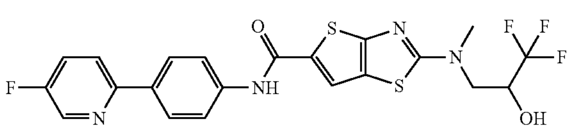 | Pale yellow solid; $^1$H NMR (400 MHz, acetone-d$_6$) δ 9.59 (s, 1H), 8.54 (d, J = 2.8 Hz, 1H), 8.05-8.08 (m, 3H), 7.96-8.00 (m, 1H), 7.89 (d, J = 8.4 Hz, 2H), 7.65-7.70 (m, 1H), 5.82 (brs, 1H), 4.63-4.65 (m, 1H), 4.07 (dd, J = 14.4, 3.2 Hz, 1H), 3.69 (dd, J = 14.4, 8.8 Hz, 1H), 3.30 (s, 3H); LCMS (electrospray) m/z 497 (M + H)$^+$. |

TABLE 1-continued

Structures and Characteristics of Compounds 1-360

| No. | Structure | NMR Characterization |
|---|---|---|
| 318 | 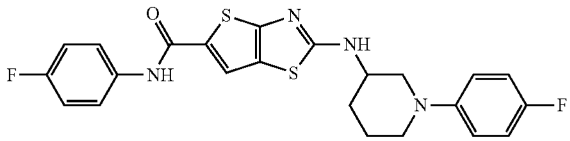 [SMILES: O=C(Nc1ccc(F)cc1)c1cc2sc(NC3CCCN(c4ccc(F)cc4)C3)nc2s1] | White solid; ¹H NMR (400 MHz, DMSO-$d_6$) δ 10.14 (brs, 1H), 8.50 (brs, 1H), 8.03 (s, 1H), 7.67-7.71 (m, 2H), 7.14-7.18 (m, 2H), 6.94-7.04 (m, 4H), 3.92-3.94 (m, 1H), 3.57-3.60 (m, 2H), 2.74-2.85 (m, 2H), 1.94-1.97 (m, 1H), 1.78-1.80 (m, 1H), 1.62-1.65 (m, 1H), 1.50-1.55 (m, 1H); LCMS (electrospray) m/z 471 (M + H)⁺. |
| 319 | 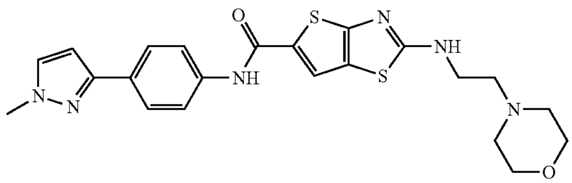 [SMILES: Cn1ccc(-c2ccc(NC(=O)c3cc4sc(NCCN5CCOCC5)nc4s3)cc2)n1] | Pale yellow solid; ¹H NMR (400 MHz, acetone-$d_6$) δ 9.41 (brs, 1H), 7.95 (s, 1H), 7.77-7.80 (m, 4H), 7.59 (s, 1H), 7.3 (brs, 1H), 6.59 (s, 1H), 3.91 (s, 3H), 3.58-3.61 (m, 6H), 2.64 (t, J = 6.0 Hz, 2H), 2.46-2.49 (m, 4H); LCMS (electrospray) m/z 469 (M + H)⁺. |
| 320 | 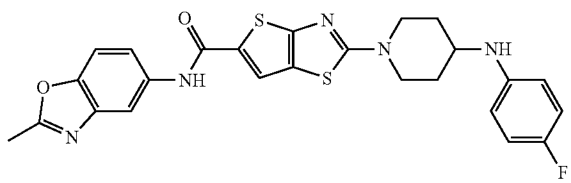 [SMILES: Cc1nc2cc(NC(=O)c3cc4sc(N5CCC(Nc6ccc(F)cc6)CC5)nc4s3)ccc2o1] | Pale yellow solid; ¹H NMR (400 MHz, DMSO-$d_6$) δ 10.23 (s, 1H), 8.14 (s, 1H), 8.04 (s, 1H), 7.58-7.59 (m, 2H), 6.88-6.93 (m, 2H), 6.58-6.61 (m, 2H), 5.44-5.46 (m, 1H), 3.94-3.97 (m, 2H), 3.50-3.52 (m, 1H), 3.32-3.38 (m, 2H), 2.58 (s, 3H), 1.99-2.03 (m, 2H), 1.43-1.45 (m, 2H); LCMS (electrospray) m/z 507 (M + H)⁺. |
| 321 | 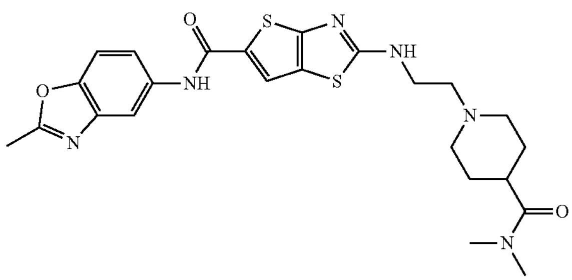 [SMILES: Cc1nc2cc(NC(=O)c3cc4sc(NCCN5CCC(C(=O)N(C)C)CC5)nc4s3)ccc2o1] | Pale yellow solid; ¹H NMR (400 MHz, DMSO-$d_6$) δ 10.18 (s, 1H), 8.31-8.34 (m, 1H), 8.05 (s, 1H), 8.03 (s, 1H), 7.58-7.61 (m, 2H), 3.42-3.46 (m, 2H), 2.98 (s, 3H), 2.89-2.92 (m, 2H), 2.78 (s, 3H), 2.58 (s, 3H), 2.51-2.55 (m, 3H), 1.96-2.02 (m, 2H), 1.53-1.58 (m, 4H); LCMS (electrospray) m/z 512 (M + H)⁺. |
| 322 | 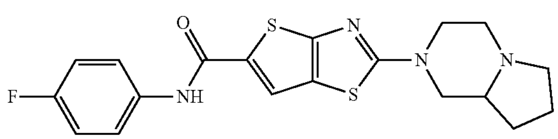 [SMILES: O=C(Nc1ccc(F)cc1)c1cc2sc(N3CCN4CCCC4C3)nc2s1] | Ivory solid; ¹H NMR (400 MHz, DMSO-$d_6$) δ 10.19 (s, 1H), 8.12 (s, 1H), 7.68-7.73 (m, 2H), 7.15-7.21 (m, 2H), 4.06-4.11 (m, 1H), 3.88-3.93 (m, 1H), 3.19-3.29 (m, 1H), 3.00-3.10 (m, 2H), 2.87-2.95 (m, 1H), 2.16-2.24 (m, 1H), 1.99-2.12 (m, 2H), 1.82-1.89 (m, 1H), 1.67-1.77 (m, 2H), 1.34-1.40 (m, 1H); LCMS (electrospray) m/z 402 (M + H)⁺. |
| 323 | 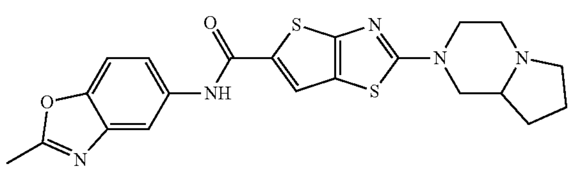 [SMILES: Cc1nc2cc(NC(=O)c3cc4sc(N5CCN6CCCC6C5)nc4s3)ccc2o1] | Ivory solid; ¹H NMR (400 MHz, DMSO-$d_6$) δ 10.25 (s, 1H), 8.15 (s, 1H), 8.05 (s, 1H), 7.56-7.64 (m, 2H), 4.06-4.11 (m, 1H), 3.88-3.93 (m, 1H), 3.19-3.29 (m, 1H), 3.00-3.08 (m, 2H), 2.87-2.95 (m, 1H), 2.59 (s, 3H), 2.16-2.24 (m, 1H), 1.99-2.12 (m, 2H), 1.82-1.87 (m, 1H), 1.66-1.77 (m, 2H), 1.34-1.40 (m, 1H); LCMS (electrospray) m/z 440 (M + H)⁺. |
| 324 | 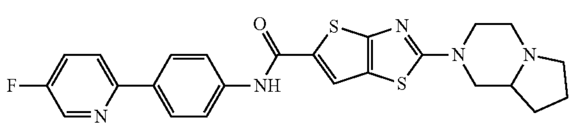 [SMILES: O=C(Nc1ccc(-c2ccc(F)cn2)cc1)c1cc2sc(N3CCN4CCCC4C3)nc2s1] | Ivory solid; ¹H NMR (400 MHz, DMSO-$d_6$) δ 10.29 (s, 1H), 8.62 (d, J = 2.0 Hz, 1H), 8.18 (s, 1H), 8.00-8.06 (m, 3H), 7.77-7.85 (m, 3H), 4.08-4.11 (m, 1H), 3.90-3.94 (m, 1H), 3.19-3.29 (m, 1H), 3.00-3.09 (m, 2H), 2.88-2.95 (m, 1H), 2.17-2.24 (m, 1H), 1.99-2.13 (m, 2H), 1.82-1.87 (m, 1H), 1.66-1.77 (m, 2H), 1.34-1.40 (m, 1H); LCMS (electrospray) m/z 479 (M + H)⁺. |
| 325 | 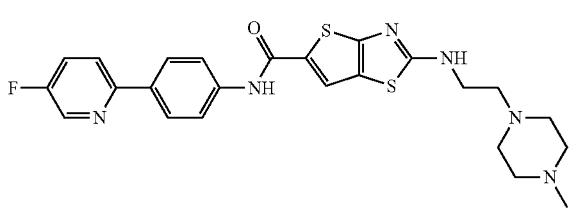 [SMILES: CN1CCN(CCNc2nc3sc(C(=O)Nc4ccc(-c5ccc(F)cn5)cc4)cc3s2)CC1] | Ivory solid; ¹H NMR (400 MHz, DMSO-$d_6$) δ 10.25 (s, 1H), 8.62 (d, J = 2.4 Hz, 1H), 8.36 (brs, 1H), 8.11 (s, 1H), 7.98-8.06 (m, 3H), 7.77-7.86 (m, 3H), 3.42-3.48 (m, 2H), 2.49-2.54 (m, 2H), 2.37-2.46 (m, 4H), 2.27-2.35 (m, 4H), 2.14 (s, 3H); LCMS (electrospray) m/z 497 (M + H)⁺. |

TABLE 1-continued

Structures and Characteristics of Compounds 1-360

| No. | Structure | NMR Characterization |
|---|---|---|
| 326 | 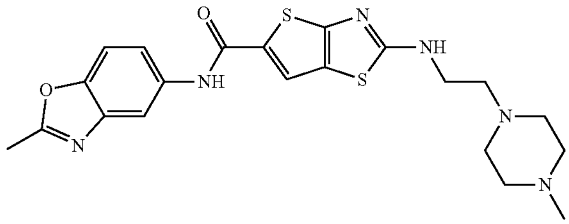 | Ivory solid; ¹H NMR (400 MHz, DMSO-d₆) δ 10.19 (s, 1H), 8.33 (brs, 1H), 8.07 (s, 1H), 8.04 (s, 1H), 3.43-3.47 (m, 2H), 2.59 (s, 3H), 2.49-2.54 (m, 2H), 2.37-2.44 (m, 4H), 2.27-2.34 (m, 4H), 2.14 (s, 3H); LCMS (electrospray) m/z 457 (M + H)⁺. |
| 327 | 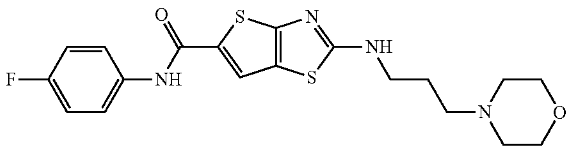 [SMILES: O=C(Nc1ccc(F)cc1)c1cc2sc(NCCCN3CCOCC3)nc2s1] | White solid; ¹H NMR (400 MHz, DMSO-d₆) δ 10.14 (s, 1H), 8.41 (brs, 1H), 8.04 (s, 1H), 7.67-7.73 (m, 2H), 7.14-7.20 (m, 2H), 3.54-2.59 (m, 4H), 3.30-3.34 (m, 2H), 2.30-2.38 (m, 6H), 1.71-1.77 (m, 2H); LCMS (electrospray) m/z 420 (M + H)⁺. |
| 328 | 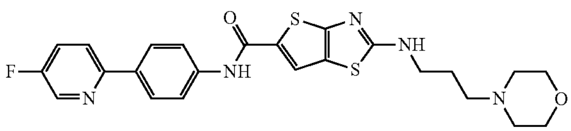 [SMILES: O=C(Nc1ccc(-c2ccc(F)cn2)cc1)c1cc2sc(NCCCN3CCOCC3)nc2s1] | Ivory solid; ¹H NMR (400 MHz, DMSO-d₆) δ 10.24 (s, 1H), 8.62 (s, 1H), 8.43 (brs, 1H), 8.10 (s, 1H), 7.98-8.11 (m, 3H), 7.78-7.85 (m, 3H), 3.54-2.59 (m, 4H), 3.29-3.34 (m, 2H), 2.32-2.39 (m, 6H), 1.71-1.76 (m, 2H); LCMS (electrospray) m/z 497 (M + H)⁺. |
| 329 | 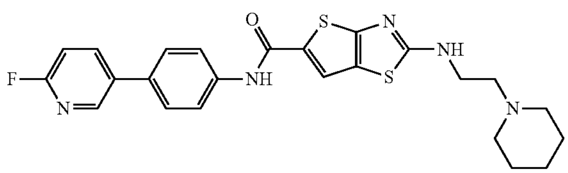 [SMILES: O=C(Nc1ccc(-c2ccc(F)nc2)cc1)c1cc2sc(NCCN3CCCCC3)nc2s1] | Ivory solid; ¹H NMR (400 MHz, DMSO-d₆) δ 10.23 (s, 1H), 8.55 (s, 1H), 8.36 (brs, 1H), 8.25-8.30 (m, 1H), 8.10 (s, 1H), 7.85 (d, J = 8.8 Hz, 2H), 7.72 (d, J = 8.8 Hz, 2H), 7.28 (d, J = 8.4 Hz, 1H), 3.42-3.47 (m, 2H), 2.48-2.52 (m, 2H), 2.37-2.42 (m, 4H), 1.46-1.51 (m, 4H), 1.36-1.41 (m, 2H); LCMS (electrospray) m/z 482 (M + H)⁺. |
| 330 | 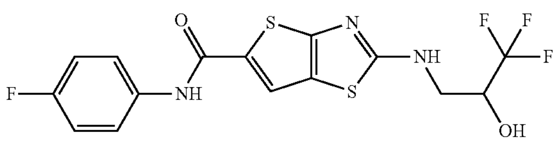 [SMILES: O=C(Nc1ccc(F)cc1)c1cc2sc(NCC(O)C(F)(F)F)nc2s1] | White solid; ¹H NMR (400 MHz, DMSO-d₆) δ 10.18 (s, 1H), 8.65 (brt, J = 5.2 Hz, 1H), 8.06 (s, 1H), 7.69-7.72 (m, 2H), 7.18 (dd, J = 8.8, 8.8 Hz, 2H), 6.64 (d, J = 6.4 Hz, 1H), 4.27-4.29 (m, 1H), 3.71-3.74 (m, 1H), 3.39-3.45 (m, 1H); LCMS (electrospray) m/z 406 (M + H)⁺. |
| 331 | 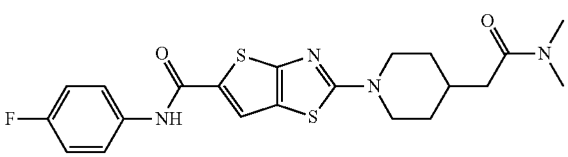 [SMILES: CN(C)C(=O)CC1CCN(c2nc3sc(C(=O)Nc4ccc(F)cc4)cc3s2)CC1] | White solid; ¹H NMR (400 MHz, DMSO-d₆) δ 10.19 (s, 1H), 8.12 (s, 1H), 7.70-8.12 (m, 2H), 7.16-7.20 (m, 2H), 3.95-3.98 (m, 2H), 3.16-3.22 (m, 2H), 2.96 (s, 3H), 2.82 (s, 3H), 2.27-2.29 (m, 2H), 1.99-2.01 (m, 1H), 1.79-1.82 (m, 2H), 1.23-1.30 (m, 2H); LCMS (electrospray) m/z 447 (M + H). |
| 332 | 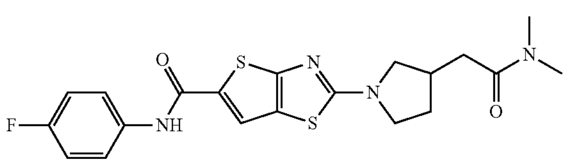 [SMILES: CN(C)C(=O)CC1CCN(c2nc3sc(C(=O)Nc4ccc(F)cc4)cc3s2)C1] | White solid; ¹H NMR (400 MHz, DMSO-d₆) δ 10.17 (s, 1H), 8.12 (s, 1H), 7.69-7.73 (m, 2H), 7.16-7.20 (m, 2H), 3.69-3.74 (m, 1H), 3.58-3.60 (m, 1H), 3.46-3.50 (m, 1H), 3.11-3.15 (m, 1H), 2.96 (s, 3H), 2.83 (s, 3H), 2.65-2.70 (m, 1H), 2.50-2.60 (m, 2H), 2.19-2.23 (m, 1H), 1.73-1.78 (m, 1H); LCMS (electrospray) m/z 433 (M + H)⁺. |
| 333 | 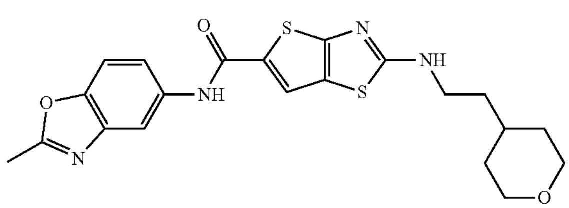 | Beige solid; ¹H NMR (400 MHz, acetone-d₆) δ 9.50 (s, 1H), 8.14 (s, 1H), 7.95 (s, 1H), 7.64 (d, J = 8.4 Hz, 1H), 7.50 (d, J = 8.4 Hz, 1H), 7.43 (s, 1H), 3.84-3.88 (m, 2H), 3.50-3.55 (m, 2H), 3.29-3.34 (m, 2H), 2.59 (s, 3H), 1.65-1.68 (m, 5H), 1.25-1.28 (m, 2H); LCMS (electrospray) m/z 443 (M + H)⁺. |
| 334 | 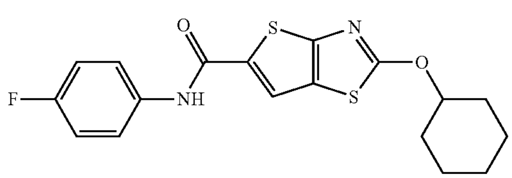 [SMILES: O=C(Nc1ccc(F)cc1)c1cc2sc(OC3CCCCC3)nc2s1] | White solid; ¹H NMR (400 MHz, DMSO-d₆) δ 10.40 (s, 1H), 8.19 (s, 1H), 7.71-7.74 (m, 2H), 7.18-7.22 (m, 2H), 5.07-5.09 (m, 1H), 2.04-2.07 (m, 2H), 1.70-1.74 (m, 2H), 1.55-1.62 (m, 3H), 1.31-1.43 (m, 3H); LCMS (electrospray) m/z 377 (M + H). |

TABLE 1-continued

Structures and Characteristics of Compounds 1-360

| No. | Structure | NMR Characterization |
| --- | --- | --- |
| 335 | 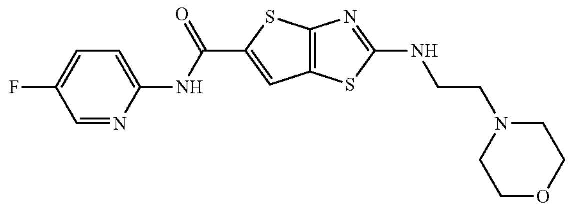 [SMILES: O=C(Nc1ccc(F)cn1)c1cc2sc(NCCN3CCOCC3)nc2s1] | Yellow solid; ¹H NMR (400 MHz, DMSO-d₆) δ 10.86 (s, 1H), 8.42 (brs, 1H), 8.38 (d, J = 2.8 Hz, 1H), 8.27 (s, 1H), 8.15 (dd, 8.8, 2.8 Hz, 1H), 7.71-7.79 (m, 1H), 3.55-3.59 (m, 4H), 3.44-3.49 (m, 2H), 2.50-2.54 (m, 2H), 2.38-2.43 (m, 4H); LCMS (electrospray) m/z 407 (M + H)⁺. |
| 336 | 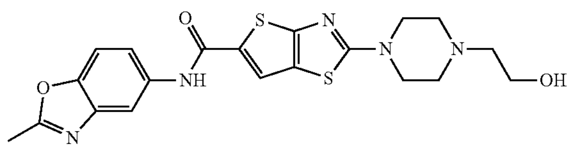 [SMILES: Cc1nc2cc(NC(=O)c3cc4sc(N5CCN(CCO)CC5)nc4s3)ccc2o1] | Ivory solid; ¹H NMR (400 MHz, DMSO-d₆) δ 10.25 (s, 1H), 8.15 (s, 1H), 8.05 (s, 1H), 7.58-7.62 (m, 2H), 4.47 (brs, 1H), 3.52-3.56 (m, 6H), 2.60 (s, 3H), 2.53-2.59 (m, 4H), 2.43-2.48 (m, 2H); LCMS (electrospray) m/z 444 (M + H)⁺. |
| 337 | 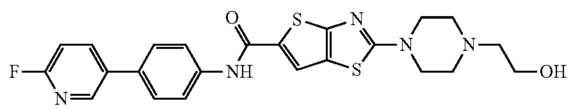 [SMILES: O=C(Nc1ccc(-c2ccc(F)nc2)cc1)c1cc2sc(N3CCN(CCO)CC3)nc2s1] | While solid; ¹H NMR (400 MHz, DMSO-d₆) δ 10.30 (s, 1H), 8.55 (s, 1H), 8.27-8.31 (m, 1H), 8.18 (s, 1H), 7.85 (d, J = 8.0 Hz, 2H), 7.73 (d, J = 8.0 Hz, 2H), 7.28 (d, J = 8.4 Hz, 1H), 4.71 (brs, 1H), 3.52-3.56 (m, 6H), 2.53-2.59 (m, 4H), 2.41-2.47 (m, 2H); LCMS (electrospray) m/z 483 (M + H)⁺. |
| 338 | 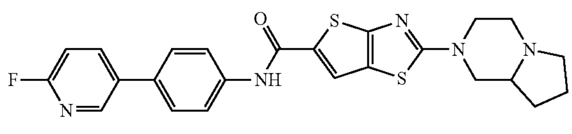 [SMILES: O=C(Nc1ccc(-c2ccc(F)nc2)cc1)c1cc2sc(N3CCN4CCCC4C3)nc2s1] | Pale yellow solid; ¹H NMR (400 MHz, DMSO-d₆) δ 10.26 (s, 1H), 8.53 (s, 1H), 8.24-8.29 (m, 1H), 8.16 (s, 1H), 7.84 (d, J = 8.4 Hz, 2H), 7.71 (d, J = 8.4 Hz, 2H), 7.25 (d, J = 8.4 Hz, 1H), 4.05-4.09 (m, 1H), 3.89-3.95 (m, 1H), 3.19-3.26 (m, 1H), 3.00-3.09 (m, 2H), 2.86-2.93 (m, 1H), 2.17-2.22 (m, 1H), 2.00-2.09 (m, 2H), 1.81-1.85 (m, 1H), 1.66-1.72 (m, 2H), 1.34-1.39 (m, 1H); LCMS (electrospray) m/z 480 (M + H)⁺. |
| 339 | 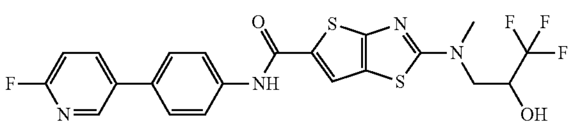 [SMILES: CN(CC(O)C(F)(F)F)c1nc2sc(C(=O)Nc3ccc(-c4ccc(F)nc4)cc3)cc2s1] | Pale yellowsolid; ¹H NMR (400 MHz, acetone-d₆) δ 9.59 (s, 1H), 8.50 (s, 1H), 8.20-8.24 (m, 1H), 8.04 (s, 1H), 7.91 (d, J = 8.4 Hz, 2H), 7.67 (d, J = 8.4 Hz, 2H), 7.14-7.17 (m, 1H), 5.80 (d, J = 6.4 Hz, 1H), 4.62-4.66 (m, 1H), 4.06-4.12 (m, 1H), 3.69-3.75 (m, 1H), 3.29 (s, 3H); LCMS (electrospray) m/z 497 (M + H)⁺. |
| 340 | 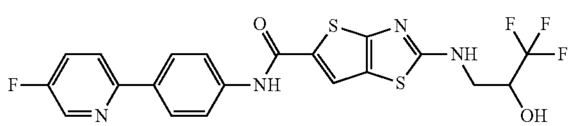 [SMILES: O=C(Nc1ccc(-c2ccc(F)cn2)cc1)c1cc2sc(NCC(O)C(F)(F)F)nc2s1] | Orange solid; ¹H NMR (400 MHz, DMSO-d₆) δ 10.28 (s, 1H), 8.68 (brt, J = 5.2 Hz, 1H), 8.62 (d, J = 1.6 Hz, 1H), 8.12 (s, 1H), 8.00-8.06 (m, 3H), 7.78-7.85 (m, 3H), 6.65 (d, J = 6.4 Hz, 1H), 4.26-4.29 (m, t 1H), 3.71-3.75 (m, 1H), 3.27-3.35 (m, 1H); LCMS (electrospray) m/z 483 (M + H)⁺. |
| 341 | 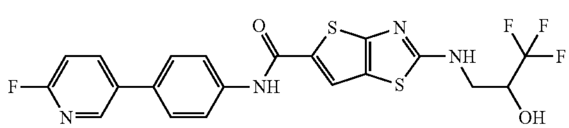 | Yellow solid; ¹H NMR (400 MHz, DMSO-d₆) δ 10.26 (s, 1H), 8.68 (brt, J = 4.8 Hz, 1H), 8.55 (s, 1H), 8.26-8.30 (m, 1H), 8.11 (s, 1H), 7.83 (d, J = 8.4 Hz, 2H), 7.71 (d, J = 8.4 Hz, 2H), 7.26 (dd, J = 8.0, 2.0 Hz, 1H), 6.65 (d, J = 6.0 Hz, 1H), 4.27-4.30 (m, 1H), 3.72-3.75 (m, 1H), 3.40-3.46 (m, 1H); LCMS (electrospray) m/z 483 (M + H)⁺. |
| 342 | 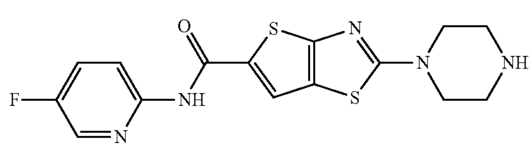 [SMILES: O=C(Nc1ccc(F)cn1)c1cc2sc(N3CCNCC3)nc2s1] | Pale yellow solid; ¹H NMR (400 MHz, DMSO-d₆) δ 10.90 (s, 1H), 8.37 (s, 1H), 8.33 (s, 1H), 8.12-8.15 (m, 1H), 7.74-7.79 (m, 1H), 3.44-3.46 (m, 4H), 2.78-2.80 (m, 4H); LCMS (electrospray) m/z 363 (M + H)⁺. |
| 343 | 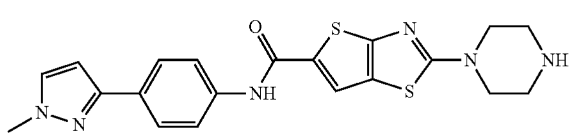 [SMILES: Cn1ccc(-c2ccc(NC(=O)c3cc4sc(N5CCNCC5)nc4s3)cc2)n1] | Pale yellow solid; ¹H NMR (400 MHz, DMSO-d₆) δ 10.17 (s, 1H), 8.14 (s, 1H), 7.72-7.73 (m, 3H), 7.68-7.69 (m, 2H), 6.62-6.63 (m, 1H), 3.85 (s, 3H), 3.31-3.46 (m, 4H), 2.78-2.81 (m, 4H); LCMS (electrospray) m/z 424 (M + H)⁺. |
| 344 | 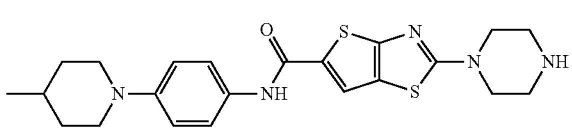 [SMILES: CC1CCN(c2ccc(NC(=O)c3cc4sc(N5CCNCC5)nc4s3)cc2)CC1] | Pale yellow solid; ¹H NMR (400 MHz, DMSO-d₆) δ 9.92 (s, 1H), 8.06 (s, 1H), 7.49 (d, J = 8.8 Hz, 2H), 6.89 (d, J = 8.8 Hz, 2H), 3.57-3.60 (m, 2H), 3.42-3.45 (m, 4H), 2.78-2.80 (m, 4H), 2.56-2.59 (m, 2H), 1.65-1.68 (m, 2H), 1.43-1.47 (m, 1H), 1.16-1.26 (m, 2H), 0.91-0.93 (m, 3H); LCMS (electrospray) m/z 441 (M + H)⁺. |

TABLE 1-continued

Structures and Characteristics of Compounds 1-360

| No. | Structure | NMR Characterization |
|---|---|---|
| 345 | 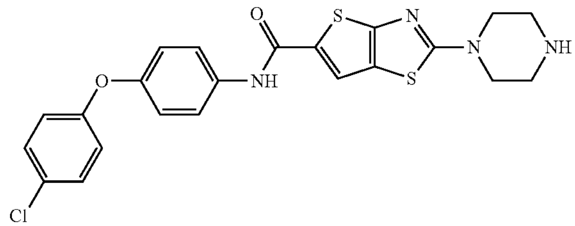 [SMILES: O=C(Nc1ccc(Oc2ccc(Cl)cc2)cc1)c1cc2sc(N3CCNCC3)nc2s1] | Pale yellow solid; $^1$H NMR (400 MHz, DMSO-d$_6$) δ 10.17 (s, 1H), 8.11 (s, 1H), 7.72 (d, J = 8.8 Hz, 2H), 7.40 (d, J = 8.0 Hz, 2H), 7.00 (d, J = 8.0 Hz, 2H), 6.99 (d, J = 8.8 Hz, 2H), 3.43-3.46 (m, 4H), 2.78-2.81 (m, 4H); LCMS (electrospray) m/z 470 (M + H)$^+$. |
| 346 | 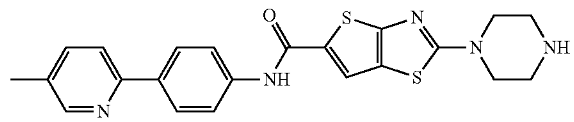 [SMILES: Cc1ccc(-c2ccc(NC(=O)c3cc4sc(N5CCNCC5)nc4s3)cc2)nc1] | Pale yellow solid; $^1$H NMR (400 MHz, DMSO-d$_6$) δ 10.25 (s, 1H), 8.46 (s, 1H), 8.16 (s, 1H), 8.03-8.05 (tn, 2H), 7.80-7.83 (m, 3H), 7.64-7.67 (m, 1H), 3.44-3.47 (m, 4H), 2.79-2.81 (m, 4H), 2.31 (s, 3H); LCMS (electrospray) m/z 435 (M + H)$^+$. |
| 347 | 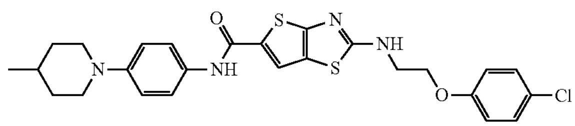 [SMILES: CC1CCN(c2ccc(NC(=O)c3cc4sc(NCCOc5ccc(Cl)cc5)nc4s3)cc2)CC1] | Pale brown solid; $^1$H NMR (400 MHz, DMSO-d$_6$) δ 9.88 (s, 1H), 8.60 (s, 1H), 7.99 (s, 1H), 7.48 (d, J = 9.2 Hz, 2H), 7.31 (d, J = 8.8 Hz, 2H), 6.99 (d, J = 8.8 Hz, 2H), 6.88 (d, J = 9.2 Hz, 2H), 4.14 (t, J = 5.2 Hz, 2H), 3.71-3.73 (m, 2H), 3.57-3.60 (m, 2H), 2.55-2.61 (m, 2H), 1.65-1.68 (m, 2H), 1.45-1.46 (m, 1H), 1.16-1.26 (m, 2H), 0.91-0.93 (m, 3H); LCMS (electrospray) m/z 526 (M + H)$^+$. |
| 348 | 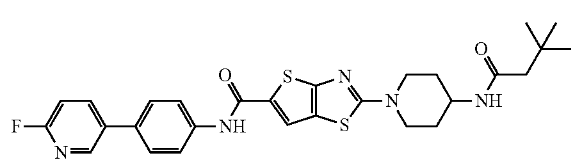 [SMILES: CC(C)(C)CC(=O)NC1CCN(c2nc3sc(C(=O)Nc4ccc(-c5ccc(F)nc5)cc4)cc3s2)CC1] | Pale brown solid; $^1$H NMR (400 MHz, DMSO-d$_6$) δ 10.29 (s, 1H), 8.53 (s, 1H), 8.26-8.27 (m, 1H), 8.17 (s, 1H), 7.84 (d, J = 8.8 Hz, 2H), 7.74-7.76 (m, 1H), 7.71 (d, J = 8.8 Hz, 2H), 7.24-7.27 (m, 1H), 3.90-3.93 (m, 4H), 3.27-3.28 (m, 1H), 1.93 (s, 2H), 1.83-1.86 (m, 2H), 1.44-1.46 (m, 2H), 0.94 (s, 9H); LCMS (electrospray) m/z 551 (M + H)$^+$. |
| 349 | 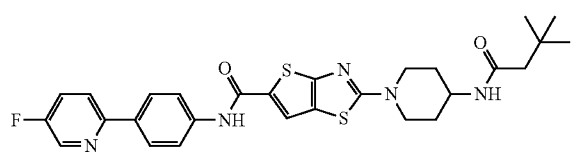 | Pale brown solid; $^1$H NMR (400 MHz, DMSO-d$_6$) δ 10.29 (s, 1H), 8.61 (s, 1H), 8.17 (s, 1H), 8.04 (d, J = 8.4 Hz, 2H), 7.99-8.01 (m, 1H), 7.83 (d, J = 8.4 Hz, 2H), 7.78-7.81 (m, 1H), 7.74-7.77 (m, 1H), 3.90-3.93 (m, 4H), 3.27-3.28 (m, 1H), 1.93 (s, 2H), 1.83-1.86 (m, 2H), 1.44-1.46 (m, 2H), 0.94 (s, 9H); LCMS (electrospray) m/z 551 (M + H)$^+$. |
| 350 | 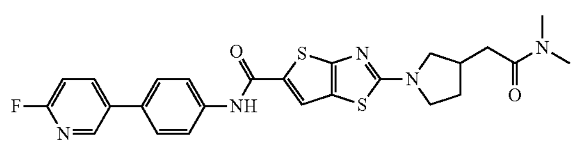 [SMILES: CN(C)C(=O)CC1CCN(c2nc3sc(C(=O)Nc4ccc(-c5ccc(F)nc5)cc4)cc3s2)C1] | White solid; $^1$H NMR (400 MHz, DMSO-d$_6$) δ 10.26 (s, 1H), 8.55 (s, 1H), 8.26-8.29 (m, 1H), 8.17 (s, 1H), 7.85 (d, J = 8.8 Hz, 2H), 7.72 (d, J = 8.8 Hz, 2H), 7.26-7.28 (m, 1H), 3.71-3.74 (m, 1H), 3.59-3.61 (m, 1H), 3.47-3.49 (m, 1H), 3.12-3.17 (m, 1H), 2.97 (s, 3H), 2.84 (s, 3H), 2.67-2.69 (m, 1H), 2.53-2.60 (m, 2H), 2.20-2.22 (m, 1H), 1.75-1.77 (m, 1H); LCMS (electrospray) m/z 510 (M + H). |
| 351 | 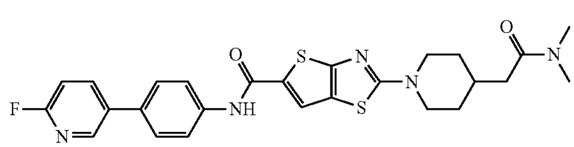 [SMILES: CN(C)C(=O)CC1CCN(c2nc3sc(C(=O)Nc4ccc(-c5ccc(F)nc5)cc4)cc3s2)CC1] | White solid; $^1$H NMR (400 MHz, DMSO-d$_6$) δ 10.27 (s, 1H), 8.55 (s, 1H), 8.28-8.29 (m, 1H), 8.17 (s, 1H), 7.85 (d, J = 8.8 Hz, 2H), 7.72 (d, J = 8.8 Hz, 2H), 7.26-7.28 (m, 1H), 3.95-3.99 (m, 2H), 3.17-3.26 (m, 2H), 2.96 (s, 3H), 2.82 (s, 3H), 2.27-2.29 (m, 2H), 1.99-2.02 (m, 1H), 1.80-1.82 (m, 2H), 1.23-1.29 (m, 2H); LCMS (electrospray) m/z 524 (M + H). |
| 352 | 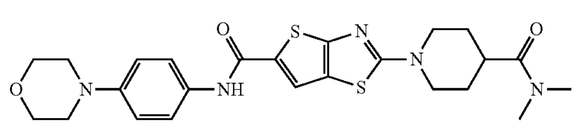 [SMILES: CN(C)C(=O)C1CCN(c2nc3sc(C(=O)Nc4ccc(N5CCOCC5)cc4)cc3s2)CC1] | White solid; $^1$H NMR (400 MHz, DMSO-d$_6$) δ 9.95 (s, 1H), 8.06 (s, 1H), 7.52 (d, J = 8.8 Hz, 2H), 6.90 (d, J = 8.8 Hz, 2H), 3.96-3.99 (m, 2H), 3.70-3.72 (m, 4H), 3.21-3.24 (m, 2H), 3.04 (s, 3H), 3.03-3.06 (m, 4H), 3.93-3.98 (m, 1H), 2.80 (s, 3H), 1.73-1.76 (m, 2H), 1.58-1.64 (m, 2H); LCMS (electrospray) m/z 500 (M + H)$^+$. |
| 353 | 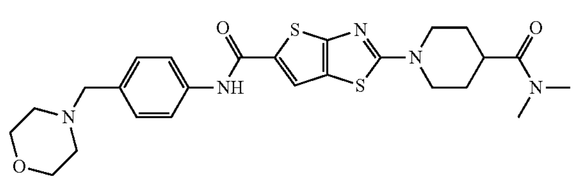 [SMILES: CN(C)C(=O)C1CCN(c2nc3sc(C(=O)Nc4ccc(CN5CCOCC5)cc4)cc3s2)CC1] | Pale yellow solid; $^1$H NMR (400 MHz, DMSO-d$_6$) δ 10.12 (brs, 1H), 8.13 (s, 1H), 7.63 (d, J = 8.0 Hz, 2H), 7.23 (d, J = 8.0 Hz, 2H), 3.96-3.99 (m, 2H), 3.53-3.56 (m, 4H), 3.39 (s, 2H), 3.20-3.27 (m, 2H), 3.04 (s, 3H), 2.93-2.99 (m, 1H), 2.80 (s, 3H), 2.30-2.34 (m, 4H), 1.73-1.76 (m, 2H), 1.55-1.63 (m, 2H); LCMS (electrospray) m/z 514 (M + H)$^+$. |

TABLE 1-continued

Structures and Characteristics of Compounds 1-360

| No. | Structure | NMR Characterization |
|---|---|---|
| 354 | 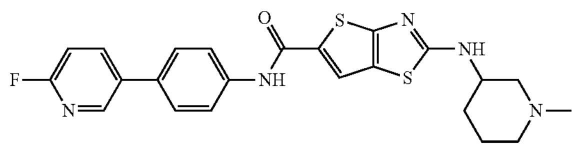 [SMILES: CN1CCCC(Nc2nc3sc(C(=O)Nc4ccc(-c5ccc(F)nc5)cc4)cc3s2)C1] | Pale yellow solid; ¹H NMR (400 MHz, methanol-$d_6$) δ 8.42 (s, 1H), 8.15-8.19 (m, 1H), 7.91 (s, 1H), 7.78 (d, J = 8.4 Hz, 2H), 7.61 (d, J = 8.4 Hz, 2H), 7.11-7.13 (m, 1H), 4.13-4.16 (m, 1H), 3.59-3.61 (m, 1H), 2.94-2.96 (m, 2H), 2.81 (s, 3H), 2.05-2.13 (m, 2H), 1.83-1.96 (m, 2H), 1.64-1.68 (m, 1H); LCMS (electrospray) m/z 468 (M + H)⁺. |
| 355 | 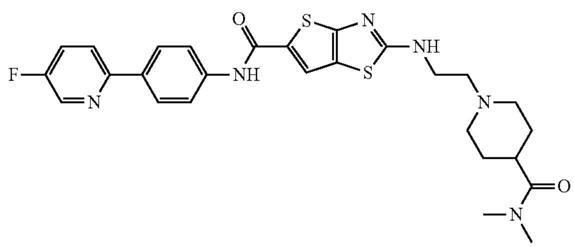 [SMILES: CN(C)C(=O)C1CCN(CCNc2nc3sc(C(=O)Nc4ccc(-c5ccc(F)cn5)cc4)cc3s2)CC1] | Pale yellow solid; ¹H NMR (400 MHz, DMSO-$d_6$) δ 10.23 (s, 1H), 8.62-8.63 (m, 1H), 8.35-8.36 (m, 1H), 8.10 (s, 1H), 8.06 (s, 1H), 8.04 (s, 1H), 8.00-8.02 (m, 1H), 7.85 (s, 1H), 7.83 (s, 1H), 7.77-7.82 (m, 1H), 3.46-3.47 (m, 2H), 3.00 (s, 3H), 2.91-2.93 (m, 2H), 2.80 (s, 3H), 2.52-2.53 (m, 3H), 1.98-2.04 (m, 2H), 1.55-1.60 (m, 4H); LCMS (electrospray) m/z 553 (M + H)⁺. |
| 356 | 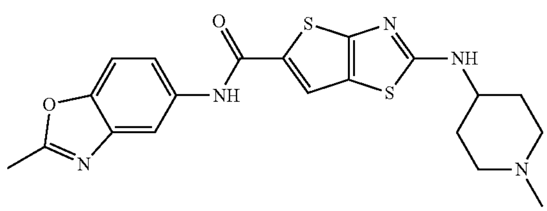 | White solid; ¹H NMR (400 MHz, DMSO-$d_6$) δ 10.19 (s, 1H), 8.36 (d, J = 7.2 Hz, 1H), 8.04-8.06 (m, 2H), 7.60-7.63 (m, 2H), 4.43 (brs, 1H), 3.61-3.63 (m, 1H), 2.70-2.73 (m, 2H), 2.59 (s, 3H), 2.16 (s, 3H), 1.93-2.03 (m, 4H), 1.46-1.54 (m, 2H); LCMS (electrospray) m/z 428 (M + H)⁺. |
| 357 | 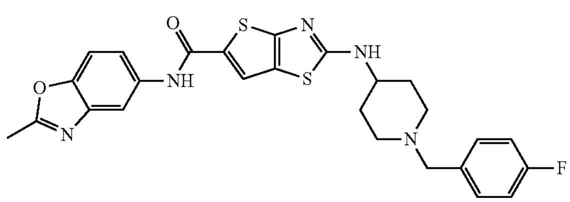 [SMILES: Cc1nc2cc(NC(=O)c3cc4sc(NC5CCN(Cc6ccc(F)cc6)CC5)nc4s3)ccc2o1] | White solid; ¹H NMR (400 MHz, DMSO-$d_6$) δ 10.18 (s, 1H), 8.38 (d, J = 7.2 Hz, 1H), 8.04 (d, J = 7.2 Hz, 2H), 7.59-7.62 (m, 2H), 7.31-7.35 (m, 2H), 7.12-7.16 (m, 2H), 3.65-3.68 (m, 1H), 3.45 (s, 2H), 2.74-2.77 (m, 2H), 2.59 (s, 3H), 2.06-2.11 (m, 2H), 1.94-1.97 (m, 2H), 1.46-1.54 (m, 2H); LCMS (electrospray) m/z 522 (M + H)⁺. |
| 358 | 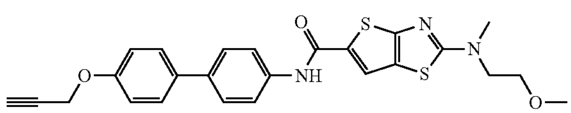 | Pale yellow solid; ¹H NMR (400 MHz, DMSO-$d_6$) δ 10.19 (s, 1H), 8.15 (s, 1H), 7.77 (d, J = 8.8 Hz, 2H), 7.60-7.62 (m, 4H), 7.05 (d, J = 8.4 Hz, 2H), 4.83 (s, 2H), 3.70-3.73 (m, 2H), 3.58-3.61 (m, 3H), 3.28 (s, 3H), 3.15 (s, 3H); LCMS (electrospray) m/z 478 (M + H)⁺. |
| 359 | 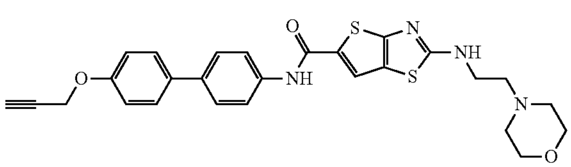 [SMILES: C#CCOc1ccc(-c2ccc(NC(=O)c3cc4sc(NCCN5CCOCC5)nc4s3)cc2)cc1] | Pale yellow solid; ¹H NMR (400 MHz, DMSO-$d_6$) δ 10.13 (s, 1H), 8.34 (brs, 1H), 8.07 (s, 1H), 7.74 (d, J = 8.4 Hz, 2H), 7.58-7.61 (m, 4H), 7.03 (d, J = 8.4 Hz, 2H), 4.81 (s, 2H), 3.55-3.57 (m, 5H), 3.45-3.46 (m, 2H), 2.48-2.53 (m, 2H), 2.39-2.42 (m, 4H); LCMS (electrospray) m/z 519 (M + H)⁺. |
| 360 | 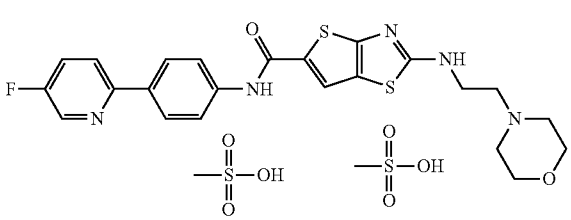 | ¹H NMR (400 MHz, DMSO-$d_6$) δ 10.31 (s, 1H), 9.71 (brs, 1H), 8.59-8.63 (m, 2H), 8.16 (s, 1H), 8.01-8.06 (m, 3H), 7.78-7.85 (m, 3H), 3.99-4.02 (m, 2H), 3.77-3.79 (m, 2H), 3.65-3.71 (m, 2H), 3.51-3.54 (m, 2H), 3.40-3.42 (m, 2H), 3.15-3.18 (m, 2H), 2.37 (s, 6H). |

TABLE 2

In vitro growth fluorescence assay (QUM and Intracellular growth assay (QIM) data of compounds 1-360

| # cpds | QUM (MIC$_{50}$, uM) | QIM (MIC$_{50}$, uM) |
|---|---|---|
| 1 | + | + |
| 2 | + | + |
| 3 | ++ | +++ |
| 4 | + | + |
| 5 | + | + |
| 6 | ++ | ++ |
| 7 | + | + |
| 8 | ++ | ++ |
| 9 | + | + |
| 10 | + | + |
| 11 | + | + |
| 12 | + | + |
| 13 | ++ | +++ |
| 14 | ++ | +++ |
| 15 | + | + |
| 16 | + | + |
| 17 | ++ | + |
| 18 | ++ | + |
| 19 | ++ | + |
| 20 | ++ | + |
| 21 | + | + |
| 22 | ++ | ++ |
| 23 | + | + |
| 24 | ++ | + |
| 25 | + | ++ |
| 26 | + | + |
| 27 | + | ++ |
| 28 | + | ++ |
| 29 | ++ | ++ |
| 30 | + | N/D |
| 31 | + | N/D |
| 32 | ++ | +++ |
| 33 | + | N/D |
| 34 | + | N/D |
| 35 | +++ | +++ |
| 36 | ++ | +++ |
| 37 | + | + |
| 38 | ++ | +++ |
| 39 | + | +++ |
| 40 | ++ | +++ |
| 41 | + | +++ |
| 42 | ++ | +++ |
| 43 | ++ | +++ |
| 44 | + | +++ |
| 45 | ++ | +++ |
| 46 | ++ | +++ |
| 47 | +++ | +++ |
| 48 | +++ | +++ |
| 49 | ++ | +++ |
| 50 | +++ | +++ |
| 51 | ++ | ++ |
| 52 | + | ++ |
| 53 | +++ | +++ |
| 54 | +++ | +++ |
| 55 | + | +++ |
| 56 | ++ | ++ |
| 57 | ++ | ++ |
| 58 | ++ | +++ |
| 59 | + | + |
| 60 | ++ | ++ |
| 61 | ++ | +++ |
| 62 | + | ++ |
| 63 | + | +++ |
| 64 | + | ++ |
| 65 | + | ++ |
| 66 | ++ | +++ |
| 67 | ++ | +++ |
| 68 | + | +++ |
| 69 | + | + |
| 70 | + | + |
| 71 | + | + |
| 72 | ++ | +++ |
| 73 | + | + |
| 74 | +++ | +++ |
| 75 | ++ | + |
| 76 | +++ | +++ |
| 77 | ++ | +++ |
| 78 | +++ | +++ |
| 79 | + | +++ |
| 80 | ++ | +++ |
| 81 | + | + |
| 82 | + | ++ |
| 83 | +++ | +++ |
| 84 | +++ | +++ |
| 85 | +++ | +++ |
| 86 | +++ | +++ |
| 87 | ++ | ++ |
| 88 | + | + |
| 89 | + | + |
| 90 | +++ | +++ |
| 91 | + | +++ |
| 92 | ++ | ++ |
| 93 | + | + |
| 94 | + | + |
| 95 | + | +++ |
| 96 | +++ | +++ |
| 97 | ++ | ++ |
| 98 | + | + |
| 99 | ++ | +++ |
| 100 | ++ | +++ |
| 101 | ++ | +++ |
| 102 | + | + |
| 103 | +++ | +++ |
| 104 | +++ | +++ |
| 105 | ++ | +++ |
| 106 | + | +++ |
| 107 | + | +++ |
| 108 | ++ | +++ |
| 109 | + | + |
| 110 | ++ | +++ |
| 111 | ++ | +++ |
| 112 | + | +++ |
| 113 | + | + |
| 114 | ++ | +++ |
| 115 | ++ | +++ |
| 116 | + | ++ |
| 117 | + | + |
| 118 | + | +++ |
| 119 | + | +++ |
| 120 | +++ | +++ |
| 121 | + | +++ |
| 122 | +++ | +++ |
| 123 | + | + |
| 124 | +++ | +++ |
| 125 | +++ | +++ |
| 126 | ++ | + |
| 127 | +++ | +++ |
| 128 | + | + |
| 129 | ++ | +++ |
| 130 | ++ | +++ |
| 131 | + | + |
| 132 | + | +++ |
| 133 | ++ | +++ |
| 134 | +++ | +++ |
| 135 | ++ | +++ |
| 136 | +++ | +++ |
| 137 | +++ | ++ |
| 138 | +++ | +++ |
| 139 | ++ | ++ |
| 140 | ++ | ++ |
| 141 | + | + |
| 142 | +++ | +++ |
| 143 | +++ | +++ |
| 144 | +++ | +++ |
| 145 | ++ | +++ |
| 146 | ++ | +++ |
| 147 | + | + |
| 148 | + | + |

TABLE 2-continued

In vitro growth fluorescence assay (QUM and Intracellular growth assay (QIM) data of compounds 1-360

| # cpds | QUM (MIC$_{50}$, uM) | QIM (MIC$_{50}$, uM) |
|---|---|---|
| 149 | ++ | ++ |
| 150 | + | + |
| 151 | ++ | +++ |
| 152 | ++ | ++ |
| 153 | +++ | +++ |
| 154 | +++ | +++ |
| 155 | + | +++ |
| 156 | ++ | +++ |
| 157 | + | + |
| 158 | ++ | +++ |
| 159 | ++ | +++ |
| 160 | + | +++ |
| 161 | + | +++ |
| 162 | ++ | +++ |
| 163 | + | + |
| 164 | + | + |
| 165 | + | ++ |
| 166 | + | + |
| 167 | ++ | +++ |
| 168 | ++ | +++ |
| 169 | ++ | ++ |
| 170 | + | + |
| 171 | + | +++ |
| 172 | + | + |
| 173 | + | + |
| 174 | ++ | +++ |
| 175 | + | + |
| 176 | + | + |
| 177 | ++ | +++ |
| 178 | ++ | ++ |
| 179 | + | + |
| 180 | ++ | +++ |
| 181 | + | + |
| 182 | + | + |
| 183 | + | +++ |
| 184 | + | + |
| 185 | + | + |
| 186 | + | +++ |
| 187 | + | + |
| 188 | +++ | +++ |
| 189 | + | + |
| 190 | + | + |
| 191 | + | + |
| 192 | ++ | ++ |
| 193 | + | +++ |
| 194 | ++ | +++ |
| 195 | + | +++ |
| 196 | ++ | ++ |
| 197 | + | +++ |
| 198 | + | + |
| 199 | ++ | +++ |
| 200 | + | + |
| 201 | +++ | ++ |
| 202 | +++ | +++ |
| 203 | +++ | +++ |
| 204 | +++ | +++ |
| 205 | + | + |
| 206 | + | +++ |
| 207 | ++ | +++ |
| 208 | +++ | +++ |
| 209 | +++ | +++ |
| 210 | + | + |
| 211 | +++ | +++ |
| 212 | ++ | +++ |
| 213 | +++ | +++ |
| 214 | + | +++ |
| 215 | +++ | +++ |
| 216 | +++ | +++ |
| 217 | ++ | +++ |
| 218 | + | +++ |
| 219 | ++ | +++ |
| 220 | + | +++ |
| 221 | ++ | +++ |
| 222 | ++ | +++ |
| 223 | ++ | ++ |
| 224 | ++ | +++ |
| 225 | ++ | +++ |
| 226 | + | +++ |
| 227 | ++ | + |
| 228 | +++ | +++ |
| 229 | + | ++ |
| 230 | + | + |
| 231 | +++ | +++ |
| 232 | ++ | +++ |
| 233 | ++ | +++ |
| 234 | ++ | +++ |
| 235 | + | +++ |
| 236 | + | +++ |
| 237 | +++ | +++ |
| 238 | ++ | +++ |
| 239 | ++ | +++ |
| 240 | + | +++ |
| 241 | + | +++ |
| 242 | ++ | +++ |
| 243 | + | +++ |
| 244 | + | +++ |
| 245 | ++ | +++ |
| 246 | ++ | +++ |
| 247 | ++ | +++ |
| 248 | ++ | +++ |
| 249 | + | +++ |
| 250 | + | +++ |
| 251 | ++ | +++ |
| 252 | ++ | +++ |
| 253 | N/D | ++ |
| 254 | N/D | +++ |
| 255 | N/D | + |
| 256 | N/D | +++ |
| 257 | N/D | + |
| 258 | ++ | +++ |
| 259 | N/D | +++ |
| 260 | ++ | +++ |
| 261 | +++ | +++ |
| 262 | +++ | +++ |
| 263 | + | + |
| 264 | N/D | ++ |
| 265 | +++ | +++ |
| 266 | +++ | +++ |
| 267 | ++ | ++ |
| 268 | N/D | +++ |
| 269 | + | + |
| 270 | + | + |
| 271 | +++ | +++ |
| 272 | +++ | +++ |
| 273 | ++ | +++ |
| 274 | ++ | +++ |
| 275 | ++ | +++ |
| 276 | + | +++ |
| 277 | N/D | +++ |
| 278 | N/D | +++ |
| 279 | N/D | ++ |
| 280 | N/D | + |
| 281 | N/D | ++ |
| 282 | N/D | +++ |
| 283 | N/D | +++ |
| 284 | +++ | +++ |
| 285 | N/D | +++ |
| 286 | N/D | + |
| 287 | +++ | +++ |
| 288 | +++ | +++ |
| 289 | ++ | +++ |
| 290 | + | +++ |
| 291 | +++ | +++ |
| 292 | ++ | +++ |
| 293 | N/D | +++ |
| 294 | + | +++ |
| 295 | + | + |
| 296 | ++ | +++ |

TABLE 2-continued

In vitro growth fluorescence assay (QUM and Intracellular growth assay (QIM) data of compounds 1-360

| # cpds | QUM (MIC$_{50}$, uM) | QIM (MIC$_{50}$, uM) |
|---|---|---|
| 297 | + | ++ |
| 298 | +++ | +++ |
| 299 | +++ | +++ |
| 300 | N/D | + |
| 301 | + | +++ |
| 302 | ++ | +++ |
| 303 | N/D | + |
| 304 | + | +++ |
| 305 | + | +++ |
| 306 | + | +++ |
| 307 | +++ | +++ |
| 308 | +++ | +++ |
| 309 | ++ | +++ |
| 310 | + | + |
| 311 | + | ++ |
| 312 | + | + |
| 313 | + | ++ |
| 314 | +++ | +++ |
| 315 | ++ | +++ |
| 316 | ++ | +++ |
| 317 | ++ | +++ |
| 318 | + | +++ |
| 319 | ++ | +++ |
| 320 | ++ | +++ |
| 321 | + | ++ |
| 322 | ++ | N/D |
| 323 | +++ | +++ |
| 324 | +++ | +++ |
| 325 | ++ | +++ |
| 326 | + | + |
| 327 | ++ | ++ |
| 328 | +++ | +++ |
| 329 | ++ | +++ |
| 330 | ++ | +++ |
| 331 | +++ | +++ |
| 332 | +++ | +++ |
| 333 | ++ | +++ |
| 334 | ++ | +++ |
| 335 | ++ | ++ |
| 336 | ++ | +++ |
| 337 | +++ | +++ |
| 338 | +++ | +++ |
| 339 | +++ | +++ |
| 340 | ++ | +++ |
| 341 | ++ | +++ |
| 342 | ++ | +++ |
| 343 | ++ | +++ |
| 344 | ++ | +++ |
| 345 | ++ | +++ |
| 346 | ++ | +++ |
| 347 | + | + |
| 348 | + | +++ |
| 349 | + | +++ |
| 350 | +++ | +++ |
| 351 | +++ | +++ |
| 352 | +++ | N/D |
| 353 | ++ | N/D |
| 354 | ++ | N/D |
| 355 | ++ | N/D |
| 356 | + | N/D |
| 357 | ++ | N/D |
| 358 | +++ | +++ |
| 359 | ++ | +++ |
| 360 | +++ | +++ |

Activity range:
+++ indicates <1 uM,
++ indicates between 1-20 uM,
+ indicates >20 uM

TABLE 3

Antibacterial activity of selected compounds

| # of cpd | MDR-33 | MDR-137 | MDR-146 |
|---|---|---|---|
| 83 | +++ | +++ | +++ |
| 127 | +++ | +++ | +++ |
| 144 | +++ | +++ | +++ |
| 202 | +++ | +++ | +++ |

MDR-33, 137 and 146: clinical isolates of multidrug-resistance tuberculosis
Activity range:
+++ indicates <2 times of MIC50 on wild type strain (H37Rv),
++ indicates between 2 times and 5 times of MIC50 on wild type strain (H37Rv),
+ indicates >5 times of MIC50 on wild type strain (H37Rv)

REFERENCES

Andries K. et al. A diarylquinoline drug active on the ATP synthase of *Mycobacterium tuberculosis* (2005). *Science* 307, 223-227.

Arain, T. M., Resconi, A. E., Singh, D. C., and Stover, C. K. (1996). Reporter gene technology to assess activity of antimycobacterial agents in macrophages. Antimicrob Agents Chemother 40, 1542-1544.

Brodin, P., Christophe, T., No, Z., Kim, J., Genovesio, A., Fenistein, D. P. C., Jeon, H., Ewann, F. A., Kang, S., Lee, S., Seo, M. J., Park, E., Contreras Dominguez, M., Nam, J., Kim, E. Anti-Infective Compounds. WO 2010/003533A1.

Chaisson, R. E. & Nuermberger, E. L. Confronting multidrug-resistant tuberculosis (2012). *N Engl J Med* 366, 2223-2224.

Diacon, A. H. et al. Randomized pilot trial of eight weeks of bedaquiline (TMC207) treatment for multidrug-resistant tuberculosis: long-term outcome, tolerability, and effect on emergence of drug resistance (2012). *Antimicrob Agents Chemother* 56, 3271-3276.

Gler, M. T. et al. Delamanid for multidrug-resistant pulmonary tuberculosis (2012). *N Engl J Med* 366, 2151-2160.

Houben, E. N., Nguyen, L., and Pieters, J. (2006). Interaction of pathogenic mycobacteria with the host immune system. Curr Opin Microbiol 9, 76-85.

Pethe, K. et al. Discovery of Q203, a potent clinical candidate for the treatment of tuberculosis (2013). Nat Med. 19(9), 1157-1160.

Rohde, K. H., Abramovitch, R. B., and Russell, D. G. (2007). *Mycobacterium tuberculosis* invasion of macrophages: linking bacterial gene expression to environmental cues. Cell Host Microbe 2, 352-364.

Stanley, S. A. et al. Identification of novel inhibitors of *M. tuberculosis* growth using whole cell based high-throughput screening (2012). *ACS Chem Biol* 7, 1377-1384.

Stover, C. K., Arrener, P., VanDevanter, D. R., Sherman, D. R., Arain, T. M., Langhorne, M. H., Anderson, S. W., Towell, J. A., Yuan, Y., McMurray, D. N., Kreiswirth, B. N., Barry, C. E., Baker, W. R. (2000). A small-molecule nitroimidazopyran drug candidate for the treatment of tuberculosis. Naure 405, 962-6.

The invention claimed is:

1. A method of treatment of a bacterial infection comprising the application, to a person in need of such treatment, of a suitable amount of a compound having the general formula I:

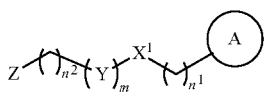

wherein
$n^1$ and $n^2$ are independently 0, 1, 2, or 3;
m is 0 or 1;
A is a moiety selected from the group consisting of

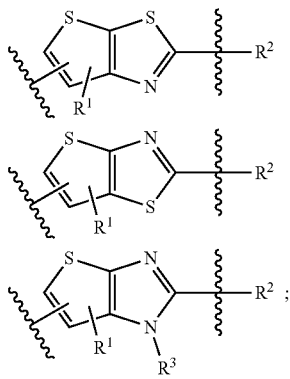

$R^1$ is selected from the group consisting of hydrogen, halogen, $C_1$-$C_{10}$ alkyl, $C_3$-$C_{10}$cycloalkyl, $C_1$-$C_3$haloalkyl, hydroxyl, —$OR^3$, —CN, —$NO_2$, —$NH_2$, —$NR^bR^c$, aryl, heteroaryl and heterocyclyl wherein each of said alkyl, cycloalkyl, aryl heteroaryl and heterocyclyl is optionally substituted with one to four $R^a$ groups;

$R^2$ is selected from the group consisting of hydrogen, halogen, $C_1$-$C_{10}$ alkyl, $C_3$-$C_{10}$cycloalkyl, $C_1$-$C_3$haloalkyl, hydroxyl, —$OR_3$, —CN, —$NO_2$, —$NH_2$, —$NR^bR^c$, —$NR^6C(O)R^c$, —$(NR^d)(V)_pR^e$, aryl, heteroaryl, heterocyclyl and groups of formula Ia shown below,
wherein each of said alkyl, cycloalkyl, aryl, heteroaryl and heterocyclyl is optionally substituted with one to four $R^a$ groups;

formula Ia

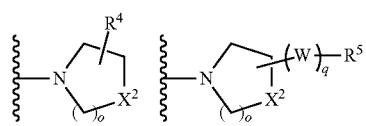

wherein,
is independently, at each occurrence, 0, 1, 2 or 3;
p is 0 or 1,
q is 0 or 1;
$X^1$ is C=O, O, S, —$S(O)_2$—, —$S(O)_2NR^6$—, —C(O)O—, —$C(O)NR^6$—, —NHC(O)— or —$(NR^6)$—;
$X^2$ is $CR^bR^c$, O, S, or $NR^6$;
Y is $C_1$-$C_6$ alkylene, O, S or $NR^6$;
V and W are independently, at each occurrence, $C_1$-$C_6$ alkylene;
$R^3$ is selected from the group consisting of hydrogen, $C_1$-$C_{10}$ alkyl, $C_3$-$C_{10}$cycloalkyl, $C_1$-$C_{10}$ haloalkyl $C_1$-$C_6$alkyl-O-alkyl, $C_2$-$C_{10}$ alkenyl, $C_3$-$C_{10}$ cycloalkenyl, $C_2$-$C_{10}$ alkynyl, aryl, heteroaryl and heterocyclyl,
wherein each of said alkyl, cycloalkyl, aryl, heteroaryl and heterocyclyl is optionally substituted with one to four $R^a$ groups;

$R^4$ is selected from the group consisting of hydrogen, halogen, $C_1$-$C_{10}$ alkyl, $C_3$-$C_{10}$cycloalkyl, $C_1$-$C_3$haloalkyl, hydroxyl, —$OR^6$, —CN, —$NO_2$, —$NH_2$, —$NR^bR^c$, —$N(R^6)C(O)R^6$, —$C(O)R^6$, —$C(O)OR^6$, —$C(O)NR^bR^c$, —$S(O)R^6$, —$S(O)_2R^6$, —$S(O)_2NR^bR^c$, aryl, heteroaryl and heterocyclyl wherein each of said alkyl, cycloalkyl, —$OR^6$ aryl, heteroaryl and heterocyclyl is optionally substituted with one to four $R^a$ groups;

$R^5$ is selected from the group consisting of hydrogen, halogen, $C_1$-$C_{10}$ alkyl, $C_3$-$C_{10}$cycloalkyl, $C_1$-$C_3$haloalkyl, hydroxyl, —$OR^6$, —CN, —$NO_2$, —$NH_2$, —$NR^bR^c$, —$N(R^6)C(O)R^6$, —$N(R^6)C(O)OR^6$, —$C(O)R^6$, —$C(O)OR^6$, —$C(O)NR^bR^c$, —$CHOHR^6$, —S(O) $R^6$, —$S(O)_2R^6$, —$S(O)_2NR^bR^c$, aryl, heteroaryl and heterocyclyl wherein each of said alkyl, cycloalkyl, aryl, heteroaryl, and heterocyclyl is optionally substituted with one to four $R^a$ groups;

$R^6$ is independently, at each occurrence, selected from the group consisting of hydrogen, $C_1$-$C_{10}$ alkyl, $C_3$-$C_{10}$cycloalkyl, $C_1$-$C_3$haloalkyl, aryl, heteroaryl and heterocyclyl, wherein each of said alkyl, cycloalkyl, aryl, heteroaryl and heterocyclyl is optionally substituted with one to four $R^a$ groups;

Z is selected from the group consisting of $C_1$-$C_{10}$ alkyl, $C_3$-$C_{10}$cycloalkyl, $C_1$-$C_3$haloalkyl, $OR^7$, aryloxy, aryl, heteroaryl, heterocyclyl, and groups of formula Ib shown below, wherein each of said alkyl, cycloalkyl, aryl, heteroaryl, heterocyclyl and groups of formula Ib is optionally substituted with one to four $R^a$ groups;

Formula Ib

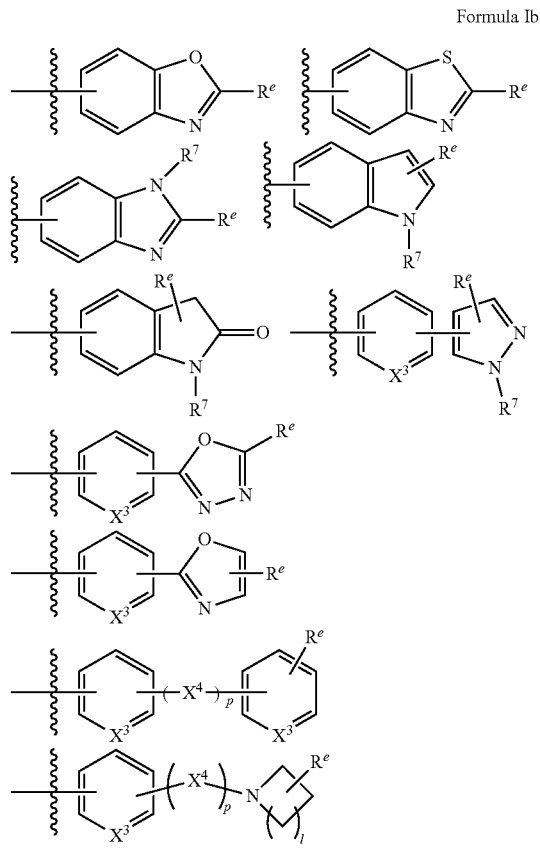

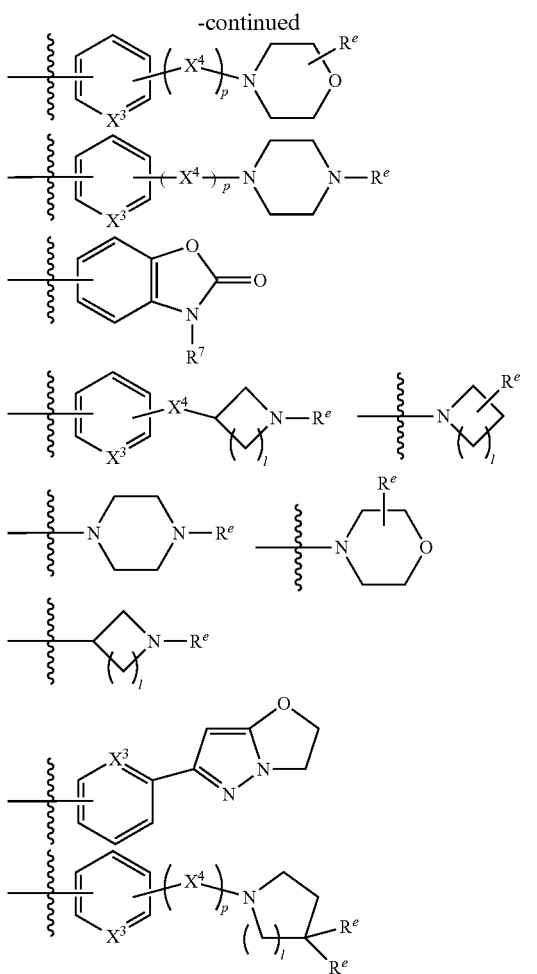

wherein, p is 0 or 1;

l is 1, 2 or 3;

$X^3$ is, independently at each occurrence, CH or N;

$X^4$ is C=O, $CR^bR^c$, O, S, or $NR^7$;

$R^e$, if denoted in formula Ib, may also occur twice as substituent at the same carbon atom wherein $R^e$ is independently selected at each occurrence;

$R^a$ is independently, at each occurrence, selected from the group consisting of hydrogen, halogen, $C_1$-$C_3$ alkyl, $C_1$-$C_4$ alkoxy, $C_1$-$C_4$ alkoxy substituted with aryl, $C_1$-$C_3$ haloalkyl, hydroxyl, $C_1$-$C_3$ alkylhydroxyl, —CN, $NO_2$, —$NR^bR^c$, —C(O)$NR^bR^c$, —$OR^c$, —C(O) $R^c$, —C(O) $OR^c$, sulfonyl, sulfoxide, $C_3$-$C_{10}$ cycloalkyl, heterocyclyl, heteroaryl and aryl, wherein each of said alkyl, cycloalkyl, aryl, heteroaryl and heterocyclyl is optionally substituted with one to four $C_1$-$C_3$ alkyl, $C_1$-$C_4$ alkoxy, aryl, halogen, $C_1$-$C_3$ haloalkyl, hydroxyl, —$NH_2$, wherein such substitution, if present, may occur in such a manner that there is more than one substituent, per carbon atom, and wherein these substituents may be the same or different;

$R^b$ and $R^c$ are independently, at each occurrence selected from the group consisting of hydrogen, $C_1$-$C_{10}$ alkyl, $C_3$-$C_{10}$ cycloalkyl, $C_1$-$C_6$ alkyl-O-alkyl, $C_2$-$C_{10}$ alkenyl, $C_1$-$C_4$ alkoxy, $C_1$-$C_3$ alkylhydroxyl, $C_3$-$C_{10}$ cycloalkenyl, $C_2$-$C_{10}$ alkynyl, $C_1$-$C_{10}$ haloalkyl, aryl, alkylaryl, heteroaryl, and heterocyclyl, wherein each of said alkyl, cycloalkyl, aryl, heteroaryl and heterocyclyl is optionally substituted with one to four $C_1$-$C_3$ alkyl, $C_1$-$C_4$ alkoxy, halogen, aryloxy, $C_1$-$C_3$ haloalkyl, hydroxyl, $C_1$-$C_3$ alkylhydroxyl, —CN, —$NO_2$, —$NH_2$, sulfonyl, sulfoxide, $C_3$-$C_{10}$ cycloalkyl, heterocyclyl, aryl, heteroaryl, wherein such substitution, if present, may occur in such a manner that there is more than one substituent per carbon atom, wherein such substituents may be the same or different; or $R^b$ and $R^c$ are connected to each other to make a four, five or six membered saturated or unsaturated cyclic or heterocyclic ring, or they are connected to make a fused cyclic or heterocyclic ring structure;

$R^d$ is independently, at each occurrence, selected from the group consisting of hydrogen, $C_1$-$C_{10}$ alkyl, $C_3$-$C_{10}$ cycloalkyl, $C_1$-$C_3$ haloalkyl, aryl, heteroaryl and heterocyclyl, wherein each of said alkyl, cycloalkyl, aryl, heteroaryl and heterocyclyl is optionally substituted with one to four $R^a$ groups;

$R^d$ is independently, at each occurrence, selected from the group consisting of hydrogen, halogen, $C_1$-$C_{10}$ alkyl, $C_3$-$C_{10}$ cycloalkyl, $C_1$-$C_3$ haloalkyl, hydroxyl, —$OR^7$, —CN, —$(CH_2)_1R^7$, with l being 0, 1, 2 or 3, —$NO_2$, —$NH_2$, —$NR^bR^c$, —$N(R^7)C(O)R^7$, —$C(O)R^7$, —$C(O)OR^7$, —$C(O)NR^bR^c$, —S(O) $R^7$, —$S(O)_2R^7$, —$S(O)_2NR^bR^c$, aryl, heteroaryl and heterocyclyl, wherein each of said alkyl, cycloalkyl, aryl, heteroaryl and heterocyclyl is optionally substituted with one to four $R^a$ groups;

$R^7$ is independently, at each occurrence, selected from the group consisting of hydrogen, $C_1$-$C_{10}$ alkyl, $C_3$-$C_{10}$ cycloalkyl, $C_1$-$C_3$ haloalkyl, aryl, heteroaryl, and heterocyclyl, wherein each of said alkyl, cycloalkyl, aryl, heteroaryl and heterocyclyl is optionally substituted with one to four $R^a$ groups;

and pharmaceutically acceptable salts thereof.

2. The method according to claim 1, wherein said suitable amount is from 0.01 mg/kg body weight to 1 g/kg body weight.

3. The method, according to claim 1, wherein the bacterial infection is Tuberculosis.

4. The method, according to claim 1, wherein the compound is selected from:

a) a compound having the general formula

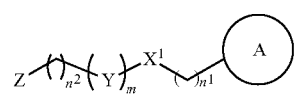

wherein $n^1$ and $n^2$ are independently 0, 1, 2, or 3;

m is 0 or 1;

A is a moiety selected from the group consisting of

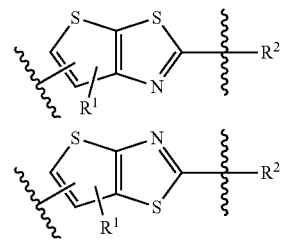

-continued

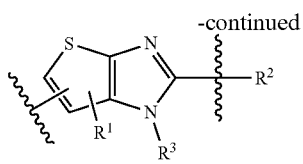

R¹ is selected from the group consisting of hydrogen, halogen, $C_1$-$C_{10}$ alkyl, $C_3$-$C_{10}$cycloalkyl, $C_1$-$C_3$haloalkyl, hydroxyl, —OR³, —CN, —NO₂, —NH₂, —NR$^b$R$^c$, aryl, heteroaryl and heterocyclyl wherein each of said alkyl, cycloalkyl, aryl heteroaryl and heterocyclyl is optionally substituted with one to four R$^a$ groups;

R² is selected from the group consisting of hydrogen, halogen, $C_1$-$C_{10}$ alkyl, $C_3$-$C_{10}$cycloalkyl, $C_1$-$C_3$haloalkyl, hydroxyl, —OR₃, —CN, —NO₂, —NH₂, —NR$^b$R$^c$, —NR⁶C(O)R$^c$, —(NR$^d$)(V)$_p$R$^e$, aryl, heteroaryl, heterocyclyl and groups of formula Ia shown below, wherein each of said alkyl, cycloalkyl, aryl, heteroaryl and heterocyclyl is optionally substituted with one to four R$^a$ groups;

formula Ia

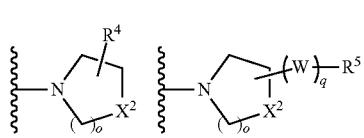

wherein,
is independently, at each occurrence, 0, 1, 2 or 3;
p is 0 or 1,
q is 0 or 1;
X¹ is C=O, O, S, —S(O)₂—, —S(O)₂NR⁶—, —C(O)O—, —C(O)NR⁶—, —NHC(O)— or —(NR⁶)—;
X² is CR$^b$R$^c$, O, S, or NR⁶;
Y is $C_1$-$C_6$ alkylene, O, S or NR⁶;
V and W are independently, at each occurrence, $C_1$-$C_6$ alkylene;
R³ is selected from the group consisting of hydrogen, $C_1$-$C_{10}$ alkyl, $C_3$-$C_{10}$cycloalkyl, $C_1$-$C_{10}$ haloalkyl $C_1$-$C_6$alkyl-O-alkyl, $C_2$-$C_{10}$ alkenyl, $C_3$-$C_{10}$ cycloalkenyl, $C_2$-$C_{10}$ alkynyl, aryl, heteroaryl and heterocyclyl, wherein each of said alkyl, cycloalkyl, aryl, heteroaryl and heterocyclyl is optionally substituted with one to four R$^a$ groups;

R⁴ is selected from the group consisting of hydrogen, halogen, $C_1$-$C_{10}$ alkyl, $C_3$-$C_{10}$cycloalkyl, $C_1$-$C_3$haloalkyl, hydroxyl, —OR⁶, —CN, —NO₂, —NH₂, —NR$^b$R$^c$, —N(R⁶)C(O)R⁶, —C(O)R⁶, —C(O)OR⁶, —C(O)NR$^b$R$^c$, —S(O)R⁶, —S(O)₂R⁶, —S(O)₂NR$^b$R$^c$, aryl, heteroaryl and heterocyclyl wherein each of said alkyl, cycloalkyl, —OR⁶ aryl, heteroaryl and heterocyclyl is optionally substituted with one to four R$^a$ groups;

R⁵ is selected from the group consisting of hydrogen, halogen, $C_1$-$C_{10}$ alkyl, $C_3$-$C_{10}$cycloalkyl, $C_1$-$C_3$haloalkyl, hydroxyl, —OR⁶, —CN, —NO₂, —NH₂, —NR$^b$R$^c$, —N(R⁶)C(O)R⁶, —N(R⁶)C(O)OR⁶, —C(O)R⁶, —C(O)OR⁶, —C(O)NR$^b$R$^c$, —CHOHR⁶, —S(O) R⁶, —S(O)₂R⁶, —S(O)₂NR$^b$R$^c$, aryl, heteroaryl and heterocyclyl wherein each of said alkyl, cycloalkyl, aryl, heteroaryl, and heterocyclyl is optionally substituted with one to four R$^a$ groups;

R⁶ is independently, at each occurrence, selected from the group consisting of hydrogen, $C_1$-$C_{10}$ alkyl, $C_3$-$C_{10}$cycloalkyl, $C_1$-$C_3$haloalkyl, aryl, heteroaryl and heterocyclyl, wherein each of said alkyl, cycloalkyl, aryl, heteroaryl and heterocyclyl is optionally substituted with one to four R$^a$ groups;

Z is selected from the group consisting of $C_1$-$C_{10}$ alkyl, $C_3$-$C_{10}$cycloalkyl, $C_1$-$C_3$haloalkyl, OR⁷, aryloxy, aryl, heteroaryl, heterocyclyl, and groups of formula Ib shown below, wherein each of said alkyl, cycloalkyl, aryl, heteroaryl, heterocyclyl and groups of formula Ib is optionally substituted with one to four R$^a$ groups;

Formula Ib

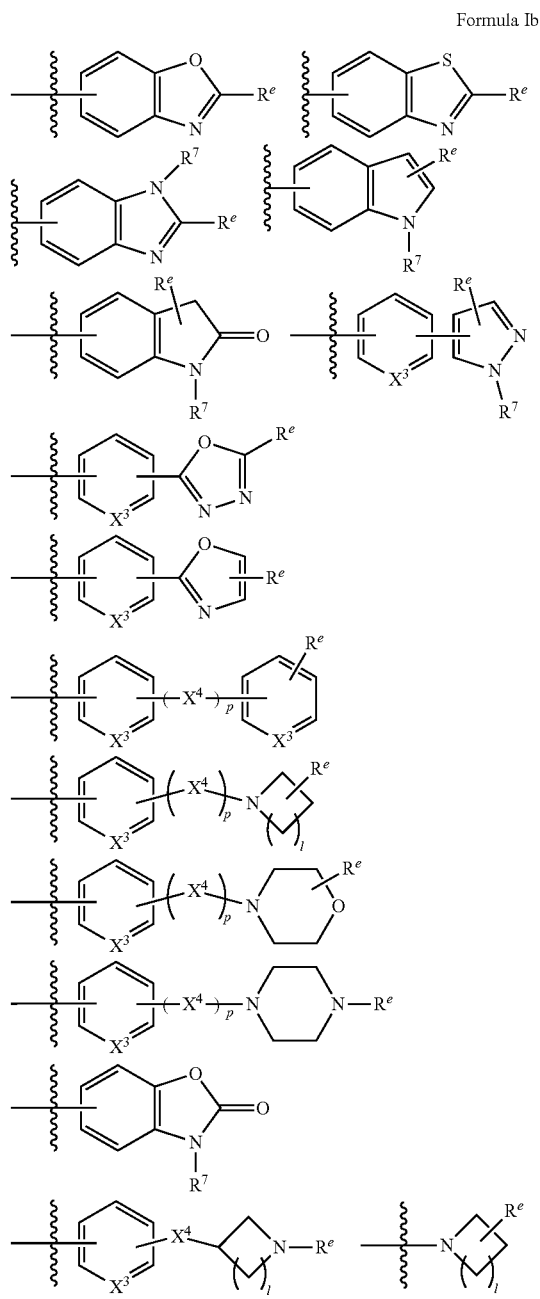

-continued

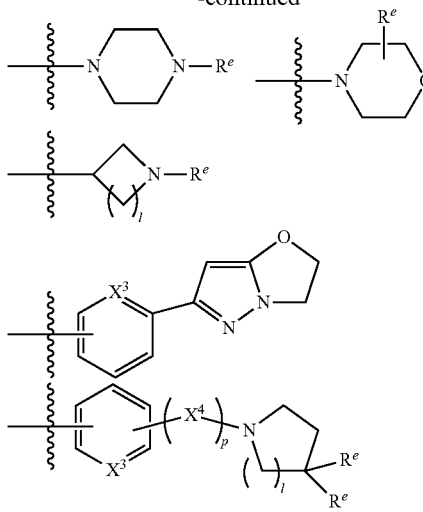

wherein, p is 0 or 1;

l is 1, 2 or 3;

$X^3$ is, independently at each occurrence, CH or N;

$X^4$ is C=O, $CR^bR^c$, O, S, or $NR^7$;

$R^e$, if denoted in formula Ib, may also occur twice as substituent at the same carbon atom wherein $R^e$ is independently selected at each occurrence;

$R^a$ is independently, at each occurrence, selected from the group consisting of hydrogen, halogen, $C_1$-$C_3$ alkyl, $C_1$-$C_4$ alkoxy, $C_1$-$C_4$ alkoxy substituted with aryl, $C_1$-$C_3$ haloalkyl, hydroxyl, $C_1$-$C_3$ alkylhydroxyl, —CN, $NO_2$, —$NR^bR^c$, —C(O)$NR^bR^c$, —$OR^c$, —C(O) $R^c$, —C(O) $OR^c$, sulfonyl, sulfoxide, $C_3$-$C_{10}$ cycloalkyl, heterocyclyl, heteroaryl and aryl, wherein each of said alkyl, cycloalkyl, aryl, heteroaryl and heterocyclyl is optionally substituted with one to four $C_1$-$C_3$ alkyl, $C_1$-$C_4$ alkoxy, aryl, halogen, $C_1$-$C_3$ haloalkyl, hydroxyl, —$NH_2$, wherein such substitution, if present, may occur in such a manner that there is more than one substituent, per carbon atom, and wherein these substituents may be the same or different;

$R^b$ and $R^c$ are independently, at each occurrence selected from the group consisting of hydrogen, $C_1$-$C_{10}$ alkyl, $C_3$-$C_{10}$ cycloalkyl, $C_1$-$C_6$ alkyl-O-alkyl, $C_2$-$C_{10}$ alkenyl, $C_1$-$C_4$ alkoxy, $C_1$-$C_3$ alkylhydroxyl, $C_3$-$C_{10}$ cycloalkenyl, $C_2$-$C_{10}$ alkynyl, $C_1$-$C_{10}$ haloalkyl, aryl, alkylaryl, heteroaryl, and heterocyclyl, wherein each of said alkyl, cycloalkyl, aryl, heteroaryl and heterocyclyl is optionally substituted with one to four $C_1$-$C_3$ alkyl, $C_1$-$C_4$ alkoxy, halogen, aryloxy, $C_1$-$C_3$ haloalkyl, hydroxyl, $C_1$-$C_3$ alkylhydroxyl, —CN, —$NO_2$, —$NH_2$, sulfonyl, sulfoxide, $C_3$-$C_{10}$ cycloalkyl, heterocyclyl, aryl, heteroaryl, wherein such substitution, if present, may occur in such a manner that there is more than one substituent per carbon atom, wherein such substituents may be the same or different; or $R^b$ and $R^c$ are connected to each other to make a four, five or six membered saturated or unsaturated cyclic or heterocyclic ring, or they are connected to make a fused cyclic or heterocyclic ring structure;

$R^d$ is independently, at each occurrence, selected from the group consisting of hydrogen, $C_1$-$C_{10}$ alkyl, $C_3$-$C_{10}$ cycloalkyl, $C_1$-$C_3$ haloalkyl, aryl, heteroaryl and heterocyclyl, wherein each of said alkyl, cycloalkyl, aryl, heteroaryl and heterocyclyl is optionally substituted with one to four $R^a$ groups;

$R^e$ is independently, at each occurrence, selected from the group consisting of hydrogen, halogen, $C_1$-$C_{10}$ alkyl, $C_3$-$C_{10}$ cycloalkyl, $C_1$-$C_3$ haloalkyl, hydroxyl, —$OR^7$, —CN, —$(CH_2)_1R^7$, with 1 being 0, 1, 2 or 3, —$NO_2$, —$NH_2$, —$NR^bR^c$, —$N(R^7)C(O)R^7$, —$C(O)R^7$, —$C(O)OR^7$, —$C(O)NR^bR^c$, —S(O) $R^7$, —$S(O)_2R^7$, —$S(O)_2NR^bR^c$, aryl, heteroaryl and heterocyclyl, wherein each of said alkyl, cycloalkyl, aryl, heteroaryl and heterocyclyl is optionally substituted with one to four $R^a$ groups;

$R^7$ is independently, at each occurrence, selected from the group consisting of hydrogen, $C_1$-$C_{10}$ alkyl, $C_3$-$C_{10}$ cycloalkyl, $C_1$-$C_3$ haloalkyl, aryl, heteroaryl, and heterocyclyl, wherein each of said alkyl, cycloalkyl, aryl, heteroaryl and heterocyclyl is optionally substituted with one to four $R^a$ groups;

and pharmaceutically acceptable salts thereof;

b) a compound having the general formula II:

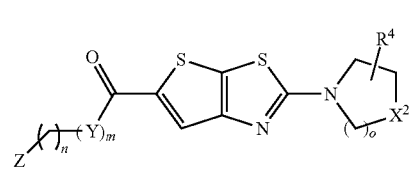

II wherein n is 0, 1, 2 or 3;

m is 0 or 1;

o is 0, 1, 2 or 3;

$X^2$ is $CR^bR^c$, O, S, or $NR^6$;

Y is $C_1$-$C_6$ alkylene, O, S or $NR^6$;

$R^4$ is selected from the group consisting of hydrogen, halogen, $C_1$-$C_{10}$ alkyl, $C_3$-$C_{10}$cycloalkyl, $C_1$-$C_3$haloalkyl, hydroxyl, —$OR^6$, —CN, —$NO_2$, —$NH_2$, —$NR^bR^c$, —$N(R^6)C(O)R^6$, —$C(O)R^6$, —$C(O)OR^6$, —$C(O)NR^bR^c$, —$S(O)R^6$, —$S(O)_2R^6$, —$S(O)_2NR^bR^e$, aryl, heteroaryl and heterocyclyl wherein each of said alkyl, cycloalkyl, —$OR^6$ aryl, heteroaryl and heterocyclyl is optionally substituted with one to four $R^a$ groups;

$R^6$ is independently, at each occurrence, selected from the group consisting of hydrogen, $C_1$-$C_{10}$ alkyl, $C_3$-$C_{10}$cycloalkyl, $C_1$-$C_3$haloalkyl, aryl, heteroaryl and heterocyclyl, wherein each of said alkyl, cycloalkyl, aryl, heteroaryl and heterocyclyl is optionally substituted with one to four $R^a$ groups;

Z is selected from the group consisting of $C_1$-$C_{10}$ alkyl, $C_3$-$C_{10}$cycloalkyl, $C_1$-$C_3$haloalkyl, $OR^6$, aryloxy, aryl, heteroaryl, heterocyclyl, and groups of formula Ib shown below, wherein each of said alkyl, cycloalkyl, aryl, heteroaryl, heterocyclyl and groups of formula Ib is optionally substituted with one to four $R^a$ groups;

Formula Ib

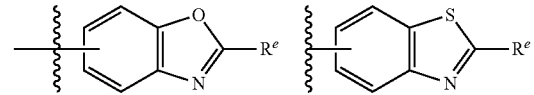

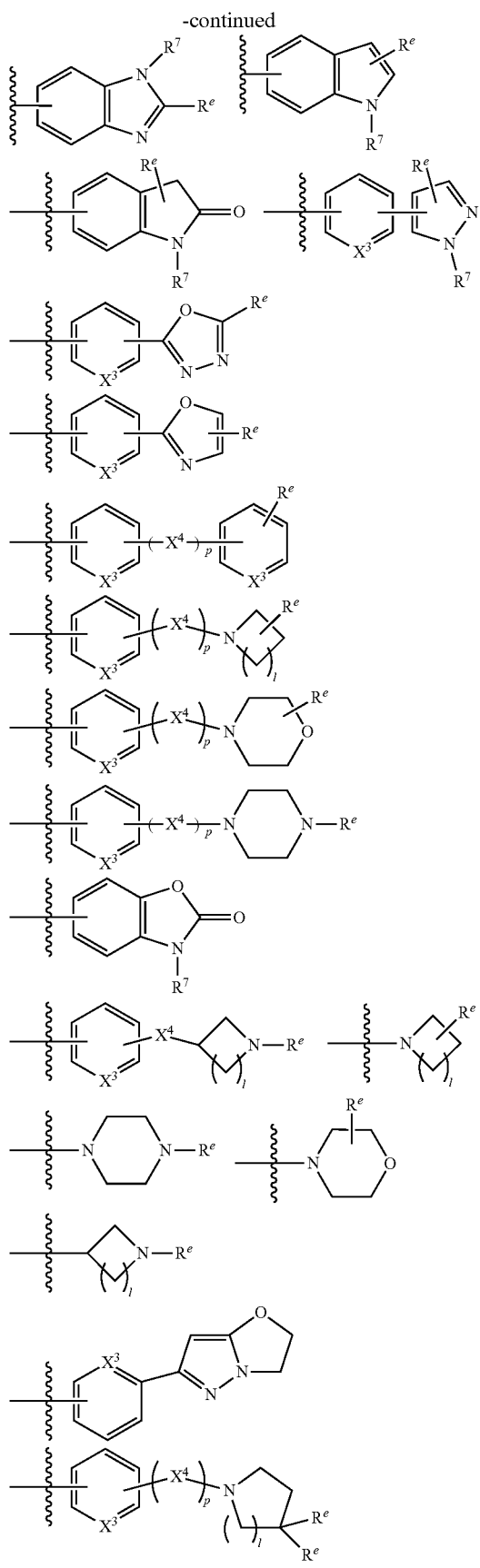

-continued wherein,
p is 0 or 1;
l is 1, 2 or 3;
$X^3$ is, independently at each occurrence, CH or N;
$X^4$ is C=O, $CR^bR^c$, O, S, or $NR^7$;
$R^c$, if denoted in formula Ib, may also occur twice as substituent at the same carbon atom wherein $R^e$ is independently selected at each occurrence;
$R^a$ is independently, at each occurrence, selected from the group consisting of hydrogen, halogen, $C_1$-$C_3$ alkyl, $C_1$-$C_4$ alkoxy, $C_1$-$C_4$ alkoxy substituted with aryl, $C_1$-$C_3$ haloalkyl, hydroxyl, $C_1$-$C_3$ alkylhydroxyl, —CN, $NO_2$, —$NR^bR^c$, —$C(O)NR^bR^c$, —$OR^c$, —C(O) $R^c$, —C(O) $OR^c$, sulfonyl, sulfoxide, $C_3$-$C_{10}$ cycloalkyl, heterocyclyl, heteroaryl and aryl, wherein each of said alkyl, cycloalkyl, aryl, heteroaryl and heterocyclyl is optionally substituted with one to four $C_1$-$C_3$ alkyl, $C_1$-$C_4$ alkoxy, aryl, halogen, $C_1$-$C_3$ haloalkyl, hydroxyl, —$NH_2$, wherein such substitution, if present, may occur in such a manner that there is more than one substituent, e.g. two or three substituents, per carbon atom, wherein such two or three substituents may be the same or different;
$R^b$ and $R^c$ are independently, at each occurrence selected from the group consisting of hydrogen, $C_1$-$C_{10}$ alkyl, $C_3$-$C_{10}$ cycloalkyl, $C_1$-$C_6$ alkyl-O-alkyl, $C_2$-$C_{10}$ alkenyl, $C_1$-$C_4$ alkoxy, $C_1$-$C_3$ alkylhydroxyl, $C_3$-$C_{10}$ cycloalkenyl, $C_2$-$C_{10}$ alkynyl, $C_1$-$C_{10}$ haloalkyl, aryl, alkylaryl, heteroaryl, and heterocyclyl, wherein each of said alkyl, cycloalkyl, aryl, heteroaryl and heterocyclyl is optionally substituted with one to four $C_1$-$C_3$ alkyl, $C_1$-$C_4$ alkoxy, halogen, aryloxy, $C_1$-$C_3$ haloalkyl, hydroxyl, $C_1$-$C_3$ alkylhydroxyl, —CN, —$NO_2$, —$NH_2$, sulfonyl, sulfoxide, $C_3$-$C_{10}$ cycloalkyl, heterocyclyl, aryl, heteroaryl, wherein such substitution, if present, may occur in such a manner that there is more than one substituent per carbon atom, wherein such substituents may be the same or different or they are connected to make a fused cyclic or heterocyclic ring structure; or
$R^b$ and $R^c$ are connected to each other to make a four, five or six membered saturated or unsaturated cyclic or heterocyclic ring, or they are connected to make a fused cyclic or heterocyclic ring structure;
$R^e$ is independently, at each occurrence, selected from the group consisting of hydrogen, halogen, $C_1$-$C_{10}$ alkyl, $C_3$-$C_{10}$ cycloalkyl, $C_1$-$C_3$ haloalkyl, hydroxyl, —$OR^7$, —CN, —$(CH_2)_l R^7$, with l being 0, 1, 2 or 3, —$NO_2$, —$NH_2$, —$NR^bR^c$, —$N(R^7)C(O)R^7$, —$C(O)R^7$, —$C(O)OR^7$, —$C(O)NR^bR^c$, —S(O) $R^7$, —$S(O)_2R^7$, —$S(O)_2NR^bR^c$, aryl, heteroaryl and heterocyclyl, wherein each of said alkyl, cycloalkyl, aryl, heteroaryl and heterocyclyl is optionally substituted with one to four $R^a$ groups;
$R^7$ is independently, at each occurrence, selected from the group consisting of hydrogen, $C_1$-$C_{10}$ alkyl, $C_3$-$C_{10}$ cycloalkyl, $C_1$-$C_3$ haloalkyl, aryl, heteroaryl, and heterocyclyl, wherein each of said alkyl, cycloalkyl, aryl, heteroaryl and heterocyclyl is optionally substituted with one to four $R^a$ groups;
and pharmaceutically acceptable salts thereof;
b) a compound having the general formula II:

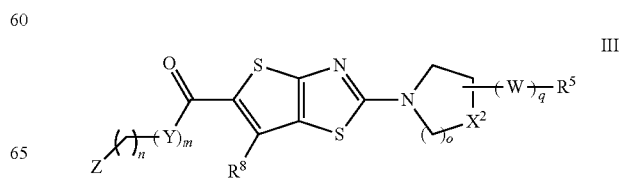

III wherein
n is 0, 1, 2 or 3;
m is 0 or 1;
o is 0, 1, 2 or 3;
q is 0 or 1;
$X^2$ is $CR^bR^c$, O, S, or $NR^6$;
Y is $C_1$-$C_6$ alkylene, O, S or $NR^6$;
W is $C_1$-$C_6$ alkylene;
$R^5$ is selected from the group consisting of hydrogen, halogen, $C_1$-$C_{10}$ alkyl, $C_3$-$C_{10}$cycloalkyl, $C_1$-$C_3$haloalkyl, hydroxyl, —$OR^6$, —CN, —$NO_2$, —$NH_2$, —$NR^bR^c$, —$N(R^6)C(O)R^6$, —$N(R^6)C(O)OR^6$, —$C(O)R^6$, —$C(O)OR^6$, —$C(O)NR^bR^c$, —$CHOHR^6$, —S(O) $R^6$, —$S(O)_2R^6$, —$S(O)_2NR^bR^c$, aryl, heteroaryl and heterocyclyl wherein each of said alkyl, cycloalkyl, aryl, heteroaryl, and heterocyclyl is optionally substituted with one to four $R^a$ groups;
$R^6$ is independently, at each occurrence, selected from the group consisting of hydrogen, $C_1$-$C_{10}$ alkyl, $C_3$-$C_{10}$cycloalkyl, $C_1$-$C_3$haloalkyl, aryl, heteroaryl and heterocyclyl, wherein each of said alkyl, cycloalkyl, aryl, heteroaryl and heterocyclyl is optionally substituted with one to four $R^a$ groups;
$R^8$ is selected from the group consisting of hydrogen, halogen, $C_1$-$C_{10}$ alkyl, $C_3$-$C_{10}$ cycloalkyl, $C_1$-$C_3$ haloalkyl, hydroxyl, —$OR^9$, —CN, —$NO_2$, —$NH_2$, aryl, heteroaryl and heterocyclyl group wherein each of said alkyl, cycloalkyl, aryl, heteroaryl and heterocyclyl is optionally substituted with one to four $R^a$ groups;
$R^9$ is selected from the group consisting of $C_1$-$C_{10}$ alkyl, $C_3$-$C_{10}$ cycloalkyl, $C_1$-$C_3$ haloalkyl, aryl, heteroaryl and heterocyclyl group wherein each of said alkyl, cycloalkyl, aryl, heteroaryl and heterocyclyl is optionally substituted with one to four $R^a$ groups;
Z is selected from the group consisting of $C_1$-$C_{10}$ alkyl, $C_3$-$C_{10}$ cycloalkyl, $C_1$-$C_3$ haloalkyl, $OR^6$, aryloxy, aryl, heteroaryl, heterocyclyl, and groups of formula Ib shown below, wherein each of said alkyl, cycloalkyl, aryl, heteroaryl, heterocyclyl and groups of formula Ib is optionally substituted with one to four $R^a$ groups;

Formula Ib

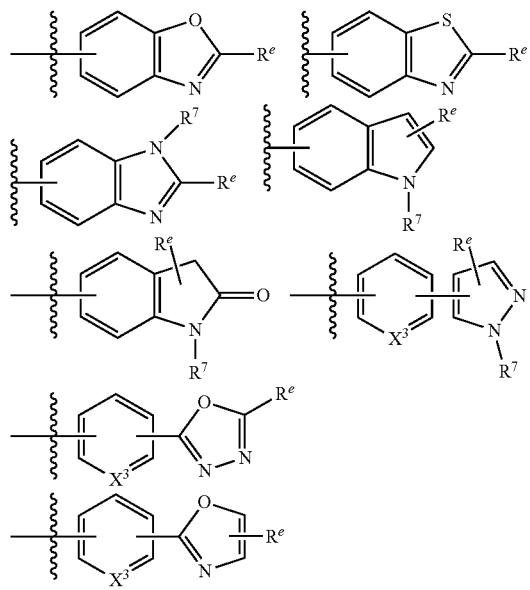

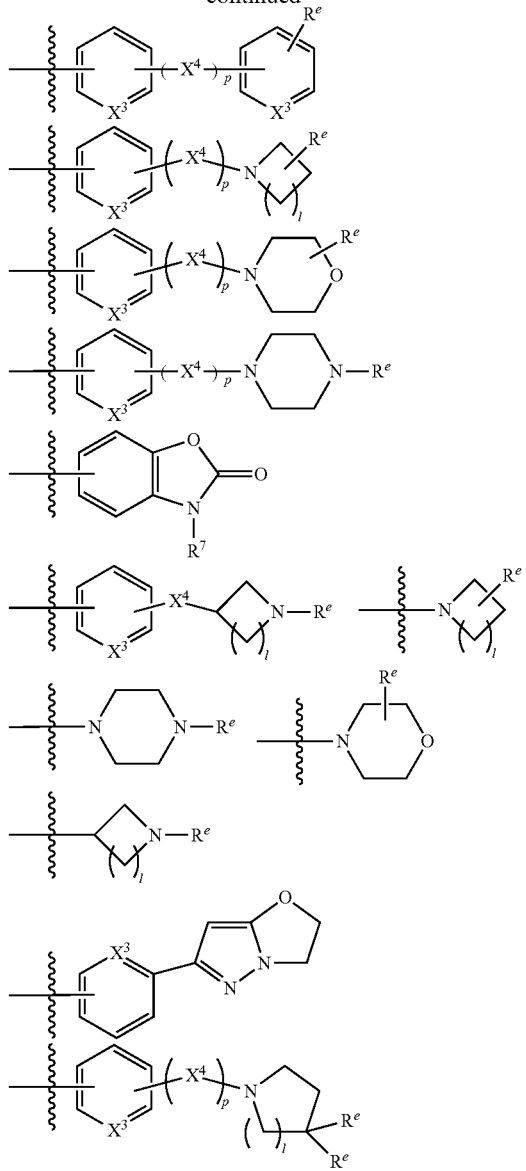

p is 0 or 1;
l is 1, 2 or 3;
$X^3$ is, independently at each occurrence, CH or N;
$X^4$ is C=O, $CR^bR^c$, O, S, or $NR^7$;
$R^c$, if denoted in formula Ib, may also occur twice as substituent at the same carbon atom wherein $R^e$ is independently selected at each occurrence;
$R^a$ is independently, at each occurrence, selected from the group consisting of hydrogen, halogen, $C_1$-$C_3$ alkyl, $C_1$-$C_4$ alkoxy, $C_1$-$C_4$ alkoxy substituted with aryl, $C_1$-$C_3$ haloalkyl, hydroxyl, $C_1$-$C_3$ alkylhydroxyl, —CN, $NO_2$, —$NR^bR^c$, —$C(O)NR^bR^c$, —$OR^c$, —$C(O)$ $R^c$, —$C(O)$ $OR^c$, sulfonyl, sulfoxide, $C_3$-$C_{10}$ cycloalkyl, heterocyclyl, heteroaryl and aryl, benzyl, alkylaryl wherein each of said alkyl, cycloalkyl, aryl, heteroaryl and heterocyclyl is optionally substituted with one to four $C_1$-$C_3$ alkyl, $C_1$-$C_4$ alkoxy, halogen, $C_1$-$C_3$ haloalkyl, hydroxyl, —$NH_2$, wherein such substitution, if present, may occur in such a manner that there is more than one substituent, per carbon atom, wherein such substituents may be the same or different;

$R^b$ and $R^c$ are independently, at each occurrence selected from the group consisting of hydrogen, $C_1$-$C_{10}$ alkyl, $C_3$-$C_{10}$ cycloalkyl, $C_1$-$C_6$ alkyl-O-alkyl, $C_2$-$C_{10}$ alkenyl, $C_1$-$C_4$ alkoxy, $C_1$-$C_3$ alkylhydroxyl, $C_3$-$C_{10}$ cycloalkenyl, $C_2$-$C_{10}$ alkynyl, $C_1$-$C_{10}$ haloalkyl, aryl, alkylaryl, heteroaryl, and heterocyclyl, wherein each of said alkyl, cycloalkyl, aryl, heteroaryl and heterocyclyl is optionally substituted with one to four $C_1$-$C_3$ alkyl, $C_1$-$C_4$ alkoxy, halogen, aryloxy, $C_1$-$C_3$ haloalkyl, hydroxyl, $C_1$-$C_3$ alkylhydroxyl, —CN, —NO₂, —NH₂, sulfonyl, sulfoxide, $C_3$-$C_{10}$ cycloalkyl, heterocyclyl, aryl, heteroaryl, wherein such substitution, if present, may occur in such a manner that there is more than one substituent per carbon atom, wherein such substituents may be the same or different; or $R^b$ and $R^c$ are connected to each other to make a four, five or six membered saturated or unsaturated cyclic or heterocyclic ring, or they are connected to make a fused cyclic or heterocyclic ring structure;

$R^e$ is independently, at each occurrence, selected from the group consisting of hydrogen, halogen, $C_1$-$C_{10}$ alkyl, $C_3$-$C_{10}$ cycloalkyl, $C_1$-$C_3$ haloalkyl, hydroxyl, —OR⁷, —CN, —(CH₂)₁R⁷, with 1 being 0, 1, 2 or 3, —NO₂, —NH₂, —NR$^b$R$^c$, —N(R⁷)C(O)R⁷, —C(O)R⁷, —C(O)OR⁷, —C(O)NR$^b$R$^c$, —S(O) R⁷, —S(O)₂R⁷, —S(O)₂NR$^b$R$^c$, aryl, heteroaryl and heterocyclyl, wherein each of said alkyl, cycloalkyl, aryl, heteroaryl and heterocyclyl is optionally substituted with one to four R$^a$ groups;

R⁷ is independently, at each occurrence, selected from the group consisting of hydrogen, $C_1$-$C_{10}$ alkyl, $C_3$-$C_{10}$ cycloalkyl, $C_1$-$C_3$ haloalkyl, aryl, heteroaryl, and heterocyclyl, wherein each of said alkyl, cycloalkyl, aryl, heteroaryl and heterocyclyl is optionally substituted with one to four R$^a$ groups;

and pharmaceutically acceptable salts thereof;

d) a compound having the general formula IV:

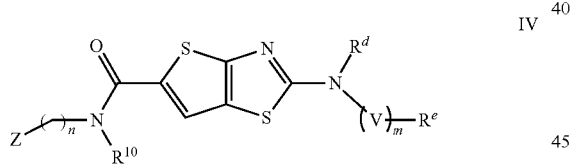

IV wherein
n is 0, 1, 2 or 3;
m is 0 or 1;
V is $C_1$-$C_6$ alkylene
$R^{10}$ and $R^d$ are independently at each occurrence, selected from the group consisting of hydrogen, $C_1$-$C_{10}$ alkyl, $C_3$-$C_{10}$ cycloalkyl, $C_1$-$C_3$ haloalkyl, aryl, heteroaryl and heterocyclyl, wherein each of said alkyl, cycloalkyl, aryl, heteroaryl and heterocyclyl is optionally substituted with one to four R$^a$ groups;

$R^e$ is independently, at each occurrence, selected from the group consisting of hydrogen, halogen, $C_1$-$C_{10}$ alkyl, $C_3$-$C_{10}$ cycloalkyl, $C_1$-$C_3$ haloalkyl, hydroxyl, —OR⁷, —CN, —(CH₂)₁R⁷ with 1 being 0, 1, 2 or 3, —NO₂, —NH₂, —NR$^b$R$^c$, —N(R⁷)C(O)R⁷, —C(O)R⁷, —C(O)OR⁷, —C(O)NR$^b$R$^c$, —S(O) R⁷, —S(O)₂R⁷, —S(O)₂NR$^b$R$^c$, aryl, heteroaryl and heterocyclyl, wherein each of said alkyl, cycloalkyl, aryl, heteroaryl and heterocyclyl is optionally substituted with one to four R$^a$ groups;

R⁷ is independently, at each occurrence, selected from the group consisting of hydrogen, $C_1$-$C_{10}$ alkyl, $C_3$-$C_{10}$ cycloalkyl, $C_1$-$C_3$ haloalkyl, aryl, heteroaryl and heterocyclyl, wherein each of said alkyl, cycloalkyl, aryl, heteroaryl and heterocyclyl is optionally substituted with one to four R$^a$ groups;

Z is selected from the group consisting of $C_1$-$C_{10}$ alkyl, $C_3$-$C_{10}$ cycloalkyl, $C_1$-$C_3$ haloalkyl, OR⁷, aryloxy, aryl, heteroaryl, heterocyclyl, and groups of formula Ib shown below, wherein each of said alkyl, cycloalkyl, aryl, heteroaryl, heterocyclyl and groups of formula Ib is optionally substituted with one to four R$^a$ groups;

Formula Ib

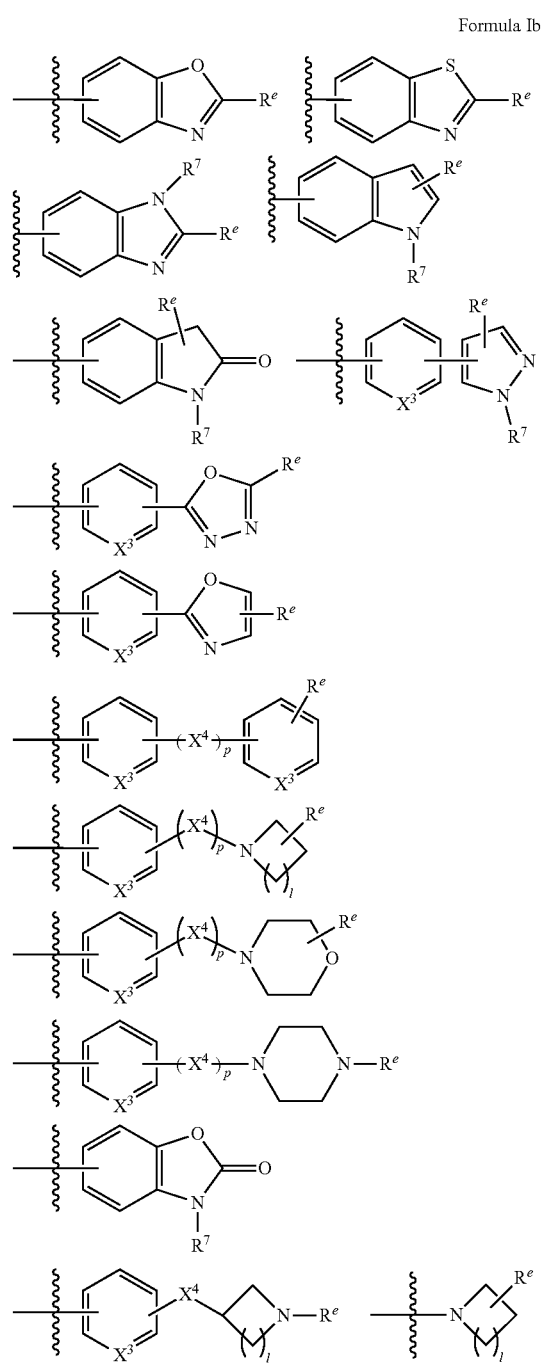

-continued

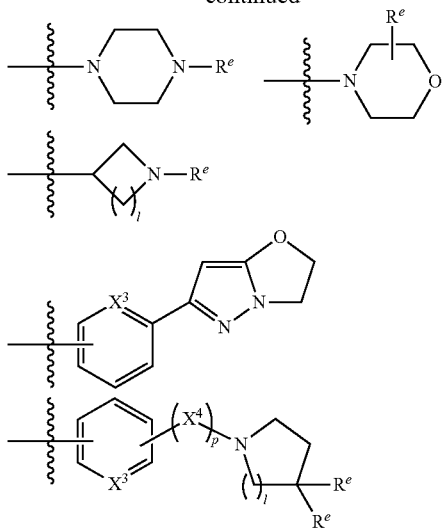

wherein,
p is 0 or 1;
l is 1, 2 or 3;
$X^3$ is, independently at each occurrence, CH or N;
$X^4$ is C=O, $CR^bR^c$, O, S, or $NR^7$;
$R^c$, if denoted in formula Ib, may also occur twice as substituent at the same carbon atom wherein $R^e$ is independently selected at each occurrence;
$R^a$ is independently, at each occurrence, selected from the group consisting of hydrogen, halogen, $C_1$-$C_3$ alkyl, $C_1$-$C_4$ alkoxy, $C_1$-$C_4$ alkoxy substituted with aryl, $C_1$-$C_3$ haloalkyl, hydroxyl, $C_1$-$C_3$ alkylhydroxyl, —CN, $NO_2$, —$NR^bR^c$, —C(O)$NR^bR^c$, —$OR^c$, —C(O) $R^c$, —C(O) $OR^c$, sulfonyl, sulfoxide, $C_3$-$C_{10}$ cycloalkyl, heterocyclyl, heteroaryl and aryl, alkylaryl wherein each of said alkyl, cycloalkyl, aryl, heteroaryl and heterocyclyl is optionally substituted with one to four $C_1$-$C_3$ alkyl, $C_1$-$C_4$ alkoxy, halogen, $C_1$-$C_3$ haloalkyl, hydroxyl, —$NH_2$, wherein such substitution, if present, may occur in such a manner that there is more than one substituent, per carbon atom, wherein such substituents may be the same or different;
$R^b$ and $R^c$ are independently, at each occurrence selected from the group consisting of hydrogen, $C_1$-$C_{10}$ alkyl, $C_3$-$C_{10}$ cycloalkyl, $C_1$-$C_6$ alkyl-O-alkyl, $C_2$-$C_{10}$ alkenyl, $C_1$-$C_4$ alkoxy, $C_1$-$C_3$ alkylhydroxyl, $C_3$-$C_{10}$ cycloalkenyl, $C_2$-$C_{10}$ alkynyl, $C_1$-$C_{10}$ haloalkyl, aryl, alkylaryl, heteroaryl, and heterocyclyl, wherein each of said alkyl, cycloalkyl, aryl, heteroaryl and heterocyclyl is optionally substituted with one to four $C_1$-$C_3$ alkyl, $C_1$-$C_4$ alkoxy, halogen, aryloxy, $C_1$-$C_3$ haloalkyl, hydroxyl, $C_1$-$C_3$ alkylhydroxyl, —CN, —$NO_2$, —$NH_2$, sulfonyl, sulfoxide, $C_3$-$C_{10}$ cycloalkyl, heterocyclyl, aryl, heteroaryl, wherein such substitution, if present, may occur in such a manner that there is more than one substituent per carbon atom, wherein such substituents may be the same or different; or
$R^b$ and $R^c$ are connected to each other to make a four, five or six membered saturated or unsaturated cyclic or heterocyclic ring, or they are connected to make a fused cyclic or heterocyclic ring structure;
$R^d$ is independently, at each occurrence, selected from the group consisting of hydrogen, $C_1$-$C_{10}$ alkyl, $C_3$-$C_{10}$ cycloalkyl, $C_1$-$C_3$ haloalkyl, aryl, heteroaryl and heterocyclyl group, wherein each of said alkyl, cycloalkyl, aryl, heteroaryl and heterocyclyl is optionally substituted with one to four $R^a$ groups;

$R^e$ is independently, at each occurrence, selected from the group consisting of hydrogen, halogen, $C_1$-$C_{10}$ alkyl, $C_3$-$C_{10}$ cycloalkyl, $C_1$-$C_3$ haloalkyl, hydroxyl, —$OR^7$, —CN, —$(CH_2)_1R^7$, with 1 being 0, 1, 2 or 3, —$NO_2$, —$NH_2$, —$NR^bR^c$, —$N(R^7)C(O)R^7$, —$C(O)R^7$, —$C(O)OR^7$, —$C(O)NR^bR^c$, —$S(O) R^7$, —$S(O)_2R^7$, —$S(O)_2NR^bR^c$, aryl, heteroaryl and heterocyclyl, wherein each of said alkyl, cycloalkyl, aryl, heteroaryl and heterocyclyl is optionally substituted with one to four $R^a$ groups;
$R^7$ is independently, at each occurrence, selected from the group consisting of hydrogen, $C_1$-$C_{10}$ alkyl, $C_3$-$C_{10}$ cycloalkyl, $C_1$-$C_3$ haloalkyl, aryl, heteroaryl, and heterocyclyl, wherein each of said alkyl, cycloalkyl, aryl, heteroaryl and heterocyclyl is optionally substituted with one to four $R^a$ groups;

and pharmaceutically acceptable salts thereof.

5. A method of treatment of a bacterial infection comprising the application, to a person in need of such treatment, of a suitable amount of a compound selected from

| Compound No. | Structure |
|---|---|
| 3 | ![structure] |
| 6 | ![structure] |
| 8 | ![structure] |
| 13 | ![structure] |
| 14 | ![structure] |
| 18 | ![structure] |

| Compound No. | Structure |
|---|---|
| 19 | 4-carboxyphenyl amide of thieno[2,3-d]thiazole-5-carboxylic acid, 2-piperidinyl |
| 20 | N-methyl-N-(3,4-difluorophenyl) amide of thieno[2,3-d]thiazole-5-carboxylic acid, 2-piperidinyl |
| 22 | N-(2-(4-methoxyphenyl)ethyl) amide of thieno[2,3-d]thiazole-5-carboxylic acid, 2-piperidinyl |
| 24 | methyl 1-(thieno[2,3-d]thiazole-5-carbonyl)piperidine-4-carboxylate, 2-piperidinyl |
| 25 | N-phenyl amide of thieno[2,3-d]thiazole-5-carboxylic acid, 2-piperidinyl |
| 27 | N-(4-methoxyphenyl) amide of thieno[2,3-d]thiazole-5-carboxylic acid, 2-morpholinyl |
| 28 | (3-amino-1H-pyrazol-1-yl)(2-piperidinyl-thieno[2,3-d]thiazol-5-yl)methanone |
| 29 | N-(4-chlorophenyl) amide of thieno[2,3-d]thiazole-5-carboxylic acid, 2-piperidinyl |

| Compound No. | Structure |
|---|---|
| 32 | N-(4-cyanophenyl) amide of thieno[2,3-d]thiazole-5-carboxylic acid, 2-piperidinyl |
| 35 | N-(4-methoxyphenyl) amide of thieno[2,3-d]thiazole-5-carboxylic acid, 2-piperidinyl |
| 36 | N-(3,4-difluorophenyl) amide of thieno[2,3-d]thiazole-5-carboxylic acid, 2-piperidinyl |
| 38 | N-(4-ethylphenyl) amide of thieno[2,3-d]thiazole-5-carboxylic acid, 2-piperidinyl |
| 39 | N-(biphenyl-4-yl) amide of thieno[2,3-d]thiazole-5-carboxylic acid, 2-piperidinyl |
| 40 | N-(quinolin-6-yl) amide of thieno[2,3-d]thiazole-5-carboxylic acid, 2-piperidinyl |
| 41 | N-(4-trifluoromethylphenyl) amide of thieno[2,3-d]thiazole-5-carboxylic acid, 2-piperidinyl |
| 42 | N-(2-(4-methoxyphenyl)ethyl) amide of thieno[2,3-d]thiazole-5-carboxylic acid, 2-piperidinyl |
| 43 | N-(2-(4-methoxycarbonylphenyl)ethyl) amide of thieno[2,3-d]thiazole-5-carboxylic acid, 2-piperidinyl |

-continued
| Compound No. | Structure |
|---|---|
| 44 | 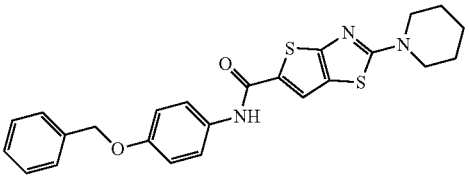 [SMILES: O=C(Nc1ccc(OCc2ccccc2)cc1)c1cc2sc(N3CCCCC3)nc2s1] |
| 45 | 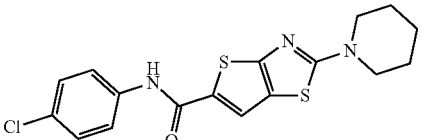 |
| 46 | 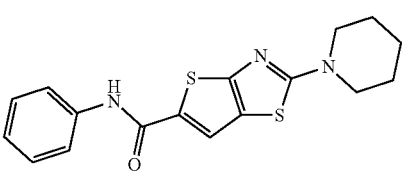 [SMILES: O=C(Nc1ccccc1)c1cc2sc(N3CCCCC3)nc2s1] |
| 47 | 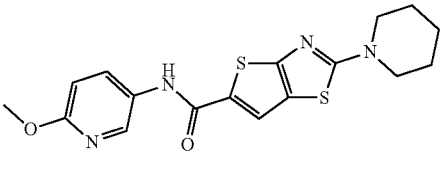 [SMILES: COc1ccc(NC(=O)c2cc3sc(N4CCCCC4)nc3s2)cn1] |
| 48 | 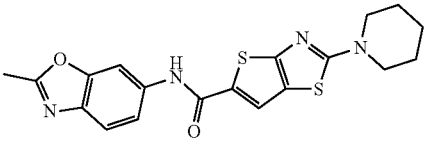 [SMILES: Cc1nc2ccc(NC(=O)c3cc4sc(N5CCCCC5)nc4s3)cc2o1] |
| 49 | 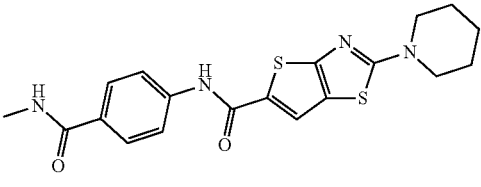 [SMILES: CNC(=O)c1ccc(NC(=O)c2cc3sc(N4CCCCC4)nc3s2)cc1] |
| 50 | 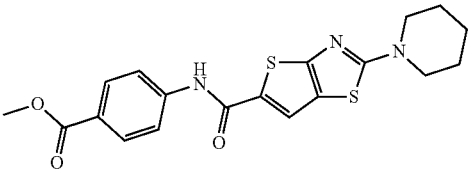 [SMILES: COC(=O)c1ccc(NC(=O)c2cc3sc(N4CCCCC4)nc3s2)cc1] |
| 51 | 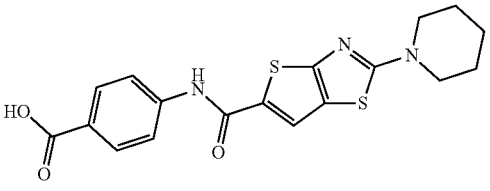 [SMILES: O=C(O)c1ccc(NC(=O)c2cc3sc(N4CCCCC4)nc3s2)cc1] |
-continued
| Compound No. | Structure |
|---|---|
| 52 | 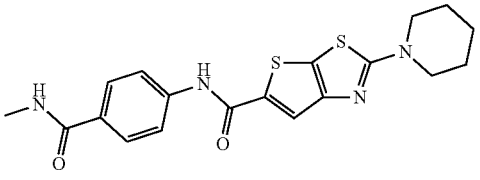 [SMILES: CNC(=O)c1ccc(NC(=O)c2cc3nc(N4CCCCC4)sc3s2)cc1] |
| 53 | 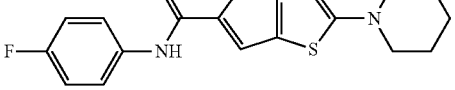 |
| 54 | 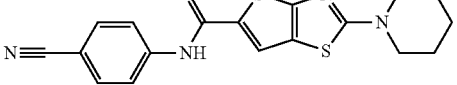 |
| 55 | 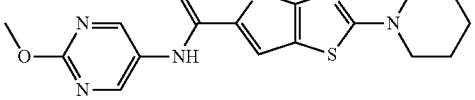 |
| 56 | 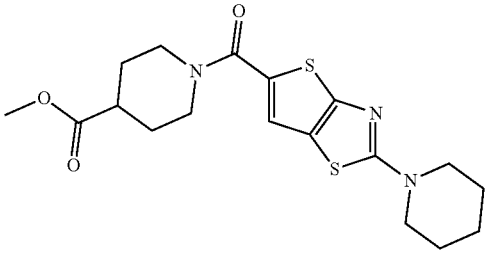 [SMILES: COC(=O)C1CCN(C(=O)c2cc3sc(N4CCCCC4)nc3s2)CC1] |
| 57 | 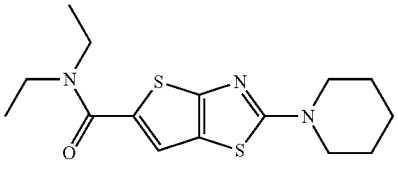 [SMILES: CCN(CC)C(=O)c1cc2sc(N3CCCCC3)nc2s1] |
| 58 | 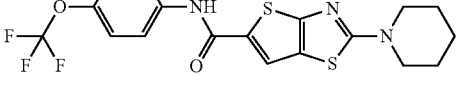 |
| 60 | 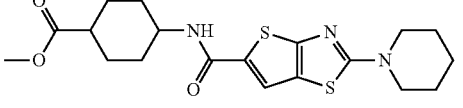 |
| 61 | 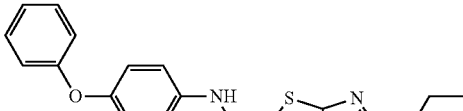 |
| 62 | 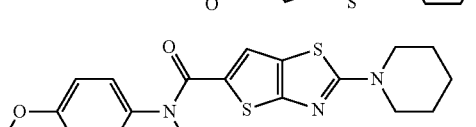 |

-continued
| Compound No. | Structure |
|---|---|
| 63 | 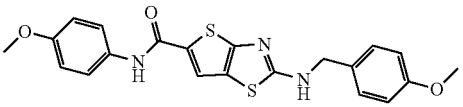 |
| 64 | 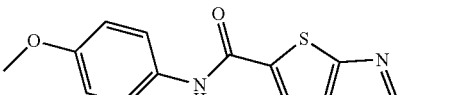 |
| 65 | 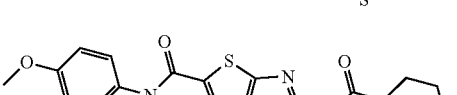 |
| 66 | 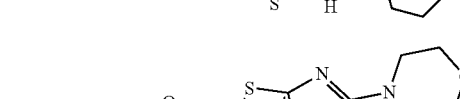 |
| 67 | 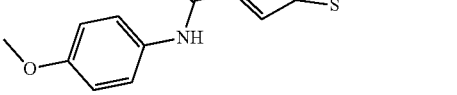 |
| 68 | 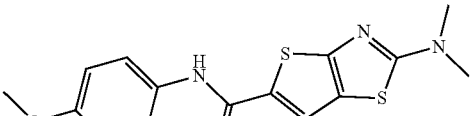 |
| 72 | 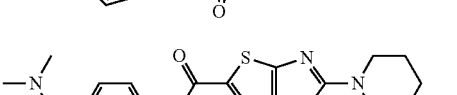 |
| 74 | 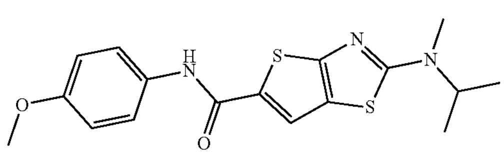 [SMILES: COc1ccc(NC(=O)c2cc3sc(N(C)C(C)C)nc3s2)cc1] |
| 75 | 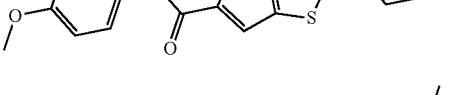 |
| 76 | 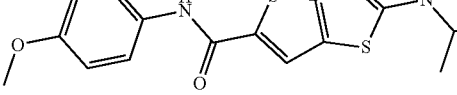 |
| 77 | 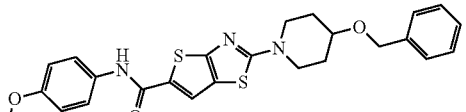 |
| 78 |  |
| 79 | 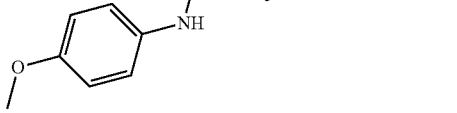 |
| 80 | 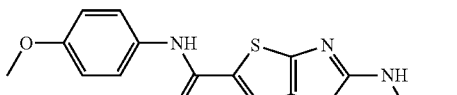 |
| 82 |  |
| 83 | 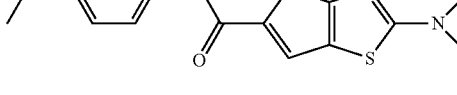 |
| 84 | 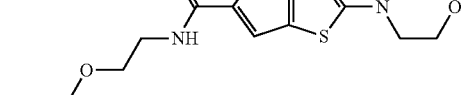 |
| 85 |  |
| 86 | 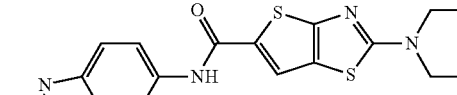 |

-continued

| Compound No. | Structure |
|---|---|
| 87 | 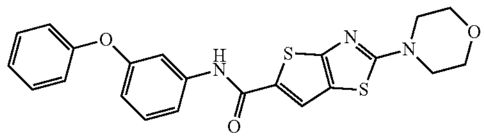 [SMILES: O=C(Nc1cccc(Oc2ccccc2)c1)c1cc2sc(N3CCOCC3)nc2s1] |
| 90 | 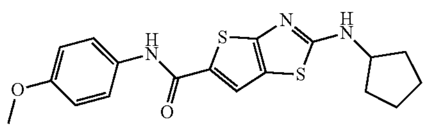 [SMILES: COc1ccc(NC(=O)c2cc3sc(NC4CCCC4)nc3s2)cc1] |
| 91 | 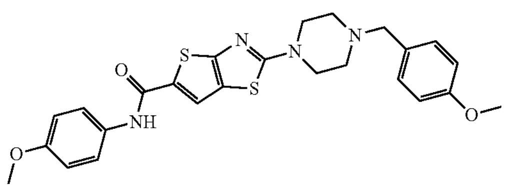 |
| 92 | 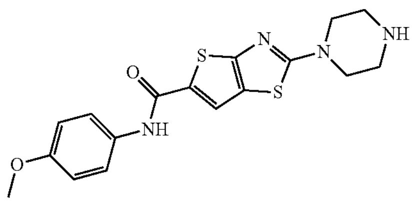 [SMILES: COc1ccc(NC(=O)c2cc3sc(N4CCNCC4)nc3s2)cc1] |
| 95 | 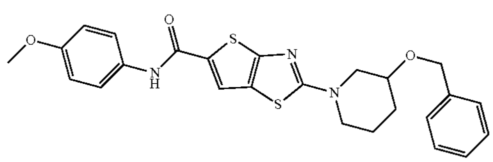 [SMILES: COc1ccc(NC(=O)c2cc3sc(N4CCCC(OCc5ccccc5)C4)nc3s2)cc1] |
| 96 | 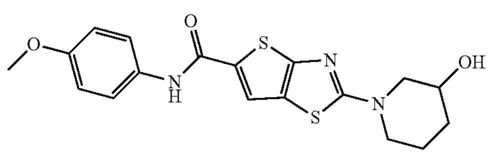 [SMILES: COc1ccc(NC(=O)c2cc3sc(N4CCCC(O)C4)nc3s2)cc1] |
| 97 | 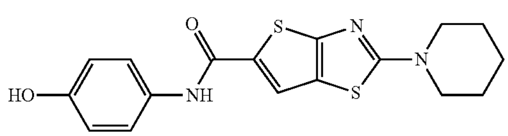 [SMILES: O=C(Nc1ccc(O)cc1)c1cc2sc(N3CCCCC3)nc2s1] |
| 99 | 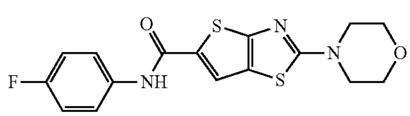 [SMILES: O=C(Nc1ccc(F)cc1)c1cc2sc(N3CCOCC3)nc2s1] |
| 100 | 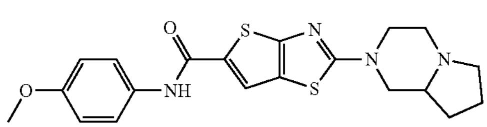 [SMILES: COc1ccc(NC(=O)c2cc3sc(N4CCN5CCCC5C4)nc3s2)cc1] |

-continued

| Compound No. | Structure |
|---|---|
| 101 | 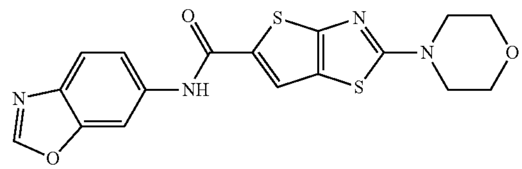 [SMILES: O=C(Nc1ccc2ncoc2c1)c1cc2sc(N3CCOCC3)nc2s1] |
| 102 | 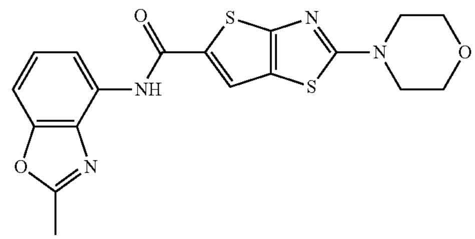 [SMILES: Cc1nc2c(NC(=O)c3cc4sc(N5CCOCC5)nc4s3)cccc2o1] |
| 103 | 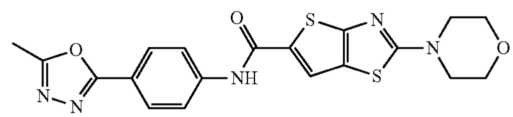 [SMILES: Cc1nnc(-c2ccc(NC(=O)c3cc4sc(N5CCOCC5)nc4s3)cc2)o1] |
| 104 | 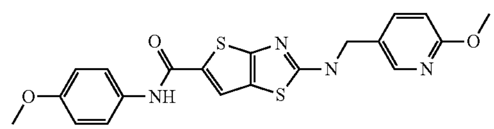 |
| 105 | 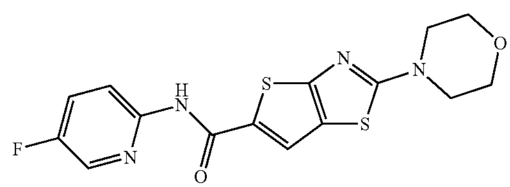 [SMILES: O=C(Nc1ccc(F)cn1)c1cc2sc(N3CCOCC3)nc2s1] |
| 106 | 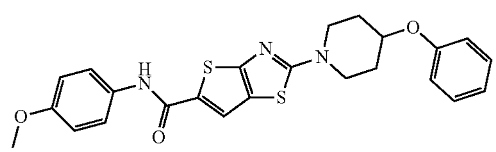 [SMILES: COc1ccc(NC(=O)c2cc3sc(N4CCC(Oc5ccccc5)CC4)nc3s2)cc1] |
| 107 | 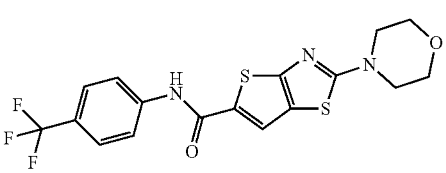 [SMILES: O=C(Nc1ccc(C(F)(F)F)cc1)c1cc2sc(N3CCOCC3)nc2s1] |
| 108 | 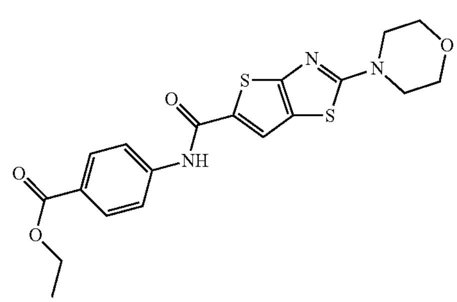 [SMILES: CCOC(=O)c1ccc(NC(=O)c2cc3sc(N4CCOCC4)nc3s2)cc1] |

-continued

| Compound No. | Structure |
|---|---|
| 110 | 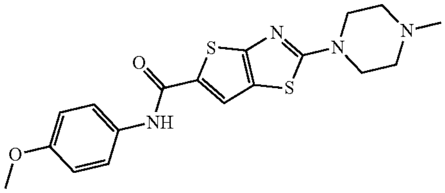 |
| 111 | 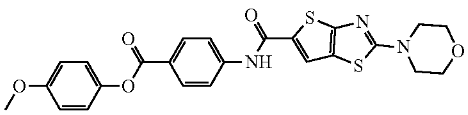 [SMILES: COc1ccc(OC(=O)c2ccc(NC(=O)c3cc4sc(N5CCOCC5)nc4s3)cc2)cc1] |
| 112 | 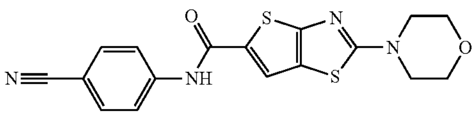 [SMILES: N#Cc1ccc(NC(=O)c2cc3sc(N4CCOCC4)nc3s2)cc1] |
| 114 | 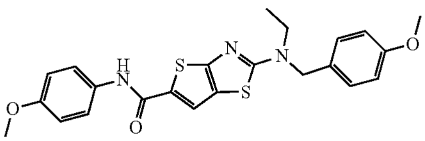 |
| 115 | 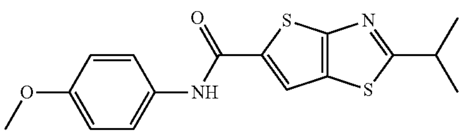 |
| 116 | 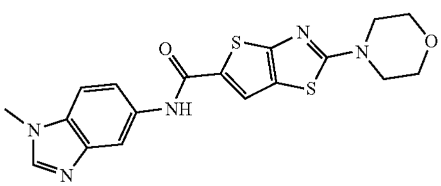 [SMILES: Cn1cnc2cc(NC(=O)c3cc4sc(N5CCOCC5)nc4s3)ccc21] |
| 118 | 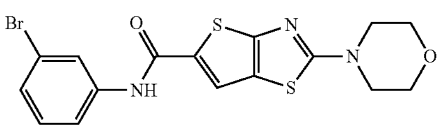 [SMILES: O=C(Nc1cccc(Br)c1)c1cc2sc(N3CCOCC3)nc2s1] |
| 119 | 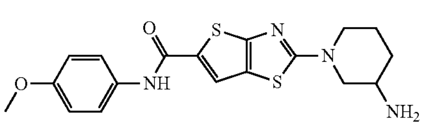 |
| 120 | 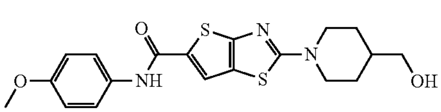 [SMILES: COc1ccc(NC(=O)c2cc3sc(N4CCC(CO)CC4)nc3s2)cc1] |
| 121 | 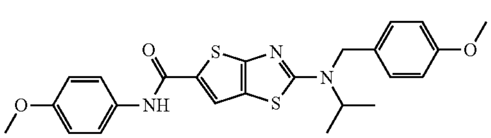 |

-continued

| Compound No. | Structure |
|---|---|
| 122 | 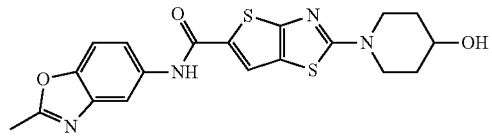 [SMILES: Cc1nc2cc(NC(=O)c3cc4sc(N5CCC(O)CC5)nc4s3)ccc2o1] |
| 124 | 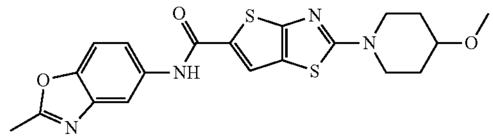 |
| 125 | 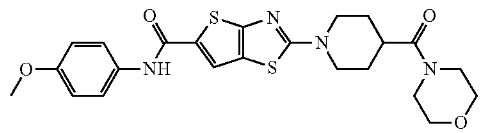 [SMILES: COc1ccc(NC(=O)c2cc3sc(N4CCC(C(=O)N5CCOCC5)CC4)nc3s2)cc1] |
| 126 | 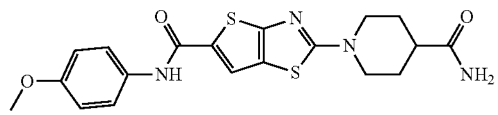 [SMILES: COc1ccc(NC(=O)c2cc3sc(N4CCC(C(N)=O)CC4)nc3s2)cc1] |
| 127 | 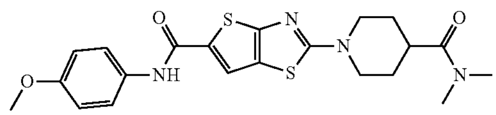 |
| 129 | 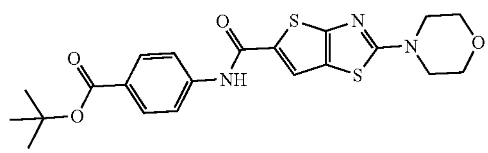 [SMILES: CC(C)(C)OC(=O)c1ccc(NC(=O)c2cc3sc(N4CCOCC4)nc3s2)cc1] |
| 130 | 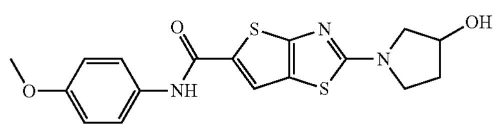 [SMILES: COc1ccc(NC(=O)c2cc3sc(N4CCC(O)C4)nc3s2)cc1] |
| 132 | 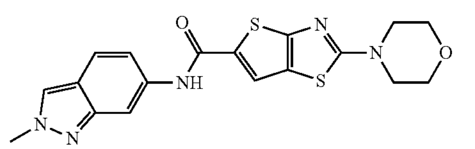 [SMILES: Cn1cc2ccc(NC(=O)c3cc4sc(N5CCOCC5)nc4s3)cc2n1] |
| 133 | 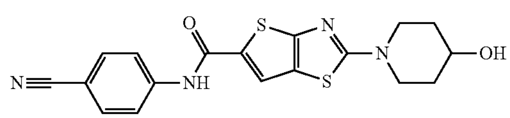 [SMILES: N#Cc1ccc(NC(=O)c2cc3sc(N4CCC(O)CC4)nc3s2)cc1] |
| 134 | 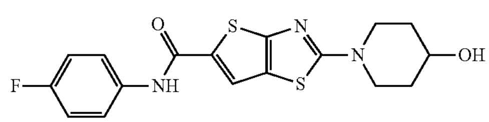 [SMILES: O=C(Nc1ccc(F)cc1)c1cc2sc(N3CCC(O)CC3)nc2s1] |
| 135 | 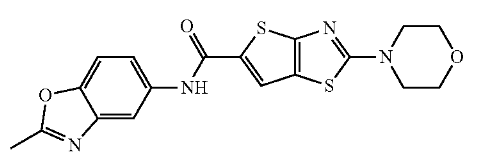 [SMILES: Cc1nc2cc(NC(=O)c3cc4sc(N5CCOCC5)nc4s3)ccc2o1] |

-continued

| Compound No. | Structure |
|---|---|
| 136 | 4-fluorophenyl thieno[2,3-d]thiazole-5-carboxamide with 2-(4-(N,N-dimethylcarbamoyl)piperidin-1-yl) |
| 137 | 6-fluoropyridin-3-yl thieno[2,3-d]thiazole-5-carboxamide with 2-(4-(N,N-dimethylcarbamoyl)piperidin-1-yl) |
| 138 | 2-methylbenzo[d]oxazol-5-yl thieno[2,3-d]thiazole-5-carboxamide with 2-(4-(N,N-dimethylcarbamoyl)piperidin-1-yl) |
| 139 | 4-fluorophenyl thieno[2,3-d]thiazole-5-carboxamide with 2-(piperazin-1-yl) |
| 140 | 2-methylbenzo[d]oxazol-5-yl thieno[2,3-d]thiazole-5-carboxamide with 2-(piperazin-1-yl) |
| 142 | 4-fluorophenyl thieno[2,3-d]thiazole-5-carboxamide with 2-(4-(hydroxymethyl)piperidin-1-yl) |
| 143 | 6-fluoropyridin-3-yl thieno[2,3-d]thiazole-5-carboxamide with 2-(4-(hydroxymethyl)piperidin-1-yl) |
| 144 | 2-methylbenzo[d]oxazol-5-yl thieno[2,3-d]thiazole-5-carboxamide with 2-(4-(hydroxymethyl)piperidin-1-yl) |
| 145 | 4-(1-methyl-1H-pyrazol-3-yl)phenyl thieno[2,3-d]thiazole-5-carboxamide with 2-morpholino |
| 146 | 4-(4-chlorophenoxy)phenyl thieno[2,3-d]thiazole-5-carboxamide with 2-morpholino |
| 149 | 4-methoxyphenyl thieno[2,3-d]thiazole-5-carboxamide with 2-(4-carboxypiperidin-1-yl) |

-continued

| Compound No. | Structure |
|---|---|
| 151 | 2-methylbenzo[d]oxazol-5-yl thieno[2,3-d]thiazole-5-carboxamide with 2-(3-ethylmorpholino) |
| 152 | 2-methylbenzo[d]oxazol-5-yl thieno[2,3-d]thiazole-5-carboxamide with 2-(2-(hydroxymethyl)morpholino) |
| 153 | 2-methylbenzo[d]oxazol-5-yl thieno[2,3-d]thiazole-5-carboxamide with 2-(2-ethylmorpholino) |
| 154 | 4-(5-methyloxazol-2-yl)phenyl thieno[2,3-d]thiazole-5-carboxamide with 2-morpholino |
| 155 | 4-(1-(tetrahydro-2H-pyran-2-yl)-1H-pyrazol-3-yl)phenyl thieno[2,3-d]thiazole-5-carboxamide with 2-morpholino |
| 156 | 4-(1H-pyrazol-3-yl)phenyl thieno[2,3-d]thiazole-5-carboxamide with 2-morpholino |
| 158 | 4-(4-fluoro-1-(4-methoxybenzyl)-1H-pyrazol-3-yl)phenyl thieno[2,3-d]thiazole-5-carboxamide with 2-morpholino |
| 159 | 4-(4-fluoro-1H-pyrazol-3-yl)phenyl thieno[2,3-d]thiazole-5-carboxamide with 2-morpholino, trifluoroacetic acid salt |
| 160 | 5-phenyl-1H-pyrazol-3-yl thieno[2,3-d]thiazole-5-carboxamide with 2-morpholino |
| 161 | 4-(6-methylpyridin-3-yl)phenyl thieno[2,3-d]thiazole-5-carboxamide with 2-morpholino |

-continued
| Compound No. | Structure |
|---|---|
| 162 | 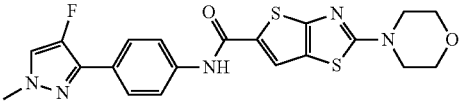 [SMILES: Cn1cc(F)c(-c2ccc(NC(=O)c3cc4sc(N5CCOCC5)nc4s3)cc2)n1] |
| 165 | 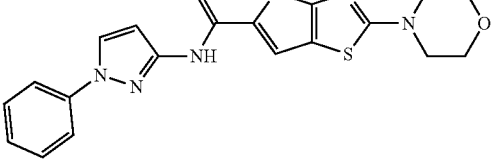 |
| 167 | 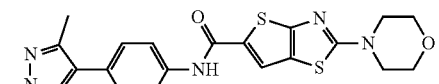 |
| 168 | 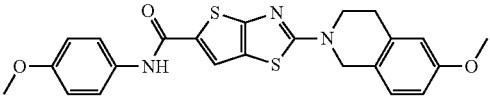 |
| 169 | 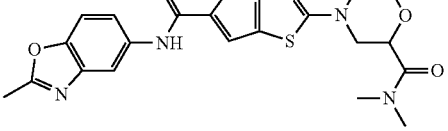 |
| 171 | 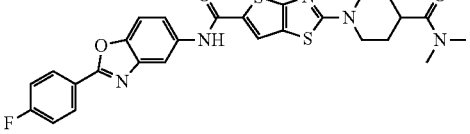 |
| 174 | 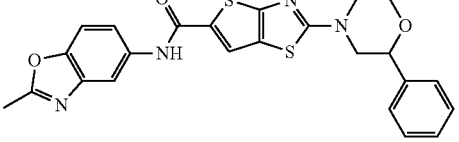 |
| 177 | 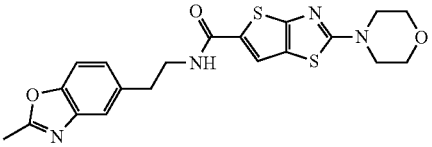 [SMILES: Cc1nc2cc(CCNC(=O)c3cc4sc(N5CCOCC5)nc4s3)ccc2o1] |
| 178 | 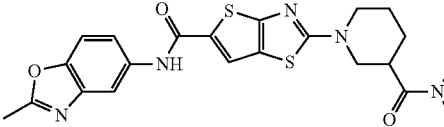 |
| 180 | 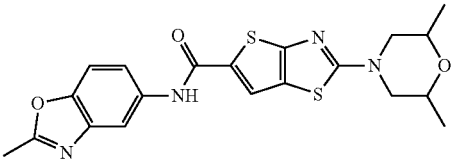 |
-continued
| Compound No. | Structure |
|---|---|
| 183 | 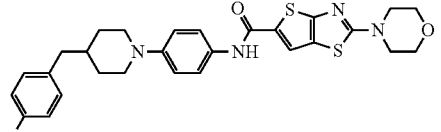 |
| 186 | 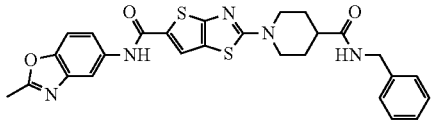 [SMILES: Cc1nc2cc(NC(=O)c3cc4sc(N5CCC(C(=O)NCc6ccccc6)CC5)nc4s3)ccc2o1] |
| 188 | 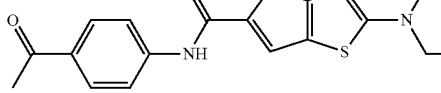 |
| 192 | 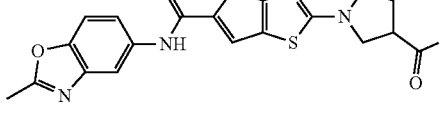 |
| 193 | 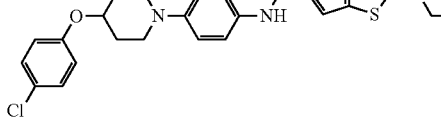 |
| 194 | 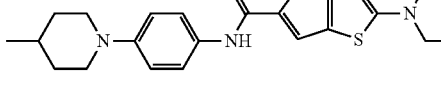 |
| 195 | 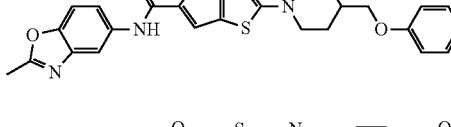 |
| 196 | 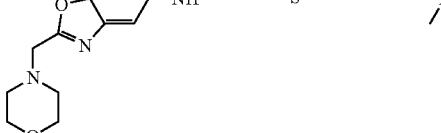 |
| 197 | 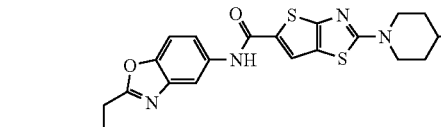 |

| Compound No. | Structure |
|---|---|
| 199 |  |
| 201 | 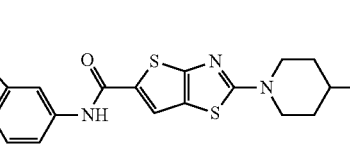 |
| 202 | 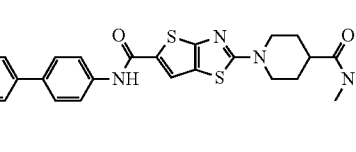 |
| 203 | 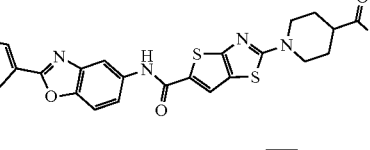 |
| 204 | 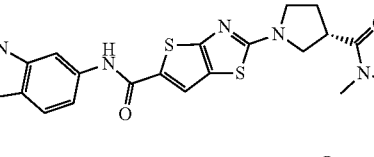 |
| 206 | 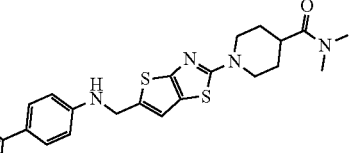 |
| 207 | 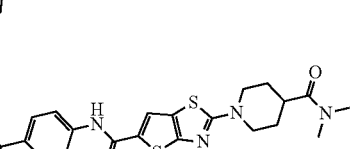 |
| 208 | 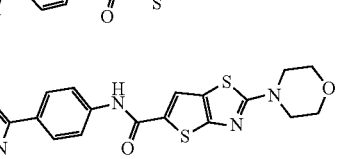 HCl |
| 209 | 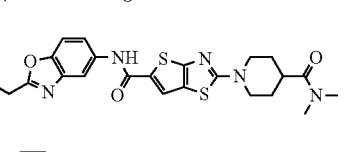 |
| 211 | 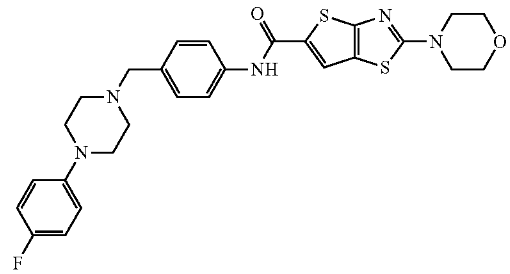 [SMILES: O=C(Nc1ccc(CN2CCN(c3ccc(F)cc3)CC2)cc1)c1cc2sc(N3CCOCC3)nc2s1] |
| 212 | 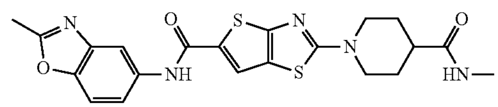 |
| 213 | 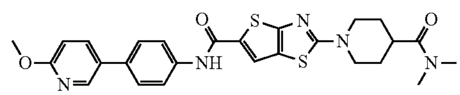 |
| 214 | 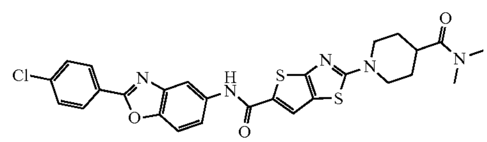 [SMILES: CN(C)C(=O)C1CCN(c2nc3sc(C(=O)Nc4ccc5oc(-c6ccc(Cl)cc6)nc5c4)cc3s2)CC1] |
| 215 | 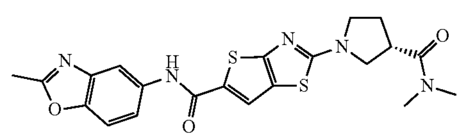 |
| 216 | 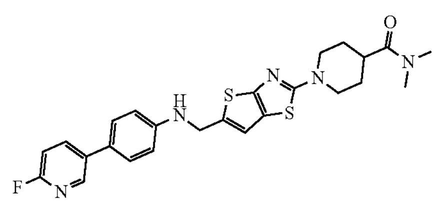 [SMILES: CN(C)C(=O)C1CCN(c2nc3sc(CNc4ccc(-c5ccc(F)nc5)cc4)cc3s2)CC1] |
| 217 | 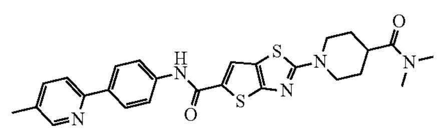 |
| 218 | 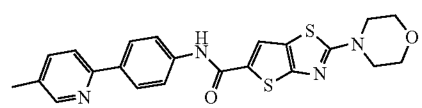 [SMILES: Cc1ccc(-c2ccc(NC(=O)c3cc4sc(N5CCOCC5)nc4s3)cc2)nc1] |
| 219 | 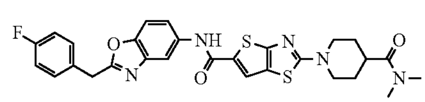 [SMILES: CN(C)C(=O)C1CCN(c2nc3sc(C(=O)Nc4ccc5oc(Cc6ccc(F)cc6)nc5c4)cc3s2)CC1] |
| 220 | 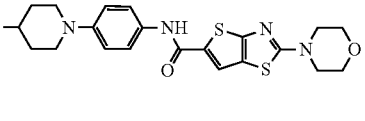 |

-continued

| Compound No. | Structure |
|---|---|
| 221 | (structure) |
| 222 | (structure) |
| 223 | (structure) |
| 224 | (structure) |
| 225 | (structure) |
| 226 | (structure) |
| 227 | (structure) |
| 228 | (structure) |

-continued

| Compound No. | Structure |
|---|---|
| 229 | (structure) |
| 231 | (structure) |
| 232 | (structure) |
| 233 | (structure) |
| 234 | (structure) |
| 235 | (structure) |
| 236 | (structure) |
| 237 | (structure) |
| 238 | (structure) |

-continued

| Compound No. | Structure |
|---|---|
| 239 | (structure) |
| 240 | (structure) |
| 241 | (structure) |
| 242 | (structure) |
| 243 | (structure) |
| 244 | (structure) |
| 245 | (structure) |
| 246 | (structure) |
| 247 | (structure) |
| 248 | (structure) |
| 249 | (structure) |

-continued

| Compound No. | Structure |
|---|---|
| 250 | (structure) |
| 251 | (structure) |
| 252 | (structure) |
| 253 | (structure) |
| 254 | (structure) |
| 256 | (structure) |
| 258 | (structure) HCl |
| 259 | (structure) HCl |
| 260 | (structure) |
| 261 | (structure) |
| 262 | (structure) |

-continued

| Compound No. | Structure |
|---|---|
| 264 | 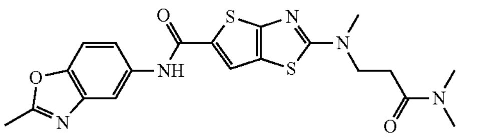 |
| 265 | 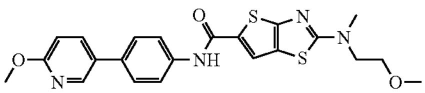 |
| 266 | 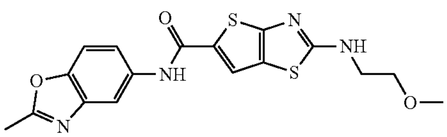 |
| 267 | 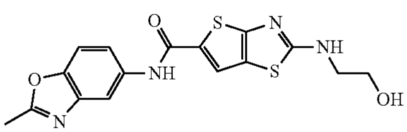 [SMILES: Cc1nc2cc(NC(=O)c3cc4sc(NCCO)nc4s3)ccc2o1] |
| 268 | 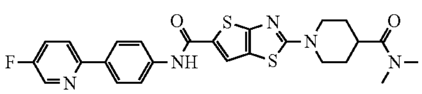 [SMILES: CN(C)C(=O)C1CCN(c2nc3sc(C(=O)Nc4ccc(-c5ccc(F)cn5)cc4)cc3s2)CC1] |
| 271 | 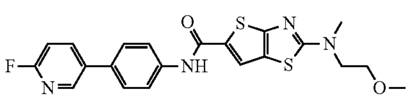 [SMILES: COCCN(C)c1nc2sc(C(=O)Nc3ccc(-c4ccc(F)nc4)cc3)cc2s1] |
| 272 | 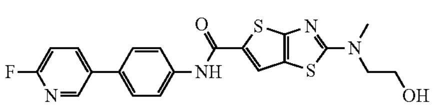 |
| 273 | 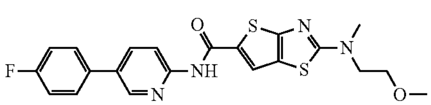 [SMILES: COCCN(C)c1nc2sc(C(=O)Nc3ccc(-c4ccc(F)cc4)cn3)cc2s1] |
| 274 | 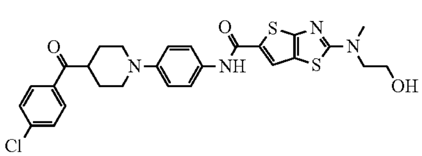 [SMILES: CN(CCO)c1nc2sc(C(=O)Nc3ccc(N4CCC(C(=O)c5ccc(Cl)cc5)CC4)cc3)cc2s1] |
| 275 | 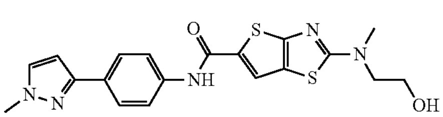 [SMILES: CN(CCO)c1nc2sc(C(=O)Nc3ccc(-c4ccn(C)n4)cc3)cc2s1] |
| 276 | 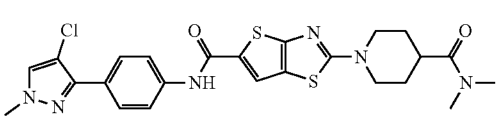 |

-continued

| Compound No. | Structure |
|---|---|
| 277 | 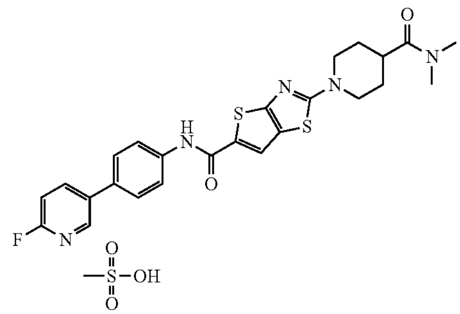 |
| 278 | 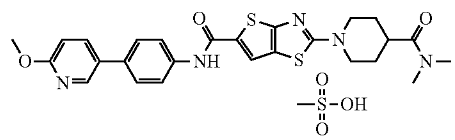 |
| 279 | 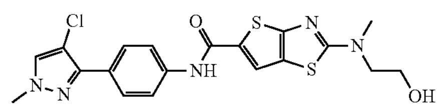 |
| 281 | 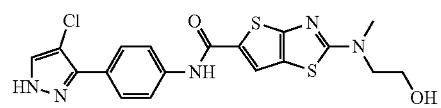 [SMILES: CN(CCO)c1nc2sc(C(=O)Nc3ccc(-c4n[nH]cc4Cl)cc3)cc2s1] |
| 282 | 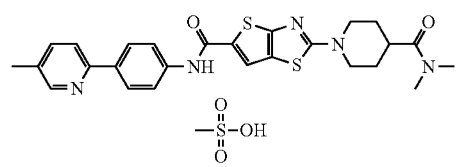 |
| 283 | 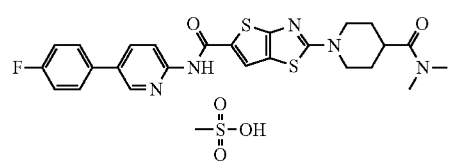 |
| 284 | 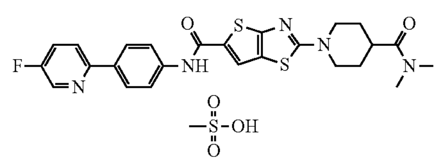 |
| 285 | 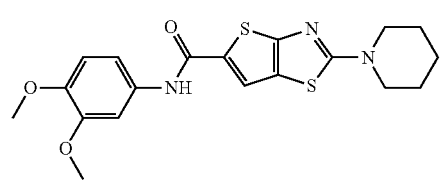 [SMILES: COc1ccc(NC(=O)c2cc3sc(N4CCCCC4)nc3s2)cc1OC] |
| 287 | 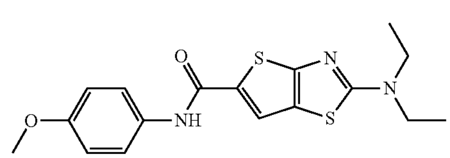 [SMILES: CCN(CC)c1nc2sc(C(=O)Nc3ccc(OC)cc3)cc2s1] |

-continued
| Compound No. | Structure |
|---|---|
| 288 | 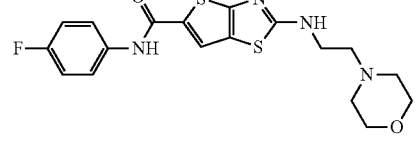 |
| 289 | 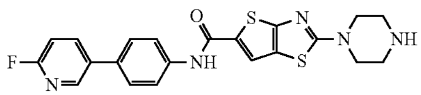 |
| 290 | 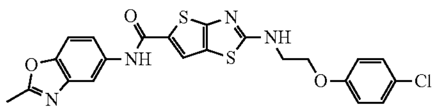 [SMILES: Cc1nc2cc(NC(=O)c3cc4sc(NCCOc5ccc(Cl)cc5)nc4s3)ccc2o1] |
| 291 | 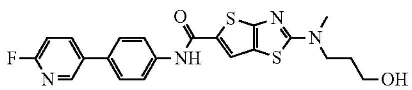 |
| 292 | 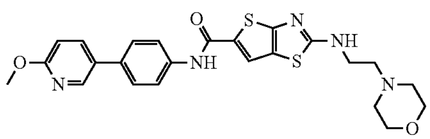 [SMILES: COc1ccc(-c2ccc(NC(=O)c3cc4sc(NCCN5CCOCC5)nc4s3)cc2)cn1] |
| 293 | 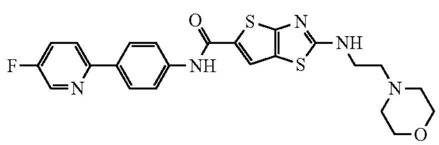 |
| 294 | 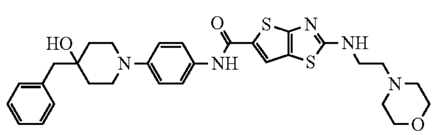 [SMILES: O=C(Nc1ccc(N2CCC(O)(Cc3ccccc3)CC2)cc1)c1cc2sc(NCCN3CCOCC3)nc2s1] |
| 296 | 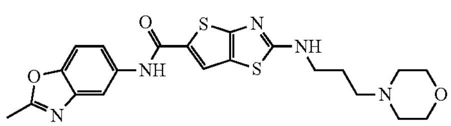 [SMILES: Cc1nc2cc(NC(=O)c3cc4sc(NCCCN5CCOCC5)nc4s3)ccc2o1] |
| 297 | 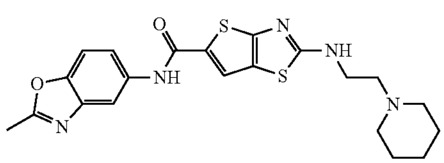 [SMILES: Cc1nc2cc(NC(=O)c3cc4sc(NCCN5CCCCC5)nc4s3)ccc2o1] |
| 298 | 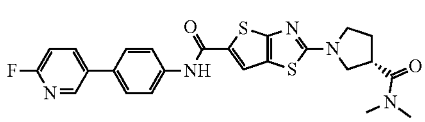 [SMILES: CN(C)C(=O)[C@H]1CCN(c2nc3sc(C(=O)Nc4ccc(-c5ccc(F)nc5)cc4)cc3s2)C1] |
| 299 | 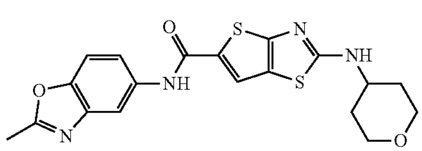 [SMILES: Cc1nc2cc(NC(=O)c3cc4sc(NC5CCOCC5)nc4s3)ccc2o1] |
| 301 | 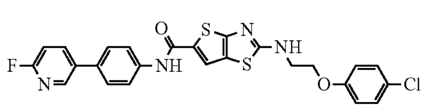 [SMILES: O=C(Nc1ccc(-c2ccc(F)nc2)cc1)c1cc2sc(NCCOc3ccc(Cl)cc3)nc2s1] |
-continued
| Compound No. | Structure |
|---|---|
| 302 | 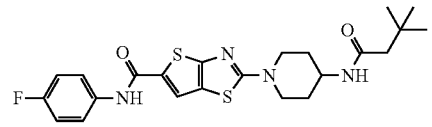 |
| 304 | 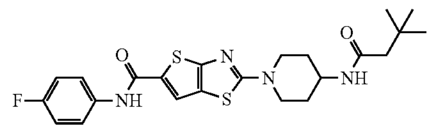 [SMILES: CC(C)(C)CC(=O)NC1CCN(c2nc3sc(C(=O)Nc4ccc(F)cc4)cc3s2)CC1] |
| 305 | 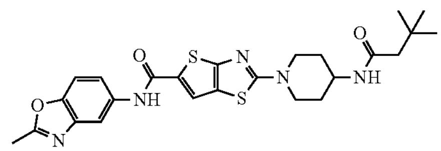 [SMILES: Cc1nc2cc(NC(=O)c3cc4sc(N5CCC(NC(=O)CC(C)(C)C)CC5)nc4s3)ccc2o1] |
| 306 | 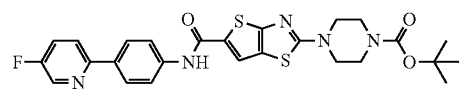 |
| 307 | 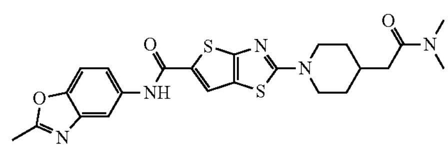 |
| 308 | 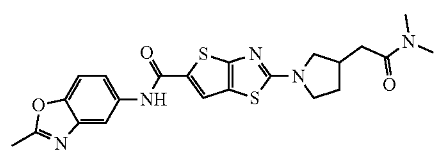 |
| 309 | 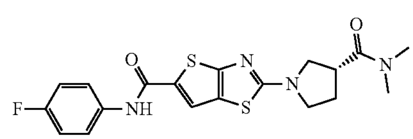 [SMILES: CN(C)C(=O)[C@@H]1CCN(c2nc3sc(C(=O)Nc4ccc(F)cc4)cc3s2)C1] |
| 311 | 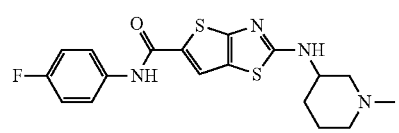 [SMILES: CN1CCCC(Nc2nc3sc(C(=O)Nc4ccc(F)cc4)cc3s2)C1] |
| 313 | 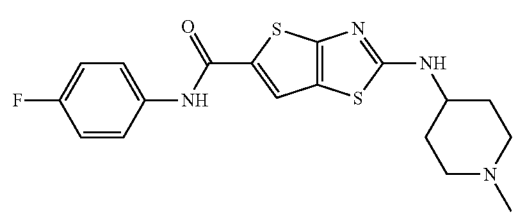 [SMILES: CN1CCC(Nc2nc3sc(C(=O)Nc4ccc(F)cc4)cc3s2)CC1] |

-continued

| Compound No. | Structure |
|---|---|
| 314 | 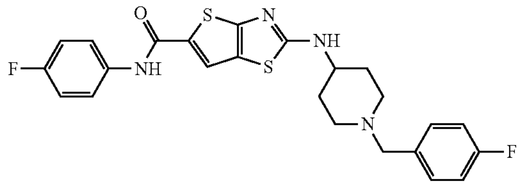 [SMILES: O=C(Nc1ccc(F)cc1)c1cc2sc(NC3CCN(Cc4ccc(F)cc4)CC3)nc2s1] |
| 315 | 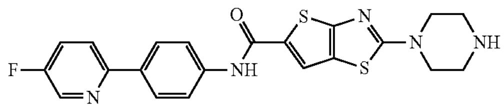 [SMILES: O=C(Nc1ccc(-c2ccc(F)cn2)cc1)c1cc2sc(N3CCNCC3)nc2s1] |
| 316 | 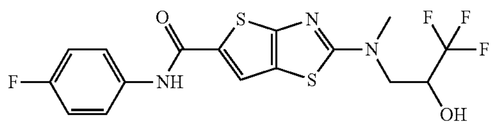 [SMILES: CN(CC(O)C(F)(F)F)c1nc2sc(C(=O)Nc3ccc(F)cc3)cc2s1] |
| 317 | 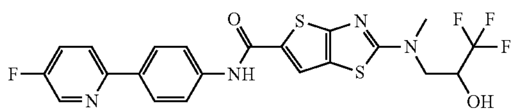 |
| 318 | 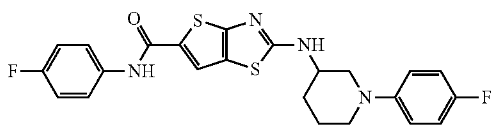 [SMILES: O=C(Nc1ccc(F)cc1)c1cc2sc(NC3CCCN(c4ccc(F)cc4)C3)nc2s1] |
| 319 | 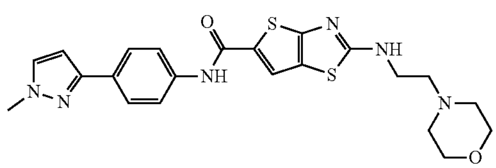 [SMILES: Cn1ccc(-c2ccc(NC(=O)c3cc4sc(NCCN5CCOCC5)nc4s3)cc2)n1] |
| 320 | 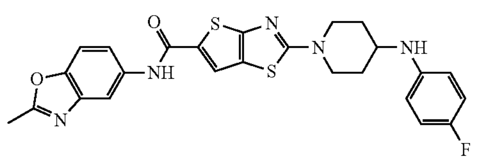 |
| 321 | 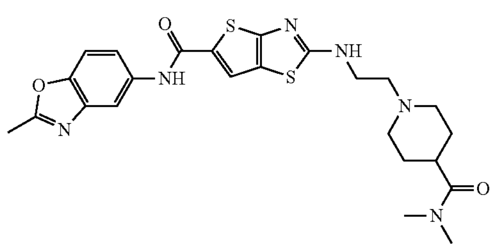 [SMILES: Cc1nc2cc(NC(=O)c3cc4sc(NCCN5CCC(C(=O)N(C)C)CC5)nc4s3)ccc2o1] |
| 322 | 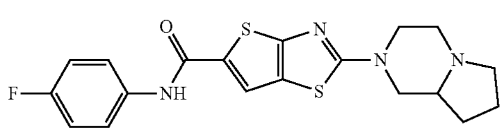 [SMILES: O=C(Nc1ccc(F)cc1)c1cc2sc(N3CCN4CCCC4C3)nc2s1] |
| 323 | 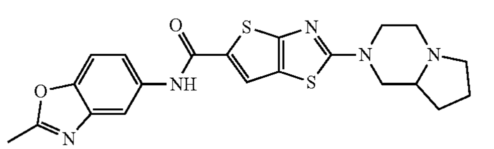 [SMILES: Cc1nc2cc(NC(=O)c3cc4sc(N5CCN6CCCC6C5)nc4s3)ccc2o1] |

-continued

| Compound No. | Structure |
|---|---|
| 324 | 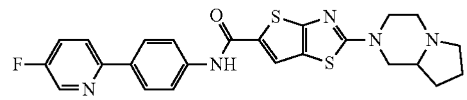 [SMILES: O=C(Nc1ccc(-c2ccc(F)cn2)cc1)c1cc2sc(N3CCN4CCCC4C3)nc2s1] |
| 325 | 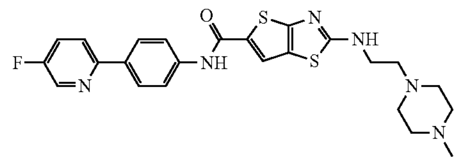 [SMILES: CN1CCN(CCNc2nc3sc(C(=O)Nc4ccc(-c5ccc(F)cn5)cc4)cc3s2)CC1] |
| 327 | 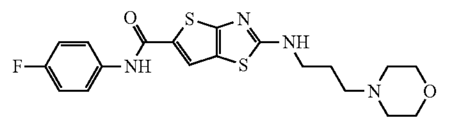 [SMILES: O=C(Nc1ccc(F)cc1)c1cc2sc(NCCCN3CCOCC3)nc2s1] |
| 328 | 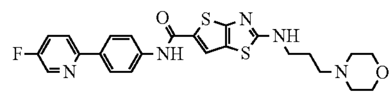 [SMILES: O=C(Nc1ccc(-c2ccc(F)cn2)cc1)c1cc2sc(NCCCN3CCOCC3)nc2s1] |
| 329 | 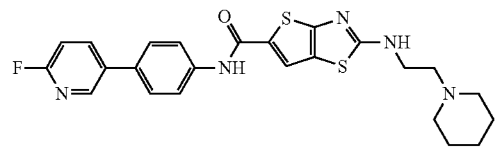 [SMILES: O=C(Nc1ccc(-c2ccc(F)nc2)cc1)c1cc2sc(NCCN3CCCCC3)nc2s1] |
| 330 | 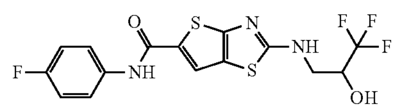 [SMILES: O=C(Nc1ccc(F)cc1)c1cc2sc(NCC(O)C(F)(F)F)nc2s1] |
| 331 | 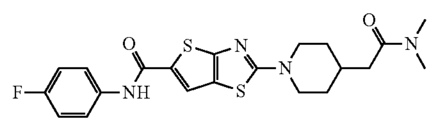 [SMILES: CN(C)C(=O)CC1CCN(c2nc3sc(C(=O)Nc4ccc(F)cc4)cc3s2)CC1] |
| 332 | 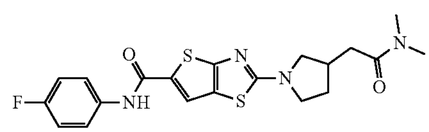 [SMILES: CN(C)C(=O)CC1CCN(c2nc3sc(C(=O)Nc4ccc(F)cc4)cc3s2)C1] |
| 333 | 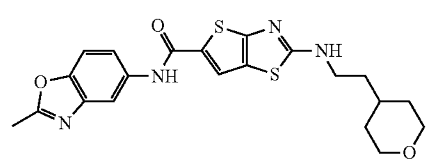 [SMILES: Cc1nc2cc(NC(=O)c3cc4sc(NCCC5CCOCC5)nc4s3)ccc2o1] |
| 334 | 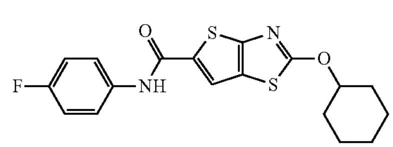 [SMILES: O=C(Nc1ccc(F)cc1)c1cc2sc(OC3CCCCC3)nc2s1] |
| 335 | 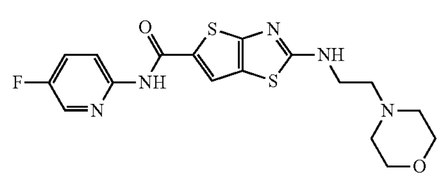 [SMILES: O=C(Nc1ccc(F)cn1)c1cc2sc(NCCN3CCOCC3)nc2s1] |

TABLE -continued

| Compound No. | Structure |
|---|---|
| 336 | 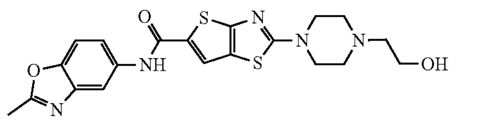 [SMILES: Cc1nc2cc(NC(=O)c3cc4sc(N5CCN(CCO)CC5)nc4s3)ccc2o1] |
| 337 | 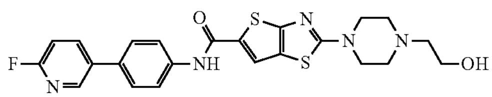 |
| 338 | 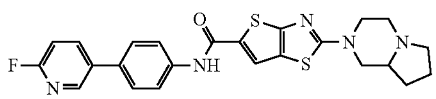 |
| 339 | 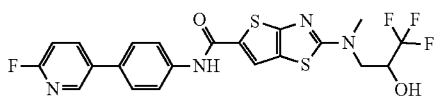 [SMILES: CN(CC(O)C(F)(F)F)c1nc2sc(C(=O)Nc3ccc(-c4ccc(F)nc4)cc3)cc2s1] |
| 340 | 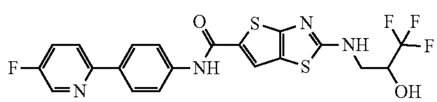 [SMILES: O=C(Nc1ccc(-c2ccc(F)cn2)cc1)c1cc2sc(NCC(O)C(F)(F)F)nc2s1] |
| 341 | 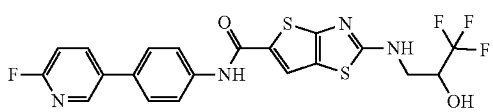 [SMILES: O=C(Nc1ccc(-c2ccc(F)nc2)cc1)c1cc2sc(NCC(O)C(F)(F)F)nc2s1] |
| 342 | 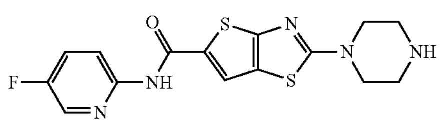 [SMILES: O=C(Nc1ccc(F)cn1)c1cc2sc(N3CCNCC3)nc2s1] |
| 343 | 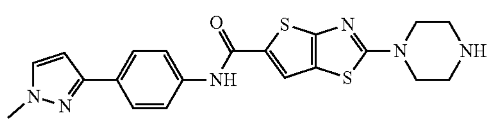 [SMILES: Cn1ccc(-c2ccc(NC(=O)c3cc4sc(N5CCNCC5)nc4s3)cc2)n1] |
| 344 | 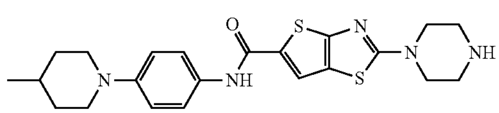 [SMILES: CC1CCN(c2ccc(NC(=O)c3cc4sc(N5CCNCC5)nc4s3)cc2)CC1] |
| 345 | 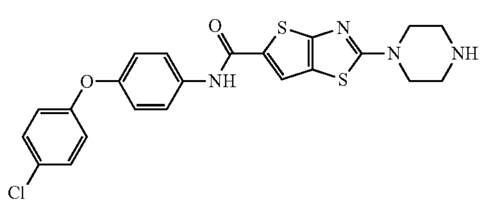 [SMILES: O=C(Nc1ccc(Oc2ccc(Cl)cc2)cc1)c1cc2sc(N3CCNCC3)nc2s1] |
| 346 | 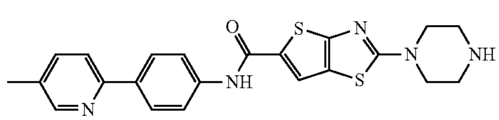 [SMILES: Cc1ccc(-c2ccc(NC(=O)c3cc4sc(N5CCNCC5)nc4s3)cc2)nc1] |
| 348 | 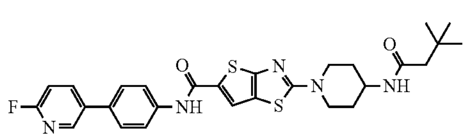 [SMILES: CC(C)(C)CC(=O)NC1CCN(c2nc3sc(C(=O)Nc4ccc(-c5ccc(F)nc5)cc4)cc3s2)CC1] |
| 349 | 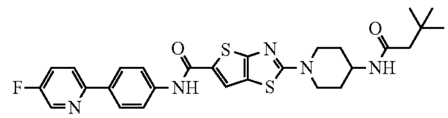 [SMILES: CC(C)(C)CC(=O)NC1CCN(c2nc3sc(C(=O)Nc4ccc(-c5ccc(F)cn5)cc4)cc3s2)CC1] |
| 350 | 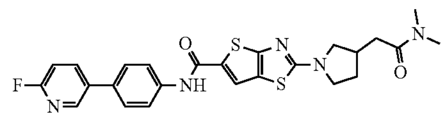 [SMILES: CN(C)C(=O)CC1CCN(c2nc3sc(C(=O)Nc4ccc(-c5ccc(F)nc5)cc4)cc3s2)C1] |
| 351 | 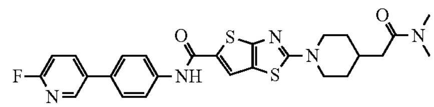 [SMILES: CN(C)C(=O)CC1CCN(c2nc3sc(C(=O)Nc4ccc(-c5ccc(F)nc5)cc4)cc3s2)CC1] |
| 352 | 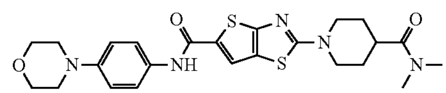 [SMILES: CN(C)C(=O)C1CCN(c2nc3sc(C(=O)Nc4ccc(N5CCOCC5)cc4)cc3s2)CC1] |
| 353 | 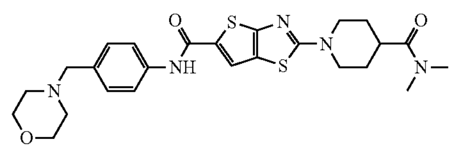 [SMILES: CN(C)C(=O)C1CCN(c2nc3sc(C(=O)Nc4ccc(CN5CCOCC5)cc4)cc3s2)CC1] |
| 354 | 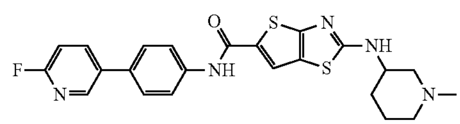 |
| 355 | 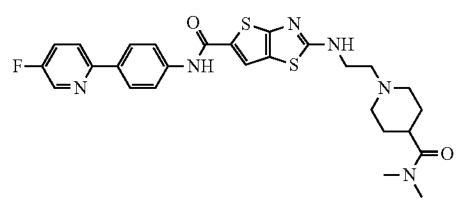 [SMILES: CN(C)C(=O)C1CCN(CCNc2nc3sc(C(=O)Nc4ccc(-c5ccc(F)cn5)cc4)cc3s2)CC1] |
| 357 | 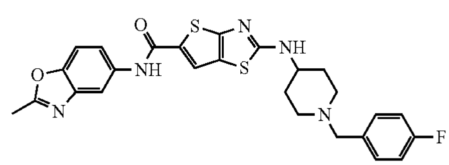 [SMILES: Cc1nc2cc(NC(=O)c3cc4sc(NC5CCN(Cc6ccc(F)cc6)CC5)nc4s3)ccc2o1] |
| 358 | 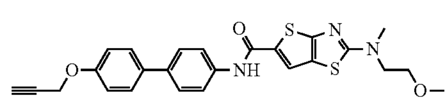 |
| 359 | 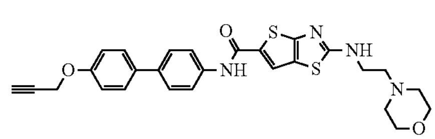 [SMILES: C#CCOc1ccc(-c2ccc(NC(=O)c3cc4sc(NCCN5CCOCC5)nc4s3)cc2)cc1] |

| Compound No. | Structure |
|---|---|
| 360 | 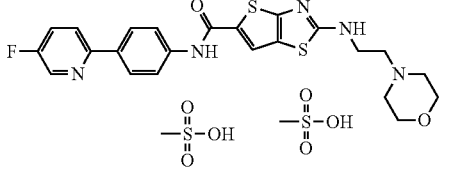 |
and pharmaceutically acceptable salts thereof.
* * * * *